(12) United States Patent
Van Der Ploeg et al.

(10) Patent No.: US 12,263,202 B2
(45) Date of Patent: Apr. 1, 2025

(54) METHOD OF TREATING MELANOCORTIN-4 RECEPTOR PATHWAY-ASSOCIATED DISORDERS

(71) Applicants: CHARITÉ—UNIVERSITÄTSMEDIZIN BERLIN, Berlin (DE); RHYTHM PHARMACEUTICALS, INC., Boston, MA (US)

(72) Inventors: Leonardus H. T. Van Der Ploeg, Newton, MA (US); Bart Henderson, Belmont, MA (US)

(73) Assignee: RHYTHM PHARMACEUTICALS, INC., Boston, MA (US)

( * ) Notice: Subject to any disclaimer, the term of this patent is extended or adjusted under 35 U.S.C. 154(b) by 505 days.

(21) Appl. No.: 17/171,563

(22) Filed: Feb. 9, 2021

(65) Prior Publication Data

US 2021/0169970 A1 Jun. 10, 2021

Related U.S. Application Data

(63) Continuation of application No. 15/764,725, filed as application No. PCT/US2016/054457 on Sep. 29, 2016, now Pat. No. 10,960,046.

(60) Provisional application No. 62/235,003, filed on Sep. 30, 2015.

(51) Int. Cl.
| | | |
|---|---|---|
| *A61K 38/00* | (2006.01) | |
| *A61K 9/00* | (2006.01) | |
| *A61K 38/12* | (2006.01) | |
| *A61P 3/04* | (2006.01) | |
| *A61P 3/10* | (2006.01) | |
| *C07K 7/06* | (2006.01) | |
| *C07K 7/54* | (2006.01) | |
| *C07K 14/685* | (2006.01) | |
| *C07K 14/72* | (2006.01) | |

(52) U.S. Cl.
CPC ............ *A61K 38/12* (2013.01); *A61K 9/0019* (2013.01); *A61P 3/04* (2018.01); *A61P 3/10* (2018.01); *C07K 7/06* (2013.01); *C07K 7/54* (2013.01); *C07K 14/685* (2013.01); *C07K 14/723* (2013.01)

(58) Field of Classification Search
CPC ......... A61K 38/12; A61K 9/0019; A61P 3/04; A61P 3/10; C07K 14/685; C07K 14/723
See application file for complete search history.

(56) References Cited

U.S. PATENT DOCUMENTS

| | | | |
|---|---|---|---|
| 6,603,058 | B1 | 8/2003 | Brennan et al. |
| 10,196,425 | B2 | 2/2019 | Sharma et al. |
| 2003/0144174 | A1 | 7/2003 | Brennan et al. |
| 2014/0329743 | A1 | 11/2014 | Tartaglia et al. |

FOREIGN PATENT DOCUMENTS

| | | |
|---|---|---|
| CA | 2793119 A1 | 1/2007 |
| JP | 2011-501963 A | 1/2011 |
| JP | 2018-531937 A | 11/2018 |
| WO | 2007/008704 A2 | 1/2007 |
| WO | 2010/144344 A2 | 12/2010 |
| WO | 11/017209 A1 | 2/2011 |
| WO | 2011/060352 A1 | 5/2011 |
| WO | 2013/102047 A1 | 7/2013 |
| WO | 2014/144260 A1 | 9/2014 |
| WO | 2014/144842 A2 | 9/2014 |

OTHER PUBLICATIONS

Seo et al. Human Molecular Genetics, 2009, vol. 18, No. 7 1323-1331.*
Chen (J Clin Endocrinol Metab. Apr. 2015; 100(4): 1639-1645).*
Keith Gottesdiener "2014 FPWR Research Conference" Nov. 16, 2014, pp. 1-15.
International Search Report for PCT/US2016/054457 mailed Dec. 6, 2016.
2014 FPWR Research Conference Foundation for Prader-Willi Research; https://www.fpwr.org/events/2014-fpwr-research-conference; Nov. 1, 2014, pp. 1-8.
Index of /wp-content/uploads/2014/11; Nov. 22, 2014, pp. 1-23.
Rhythm Initiates Two Phase 2 Clinical Trails of Setmelanotide (RM-493) in Rare Genetic Disorders of Obesity Caused by MC4 Pathway Deficiencies—Rhythm Pharmaceuticals; Jun. 4, 2015 pp. 1-2.
Kühnen et al "RM-493, a Melancortin-4 Receptor (MC4R) Agonist, is being Therapeutically Evaluated in Patients with Deficiencies in the Leptin—Proopiomelanocortin (POMC)—MC4R Hypothalamic Pathway, Including Prader-Willi Syndrome (PWS)" ESPE Abstracts, Oct. 1, 2015, pp. 1-2.
Wikipedia, Setmelanotide: https://en.wikipedia.org/w/index.php?title=Setmelanotide&oldid=683313790; Sep. 29, 2015, pp. 1-3.
Rhythm: MC4/RM-493; Aug. 17, 2015, pp. 1.
Mercer et al "Magel2 is Required for Leptin-Mediated Depolarization of POMC Neurons in the Hypothalamic Arcuate Nucleus in Mice" PLoS Genetis, vol. 9, No. 1, Jan. 2013, pp. 1-10.
Wikipedia, Melanotan II: https://de.wikipedia.org/w/index.php?title=Melanotan_II&oldid=139806007; Mar. 15, 2015, pp. 1-3.
Clinical Trial: NCT02311673 on Aug. 3, 2015, pp. 1-5.
Schaaf et al "Truncating Mutations of MAGEL2 cause Prader-Willi Phenotypes and Autism" Nature Genetics, vol. 45, No. 11, Nov. 2013, pp. 1405-1405.
Keith Gottesdiener "Project Information 1R01FD005094-01A1" Jul. 10, 2015, pp. 1-2.
Zeng et al "Structure-activity relationshipds of beta-MSH derived melanocortin-4 receptor peptide agonists" Current Topics in Medical Chemistry, vol. 7, No. 11, Jun. 2007, pp. 1052-1067.

(Continued)

*Primary Examiner* — Jeanette M Lieb
(74) *Attorney, Agent, or Firm* — Lando & Anastasi, LLP

(57) ABSTRACT

The disclosure is related to a method of treating a disorder, such as Prader Willi Syndrome (PWS), obesity or hyperphagia, in a subject using a melanocortin-4 receptor (MC4R) agonist. Also described is method of treating a subject having a deficiency in the pro-opiomelanocortin (POMC)-MC4R pathway, such as a POMC-null or a PCSK-null subject, using a MC4R agonist.

21 Claims, 5 Drawing Sheets

Specification includes a Sequence Listing.

(56) References Cited

OTHER PUBLICATIONS

Al-Obeidi et al, "Potent and Prolonged Acting Cyclic actam Analogues of a-Melanotropin: Design Based on Molecular Dynamics" Journal of Medical Chemisty, vol. 32, No. 12, 1989, pp. 2555-2561.
Chen et al, "RM-493, a Melanocortin-4 Receptor (MC4R) Agonist, Increases Resting Energy Expenditure in Obese Individuals" Journal of Clinical Endocrinology and Metabolism, vol. 100, No. 4, 2015, pp. 1639-1645.
International Search Report and Writen Opinion for PCT/US2016/054455 mailed Oct. 31, 2016.
Dubern et al., "Mutational analysis of the pro-opiomelanocortin gene in French obese children led to the identification of a novel deleterious heterozygous mutation located in the a-Melanocyte stimulation hormone domain" Pediatric Research, 2008, vol. 63, No. 2, pp. 211-216.
Search Report and Written Opinion for Singapore Patent Application No. 11201802526W dated Aug. 13, 2019.
Kulanuwat et al., "Association between rs155971 in the PCSK1 gene and the lipid profile of obese Thai children: a family-based study" Genetics and Molecular Research, 2015, vol. 14, No. 3, pp. 9136-9144.
Ghoussaini et al., "Analysis of the SIM1 contribution to polygenic obesity in the French population" Obesity, 2010, vol. 18, pp. 1670-1675.
Weigle et al., "Obesity genes and the regulation of body fat content" BioEssays, 1996, vol. 18, No. 11, Abstract.
Colmers et al., "Leptin signaling defects in a mouse model of Prader-Willi syndrome, An orphan genetic obesity syndrome No. more?" Rare Diseases, 2013, e24421.
Yuan et al., "Identification of polymorphic loci in the promoter region of the serotonin 5-HT2C receptor gene and their association with obesity and type II diabetes" Diabetologia, 2000, vol. 43, pp. 373-376.
Sharma et al., "Current mechanistic and pharmacodynamic understanding of melanocortin-4 receptor activation" Molecules, 2019, vol. 24, No. 10, 14 pages.
Anonymous: "History of Changes for Study: NCT02507492", Jul. 22, 2015, pp. 1-3, XP055713577, Retrieved from the Internet: URL:https://clinicaltrials.gov/ct2/history/NCT02507492?V_1=View#StudyPageTop.
Anonymous: "RM-493-Supplementation-Therapy", Nov. 28, 2014, pp. 1-5, XP055713588, Retrieved from the Internet: URL:https://www.clinicaltrialsregister.eu/ctr-search/trial/2014-002392-28/DE.
Müller et al., "Metabolic precision medicines curing POMC deficiency" Cell Metabolism, 2016, vol. 24, No. 2, pp. 194-195.
Gottesdiener et al., "T-P-3134: Analysis of the Synthetic PeptideSetrnelanotide (RM-493),a Melanocortin-4 Receptor (MC4R) Agonist, on Cardiovascular Parameters in Three Phase 1b/2a Studies", Nov. 6, 2015, XP055713763, Retrieved from the Internet: URL:http://web.archive.org/web/20171209164909if_fhttp://www.rhythmtx.com:80/wp-content/uploads/2015/12/ObesityWeek-2015-Rhythm-Ph1b-Data-.pdf.
Kühnen et al., "Proopoimelanocortin deficiency treated with a melanocortin-4 receptor agonist" New England Journal of Medicine, 2016, vol. 375, No. 3, pp. 240-246.
Plagemann et al., "Hypothalamic proopiomelanocortin promoter methylation becomes altered by early overfeeding: an epigenetic model of obesity and the metabolic syndrome" J Physiol, 2009, vol. 587, No. 20, pp. 4963-4976.
Zhang et al., "Hypermethylation of Sp1 binding site suppresses hypothalamic POMC in neonates and may contribute to metabolic disorders in adults: impact of maternal dietary CLAs" Diabetes, vol. 63, pp. 1475-1487.
Marco et al., "High fat diet induces hypermethylation of the hypothalamic Pomc promoter and obesity in post-weaning rats" Psychoneuroendocrinology, 2013, vol. 38, Issue 12, pp. 2844-2853.
Kuehnen et al., "An alu element-associated hypermethylation variant of the POMC gene is associated with childhood obesity" PLoS Genetics, 2012, vol. 8, Issue 3, e1002543.
Hiroyuki Shimizu, "Approach to melanocortin-based—clinical practice" Journal of Japan Society for the Study of Obesity, vol. 8, No. 1, 2002, pp. 80-81.
Adan et al., "The MC4 receptor and control of appetite" Britsh Journal of Pharmacology, 2006, vol. 149, pp. 815-827.
Modi et al., "Melanocortin receptor agonists facilitate oxytocin-dependent partner preference formation in the prairie vole" Neuropsychopharmacology, 2015, vol. 40, pp. 1856-1865.

* cited by examiner

```
                               SEQUENCE LISTING

<160> NUMBER OF SEQ ID NOS: 614

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Beta-Ala

<400> SEQUENCE: 1

Xaa Asp His Phe Arg Trp Ala Lys
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: A6c

<400> SEQUENCE: 2

Xaa Asp His Phe Arg Trp Xaa Lys
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Ahx
```

```
<400> SEQUENCE: 3

Xaa Cys His Phe Arg Trp Xaa Cys
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: D-Cys

<400> SEQUENCE: 4

Phe Cys His Phe Arg Trp Ala Cys Thr
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys

<400> SEQUENCE: 5

Phe Cys His Phe Arg Trp Ala Cys Thr
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-Phe
<220> FEATURE:
```

```
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (8)..(8)
<223> OTHER INFORMATION: D-Cys

<400> SEQUENCE: 6

Phe Cys His Phe Arg Trp Xaa Cys Thr
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn

<400> SEQUENCE: 7

Xaa Cys His Phe Arg Trp Xaa Cys
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn

<400> SEQUENCE: 8

Xaa Asp His Phe Arg Trp Xaa Lys
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A6c
<220> FEATURE:
<221> NAME/KEY: MOD_RES
```

```
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 9

Xaa Asp His Phe Arg Trp Xaa Lys
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-2-Nal
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 10

Xaa Asp His Phe Arg Trp Xaa Lys
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cha
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 11

Xaa Asp His Phe Arg Trp Xaa Lys
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
```

```
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 12

Xaa Asp His Phe Arg Trp Xaa Lys
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe

<400> SEQUENCE: 13

Xaa Cys Ala His Phe Arg Trp Cys
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: Beta-Ala
<220> FEATURE:
<221> NAME/KEY: MOD_RES
<222> LOCATION: (5)..(5)
<223> OTHER INFORMATION: D-Phe

<400> SEQUENCE: 14

Xaa Cys Ala His Phe Arg Trp Cys
1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: Gaba
```

```
<220> FEATURE:
<221> NAME/KEY: MOD_RES
<222> LOCATION: (5)..(5)
<223> OTHER INFORMATION: D-Phe

<400> SEQUENCE: 15

Xaa Cys Xaa His Phe Arg Trp Cys
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (5)..(5)
<223> OTHER INFORMATION: D-Phe

<400> SEQUENCE: 16

Xaa Cys Xaa His Phe Arg Trp Cys
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (5)..(5)
<223> OTHER INFORMATION: D-Phe

<400> SEQUENCE: 17

Xaa Cys Gly His Phe Arg Trp Cys
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (5)..(5)
<223> OTHER INFORMATION: D-Phe
```

```
<400> SEQUENCE: 18

Xaa Cys Ala His Phe Arg Trp Cys
 1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe

<400> SEQUENCE: 19

Xaa Cys Ala His Phe Arg Trp Cys
 1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (3)..(3)
<223> OTHER INFORMATION: Beta-Ala
<220> FEATURE:
<221> NAME/KEY: MOD_RES
<222> LOCATION: (5)..(5)
<223> OTHER INFORMATION: D-Phe

<400> SEQUENCE: 20

Xaa Cys Ala His Phe Arg Trp Cys
 1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
```

```
<222> LOCATION: (2)..(2)
<223> OTHER INFORMATION: D-Cys
<220> FEATURE:
<221> NAME/KEY: MOD_RES
<222> LOCATION: (3)..(3)
<223> OTHER INFORMATION: Gaba
<220> FEATURE:
<221> NAME/KEY: MOD_RES
<222> LOCATION: (5)..(5)
<223> OTHER INFORMATION: D-Phe

<400> SEQUENCE: 21

Xaa Cys Xaa His Phe Arg Trp Cys
1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (5)..(5)
<223> OTHER INFORMATION: D-Phe

<400> SEQUENCE: 22

Xaa Cys Xaa His Phe Arg Trp Cys
1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (5)..(5)
<223> OTHER INFORMATION: D-Phe

<400> SEQUENCE: 23

Xaa Cys Gly His Phe Arg Trp Cys
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: D-Cys

<400> SEQUENCE: 24

Xaa Cys Ala His Phe Arg Trp Cys
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: Beta-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: D-Cys

<400> SEQUENCE: 25

Xaa Cys Ala His Phe Arg Trp Cys
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: Gaba
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: D-Cys

<400> SEQUENCE: 26
```

```
Xaa Cys Xaa His Phe Arg Trp Cys
1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: D-Cys

<400> SEQUENCE: 27

Xaa Cys Xaa His Phe Arg Trp Cys
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: D-Cys

<400> SEQUENCE: 28

Xaa Cys Gly His Phe Arg Trp Cys
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (5)..(5)
```

```
<223> OTHER INFORMATION: D-Phe
<220> FEATURE:
<221> NAME/KEY: MOD_RES
<222> LOCATION: (8)..(8)
<223> OTHER INFORMATION: D-Cys

<400> SEQUENCE: 29

Xaa Cys Ala His Phe Arg Trp Cys
1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: D-Cys

<400> SEQUENCE: 30

Xaa Cys Ala His Phe Arg Trp Cys
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (3)..(3)
<223> OTHER INFORMATION: Beta-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: D-Cys

<400> SEQUENCE: 31

Xaa Cys Ala His Phe Arg Trp Cys
1               5
```

```
<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (3)..(3)
<223> OTHER INFORMATION: Gaba
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: D-Cys

<400> SEQUENCE: 32

Xaa Cys Xaa His Phe Arg Trp Cys
1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: D-Cys

<400> SEQUENCE: 33

Xaa Cys Xaa His Phe Arg Trp Cys
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Oic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 34

Xaa Asp His Phe Arg Trp Xaa Lys
1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chg
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 35

Xaa Asp His Phe Arg Trp Xaa Lys
1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hCha
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 36

Xaa Asp His Phe Arg Trp Xaa Lys
1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Cha
```

```
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 37

Xaa Asp His Phe Arg Trp Xaa Lys
1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-hCha
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 38

Xaa Asp His Phe Arg Trp Xaa Lys
1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nip
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 39

Xaa Asp His Phe Arg Trp Xaa Lys
1               5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Phe
<220> FEATURE:
```

```
<221> NAME/KEY: MOD_RES
<222> LOCATION: (7)..(7)
<223> OTHER INFORMATION: Gaba

<400> SEQUENCE: 40

Pro Asp His Phe Arg Trp Xaa Lys
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 41

Leu Asp His Phe Arg Trp Xaa Lys
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 42

Phe Asp His Phe Arg Trp Xaa Lys
1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 43

Phe Asp His Phe Arg Trp Xaa Lys
1               5
```

```
<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Chg
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 44

Xaa Asp His Phe Arg Trp Xaa Lys
1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cha
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 45

Xaa Asp His Phe Arg Trp Xaa Lys
1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cha
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 46

Xaa Asp His Phe Arg Trp Xaa Lys
1               5
```

```
<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 47

Phe Asp His Phe Arg Trp Xaa Lys
1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-hMet
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 48

Met Asp His Phe Arg Trp Xaa Lys
1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gaba
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 49

Xaa Asp His Phe Arg Trp Xaa Lys
1               5

<210> SEQ ID NO 50
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cha
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp

<400> SEQUENCE: 50

Xaa Asp His Phe Arg Trp Ala Lys
1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hCha
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp

<400> SEQUENCE: 51

Xaa Asp His Phe Arg Trp Ala Lys
1               5

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp

<400> SEQUENCE: 52

Leu Asp His Phe Arg Trp Ala Lys
1               5

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
```

```
<223> OTHER INFORMATION: D-Phe
<220> FEATURE:
<221> NAME/KEY: MOD_RES
<222> LOCATION: (6)..(6)
<223> OTHER INFORMATION: D-Trp

<400> SEQUENCE: 53

Leu Asp His Phe Arg Trp Ala Lys
1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp

<400> SEQUENCE: 54

Phe Asp His Phe Arg Trp Ala Lys
1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: D-Ala

<400> SEQUENCE: 55

Xaa Asp His Phe Arg Trp Ala Lys
1               5

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
```

```
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Beta-Ala

<400> SEQUENCE: 56

Xaa Asp His Phe Arg Trp Ala Lys
1               5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Gaba

<400> SEQUENCE: 57

Xaa Asp His Phe Arg Trp Xaa Lys
1               5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Aha

<400> SEQUENCE: 58

Xaa Asp His Phe Arg Trp Xaa Lys
1               5

<210> SEQ ID NO 59
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Apn

<400> SEQUENCE: 59

Xaa Asp His Phe Arg Trp Xaa Lys
1               5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Apn

<400> SEQUENCE: 60

Xaa Cys His Phe Arg Trp Xaa Cys
1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Gaba
```

```
<400> SEQUENCE: 61

Xaa Cys His Phe Arg Trp Xaa Cys
1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Ahx

<400> SEQUENCE: 62

Xaa Cys His Phe Arg Trp Xaa Cys
1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Beta-Ala

<400> SEQUENCE: 63

Xaa Cys His Phe Arg Trp Ala Cys
1               5

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
```

```
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: D-Ala

<400> SEQUENCE: 64

Xaa Cys His Phe Arg Trp Ala Cys
1               5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-2-Nal

<400> SEQUENCE: 65

Xaa Cys Ala His Xaa Arg Trp Cys
1               5

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-2-Nal
<220> FEATURE:
<221> NAME/KEY: MOD_RES
<222> LOCATION: (7)..(7)
<223> OTHER INFORMATION: 2-Nal

<400> SEQUENCE: 66

Xaa Cys Ala His Xaa Arg Xaa Cys
1               5

<210> SEQ ID NO 67
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-2-Nal
<220> FEATURE:
<221> NAME/KEY: MOD_RES
<222> LOCATION: (7)..(7)
<223> OTHER INFORMATION: 1-Nal

<400> SEQUENCE: 67

Xaa Cys Ala His Xaa Arg Xaa Cys
1               5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (7)..(7)
<223> OTHER INFORMATION: 2-Nal

<400> SEQUENCE: 68

Xaa Cys Ala His Phe Arg Xaa Cys
1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe

<400> SEQUENCE: 69

Xaa Cys Ala His Phe Arg Trp Cys
1               5
```

```
<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (7)..(7)
<223> OTHER INFORMATION: 2-Nal

<400> SEQUENCE: 70

Xaa Cys Ala His Phe Arg Xaa Cys
1               5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (7)..(7)
<223> OTHER INFORMATION: 1-Nal

<400> SEQUENCE: 71

Xaa Cys Ala His Phe Arg Xaa Cys
1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
```

```
<222> LOCATION: (5)..(5)
<223> OTHER INFORMATION: D-Phe
<220> FEATURE:
<221> NAME/KEY: MOD_RES
<222> LOCATION: (7)..(7)
<223> OTHER INFORMATION: Bal

<400> SEQUENCE: 72

Xaa Cys Ala His Phe Arg Xaa Cys
1               5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Glu
<220> FEATURE:
<221> NAME/KEY: MOD_RES
<222> LOCATION: (5)..(5)
<223> OTHER INFORMATION: D-Phe

<400> SEQUENCE: 73

Xaa Cys Glu His Phe Arg Trp Cys
1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Ala

<400> SEQUENCE: 74

Xaa Asp His Phe Arg Trp Ala Lys
1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
```

```
<223> OTHER INFORMATION: D-Ala
<220> FEATURE:
<221> NAME/KEY: MOD_RES
<222> LOCATION: (5)..(5)
<223> OTHER INFORMATION: D-2-Nal
<220> FEATURE:
<221> NAME/KEY: MOD_RES
<222> LOCATION: (7)..(7)
<223> OTHER INFORMATION: Bal

<400> SEQUENCE: 75

Xaa Cys Ala His Xaa Arg Xaa Cys
1               5

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: Pen
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe

<400> SEQUENCE: 76

Xaa Xaa Ala His Phe Arg Trp Cys
1               5

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen

<400> SEQUENCE: 77

Xaa Cys Ala His Phe Arg Trp Xaa
1               5

<210> SEQ ID NO 78
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: Pen
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen

<400> SEQUENCE: 78

Xaa Xaa Ala His Phe Arg Trp Xaa
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys

<400> SEQUENCE: 79

Phe Cys His Phe Arg Trp Ala Cys Thr
1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
```

```
<223> OTHER INFORMATION: Beta-Ala
<220> FEATURE:
<221> NAME/KEY: MOD_RES
<222> LOCATION: (8)..(8)
<223> OTHER INFORMATION: D-Cys

<400> SEQUENCE: 80

Phe Cys His Tyr Arg Trp Ala Cys Thr
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys

<400> SEQUENCE: 81

Phe Cys His Phe Arg Xaa Ala Cys Thr
1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys

<400> SEQUENCE: 82

Phe Cys His Tyr Arg Trp Ala Cys Thr
1               5

<210> SEQ ID NO 83
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys

<400> SEQUENCE: 83

Phe Cys His Phe Arg Xaa Ala Cys Thr
1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys

<400> SEQUENCE: 84

Phe Cys His Tyr Arg Xaa Ala Cys Thr
1               5

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
```

```
<223> OTHER INFORMATION: D-Phe
<220> FEATURE:
<221> NAME/KEY: MOD_RES
<222> LOCATION: (7)..(7)
<223> OTHER INFORMATION: Apn

<400> SEQUENCE: 85

Xaa Cys His Phe Arg Trp Xaa Cys
1               5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe

<400> SEQUENCE: 86

Xaa Asp Ala His Phe Arg Trp Lys
1               5

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (7)..(7)
<223> OTHER INFORMATION: Bal

<400> SEQUENCE: 87

Xaa Asp Ala His Phe Arg Xaa Lys
1               5

<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
```

```
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen

<400> SEQUENCE: 88

Xaa Cys Ala His Phe Arg Trp Xaa
1               5

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Abu
<220> FEATURE:
<221> NAME/KEY: MOD_RES
<222> LOCATION: (5)..(5)
<223> OTHER INFORMATION: D-Phe

<400> SEQUENCE: 89

Xaa Cys Xaa His Phe Arg Trp Cys
1               5

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Val
<220> FEATURE:
<221> NAME/KEY: MOD_RES
<222> LOCATION: (5)..(5)
<223> OTHER INFORMATION: D-Phe

<400> SEQUENCE: 90

Xaa Cys Val His Phe Arg Trp Cys
1               5

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ile
<220> FEATURE:
<221> NAME/KEY: MOD_RES
<222> LOCATION: (5)..(5)
<223> OTHER INFORMATION: D-Phe

<400> SEQUENCE: 91

Xaa Cys Ile His Phe Arg Trp Cys
1               5

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe

<400> SEQUENCE: 92

Xaa Cys Leu His Phe Arg Trp Cys
1               5

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Tle
<220> FEATURE:
<221> NAME/KEY: MOD_RES
<222> LOCATION: (5)..(5)
<223> OTHER INFORMATION: D-Phe

<400> SEQUENCE: 93

Xaa Cys Xaa His Phe Arg Trp Cys
1               5

<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe

<400> SEQUENCE: 94

Xaa Cys Xaa His Phe Arg Trp Cys
1               5

<210> SEQ ID NO 95
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: Pen
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 95

Xaa Xaa His Phe Arg Trp Xaa Cys
1               5

<210> SEQ ID NO 96
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (8)..(8)
<223> OTHER INFORMATION: Pen

<400> SEQUENCE: 96

Xaa Cys His Phe Arg Trp Xaa Xaa
1               5

<210> SEQ ID NO 97
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: Pen
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (8)..(8)
<223> OTHER INFORMATION: Pen

<400> SEQUENCE: 97

Xaa Xaa His Phe Arg Trp Xaa Xaa
1               5

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 98

Leu Cys His Phe Arg Trp Xaa Cys
1               5

<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cha
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 99

Xaa Cys His Phe Arg Trp Xaa Cys
1               5
```

```
<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 100

Ile Cys His Phe Arg Trp Xaa Cys
1               5

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 101

Phe Cys His Phe Arg Trp Xaa Cys
1               5

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 102

Val Cys His Phe Arg Trp Xaa Cys
1               5

<210> SEQ ID NO 103
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 2-Nal
<220> FEATURE:
```

```
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 103

Xaa Cys His Phe Arg Trp Xaa Cys
1               5

<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 104

Xaa Cys His Phe Arg Trp Xaa Cys
1               5

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 105

Phe Cys His Phe Arg Trp Xaa Cys
1               5

<210> SEQ ID NO 106
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: 3-Pal
<220> FEATURE:
<221> NAME/KEY: MOD_RES
```

```
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 106

Xaa Cys Xaa Phe Arg Trp Xaa Cys
1               5

<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe

<400> SEQUENCE: 107

Xaa Cys Ala His Phe Arg Trp Cys
1               5

<210> SEQ ID NO 108
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Gaba

<400> SEQUENCE: 108

Xaa Cys His Phe Arg Trp Xaa Cys
1               5

<210> SEQ ID NO 109
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
```

```
<223> OTHER INFORMATION: D-2-Nal

<400> SEQUENCE: 109

Xaa Asp His Xaa Arg Trp Ala Lys
1               5

<210> SEQ ID NO 110
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (7)..(7)
<223> OTHER INFORMATION: Beta-Ala

<400> SEQUENCE: 110

Xaa Asp His Xaa Arg Trp Ala Lys
1               5

<210> SEQ ID NO 111
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (7)..(7)
<223> OTHER INFORMATION: Gaba

<400> SEQUENCE: 111

Xaa Cys His Xaa Arg Trp Xaa Cys
1               5

<210> SEQ ID NO 112
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (7)..(7)
<223> OTHER INFORMATION: Ahx
```

```
<400> SEQUENCE: 112

Xaa Cys His Xaa Arg Trp Xaa Cys
1               5

<210> SEQ ID NO 113
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (7)..(7)
<223> OTHER INFORMATION: Gaba

<400> SEQUENCE: 113

Phe Asp His Xaa Arg Trp Xaa Lys
1               5

<210> SEQ ID NO 114
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cha
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (7)..(7)
<223> OTHER INFORMATION: Gaba

<400> SEQUENCE: 114

Xaa Asp His Xaa Arg Trp Xaa Lys
1               5

<210> SEQ ID NO 115
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Beta-Ala

<400> SEQUENCE: 115

Xaa Asp His Phe Arg Trp Ala Lys
1               5
```

```
<210> SEQ ID NO 116
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Ahx

<400> SEQUENCE: 116

Xaa Cys His Phe Arg Trp Xaa Cys
1               5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: D-Cys

<400> SEQUENCE: 117

Phe Cys His Phe Arg Trp Ala Cys Thr
1               5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys

<400> SEQUENCE: 118
```

```
Phe Cys His Phe Arg Trp Ala Cys Thr
1               5

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (8)..(8)
<223> OTHER INFORMATION: D-Cys

<400> SEQUENCE: 119

Phe Cys His Phe Arg Trp Xaa Cys Thr
1               5

<210> SEQ ID NO 120
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn

<400> SEQUENCE: 120

Xaa Cys His Phe Arg Trp Xaa Cys
1               5

<210> SEQ ID NO 121
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
```

```
<223> OTHER INFORMATION: Apn

<400> SEQUENCE: 121

Xaa Asp His Phe Arg Trp Xaa Lys
1               5

<210> SEQ ID NO 122
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cha
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 122

Xaa Asp His Phe Arg Trp Xaa Lys
1               5

<210> SEQ ID NO 123
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 123

Xaa Asp His Phe Arg Trp Xaa Lys
1               5

<210> SEQ ID NO 124
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chg
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
```

```
<400> SEQUENCE: 124

Xaa Asp His Phe Arg Trp Xaa Lys
1               5

<210> SEQ ID NO 125
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Cha
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 125

Xaa Asp His Phe Arg Trp Xaa Lys
1               5

<210> SEQ ID NO 126
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hCha
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 126

Xaa Asp His Phe Arg Trp Xaa Lys
1               5

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Chg
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
```

```
<400> SEQUENCE: 127

Xaa Asp His Phe Arg Trp Xaa Lys
1               5

<210> SEQ ID NO 128
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba

<400> SEQUENCE: 128

Phe Asp His Phe Arg Trp Xaa Lys
1               5

<210> SEQ ID NO 129
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Gaba

<400> SEQUENCE: 129

Xaa Cys His Phe Arg Trp Xaa Cys
1               5

<210> SEQ ID NO 130
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
```

```
<222> LOCATION: (7)..(7)
<223> OTHER INFORMATION: Ahx

<400> SEQUENCE: 130

Xaa Cys His Phe Arg Trp Xaa Cys
1               5

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Beta-Ala

<400> SEQUENCE: 131

Xaa Cys His Phe Arg Trp Ala Cys
1               5

<210> SEQ ID NO 132
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: D-Ala

<400> SEQUENCE: 132

Xaa Cys His Phe Arg Trp Ala Cys
1               5

<210> SEQ ID NO 133
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-2-Nal

<400> SEQUENCE: 133

Xaa Cys Ala His Xaa Arg Trp Cys
1               5

<210> SEQ ID NO 134
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-2-Nal
<220> FEATURE:
<221> NAME/KEY: MOD_RES
<222> LOCATION: (7)..(7)
<223> OTHER INFORMATION: 2-Nal

<400> SEQUENCE: 134

Xaa Cys Ala His Xaa Arg Xaa Cys
1               5

<210> SEQ ID NO 135
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-2-Nal
<220> FEATURE:
<221> NAME/KEY: MOD_RES
<222> LOCATION: (7)..(7)
<223> OTHER INFORMATION: 1-Nal

<400> SEQUENCE: 135

Xaa Cys Ala His Xaa Arg Xaa Cys
1               5

<210> SEQ ID NO 136
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-2-Nal
<220> FEATURE:
<221> NAME/KEY: MOD_RES
<222> LOCATION: (7)..(7)
<223> OTHER INFORMATION: Bal

<400> SEQUENCE: 136

Xaa Cys Ala His Xaa Arg Xaa Cys
1               5

<210> SEQ ID NO 137
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: Pen
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe

<400> SEQUENCE: 137

Xaa Xaa Ala His Phe Arg Trp Cys
1               5

<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (8)..(8)
```

```
<223> OTHER INFORMATION: Pen

<400> SEQUENCE: 138

Xaa Cys His Phe Arg Trp Xaa Xaa
1               5

<210> SEQ ID NO 139
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-2-Nal

<400> SEQUENCE: 139

Arg Cys Ala His Xaa Arg Trp Cys
1               5

<210> SEQ ID NO 140
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe

<400> SEQUENCE: 140

Arg Cys Ala His Phe Arg Trp Cys
1               5

<210> SEQ ID NO 141
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe

<400> SEQUENCE: 141

Arg Cys Ala His Phe Arg Trp Cys
1               5

<210> SEQ ID NO 142
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen

<400> SEQUENCE: 142

Arg Cys Ala His Phe Arg Trp Xaa
1               5

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (8)..(8)
<223> OTHER INFORMATION: Pen

<400> SEQUENCE: 143

Arg Cys His Phe Arg Trp Xaa Xaa
1               5

<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (8)..(8)
<223> OTHER INFORMATION: Pen
```

```
<400> SEQUENCE: 144

Arg Cys His Phe Arg Trp Xaa Xaa
1               5

<210> SEQ ID NO 145
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen

<400> SEQUENCE: 145

Arg Cys Ala His Phe Arg Trp Xaa
1               5

<210> SEQ ID NO 146
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (4)..(4)
<223> OTHER INFORMATION: D-Phe

<400> SEQUENCE: 146

Arg Asp His Phe Arg Trp Ala Lys
1               5

<210> SEQ ID NO 147
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Phe

<400> SEQUENCE: 147

Arg Asp His Phe Arg Trp Ala Lys
1               5

<210> SEQ ID NO 148
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe

<400> SEQUENCE: 148

Xaa Cys Ala His Phe Arg Trp Gly Cys
1               5

<210> SEQ ID NO 149
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: D-Ala

<400> SEQUENCE: 149

Xaa Cys Ala His Phe Arg Trp Ala Cys
1               5

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Beta-Ala

<400> SEQUENCE: 150

Xaa Cys Ala His Phe Arg Trp Ala Cys
1               5
```

```
<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Gaba

<400> SEQUENCE: 151

Xaa Cys Ala His Phe Arg Trp Xaa Cys
1               5

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Apn

<400> SEQUENCE: 152

Xaa Cys Ala His Phe Arg Trp Xaa Cys
1               5

<210> SEQ ID NO 153
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Phe

<400> SEQUENCE: 153

Cys Glu His Phe Arg Trp Ala Cys
1               5

<210> SEQ ID NO 154
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: 2-Nal

<400> SEQUENCE: 154

Cys Glu His Phe Arg Xaa Ala Cys
1               5

<210> SEQ ID NO 155
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe

<400> SEQUENCE: 155

Cys Ala His Phe Arg Trp Ala Cys
1               5

<210> SEQ ID NO 156
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: 2-Nal

<400> SEQUENCE: 156

Cys Ala His Phe Arg Xaa Ala Cys
1               5

<210> SEQ ID NO 157
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe

<400> SEQUENCE: 157

Xaa Cys Ala His Phe Arg Trp Ala Cys
1               5

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (7)..(7)
<223> OTHER INFORMATION: Bal

<400> SEQUENCE: 158

Xaa Asp Ala His Phe Arg Xaa Ala Lys
1               5

<210> SEQ ID NO 159
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Nle
<220> FEATURE:
<221> NAME/KEY: MOD_RES
<222> LOCATION: (15)..(15)
<223> OTHER INFORMATION: D-2-Nal

<400> SEQUENCE: 159

Tyr Gly Arg Lys Lys Arg Arg Gln Arg Arg Arg Xaa Asp His Xaa Arg
1               5                   10                  15

Trp Lys

<210> SEQ ID NO 160
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (12)..(12)
<223> OTHER INFORMATION: Doc
<220> FEATURE:
<221> NAME/KEY: MOD_RES
<222> LOCATION: (13)..(13)
<223> OTHER INFORMATION: Nle
<220> FEATURE:
<221> NAME/KEY: MOD_RES
<222> LOCATION: (16)..(16)
<223> OTHER INFORMATION: D-2-Nal

<400> SEQUENCE: 160

Tyr Gly Arg Lys Lys Arg Arg Gln Arg Arg Xaa Xaa Asp His Xaa
1               5                   10                  15

Arg Trp Lys

<210> SEQ ID NO 161
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (8)..(8)
<223> OTHER INFORMATION: Beta-Ala

<400> SEQUENCE: 161

Xaa Asp His Xaa Arg Trp Lys Ala Tyr Gly Arg Lys Lys Arg Arg Gln
1               5                   10                  15

Arg Arg Arg

<210> SEQ ID NO 162
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (8)..(8)
<223> OTHER INFORMATION: Beta-Ala

<400> SEQUENCE: 162

Xaa Asp His Xaa Arg Trp Lys Ala Tyr Gly Arg Lys Lys Arg Arg Gln
1               5                   10                  15

Arg Arg Arg

<210> SEQ ID NO 163
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (8)..(8)
<223> OTHER INFORMATION: Doc
<220> FEATURE:
<221> NAME/KEY: MOD_RES
<222> LOCATION: (9)..(9)
<223> OTHER INFORMATION: Doc

<400> SEQUENCE: 163

Xaa Asp His Xaa Arg Trp Lys Xaa Xaa Tyr Gly Arg Lys Lys Arg Arg
1               5                   10                  15

Gln Arg Arg
            20

<210> SEQ ID NO 164
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-2-Nal

<400> SEQUENCE: 164

Xaa Asp His Xaa Arg Trp Lys Pro Pro Lys Asp Tyr Gly Arg Lys Lys
1               5                   10                  15

Arg Arg Gln Arg Arg
            20

<210> SEQ ID NO 165
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal

<400> SEQUENCE: 165

Cys Glu His Xaa Arg Trp Gly Cys Pro Pro Lys Asp Tyr Gly Arg Lys
1               5                   10                  15

Lys Arg Arg Gln Arg Arg Arg
            20

<210> SEQ ID NO 166
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (8)..(8)
<223> OTHER INFORMATION: Beta-Ala
<220> FEATURE:
<221> NAME/KEY: MOD_RES
<222> LOCATION: (9)..(9)
<223> OTHER INFORMATION: Beta-Ala

<400> SEQUENCE: 166

Xaa Asp His Xaa Arg Trp Lys Ala Ala Tyr Gly Arg Lys Lys Arg Arg
1               5                   10                  15

Gln Arg Arg Arg
            20

<210> SEQ ID NO 167
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (12)..(12)
<223> OTHER INFORMATION: Doc

<400> SEQUENCE: 167

Xaa Asp His Xaa Arg Trp Lys Pro Pro Lys Asp Xaa Tyr Gly Arg Lys
1               5                   10                  15

Lys Arg Arg Gln Arg Arg Arg
            20

<210> SEQ ID NO 168
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (13)..(13)
<223> OTHER INFORMATION: Doc

<400> SEQUENCE: 168

Cys Glu His Xaa Arg Trp Gly Cys Pro Pro Lys Asp Xaa Tyr Gly Arg
1               5                   10                  15
```

Lys Lys Arg Arg Gln Arg Arg Arg
            20

<210> SEQ ID NO 169
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (13)..(13)
<223> OTHER INFORMATION: Beta-Ala

<400> SEQUENCE: 169

Cys Glu His Xaa Arg Trp Ala Cys Pro Pro Lys Asp Ala Tyr Gly Arg
1               5                   10                  15

Lys Lys Arg Arg Gln Arg Arg Arg
            20

<210> SEQ ID NO 170
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (13)..(13)
<223> OTHER INFORMATION: Doc

<400> SEQUENCE: 170

Cys Glu His Xaa Arg Trp Ala Cys Pro Pro Lys Asp Xaa Tyr Gly Arg
1               5                   10                  15

Lys Lys Arg Arg Gln Arg Arg Arg
            20

<210> SEQ ID NO 171
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (8)..(8)
<223> OTHER INFORMATION: Doc
<220> FEATURE:
<221> NAME/KEY: MOD_RES
<222> LOCATION: (9)..(9)
<223> OTHER INFORMATION: Doc

<400> SEQUENCE: 171

```
Xaa Asp His Xaa Arg Trp Lys Xaa Xaa Tyr Gly Arg Lys Lys Arg Arg
1               5                   10                  15

Gln Arg Arg Arg
            20

<210> SEQ ID NO 172
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala

<400> SEQUENCE: 172

Cys Glu His Xaa Arg Xaa Ala Cys Pro Pro Lys Asp Ala Tyr Gly Arg
1               5                   10                  15

Lys Lys Arg Arg Gln Arg Arg Arg
            20

<210> SEQ ID NO 173
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala

<400> SEQUENCE: 173

Cys Glu His Xaa Arg Xaa Ala Cys Pro Pro Lys Asp Ala Arg Arg Arg
1               5                   10                  15

Arg Arg Gln Arg Arg Arg
            20

<210> SEQ ID NO 174
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
```

```
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala

<400> SEQUENCE: 174

Cys Glu His Xaa Arg Xaa Ala Cys Pro Pro Lys Asp Ala Gly Arg Arg
1               5                   10                  15

Arg Arg Arg Gln Arg Arg Arg
            20

<210> SEQ ID NO 175
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala

<400> SEQUENCE: 175

Cys Glu His Xaa Arg Xaa Ala Cys Pro Pro Lys Asp Ala Tyr Gly Arg
1               5                   10                  15

Arg Arg Arg Arg Gln Arg Arg Arg
            20

<210> SEQ ID NO 176
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (13)..(13)
<223> OTHER INFORMATION: Beta-Ala

<400> SEQUENCE: 176

Cys Glu His Xaa Arg Trp Ala Cys Pro Pro Lys Asp Ala Tyr Gly Arg
1               5                   10                  15

Lys Lys Arg Gln Arg Arg Arg Arg
            20

<210> SEQ ID NO 177
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (4)..(4)
<223> OTHER INFORMATION: D-2-Nal
<220> FEATURE:
<221> NAME/KEY: MOD_RES
<222> LOCATION: (13)..(13)
<223> OTHER INFORMATION: Beta-Ala

<400> SEQUENCE: 177

Cys Glu His Xaa Arg Trp Ala Cys Pro Pro Lys Asp Ala Tyr Gly Arg
1               5                   10                  15

Lys Lys Gln Arg Arg Arg Arg Arg
            20

<210> SEQ ID NO 178
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (13)..(13)
<223> OTHER INFORMATION: Beta-Ala

<400> SEQUENCE: 178

Cys Glu His Xaa Arg Trp Ala Cys Pro Pro Lys Asp Ala Tyr Gly Arg
1               5                   10                  15

Lys Gln Lys Arg Arg Arg Arg Arg
            20

<210> SEQ ID NO 179
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (13)..(13)
<223> OTHER INFORMATION: Beta-Ala

<400> SEQUENCE: 179

Cys Glu His Xaa Arg Trp Ala Cys Pro Pro Lys Asp Ala Tyr Gly Arg
1               5                   10                  15

Lys Lys Arg Arg Arg Arg Gln Arg
            20

<210> SEQ ID NO 180
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
```

```
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala
<220> FEATURE:
<221> NAME/KEY: MOD_RES
<222> LOCATION: (15)..(15)
<223> OTHER INFORMATION: Aib

<400> SEQUENCE: 180

Cys Glu His Xaa Arg Xaa Ala Cys Pro Pro Lys Asp Ala Tyr Xaa Arg
1               5                   10                  15

Lys Lys Arg Arg Gln Arg Arg Arg
            20

<210> SEQ ID NO 181
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala

<400> SEQUENCE: 181

Cys Glu His Xaa Arg Xaa Ala Cys Pro Pro Arg Asp Ala Arg Arg Arg
1               5                   10                  15

Arg Arg Gln Arg Arg Arg
            20

<210> SEQ ID NO 182
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala

<400> SEQUENCE: 182

Cys Glu His Xaa Arg Xaa Ala Cys Pro Pro Lys Asp Ala Arg Arg Arg
1               5                   10                  15

Arg Arg Gln Arg Arg Arg
            20

<210> SEQ ID NO 183
```

```
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala

<400> SEQUENCE: 183

Cys Glu His Xaa Arg Xaa Ala Cys Pro Pro Lys Asp Ala Arg Arg Arg
1               5                   10                  15

Arg Arg Arg Gln Arg Arg Arg
            20

<210> SEQ ID NO 184
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala

<400> SEQUENCE: 184

Cys Glu His Xaa Arg Xaa Ala Cys Pro Pro Arg Asp Ala Arg Arg Arg
1               5                   10                  15

Arg Arg Gln Arg Arg Arg
            20

<210> SEQ ID NO 185
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala

<400> SEQUENCE: 185
```

Cys Glu His Xaa Arg Xaa Ala Cys Pro Pro Lys Asp Ala Arg Arg Arg
1               5                   10                  15

Arg Arg Gln Arg Arg Arg
            20

<210> SEQ ID NO 186
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala

<400> SEQUENCE: 186

Cys Glu His Xaa Arg Xaa Ala Cys Pro Pro Lys Asp Ala Arg Arg Arg
1               5                   10                  15

Arg Arg Arg Gln Arg Arg Arg
            20

<210> SEQ ID NO 187
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala

<400> SEQUENCE: 187

Cys Glu His Xaa Arg Xaa Ala Cys Pro Pro Arg Asp Ala Arg Arg Arg
1               5                   10                  15

Arg Arg Arg Gln Arg Arg Arg
            20

<210> SEQ ID NO 188
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)

<223> OTHER INFORMATION: Bal
<220> FEATURE:
<221> NAME/KEY: MOD_RES
<222> LOCATION: (13)..(13)
<223> OTHER INFORMATION: Beta-Ala

<400> SEQUENCE: 188

Cys Glu His Xaa Arg Xaa Ala Cys Pro Pro Arg Asp Ala Arg Arg Arg
1               5                   10                  15

Arg Arg Gln Arg Arg Arg
            20

<210> SEQ ID NO 189
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala

<400> SEQUENCE: 189

Cys Glu His Xaa Arg Xaa Ala Cys Pro Pro Lys Asp Ala Arg Arg Arg
1               5                   10                  15

Arg Arg Arg Gln Arg Arg Arg
            20

<210> SEQ ID NO 190
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (13)..(13)
<223> OTHER INFORMATION: Beta-Ala

<400> SEQUENCE: 190

Cys Glu His Xaa Arg Trp Ala Cys Pro Pro Lys Asp Ala Tyr Gly Arg
1               5                   10                  15

Lys Lys Arg Arg Arg Gln Arg Arg
            20

<210> SEQ ID NO 191
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)

<223> OTHER INFORMATION: D-2-Nal
<220> FEATURE:
<221> NAME/KEY: MOD_RES
<222> LOCATION: (13)..(13)
<223> OTHER INFORMATION: Beta-Ala

<400> SEQUENCE: 191

Cys Glu His Xaa Arg Trp Ala Cys Pro Pro Lys Asp Ala Tyr Gly Arg
1               5                   10                  15

Gln Lys Lys Arg Arg Arg Arg Arg
            20

<210> SEQ ID NO 192
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (13)..(13)
<223> OTHER INFORMATION: Beta-Ala

<400> SEQUENCE: 192

Cys Glu His Xaa Arg Trp Ala Cys Pro Pro Lys Asp Ala Tyr Gly Arg
1               5                   10                  15

Lys Lys Arg Arg Arg Arg Arg Gln
            20

<210> SEQ ID NO 193
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala

<400> SEQUENCE: 193

Cys Glu His Xaa Arg Xaa Ala Cys Pro Pro Lys Asp Ala Tyr Gly Arg
1               5                   10                  15

Lys Lys Arg Arg Gln Arg Arg Arg
            20

<210> SEQ ID NO 194
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)

```
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala

<400> SEQUENCE: 194

Cys Glu His Xaa Arg Xaa Ala Cys Pro Pro Lys Asp Ala Tyr Gly Arg
1               5                   10                  15

Lys Lys Arg Arg Gln Arg Arg Arg
            20

<210> SEQ ID NO 195
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala

<400> SEQUENCE: 195

Cys Glu His Xaa Arg Xaa Ala Cys Pro Pro Lys Asp Ala Arg Arg Lys
1               5                   10                  15

Arg Arg Gln Arg Arg Arg
            20

<210> SEQ ID NO 196
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala

<400> SEQUENCE: 196

Cys Glu His Xaa Arg Xaa Ala Cys Pro Pro Lys Asp Ala Arg Lys Arg
1               5                   10                  15

Arg Arg Gln Arg Arg Arg
            20

<210> SEQ ID NO 197
<211> LENGTH: 22
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala

<400> SEQUENCE: 197

Cys Glu His Xaa Arg Xaa Ala Cys Pro Pro Lys Asp Ala Arg Arg Lys
1               5                   10                  15

Arg Arg Gln Arg Arg Arg
            20

<210> SEQ ID NO 198
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala

<400> SEQUENCE: 198

Cys Glu His Xaa Arg Xaa Ala Cys Pro Pro Lys Asp Ala Tyr Gly Arg
1               5                   10                  15

Arg Lys Arg Arg Gln Arg Arg Arg
            20

<210> SEQ ID NO 199
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala

<400> SEQUENCE: 199

Cys Glu His Xaa Arg Xaa Ala Cys Pro Pro Lys Asp Ala Gly Arg Arg
```

```
1               5                  10                 15
Lys Arg Arg Gln Arg Arg Arg
            20

<210> SEQ ID NO 200
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala

<400> SEQUENCE: 200

Cys Glu His Xaa Arg Xaa Ala Cys Pro Pro Lys Asp Ala Gly Arg Lys
1               5                  10                 15

Arg Arg Arg Gln Arg Arg Arg
            20

<210> SEQ ID NO 201
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala

<400> SEQUENCE: 201

Cys Glu His Xaa Arg Xaa Ala Cys Pro Pro Lys Asp Ala Tyr Gly Arg
1               5                  10                 15

Arg Lys Arg Arg Gln Arg Arg Arg
            20

<210> SEQ ID NO 202
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
```

```
<220> FEATURE:
<221> NAME/KEY: MOD_RES
<222> LOCATION: (13)..(13)
<223> OTHER INFORMATION: Beta-Ala

<400> SEQUENCE: 202

Cys Glu His Xaa Arg Xaa Ala Cys Pro Pro Lys Asp Ala Tyr Gly Arg
1               5                   10                  15

Lys Arg Arg Arg Gln Arg Arg Arg
            20

<210> SEQ ID NO 203
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala

<400> SEQUENCE: 203

Cys Glu His Xaa Arg Xaa Ala Cys Pro Pro Lys Asp Ala Gly Arg Arg
1               5                   10                  15

Lys Arg Arg Gln Arg Arg Arg
            20

<210> SEQ ID NO 204
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala

<400> SEQUENCE: 204

Cys Glu His Xaa Arg Xaa Ala Cys Pro Pro Lys Asp Ala Gly Arg Lys
1               5                   10                  15

Arg Arg Arg Gln Arg Arg Arg
            20

<210> SEQ ID NO 205
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala

<400> SEQUENCE: 205

Cys Glu His Xaa Arg Xaa Ala Cys Pro Pro Lys Asp Ala Arg Arg Lys
1               5                   10                  15

Arg Arg Gln Arg Arg Arg
            20

<210> SEQ ID NO 206
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala

<400> SEQUENCE: 206

Cys Glu His Xaa Arg Xaa Ala Cys Pro Pro Lys Asp Ala Arg Lys Arg
1               5                   10                  15

Arg Arg Gln Arg Arg Arg
            20

<210> SEQ ID NO 207
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala

<400> SEQUENCE: 207

Cys Glu His Xaa Arg Xaa Ala Cys Pro Pro Lys Asp Ala Tyr Gly Arg
1               5                   10                  15

Lys Arg Arg Gln Arg Arg Arg
            20
```

<210> SEQ ID NO 208
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala

<400> SEQUENCE: 208

Cys Glu His Xaa Arg Xaa Ala Cys Pro Pro Lys Asp Ala Arg Arg Lys
1               5                   10                  15

Arg Arg Gln Arg Arg Arg
            20

<210> SEQ ID NO 209
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala

<400> SEQUENCE: 209

Cys Glu His Xaa Arg Xaa Ala Cys Pro Pro Lys Asp Ala Arg Lys Arg
1               5                   10                  15

Arg Arg Gln Arg Arg Arg
            20

<210> SEQ ID NO 210
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala -continued

```
<400> SEQUENCE: 210

Cys Glu His Xaa Arg Xaa Ala Cys Pro Pro Lys Asp Ala Tyr Gly Arg
1               5                   10                  15

Arg Lys Arg Arg Gln Arg Arg Arg
            20

<210> SEQ ID NO 211
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala

<400> SEQUENCE: 211

Cys Glu His Xaa Arg Xaa Ala Cys Pro Pro Lys Asp Ala Tyr Gly Arg
1               5                   10                  15

Lys Arg Arg Gln Arg Arg Arg
            20

<210> SEQ ID NO 212
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala

<400> SEQUENCE: 212

Cys Glu His Xaa Arg Xaa Ala Cys Pro Pro Lys Asp Ala Gly Arg Arg
1               5                   10                  15

Lys Arg Arg Gln Arg Arg Arg
            20

<210> SEQ ID NO 213
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
```

```
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala

<400> SEQUENCE: 213

Cys Glu His Xaa Arg Xaa Ala Cys Pro Pro Lys Asp Ala Gly Arg Lys
1               5                   10                  15

Arg Arg Arg Gln Arg Arg Arg
            20

<210> SEQ ID NO 214
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (13)..(13)
<223> OTHER INFORMATION: Beta-Ala

<400> SEQUENCE: 214

Cys Glu His Xaa Arg Trp Ala Cys Pro Pro Lys Asp Ala Arg Arg Arg
1               5                   10                  15

Arg Arg Gln Arg Arg Arg
            20

<210> SEQ ID NO 215
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (13)..(13)
<223> OTHER INFORMATION: Beta-Ala

<400> SEQUENCE: 215

Cys Glu His Xaa Arg Trp Ala Cys Pro Pro Arg Asp Ala Arg Arg Arg
1               5                   10                  15

Arg Arg Gln Arg Arg Arg
            20

<210> SEQ ID NO 216
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
```

```
<221> NAME/KEY: MOD_RES
<222> LOCATION: (13)..(13)
<223> OTHER INFORMATION: Beta-Ala

<400> SEQUENCE: 216

Cys Glu His Xaa Arg Trp Ala Cys Pro Pro Lys Asp Ala Tyr Gly Arg
1               5                   10                  15

Arg Arg Arg Arg Gln Arg Arg Arg
            20

<210> SEQ ID NO 217
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (13)..(13)
<223> OTHER INFORMATION: Beta-Ala

<400> SEQUENCE: 217

Cys Glu His Xaa Arg Trp Ala Cys Pro Pro Arg Asp Ala Tyr Gly Arg
1               5                   10                  15

Arg Arg Arg Arg Gln Arg Arg Arg
            20

<210> SEQ ID NO 218
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (13)..(13)
<223> OTHER INFORMATION: Beta-Ala

<400> SEQUENCE: 218

Cys Glu His Xaa Arg Trp Ala Cys Pro Pro Lys Asp Ala Arg Arg Arg
1               5                   10                  15

Arg Arg Gln Arg Arg Arg Arg
            20

<210> SEQ ID NO 219
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (13)..(13)
<223> OTHER INFORMATION: Beta-Ala
```

```
<400> SEQUENCE: 219

Cys Glu His Xaa Arg Trp Ala Cys Pro Pro Arg Asp Ala Arg Arg
1               5                   10                  15

Arg Arg Gln Arg Arg Arg Arg
            20

<210> SEQ ID NO 220
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (13)..(13)
<223> OTHER INFORMATION: Beta-Ala

<400> SEQUENCE: 220

Cys Glu His Xaa Arg Trp Ala Cys Pro Pro Lys Asp Ala Tyr Gly Arg
1               5                   10                  15

Arg Arg Arg Arg Gln Arg Arg Arg Arg
            20                  25

<210> SEQ ID NO 221
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (13)..(13)
<223> OTHER INFORMATION: Beta-Ala

<400> SEQUENCE: 221

Cys Glu His Xaa Arg Trp Ala Cys Pro Pro Arg Asp Ala Tyr Gly Arg
1               5                   10                  15

Arg Arg Arg Arg Gln Arg Arg Arg Arg
            20                  25

<210> SEQ ID NO 222
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala
```

```
<400> SEQUENCE: 222

Cys Glu His Xaa Arg Xaa Ala Cys Pro Pro Lys Asp Ala Arg Arg
1               5                   10                  15

Arg Arg Gln Arg Arg Arg Arg
            20

<210> SEQ ID NO 223
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala

<400> SEQUENCE: 223

Cys Glu His Xaa Arg Xaa Ala Cys Pro Pro Arg Asp Ala Arg Arg
1               5                   10                  15

Arg Arg Gln Arg Arg Arg Arg
            20

<210> SEQ ID NO 224
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala

<400> SEQUENCE: 224

Cys Glu His Xaa Arg Xaa Ala Cys Pro Pro Arg Asp Ala Arg Arg
1               5                   10                  15

Arg Arg Arg Gln Arg Arg Arg
            20

<210> SEQ ID NO 225
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
```

```
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala

<400> SEQUENCE: 225

Cys Glu His Xaa Arg Xaa Ala Cys Pro Pro Lys Asp Ala Tyr Gly Arg
1               5                   10                  15

Arg Arg Arg Arg Gln Arg Arg Arg
            20

<210> SEQ ID NO 226
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala

<400> SEQUENCE: 226

Cys Glu His Xaa Arg Xaa Ala Cys Pro Pro Arg Asp Ala Tyr Gly Arg
1               5                   10                  15

Arg Arg Arg Arg Gln Arg Arg Arg
            20

<210> SEQ ID NO 227
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala

<400> SEQUENCE: 227

Cys Glu His Xaa Arg Xaa Ala Cys Pro Pro Lys Asp Ala Tyr Gly Arg
1               5                   10                  15

Arg Arg Arg Arg Gln Arg Arg Arg
            20                  25

<210> SEQ ID NO 228
<211> LENGTH: 25
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala

<400> SEQUENCE: 228

Cys Glu His Xaa Arg Xaa Ala Cys Pro Pro Arg Asp Ala Tyr Gly Arg
1               5                   10                  15

Arg Arg Arg Arg Gln Arg Arg Arg Arg
            20                  25

<210> SEQ ID NO 229
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala

<400> SEQUENCE: 229

Cys Glu His Xaa Arg Xaa Ala Cys Pro Pro Lys Asp Ala Tyr Gly Arg
1               5                   10                  15

Arg Arg Arg Arg Arg Gln Arg Arg Arg
            20                  25

<210> SEQ ID NO 230
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala

<400> SEQUENCE: 230

Cys Glu His Xaa Arg Xaa Ala Cys Pro Pro Arg Asp Ala Tyr Gly Arg
1               5                   10                  15
```

Arg Arg Arg Arg Arg Gln Arg Arg
        20              25

<210> SEQ ID NO 231
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala

<400> SEQUENCE: 231

Cys Glu His Xaa Arg Xaa Ala Cys Pro Pro Arg Asp Ala Arg Arg
1               5                   10                  15

Arg Arg Arg Gln Arg Arg Arg
            20

<210> SEQ ID NO 232
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala

<400> SEQUENCE: 232

Cys Glu His Xaa Arg Xaa Ala Cys Pro Pro Lys Asp Ala Arg Arg
1               5                   10                  15

Arg Arg Gln Arg Arg Arg Arg
            20

<210> SEQ ID NO 233
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES

```
<222> LOCATION: (13)..(13)
<223> OTHER INFORMATION: Beta-Ala

<400> SEQUENCE: 233

Cys Glu His Xaa Arg Xaa Ala Cys Pro Pro Arg Asp Ala Arg Arg
1               5                   10                  15

Arg Arg Gln Arg Arg Arg Arg
            20

<210> SEQ ID NO 234
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala

<400> SEQUENCE: 234

Cys Glu His Xaa Arg Xaa Ala Cys Pro Pro Lys Asp Ala Tyr Gly Arg
1               5                   10                  15

Arg Arg Arg Arg Gln Arg Arg Arg
            20

<210> SEQ ID NO 235
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala

<400> SEQUENCE: 235

Cys Glu His Xaa Arg Xaa Ala Cys Pro Pro Arg Asp Ala Tyr Gly Arg
1               5                   10                  15

Arg Arg Arg Arg Gln Arg Arg Arg
            20

<210> SEQ ID NO 236
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala

<400> SEQUENCE: 236

Cys Glu His Xaa Arg Xaa Ala Cys Pro Pro Lys Asp Ala Tyr Gly Arg
1               5                   10                  15

Arg Arg Arg Arg Arg Gln Arg Arg Arg
            20                  25

<210> SEQ ID NO 237
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala

<400> SEQUENCE: 237

Cys Glu His Xaa Arg Xaa Ala Cys Pro Pro Arg Asp Ala Tyr Gly Arg
1               5                   10                  15

Arg Arg Arg Arg Arg Gln Arg Arg Arg
            20                  25

<210> SEQ ID NO 238
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala

<400> SEQUENCE: 238

Cys Glu His Xaa Arg Xaa Ala Cys Pro Pro Lys Asp Ala Tyr Gly Arg
1               5                   10                  15

Arg Arg Arg Arg Gln Arg Arg Arg Arg
            20                  25

<210> SEQ ID NO 239
```

```
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala

<400> SEQUENCE: 239

Cys Glu His Xaa Arg Xaa Ala Cys Pro Pro Arg Asp Ala Tyr Gly Arg
1               5                   10                  15

Arg Arg Arg Arg Gln Arg Arg Arg Arg
            20                  25

<210> SEQ ID NO 240
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala

<400> SEQUENCE: 240

Cys Glu His Xaa Arg Xaa Ala Cys Pro Pro Lys Asp Ala Arg Arg Arg
1               5                   10                  15

Arg Arg Gln Arg Arg Arg Arg
            20

<210> SEQ ID NO 241
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala

<400> SEQUENCE: 241
```

```
Cys Glu His Xaa Arg Xaa Ala Cys Pro Pro Arg Asp Ala Arg Arg Arg
1               5                   10                  15

Arg Arg Gln Arg Arg Arg Arg
            20
```

<210> SEQ ID NO 242
<211> LENGTH: 24
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala

<400> SEQUENCE: 242

```
Cys Glu His Xaa Arg Xaa Ala Cys Pro Pro Arg Asp Ala Tyr Gly Arg
1               5                   10                  15

Arg Arg Arg Arg Gln Arg Arg Arg
            20
```

<210> SEQ ID NO 243
<211> LENGTH: 25
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala

<400> SEQUENCE: 243

```
Cys Glu His Xaa Arg Xaa Ala Cys Pro Pro Lys Asp Ala Tyr Gly Arg
1               5                   10                  15

Arg Arg Arg Arg Gln Arg Arg Arg Arg
            20                  25
```

<210> SEQ ID NO 244
<211> LENGTH: 25
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)

```
<223> OTHER INFORMATION: Bal
<220> FEATURE:
<221> NAME/KEY: MOD_RES
<222> LOCATION: (13)..(13)
<223> OTHER INFORMATION: Beta-Ala

<400> SEQUENCE: 244

Cys Glu His Xaa Arg Xaa Ala Cys Pro Pro Arg Asp Ala Tyr Gly Arg
1               5                   10                  15

Arg Arg Arg Arg Gln Arg Arg Arg Arg
            20                  25

<210> SEQ ID NO 245
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala

<400> SEQUENCE: 245

Cys Glu His Xaa Arg Xaa Ala Cys Pro Pro Lys Asp Ala Tyr Gly Arg
1               5                   10                  15

Arg Arg Arg Arg Arg Gln Arg Arg Arg
            20                  25

<210> SEQ ID NO 246
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala

<400> SEQUENCE: 246

Cys Glu His Xaa Arg Xaa Ala Cys Pro Pro Arg Asp Ala Tyr Gly Arg
1               5                   10                  15

Arg Arg Arg Arg Arg Gln Arg Arg Arg
            20                  25

<210> SEQ ID NO 247
<211> LENGTH: 21
<212> TYPE: PRT
<213> ORGANISM: Artificial Sequence
<220> FEATURE:
<223> OTHER INFORMATION: Description of Artificial Sequence: Synthetic
```

```
                    peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 247

Xaa Cys Ala His Phe Arg Trp Cys Xaa Xaa Tyr Gly Arg Lys Lys Arg
1               5                   10                  15

Arg Gln Arg Arg Arg
            20

<210> SEQ ID NO 248
<211> LENGTH: 20
<212> TYPE: PRT
<213> ORGANISM: Artificial Sequence
<220> FEATURE:
<223> OTHER INFORMATION: Description of Artificial Sequence: Synthetic
                    peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala

<400> SEQUENCE: 248

Xaa Cys Ala His Phe Arg Trp Cys Ala Tyr Gly Arg Lys Lys Arg Gln
1               5                   10                  15

Arg Arg Arg Arg
            20

<210> SEQ ID NO 249
<211> LENGTH: 20
<212> TYPE: PRT
<213> ORGANISM: Artificial Sequence
<220> FEATURE:
<223> OTHER INFORMATION: Description of Artificial Sequence: Synthetic
                    peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
```

```
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc

<400> SEQUENCE: 249

Xaa Cys Ala His Phe Arg Trp Cys Xaa Tyr Gly Arg Lys Lys Arg Arg
1               5                   10                  15

Gln Arg Arg Arg
            20

<210> SEQ ID NO 250
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala

<400> SEQUENCE: 250

Xaa Cys Ala His Phe Arg Trp Cys Ala Arg Arg Arg Arg Arg Gln Arg
1               5                   10                  15

Arg Arg

<210> SEQ ID NO 251
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala

<400> SEQUENCE: 251

Xaa Cys Ala His Phe Arg Trp Cys Ala Gly Arg Arg Arg Arg Arg Gln
1               5                   10                  15
```

Arg Arg Arg

<210> SEQ ID NO 252
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala

<400> SEQUENCE: 252

Xaa Cys Ala His Phe Arg Trp Cys Ala Tyr Gly Arg Arg Arg Arg
1               5                   10                  15

Gln Arg Arg Arg
            20

<210> SEQ ID NO 253
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala

<400> SEQUENCE: 253

Xaa Cys Ala His Phe Arg Trp Cys Ala Gly Arg Arg Arg Arg Gln
1               5                   10                  15

Arg Arg Arg Arg
            20

<210> SEQ ID NO 254
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)

```
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala

<400> SEQUENCE: 254

Xaa Cys Ala His Phe Arg Trp Cys Ala Tyr Gly Arg Arg Lys Arg Arg
1               5                   10                  15

Gln Arg Arg Arg
            20

<210> SEQ ID NO 255
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala

<400> SEQUENCE: 255

Xaa Cys Ala His Phe Arg Trp Cys Ala Tyr Gly Arg Lys Arg Arg
1               5                   10                  15

Gln Arg Arg Arg
            20

<210> SEQ ID NO 256
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
```

<400> SEQUENCE: 256

Xaa Cys Ala His Phe Arg Trp Cys Ala Gly Arg Arg Lys Arg Arg Gln
1               5                   10                  15

Arg Arg Arg

<210> SEQ ID NO 257
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala

<400> SEQUENCE: 257

Xaa Cys Ala His Phe Arg Trp Cys Ala Gly Arg Lys Arg Arg Gln
1               5                   10                  15

Arg Arg Arg

<210> SEQ ID NO 258
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala

<400> SEQUENCE: 258

Xaa Cys Ala His Phe Arg Trp Cys Ala Arg Arg Lys Arg Arg Gln Arg
1               5                   10                  15

Arg Arg

<210> SEQ ID NO 259
<211> LENGTH: 18
<212> TYPE: PRT
<213> ORGANISM: Artificial Sequence
<220> FEATURE:
<223> OTHER INFORMATION: Description of Artificial Sequence: Synthetic

```
            peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala

<400> SEQUENCE: 259

Xaa Cys Ala His Phe Arg Trp Cys Ala Arg Lys Arg Arg Arg Gln Arg
1               5                   10                  15

Arg Arg

<210> SEQ ID NO 260
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
<223> OTHER INFORMATION: Beta-Ala

<400> SEQUENCE: 260

Xaa Cys Ala His Phe Arg Trp Cys Ala Ala Arg Arg Arg Arg Gln
1               5                   10                  15

Arg Arg Arg

<210> SEQ ID NO 261
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
```

```
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
<223> OTHER INFORMATION: Beta-Ala

<400> SEQUENCE: 261

Xaa Cys Ala His Phe Arg Trp Cys Ala Ala Gly Arg Arg Arg Arg
1               5                   10                  15

Gln Arg Arg Arg
            20

<210> SEQ ID NO 262
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
<223> OTHER INFORMATION: Beta-Ala

<400> SEQUENCE: 262

Xaa Cys Ala His Phe Arg Trp Cys Ala Ala Tyr Gly Arg Arg Arg
1               5                   10                  15

Arg Gln Arg Arg Arg
            20

<210> SEQ ID NO 263
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
```

<223> OTHER INFORMATION: Doc

<400> SEQUENCE: 263

Xaa Cys Ala His Phe Arg Trp Cys Xaa Arg Arg Arg Arg Gln Arg
1               5                   10                  15

Arg Arg

<210> SEQ ID NO 264
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc

<400> SEQUENCE: 264

Xaa Cys Ala His Phe Arg Trp Cys Xaa Gly Arg Arg Arg Arg Gln
1               5                   10                  15

Arg Arg Arg

<210> SEQ ID NO 265
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc

<400> SEQUENCE: 265

Xaa Cys Ala His Phe Arg Trp Cys Xaa Tyr Gly Arg Arg Arg Arg
1               5                   10                  15

Gln Arg Arg Arg
            20

<210> SEQ ID NO 266
<211> LENGTH: 19
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 266

Xaa Cys Ala His Phe Arg Trp Cys Xaa Xaa Arg Arg Arg Arg Gln
1               5                   10                  15

Arg Arg Arg

<210> SEQ ID NO 267
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 267

Xaa Cys Ala His Phe Arg Trp Cys Xaa Xaa Gly Arg Arg Arg Arg
1               5                   10                  15

Gln Arg Arg Arg
                20

<210> SEQ ID NO 268
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 268

Xaa Cys Ala His Phe Arg Trp Cys Xaa Xaa Tyr Gly Arg Arg Arg Arg
1               5                   10                  15

Arg Gln Arg Arg Arg
            20

<210> SEQ ID NO 269
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala

<400> SEQUENCE: 269

Xaa Cys Ala His Phe Arg Trp Cys Ala Arg Arg Arg Arg Gln Arg
1               5                   10                  15

Arg Arg Arg

<210> SEQ ID NO 270
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
```

```
<221> NAME/KEY: MOD_RES
<222> LOCATION: (9)..(9)
<223> OTHER INFORMATION: Beta-Ala

<400> SEQUENCE: 270

Xaa Cys Ala His Phe Arg Trp Cys Ala Tyr Gly Arg Arg Arg Arg
1               5                   10                  15

Gln Arg Arg Arg Arg
            20

<210> SEQ ID NO 271
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
<223> OTHER INFORMATION: Beta-Ala

<400> SEQUENCE: 271

Xaa Cys Ala His Phe Arg Trp Cys Ala Ala Arg Arg Arg Arg Gln
1               5                   10                  15

Arg Arg Arg Arg
            20

<210> SEQ ID NO 272
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
<223> OTHER INFORMATION: Beta-Ala

<400> SEQUENCE: 272
```

-continued

```
Xaa Cys Ala His Phe Arg Trp Cys Ala Ala Gly Arg Arg Arg Arg
1               5                   10                  15

Gln Arg Arg Arg Arg
            20

<210> SEQ ID NO 273
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
<223> OTHER INFORMATION: Beta-Ala

<400> SEQUENCE: 273

Xaa Cys Ala His Phe Arg Trp Cys Ala Ala Tyr Gly Arg Arg Arg
1               5                   10                  15

Arg Gln Arg Arg Arg Arg
            20

<210> SEQ ID NO 274
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc

<400> SEQUENCE: 274

Xaa Cys Ala His Phe Arg Trp Cys Xaa Arg Arg Arg Arg Gln Arg
1               5                   10                  15

Arg Arg Arg

<210> SEQ ID NO 275
<211> LENGTH: 20
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc

<400> SEQUENCE: 275

Xaa Cys Ala His Phe Arg Trp Cys Xaa Gly Arg Arg Arg Arg Gln
1               5                   10                  15

Arg Arg Arg Arg
            20

<210> SEQ ID NO 276
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc

<400> SEQUENCE: 276

Xaa Cys Ala His Phe Arg Trp Cys Xaa Tyr Gly Arg Arg Arg Arg
1               5                   10                  15

Gln Arg Arg Arg Arg
            20

<210> SEQ ID NO 277
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
```

```
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 277

Xaa Cys Ala His Phe Arg Trp Cys Xaa Xaa Arg Arg Arg Arg Arg Gln
1               5                   10                  15

Arg Arg Arg Arg
            20

<210> SEQ ID NO 278
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 278

Xaa Cys Ala His Phe Arg Trp Cys Xaa Xaa Gly Arg Arg Arg Arg
1               5                   10                  15

Gln Arg Arg Arg Arg
            20

<210> SEQ ID NO 279
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
```

<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 279

Xaa Cys Ala His Phe Arg Trp Cys Xaa Xaa Tyr Gly Arg Arg Arg
1               5                   10                  15

Arg Gln Arg Arg Arg Arg
            20

<210> SEQ ID NO 280
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala

<400> SEQUENCE: 280

Xaa Cys His Phe Arg Trp Xaa Cys Ala Tyr Gly Arg Arg Arg Arg
1               5                   10                  15

Gln Arg Arg Arg
            20

<210> SEQ ID NO 281
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala

<400> SEQUENCE: 281

Xaa Cys His Phe Arg Trp Xaa Cys Ala Arg Arg Arg Arg Gln Arg
1               5                   10                  15

Arg Arg

```
<210> SEQ ID NO 282
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (9)..(9)
<223> OTHER INFORMATION: Beta-Ala

<400> SEQUENCE: 282
```

Xaa Asp His Phe Arg Trp Ala Lys Ala Tyr Gly Arg Arg Arg Arg
1               5                   10                  15

Gln Arg Arg Arg
            20

```
<210> SEQ ID NO 283
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (9)..(9)
<223> OTHER INFORMATION: Beta-Ala

<400> SEQUENCE: 283
```

Xaa Asp His Phe Arg Trp Ala Lys Ala Arg Arg Arg Arg Gln Arg
1               5                   10                  15

Arg Arg

```
<210> SEQ ID NO 284
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Beta-Ala
```

<400> SEQUENCE: 284

Xaa Asp His Phe Arg Trp Lys Ala Tyr Gly Arg Arg Arg Arg Gln
1               5                   10                  15

Arg Arg Arg

<210> SEQ ID NO 285
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Beta-Ala

<400> SEQUENCE: 285

Xaa Asp His Phe Arg Trp Lys Ala Gly Arg Arg Arg Arg Gln Arg
1               5                   10                  15

Arg Arg

<210> SEQ ID NO 286
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Beta-Ala

<400> SEQUENCE: 286

Xaa Asp His Phe Arg Trp Lys Ala Arg Arg Arg Arg Gln Arg Arg
1               5                   10                  15

Arg

<210> SEQ ID NO 287
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)

```
<223> OTHER INFORMATION: D-Phe
<220> FEATURE:
<221> NAME/KEY: MOD_RES
<222> LOCATION: (8)..(8)
<223> OTHER INFORMATION: Beta-Ala
<220> FEATURE:
<221> NAME/KEY: MOD_RES
<222> LOCATION: (9)..(9)
<223> OTHER INFORMATION: Beta-Ala

<400> SEQUENCE: 287

Xaa Asp His Phe Arg Trp Lys Ala Ala Tyr Gly Arg Arg Arg Arg
1               5                   10                  15

Gln Arg Arg Arg
         20

<210> SEQ ID NO 288
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Beta-Ala
<220> FEATURE:
<221> NAME/KEY: MOD_RES
<222> LOCATION: (9)..(9)
<223> OTHER INFORMATION: Beta-Ala

<400> SEQUENCE: 288

Xaa Asp His Phe Arg Trp Lys Ala Ala Gly Arg Arg Arg Arg Gln
1               5                   10                  15

Arg Arg Arg

<210> SEQ ID NO 289
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Beta-Ala
<220> FEATURE:
<221> NAME/KEY: MOD_RES
<222> LOCATION: (9)..(9)
<223> OTHER INFORMATION: Beta-Ala

<400> SEQUENCE: 289

Xaa Asp His Phe Arg Trp Lys Ala Ala Arg Arg Arg Arg Arg Gln Arg
1               5                   10                  15
```

Arg Arg

```
<210> SEQ ID NO 290
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Doc

<400> SEQUENCE: 290

Xaa Asp His Phe Arg Trp Lys Xaa Tyr Gly Arg Arg Arg Arg Gln
1               5                   10                  15

Arg Arg Arg

<210> SEQ ID NO 291
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Doc

<400> SEQUENCE: 291

Xaa Asp His Phe Arg Trp Lys Xaa Gly Arg Arg Arg Arg Gln Arg
1               5                   10                  15

Arg Arg

<210> SEQ ID NO 292
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Doc
```

<400> SEQUENCE: 292

Xaa Asp His Phe Arg Trp Lys Xaa Arg Arg Arg Arg Gln Arg Arg
1               5                   10                  15

Arg

<210> SEQ ID NO 293
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Doc
<220> FEATURE:
<221> NAME/KEY: MOD_RES
<222> LOCATION: (9)..(9)
<223> OTHER INFORMATION: Doc

<400> SEQUENCE: 293

Xaa Asp His Phe Arg Trp Lys Xaa Xaa Tyr Gly Arg Arg Arg Arg
1               5                   10                  15

Gln Arg Arg Arg
            20

<210> SEQ ID NO 294
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Doc
<220> FEATURE:
<221> NAME/KEY: MOD_RES
<222> LOCATION: (9)..(9)
<223> OTHER INFORMATION: Doc

<400> SEQUENCE: 294

Xaa Asp His Phe Arg Trp Lys Xaa Xaa Gly Arg Arg Arg Arg Gln
1               5                   10                  15

Arg Arg Arg

<210> SEQ ID NO 295
<211> LENGTH: 18
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Doc
<220> FEATURE:
<221> NAME/KEY: MOD_RES
<222> LOCATION: (9)..(9)
<223> OTHER INFORMATION: Doc

<400> SEQUENCE: 295

Xaa Asp His Phe Arg Trp Lys Xaa Xaa Arg Arg Arg Arg Gln Arg
1               5                   10                  15

Arg Arg

<210> SEQ ID NO 296
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Beta-Ala

<400> SEQUENCE: 296

Xaa Asp His Phe Arg Trp Lys Ala Tyr Gly Arg Arg Arg Arg Gln
1               5                   10                  15

Arg Arg Arg Arg
            20

<210> SEQ ID NO 297
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Beta-Ala

<400> SEQUENCE: 297

Xaa Asp His Phe Arg Trp Lys Ala Gly Arg Arg Arg Arg Gln Arg
```

```
1               5                   10                  15

Arg Arg Arg

<210> SEQ ID NO 298
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Beta-Ala

<400> SEQUENCE: 298

Xaa Asp His Phe Arg Trp Lys Ala Arg Arg Arg Arg Gln Arg Arg
1               5                   10                  15

Arg Arg

<210> SEQ ID NO 299
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Beta-Ala
<220> FEATURE:
<221> NAME/KEY: MOD_RES
<222> LOCATION: (9)..(9)
<223> OTHER INFORMATION: Beta-Ala

<400> SEQUENCE: 299

Xaa Asp His Phe Arg Trp Lys Ala Ala Tyr Gly Arg Arg Arg Arg
1               5                   10                  15

Gln Arg Arg Arg Arg
            20

<210> SEQ ID NO 300
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
```

```
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Beta-Ala
<220> FEATURE:
<221> NAME/KEY: MOD_RES
<222> LOCATION: (9)..(9)
<223> OTHER INFORMATION: Beta-Ala

<400> SEQUENCE: 300

Xaa Asp His Phe Arg Trp Lys Ala Ala Gly Arg Arg Arg Arg Gln
1               5                   10                  15

Arg Arg Arg Arg
            20

<210> SEQ ID NO 301
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Beta-Ala
<220> FEATURE:
<221> NAME/KEY: MOD_RES
<222> LOCATION: (9)..(9)
<223> OTHER INFORMATION: Beta-Ala

<400> SEQUENCE: 301

Xaa Asp His Phe Arg Trp Lys Ala Ala Arg Arg Arg Arg Gln Arg
1               5                   10                  15

Arg Arg Arg

<210> SEQ ID NO 302
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Doc

<400> SEQUENCE: 302

Xaa Asp His Phe Arg Trp Lys Xaa Tyr Gly Arg Arg Arg Arg Gln
1               5                   10                  15

Arg Arg Arg Arg
            20
```

```
<210> SEQ ID NO 303
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Doc

<400> SEQUENCE: 303

Xaa Asp His Phe Arg Trp Lys Xaa Gly Arg Arg Arg Arg Gln Arg
1               5                   10                  15

Arg Arg Arg

<210> SEQ ID NO 304
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Doc

<400> SEQUENCE: 304

Xaa Asp His Phe Arg Trp Lys Xaa Arg Arg Arg Arg Gln Arg Arg
1               5                   10                  15

Arg Arg

<210> SEQ ID NO 305
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Doc
<220> FEATURE:
<221> NAME/KEY: MOD_RES
```

```
<222> LOCATION: (9)..(9)
<223> OTHER INFORMATION: Doc

<400> SEQUENCE: 305

Xaa Asp His Phe Arg Trp Lys Xaa Xaa Tyr Gly Arg Arg Arg Arg
1               5                   10                  15

Gln Arg Arg Arg Arg
            20

<210> SEQ ID NO 306
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Doc
<220> FEATURE:
<221> NAME/KEY: MOD_RES
<222> LOCATION: (9)..(9)
<223> OTHER INFORMATION: Doc

<400> SEQUENCE: 306

Xaa Asp His Phe Arg Trp Lys Xaa Xaa Gly Arg Arg Arg Arg Gln
1               5                   10                  15

Arg Arg Arg Arg
            20

<210> SEQ ID NO 307
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Doc
<220> FEATURE:
<221> NAME/KEY: MOD_RES
<222> LOCATION: (9)..(9)
<223> OTHER INFORMATION: Doc

<400> SEQUENCE: 307

Xaa Asp His Phe Arg Trp Lys Xaa Xaa Arg Arg Arg Arg Gln Arg
1               5                   10                  15

Arg Arg Arg

<210> SEQ ID NO 308
<211> LENGTH: 20
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (9)..(9)
<223> OTHER INFORMATION: Beta-Ala

<400> SEQUENCE: 308

Xaa Asp His Phe Arg Trp Ala Lys Ala Tyr Gly Arg Arg Arg Arg
1               5                   10                  15

Gln Arg Arg Arg
            20

<210> SEQ ID NO 309
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (9)..(9)
<223> OTHER INFORMATION: Beta-Ala

<400> SEQUENCE: 309

Xaa Asp His Phe Arg Trp Ala Lys Ala Arg Arg Arg Arg Gln Arg
1               5                   10                  15

Arg Arg

<210> SEQ ID NO 310
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
```

```
<221> NAME/KEY: MOD_RES
<222> LOCATION: (7)..(7)
<223> OTHER INFORMATION: Ahx
<220> FEATURE:
<221> NAME/KEY: MOD_RES
<222> LOCATION: (9)..(9)
<223> OTHER INFORMATION: Beta-Ala

<400> SEQUENCE: 310

Xaa Cys His Phe Arg Trp Xaa Cys Ala Tyr Gly Arg Arg Arg Arg
1               5                   10                  15

Gln Arg Arg Arg
            20

<210> SEQ ID NO 311
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Ahx
<220> FEATURE:
<221> NAME/KEY: MOD_RES
<222> LOCATION: (9)..(9)
<223> OTHER INFORMATION: Beta-Ala

<400> SEQUENCE: 311

Xaa Cys His Phe Arg Trp Xaa Cys Ala Arg Arg Arg Arg Gln Arg
1               5                   10                  15

Arg Arg

<210> SEQ ID NO 312
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Beta-Ala

<400> SEQUENCE: 312
```

Phe Cys His Phe Arg Trp Ala Cys Thr Ala Tyr Gly Arg Arg Arg Arg
1               5                   10                  15

Arg Gln Arg Arg Arg
            20

<210> SEQ ID NO 313
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Beta-Ala

<400> SEQUENCE: 313

Phe Cys His Phe Arg Trp Ala Cys Thr Ala Arg Arg Arg Arg Arg Gln
1               5                   10                  15

Arg Arg Arg

<210> SEQ ID NO 314
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(9)
<223> OTHER INFORMATION: Beta-Ala

<400> SEQUENCE: 314

Xaa Cys His Phe Arg Trp Xaa Cys Ala Tyr Gly Arg Arg Arg Arg
1               5                   10                  15

Gln Arg Arg Arg
            20

<210> SEQ ID NO 315
<211> LENGTH: 18
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(9)
<223> OTHER INFORMATION: Beta-Ala

<400> SEQUENCE: 315

Xaa Cys His Phe Arg Trp Xaa Cys Ala Arg Arg Arg Arg Gln Arg
1               5                  10                 15

Arg Arg

<210> SEQ ID NO 316
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cha
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala

<400> SEQUENCE: 316

Xaa Asp His Phe Arg Trp Xaa Lys Ala Tyr Gly Arg Arg Arg Arg
1               5                  10                 15

Gln Arg Arg Arg
            20

<210> SEQ ID NO 317
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cha
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
```

```
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala

<400> SEQUENCE: 317

Xaa Asp His Phe Arg Trp Xaa Lys Ala Arg Arg Arg Arg Gln Arg
1               5                   10                  15

Arg Arg

<210> SEQ ID NO 318
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala

<400> SEQUENCE: 318

Xaa Asp His Phe Arg Trp Xaa Lys Ala Tyr Gly Arg Arg Arg Arg
1               5                   10                  15

Gln Arg Arg Arg
            20

<210> SEQ ID NO 319
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala

<400> SEQUENCE: 319

Xaa Asp His Phe Arg Trp Xaa Lys Ala Arg Arg Arg Arg Gln Arg
1               5                   10                  15

Arg Arg
```

```
<210> SEQ ID NO 320
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chg
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala

<400> SEQUENCE: 320

Xaa Asp His Phe Arg Trp Xaa Lys Ala Tyr Gly Arg Arg Arg Arg
1               5                   10                  15

Gln Arg Arg Arg
            20

<210> SEQ ID NO 321
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chg
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala

<400> SEQUENCE: 321

Xaa Asp His Phe Arg Trp Xaa Lys Ala Arg Arg Arg Arg Gln Arg
1               5                   10                  15

Arg Arg

<210> SEQ ID NO 322
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hCha
<220> FEATURE:
<221> NAME/KEY: MOD_RES
```

```
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala

<400> SEQUENCE: 322

Xaa Asp His Phe Arg Trp Xaa Lys Ala Tyr Gly Arg Arg Arg Arg
1               5                   10                  15

Gln Arg Arg Arg
            20

<210> SEQ ID NO 323
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hCha
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala

<400> SEQUENCE: 323

Xaa Asp His Phe Arg Trp Xaa Lys Ala Arg Arg Arg Arg Gln Arg
1               5                   10                  15

Arg Arg

<210> SEQ ID NO 324
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hCha
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
<223> OTHER INFORMATION: Beta-Ala
```

<400> SEQUENCE: 324

Xaa Asp His Phe Arg Trp Xaa Lys Ala Ala Tyr Gly Arg Arg Arg
1               5                   10                  15

Arg Gln Arg Arg Arg
            20

<210> SEQ ID NO 325
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hCha
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
<223> OTHER INFORMATION: Beta-Ala

<400> SEQUENCE: 325

Xaa Asp His Phe Arg Trp Xaa Lys Ala Ala Arg Arg Arg Arg Gln
1               5                   10                  15

Arg Arg Arg

<210> SEQ ID NO 326
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hCha
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Doc

<400> SEQUENCE: 326

Xaa Asp His Phe Arg Trp Xaa Lys Xaa Tyr Gly Arg Arg Arg Arg
1               5                   10                  15

Gln Arg Arg Arg
            20

```
<210> SEQ ID NO 327
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hCha
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Doc

<400> SEQUENCE: 327

Xaa Asp His Phe Arg Trp Xaa Lys Xaa Arg Arg Arg Arg Gln Arg
1               5                   10                  15

Arg Arg

<210> SEQ ID NO 328
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hCha
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 328

Xaa Asp His Phe Arg Trp Xaa Lys Xaa Xaa Tyr Gly Arg Arg Arg
1               5                   10                  15

Arg Gln Arg Arg Arg
            20

<210> SEQ ID NO 329
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: hCha
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 329

Xaa Asp His Phe Arg Trp Xaa Lys Xaa Xaa Arg Arg Arg Arg Arg Gln
1               5                   10                  15

Arg Arg Arg

<210> SEQ ID NO 330
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hCha
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala

<400> SEQUENCE: 330

Xaa Asp His Phe Arg Trp Xaa Lys Ala Tyr Gly Arg Arg Arg Arg Arg
1               5                   10                  15

Gln Arg Arg Arg Arg
            20

<210> SEQ ID NO 331
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hCha
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
```

```
<221> NAME/KEY: MOD_RES
<222> LOCATION: (9)..(9)
<223> OTHER INFORMATION: Beta-Ala

<400> SEQUENCE: 331

Xaa Asp His Phe Arg Trp Xaa Lys Ala Arg Arg Arg Arg Gln Arg
1               5                   10                  15

Arg Arg Arg

<210> SEQ ID NO 332
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hCha
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
<223> OTHER INFORMATION: Beta-Ala

<400> SEQUENCE: 332

Xaa Asp His Phe Arg Trp Xaa Lys Ala Ala Tyr Gly Arg Arg Arg
1               5                   10                  15

Arg Gln Arg Arg Arg Arg
            20

<210> SEQ ID NO 333
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hCha
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
<223> OTHER INFORMATION: Beta-Ala

<400> SEQUENCE: 333
```

```
Xaa Asp His Phe Arg Trp Xaa Lys Ala Ala Arg Arg Arg Arg Gln
1               5                   10                  15

Arg Arg Arg Arg
            20

<210> SEQ ID NO 334
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hCha
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Doc

<400> SEQUENCE: 334

Xaa Asp His Phe Arg Trp Xaa Lys Xaa Tyr Gly Arg Arg Arg Arg
1               5                   10                  15

Gln Arg Arg Arg Arg
            20

<210> SEQ ID NO 335
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hCha
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Doc

<400> SEQUENCE: 335

Xaa Asp His Phe Arg Trp Xaa Lys Xaa Arg Arg Arg Arg Gln Arg
1               5                   10                  15

Arg Arg Arg

<210> SEQ ID NO 336
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: hCha
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 336

Xaa Asp His Phe Arg Trp Xaa Lys Xaa Xaa Tyr Gly Arg Arg Arg
1               5                   10                  15

Arg Gln Arg Arg Arg Arg
                20

<210> SEQ ID NO 337
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hCha
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 337

Xaa Asp His Phe Arg Trp Xaa Lys Xaa Xaa Arg Arg Arg Arg Gln
1               5                   10                  15

Arg Arg Arg Arg
                20

<210> SEQ ID NO 338
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Chg
<220> FEATURE:
```

```
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala

<400> SEQUENCE: 338

Xaa Asp His Phe Arg Trp Xaa Lys Ala Tyr Gly Arg Arg Arg Arg
1               5                  10                  15

Gln Arg Arg Arg
            20

<210> SEQ ID NO 339
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Chg
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala

<400> SEQUENCE: 339

Xaa Asp His Phe Arg Trp Xaa Lys Ala Arg Arg Arg Arg Gln Arg
1               5                  10                  15

Arg Arg

<210> SEQ ID NO 340
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala

<400> SEQUENCE: 340

Phe Asp His Phe Arg Trp Xaa Lys Ala Tyr Gly Arg Arg Arg Arg
1               5                  10                  15

Gln Arg Arg Arg
```

```
<210> SEQ ID NO 341
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala

<400> SEQUENCE: 341

Phe Asp His Phe Arg Trp Xaa Lys Ala Arg Arg Arg Arg Gln Arg
1               5                   10                  15

Arg Arg

<210> SEQ ID NO 342
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(9)
<223> OTHER INFORMATION: Beta-Ala

<400> SEQUENCE: 342

Xaa Cys His Phe Arg Trp Xaa Cys Ala Tyr Gly Arg Arg Arg Arg
1               5                   10                  15

Gln Arg Arg Arg
            20

<210> SEQ ID NO 343
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
```

```
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(9)
<223> OTHER INFORMATION: Beta-Ala

<400> SEQUENCE: 343

Xaa Cys His Phe Arg Trp Xaa Cys Ala Arg Arg Arg Arg Gln Arg
1               5                   10                  15

Arg Arg

<210> SEQ ID NO 344
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Ahx
<220> FEATURE:
<221> NAME/KEY: MOD_RES
<222> LOCATION: (9)..(9)
<223> OTHER INFORMATION: Beta-Ala

<400> SEQUENCE: 344

Xaa Cys His Phe Arg Trp Xaa Cys Ala Tyr Gly Arg Arg Arg Arg
1               5                   10                  15

Gln Arg Arg Arg
            20

<210> SEQ ID NO 345
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
```

```
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Ahx
<220> FEATURE:
<221> NAME/KEY: MOD_RES
<222> LOCATION: (9)..(9)
<223> OTHER INFORMATION: Beta-Ala

<400> SEQUENCE: 345

Xaa Cys His Phe Arg Trp Xaa Cys Ala Arg Arg Arg Arg Gln Arg
1               5                   10                  15

Arg Arg

<210> SEQ ID NO 346
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (9)..(9)
<223> OTHER INFORMATION: Beta-Ala

<400> SEQUENCE: 346

Xaa Cys His Phe Arg Trp Ala Cys Ala Tyr Gly Arg Arg Arg Arg
1               5                   10                  15

Gln Arg Arg Arg
            20

<210> SEQ ID NO 347
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Beta-Ala
```

```
<220> FEATURE:
<221> NAME/KEY: MOD_RES
<222> LOCATION: (9)..(9)
<223> OTHER INFORMATION: Beta-Ala

<400> SEQUENCE: 347

Xaa Cys His Phe Arg Trp Ala Cys Ala Arg Arg Arg Arg Gln Arg
1               5                   10                  15

Arg Arg

<210> SEQ ID NO 348
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen
<220> FEATURE:
<221> NAME/KEY: MOD_RES
<222> LOCATION: (9)..(9)
<223> OTHER INFORMATION: Beta-Ala

<400> SEQUENCE: 348

Xaa Cys Ala His Phe Arg Trp Xaa Ala Tyr Gly Arg Arg Arg Arg
1               5                   10                  15

Gln Arg Arg Arg
            20

<210> SEQ ID NO 349
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen
<220> FEATURE:
<221> NAME/KEY: MOD_RES
<222> LOCATION: (9)..(9)
<223> OTHER INFORMATION: Beta-Ala

<400> SEQUENCE: 349
```

```
Xaa Cys Ala His Phe Arg Trp Xaa Ala Gly Arg Arg Arg Arg Gln
1               5                   10                  15

Arg Arg Arg

<210> SEQ ID NO 350
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen
<220> FEATURE:
<221> NAME/KEY: MOD_RES
<222> LOCATION: (9)..(9)
<223> OTHER INFORMATION: Beta-Ala

<400> SEQUENCE: 350

Xaa Cys Ala His Phe Arg Trp Xaa Ala Arg Arg Arg Arg Gln Arg
1               5                   10                  15

Arg Arg

<210> SEQ ID NO 351
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
<223> OTHER INFORMATION: Beta-Ala

<400> SEQUENCE: 351

Xaa Cys Ala His Phe Arg Trp Xaa Ala Ala Tyr Gly Arg Arg Arg Arg
1               5                   10                  15
```

Arg Gln Arg Arg Arg
            20

<210> SEQ ID NO 352
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
<223> OTHER INFORMATION: Beta-Ala

<400> SEQUENCE: 352

Xaa Cys Ala His Phe Arg Trp Xaa Ala Ala Gly Arg Arg Arg Arg
1               5                   10                  15

Gln Arg Arg Arg
            20

<210> SEQ ID NO 353
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
<223> OTHER INFORMATION: Beta-Ala

<400> SEQUENCE: 353

```
Xaa Cys Ala His Phe Arg Trp Xaa Ala Ala Arg Arg Arg Arg Gln
1               5                   10                  15

Arg Arg Arg

<210> SEQ ID NO 354
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen
<220> FEATURE:
<221> NAME/KEY: MOD_RES
<222> LOCATION: (9)..(9)
<223> OTHER INFORMATION: Doc

<400> SEQUENCE: 354

Xaa Cys Ala His Phe Arg Trp Xaa Xaa Tyr Gly Arg Arg Arg Arg
1               5                   10                  15

Gln Arg Arg Arg
            20

<210> SEQ ID NO 355
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen
<220> FEATURE:
<221> NAME/KEY: MOD_RES
<222> LOCATION: (9)..(9)
<223> OTHER INFORMATION: Doc

<400> SEQUENCE: 355

Xaa Cys Ala His Phe Arg Trp Xaa Xaa Gly Arg Arg Arg Arg Gln
1               5                   10                  15

Arg Arg Arg
```

```
<210> SEQ ID NO 356
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen
<220> FEATURE:
<221> NAME/KEY: MOD_RES
<222> LOCATION: (9)..(9)
<223> OTHER INFORMATION: Doc

<400> SEQUENCE: 356

Xaa Cys Ala His Phe Arg Trp Xaa Xaa Arg Arg Arg Arg Gln Arg
1               5                   10                  15

Arg Arg

<210> SEQ ID NO 357
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 357

Xaa Cys Ala His Phe Arg Trp Xaa Xaa Xaa Tyr Gly Arg Arg Arg
1               5                   10                  15

Arg Gln Arg Arg Arg
                20

<210> SEQ ID NO 358
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 358

Xaa Cys Ala His Phe Arg Trp Xaa Xaa Xaa Gly Arg Arg Arg Arg
1               5                  10                  15

Gln Arg Arg Arg
            20

<210> SEQ ID NO 359
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 359

Xaa Cys Ala His Phe Arg Trp Xaa Xaa Xaa Arg Arg Arg Arg Gln
1               5                  10                  15

Arg Arg Arg
```

```
<210> SEQ ID NO 360
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (9)..(9)
<223> OTHER INFORMATION: Beta-Ala

<400> SEQUENCE: 360

Phe Cys His Tyr Arg Trp Ala Cys Ala Tyr Gly Arg Arg Arg Arg
1               5                  10                  15

Gln Arg Arg Arg
            20

<210> SEQ ID NO 361
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (9)..(9)
<223> OTHER INFORMATION: Beta-Ala

<400> SEQUENCE: 361

Phe Cys His Tyr Arg Trp Ala Cys Ala Arg Arg Arg Arg Gln Arg
1               5                  10                  15

Arg Arg

<210> SEQ ID NO 362
<211> LENGTH: 19
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (9)..(9)
<223> OTHER INFORMATION: Beta-Ala

<400> SEQUENCE: 362

Phe Cys His Tyr Arg Trp Ala Cys Ala Gly Arg Arg Arg Arg Gln
1               5                   10                  15

Arg Arg Arg

<210> SEQ ID NO 363
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (9)..(9)
<223> OTHER INFORMATION: Beta-Ala

<400> SEQUENCE: 363

Phe Cys His Tyr Arg Trp Ala Cys Ala Arg Arg Arg Arg Gln Arg
1               5                   10                  15

Arg Arg Arg

<210> SEQ ID NO 364
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
```

<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
<223> OTHER INFORMATION: Beta-Ala

<400> SEQUENCE: 364

Phe Cys His Tyr Arg Trp Ala Cys Ala Ala Tyr Gly Arg Arg Arg
1               5                   10                  15

Arg Gln Arg Arg Arg
            20

<210> SEQ ID NO 365
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
<223> OTHER INFORMATION: Beta-Ala

<400> SEQUENCE: 365

Phe Cys His Tyr Arg Trp Ala Cys Ala Ala Arg Arg Arg Arg Gln
1               5                   10                  15

Arg Arg Arg

<210> SEQ ID NO 366
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)

```
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
<223> OTHER INFORMATION: Beta-Ala

<400> SEQUENCE: 366

Phe Cys His Tyr Arg Trp Ala Cys Ala Ala Gly Arg Arg Arg Arg
1               5                   10                  15

Gln Arg Arg Arg
            20

<210> SEQ ID NO 367
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
<223> OTHER INFORMATION: Beta-Ala

<400> SEQUENCE: 367

Phe Cys His Tyr Arg Trp Ala Cys Ala Ala Arg Arg Arg Arg Gln
1               5                   10                  15

Arg Arg Arg Arg
            20

<210> SEQ ID NO 368
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (9)..(9)
<223> OTHER INFORMATION: Doc

<400> SEQUENCE: 368

Phe Cys His Tyr Arg Trp Ala Cys Xaa Tyr Gly Arg Arg Arg Arg
1               5                   10                  15

Gln Arg Arg Arg
            20

<210> SEQ ID NO 369
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (9)..(9)
<223> OTHER INFORMATION: Doc

<400> SEQUENCE: 369

Phe Cys His Tyr Arg Trp Ala Cys Xaa Arg Arg Arg Arg Gln Arg
1               5                   10                  15

Arg Arg

<210> SEQ ID NO 370
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
```

```
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (9)..(9)
<223> OTHER INFORMATION: Doc

<400> SEQUENCE: 370

Phe Cys His Tyr Arg Trp Ala Cys Xaa Gly Arg Arg Arg Arg Gln
1               5                   10                  15

Arg Arg Arg

<210> SEQ ID NO 371
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (9)..(9)
<223> OTHER INFORMATION: Doc

<400> SEQUENCE: 371

Phe Cys His Tyr Arg Trp Ala Cys Xaa Arg Arg Arg Arg Gln Arg
1               5                   10                  15

Arg Arg Arg

<210> SEQ ID NO 372
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
```

```
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 372

Phe Cys His Tyr Arg Trp Ala Cys Xaa Xaa Tyr Gly Arg Arg Arg
1               5                   10                  15

Arg Gln Arg Arg Arg
            20

<210> SEQ ID NO 373
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 373

Phe Cys His Tyr Arg Trp Ala Cys Xaa Xaa Arg Arg Arg Arg Gln
1               5                   10                  15

Arg Arg Arg

<210> SEQ ID NO 374
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
```

```
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 374

Phe Cys His Tyr Arg Trp Ala Cys Xaa Xaa Gly Arg Arg Arg Arg
1               5                   10                  15

Gln Arg Arg Arg
            20

<210> SEQ ID NO 375
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 375

Phe Cys His Tyr Arg Trp Ala Cys Xaa Xaa Arg Arg Arg Arg Gln
1               5                   10                  15

Arg Arg Arg Arg
            20

<210> SEQ ID NO 376
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
```

<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Beta-Ala

<400> SEQUENCE: 376

Phe Cys His Tyr Arg Trp Ala Cys Thr Ala Tyr Gly Arg Arg Arg
1               5                   10                  15

Arg Gln Arg Arg Arg
            20

<210> SEQ ID NO 377
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Beta-Ala

<400> SEQUENCE: 377

Phe Cys His Tyr Arg Trp Ala Cys Thr Ala Arg Arg Arg Arg Gln
1               5                   10                  15

Arg Arg Arg

<210> SEQ ID NO 378
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES

```
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Beta-Ala
<220> FEATURE:
<221> NAME/KEY: MOD_RES
<222> LOCATION: (11)..(11)
<223> OTHER INFORMATION: Beta-Ala

<400> SEQUENCE: 378

Phe Cys His Tyr Arg Trp Ala Cys Thr Ala Ala Tyr Gly Arg Arg Arg
1               5                   10                  15

Arg Arg Gln Arg Arg Arg
            20

<210> SEQ ID NO 379
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Beta-Ala
<220> FEATURE:
<221> NAME/KEY: MOD_RES
<222> LOCATION: (11)..(11)
<223> OTHER INFORMATION: Beta-Ala

<400> SEQUENCE: 379

Phe Cys His Tyr Arg Trp Ala Cys Thr Ala Ala Arg Arg Arg Arg Arg
1               5                   10                  15

Gln Arg Arg Arg
            20

<210> SEQ ID NO 380
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
```

```
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Doc

<400> SEQUENCE: 380

Phe Cys His Tyr Arg Trp Ala Cys Thr Xaa Tyr Gly Arg Arg Arg Arg
1               5                   10                  15

Arg Gln Arg Arg Arg
            20

<210> SEQ ID NO 381
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Doc

<400> SEQUENCE: 381

Phe Cys His Tyr Arg Trp Ala Cys Thr Xaa Arg Arg Arg Arg Arg Gln
1               5                   10                  15

Arg Arg Arg

<210> SEQ ID NO 382
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
```

```
<221> NAME/KEY: MOD_RES
<222> LOCATION: (10)..(10)
<223> OTHER INFORMATION: Doc
<220> FEATURE:
<221> NAME/KEY: MOD_RES
<222> LOCATION: (11)..(11)
<223> OTHER INFORMATION: Doc

<400> SEQUENCE: 382

Phe Cys His Tyr Arg Trp Ala Cys Thr Xaa Xaa Tyr Gly Arg Arg Arg
1               5                   10                  15

Arg Arg Gln Arg Arg Arg
            20

<210> SEQ ID NO 383
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Beta-Ala

<400> SEQUENCE: 383

Phe Cys His Tyr Arg Trp Ala Cys Thr Ala Tyr Gly Arg Arg Arg Arg
1               5                   10                  15

Arg Gln Arg Arg Arg Arg
            20

<210> SEQ ID NO 384
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
```

```
<222> LOCATION: (10)..(10)
<223> OTHER INFORMATION: Beta-Ala

<400> SEQUENCE: 384

Phe Cys His Tyr Arg Trp Ala Cys Thr Ala Arg Arg Arg Arg Gln
1               5                   10                  15

Arg Arg Arg Arg
            20

<210> SEQ ID NO 385
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Beta-Ala
<220> FEATURE:
<221> NAME/KEY: MOD_RES
<222> LOCATION: (11)..(11)
<223> OTHER INFORMATION: Beta-Ala

<400> SEQUENCE: 385

Phe Cys His Tyr Arg Trp Ala Cys Thr Ala Ala Tyr Gly Arg Arg
1               5                   10                  15

Arg Arg Gln Arg Arg Arg Arg
            20

<210> SEQ ID NO 386
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
```

<223> OTHER INFORMATION: Beta-Ala
<220> FEATURE:
<221> NAME/KEY: MOD_RES
<222> LOCATION: (11)..(11)
<223> OTHER INFORMATION: Beta-Ala

<400> SEQUENCE: 386

Phe Cys His Tyr Arg Trp Ala Cys Thr Ala Ala Arg Arg Arg Arg Arg
1               5                   10                  15

Gln Arg Arg Arg Arg
            20

<210> SEQ ID NO 387
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Doc

<400> SEQUENCE: 387

Phe Cys His Tyr Arg Trp Ala Cys Thr Xaa Tyr Gly Arg Arg Arg Arg
1               5                   10                  15

Arg Gln Arg Arg Arg Arg
            20

<210> SEQ ID NO 388
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Doc

<400> SEQUENCE: 388

Phe Cys His Tyr Arg Trp Ala Cys Thr Xaa Arg Arg Arg Arg Gln
1               5                   10                  15

Arg Arg Arg Arg
            20

<210> SEQ ID NO 389
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Doc
<220> FEATURE:
<221> NAME/KEY: MOD_RES
<222> LOCATION: (11)..(11)
<223> OTHER INFORMATION: Doc

<400> SEQUENCE: 389

Phe Cys His Tyr Arg Trp Ala Cys Thr Xaa Xaa Tyr Gly Arg Arg
1               5                   10                  15

Arg Arg Gln Arg Arg Arg Arg
            20

<210> SEQ ID NO 390
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Doc
<220> FEATURE:

```
<221> NAME/KEY: MOD_RES
<222> LOCATION: (11)..(11)
<223> OTHER INFORMATION: Doc

<400> SEQUENCE: 390

Phe Cys His Tyr Arg Trp Ala Cys Thr Xaa Xaa Arg Arg Arg Arg
1               5                   10                  15

Gln Arg Arg Arg Arg
            20

<210> SEQ ID NO 391
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Beta-Ala

<400> SEQUENCE: 391

Phe Cys His Tyr Arg Xaa Ala Cys Thr Ala Tyr Gly Arg Arg Arg
1               5                   10                  15

Arg Gln Arg Arg Arg
            20

<210> SEQ ID NO 392
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
```

```
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Beta-Ala

<400> SEQUENCE: 392

Phe Cys His Tyr Arg Xaa Ala Cys Thr Ala Tyr Gly Arg Arg Arg
1               5                   10                  15

Arg Gln Arg Arg Arg Arg
            20

<210> SEQ ID NO 393
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Beta-Ala

<400> SEQUENCE: 393

Phe Cys His Tyr Arg Xaa Ala Cys Thr Ala Arg Arg Arg Arg Gln
1               5                   10                  15

Arg Arg Arg

<210> SEQ ID NO 394
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: Beta-Ala
```

```
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Beta-Ala
<220> FEATURE:
<221> NAME/KEY: MOD_RES
<222> LOCATION: (11)..(11)
<223> OTHER INFORMATION: Beta-Ala

<400> SEQUENCE: 394

Phe Cys His Tyr Arg Xaa Ala Cys Thr Ala Ala Tyr Gly Arg Arg Arg
1               5                   10                  15

Arg Arg Gln Arg Arg Arg
            20

<210> SEQ ID NO 395
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Beta-Ala
<220> FEATURE:
<221> NAME/KEY: MOD_RES
<222> LOCATION: (11)..(11)
<223> OTHER INFORMATION: Beta-Ala

<400> SEQUENCE: 395

Phe Cys His Tyr Arg Xaa Ala Cys Thr Ala Ala Arg Arg Arg Arg Arg
1               5                   10                  15

Gln Arg Arg Arg
            20

<210> SEQ ID NO 396
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
```

```
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Doc

<400> SEQUENCE: 396

Phe Cys His Tyr Arg Xaa Ala Cys Thr Xaa Tyr Gly Arg Arg Arg
1               5                  10                  15

Arg Gln Arg Arg Arg
            20

<210> SEQ ID NO 397
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Doc

<400> SEQUENCE: 397

Phe Cys His Tyr Arg Xaa Ala Cys Thr Xaa Tyr Gly Arg Arg Arg
1               5                  10                  15

Arg Gln Arg Arg Arg Arg
            20

<210> SEQ ID NO 398
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Doc

<400> SEQUENCE: 398

Phe Cys His Tyr Arg Xaa Ala Cys Thr Xaa Arg Arg Arg Arg Gln
1               5                   10                  15

Arg Arg Arg

<210> SEQ ID NO 399
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Doc
<220> FEATURE:
<221> NAME/KEY: MOD_RES
<222> LOCATION: (11)..(11)
<223> OTHER INFORMATION: Doc

<400> SEQUENCE: 399

Phe Cys His Tyr Arg Xaa Ala Cys Thr Xaa Xaa Tyr Gly Arg Arg
1               5                   10                  15

Arg Arg Gln Arg Arg Arg
            20

<210> SEQ ID NO 400
<211> LENGTH: 20
<212> TYPE: PRT
```

<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Doc
<220> FEATURE:
<221> NAME/KEY: MOD_RES
<222> LOCATION: (11)..(11)
<223> OTHER INFORMATION: Doc

<400> SEQUENCE: 400

Phe Cys His Tyr Arg Xaa Ala Cys Thr Xaa Xaa Arg Arg Arg Arg
1               5                   10                  15

Gln Arg Arg Arg
            20

<210> SEQ ID NO 401
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (10)..(10)
<223> OTHER INFORMATION: Beta-Ala

<400> SEQUENCE: 401

Xaa Cys Ala His Phe Arg Trp Gly Cys Ala Tyr Gly Arg Arg Arg
1               5                   10                  15

Arg Gln Arg Arg Arg
            20

<210> SEQ ID NO 402
<211> LENGTH: 19
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (10)..(10)
<223> OTHER INFORMATION: Beta-Ala

<400> SEQUENCE: 402

Xaa Cys Ala His Phe Arg Trp Gly Cys Ala Arg Arg Arg Arg Gln
1               5                   10                  15

Arg Arg Arg

<210> SEQ ID NO 403
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(9)
<223> OTHER INFORMATION: Beta-Ala

<400> SEQUENCE: 403

Xaa Cys His Phe Arg Trp Xaa Cys Ala Tyr Gly Arg Arg Arg Arg
1               5                   10                  15

Gln Arg Arg Arg
            20

<210> SEQ ID NO 404
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
```

```
<223> OTHER INFORMATION: Apn
<220> FEATURE:
<221> NAME/KEY: MOD_RES
<222> LOCATION: (9)..(9)
<223> OTHER INFORMATION: Beta-Ala

<400> SEQUENCE: 404

Xaa Cys His Phe Arg Trp Xaa Cys Ala Arg Arg Arg Arg Gln Arg
1               5                   10                  15

Arg Arg

<210> SEQ ID NO 405
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
<223> OTHER INFORMATION: Beta-Ala

<400> SEQUENCE: 405

Xaa Cys His Phe Arg Trp Xaa Cys Ala Ala Tyr Gly Arg Arg Arg
1               5                   10                  15

Arg Gln Arg Arg Arg
                20

<210> SEQ ID NO 406
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
<223> OTHER INFORMATION: Beta-Ala
```

```
<400> SEQUENCE: 406

Xaa Cys His Phe Arg Trp Xaa Cys Ala Ala Arg Arg Arg Arg Gln
1               5                   10                  15

Arg Arg Arg

<210> SEQ ID NO 407
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(9)
<223> OTHER INFORMATION: Beta-Ala

<400> SEQUENCE: 407

Xaa Cys His Phe Arg Trp Xaa Cys Ala Tyr Gly Arg Arg Arg Arg
1               5                   10                  15

Gln Arg Arg Arg Arg
                20

<210> SEQ ID NO 408
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(9)
<223> OTHER INFORMATION: Beta-Ala

<400> SEQUENCE: 408

Xaa Cys His Phe Arg Trp Xaa Cys Ala Arg Arg Arg Arg Gln Arg
1               5                   10                  15

Arg Arg Arg

<210> SEQ ID NO 409
<211> LENGTH: 22
<212> TYPE: PRT
<213> ORGANISM: Artificial Sequence
<220> FEATURE:
<223> OTHER INFORMATION: Description of Artificial Sequence: Synthetic
```

```
                        peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
<223> OTHER INFORMATION: Beta-Ala

<400> SEQUENCE: 409

Xaa Cys His Phe Arg Trp Xaa Cys Ala Ala Tyr Gly Arg Arg Arg Arg
1               5                   10                  15

Arg Gln Arg Arg Arg Arg
            20

<210> SEQ ID NO 410
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
<223> OTHER INFORMATION: Beta-Ala

<400> SEQUENCE: 410

Xaa Cys His Phe Arg Trp Xaa Cys Ala Ala Arg Arg Arg Arg Arg Gln
1               5                   10                  15

Arg Arg Arg Arg
            20

<210> SEQ ID NO 411
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
```

```
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(9)
<223> OTHER INFORMATION: Doc

<400> SEQUENCE: 411

Xaa Cys His Phe Arg Trp Xaa Cys Xaa Tyr Gly Arg Arg Arg Arg
1               5                   10                  15

Gln Arg Arg Arg
            20

<210> SEQ ID NO 412
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(9)
<223> OTHER INFORMATION: Doc

<400> SEQUENCE: 412

Xaa Cys His Phe Arg Trp Xaa Cys Xaa Arg Arg Arg Arg Gln Arg
1               5                   10                  15

Arg Arg

<210> SEQ ID NO 413
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
```

```
<222> LOCATION: (10)..(10)
<223> OTHER INFORMATION: Doc

<400> SEQUENCE: 413

Xaa Cys His Phe Arg Trp Xaa Cys Xaa Xaa Tyr Gly Arg Arg Arg
1               5                   10                  15

Arg Gln Arg Arg Arg
            20

<210> SEQ ID NO 414
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 414

Xaa Cys His Phe Arg Trp Xaa Cys Xaa Xaa Arg Arg Arg Arg Gln
1               5                   10                  15

Arg Arg Arg

<210> SEQ ID NO 415
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(9)
<223> OTHER INFORMATION: Doc

<400> SEQUENCE: 415

Xaa Cys His Phe Arg Trp Xaa Cys Xaa Tyr Gly Arg Arg Arg Arg
1               5                   10                  15

Gln Arg Arg Arg Arg
            20
```

```
<210> SEQ ID NO 416
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(9)
<223> OTHER INFORMATION: Doc

<400> SEQUENCE: 416

Xaa Cys His Phe Arg Trp Xaa Cys Xaa Arg Arg Arg Arg Gln Arg
1               5                   10                  15

Arg Arg Arg

<210> SEQ ID NO 417
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 417

Xaa Cys His Phe Arg Trp Xaa Cys Xaa Xaa Tyr Gly Arg Arg Arg
1               5                   10                  15

Arg Gln Arg Arg Arg Arg
                20

<210> SEQ ID NO 418
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 418

Xaa Cys His Phe Arg Trp Xaa Cys Xaa Xaa Arg Arg Arg Arg Gln
1               5                   10                  15

Arg Arg Arg Arg
            20

<210> SEQ ID NO 419
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala

<400> SEQUENCE: 419

Xaa Cys Leu His Phe Arg Trp Cys Ala Tyr Gly Arg Arg Arg Arg
1               5                   10                  15

Gln Arg Arg Arg
            20

<210> SEQ ID NO 420
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
```

```
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala

<400> SEQUENCE: 420

Xaa Cys Leu His Phe Arg Trp Cys Ala Arg Arg Arg Arg Gln Arg
1               5                   10                  15

Arg Arg

<210> SEQ ID NO 421
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
<223> OTHER INFORMATION: Beta-Ala

<400> SEQUENCE: 421

Xaa Cys Leu His Phe Arg Trp Cys Ala Ala Tyr Gly Arg Arg Arg
1               5                   10                  15

Arg Gln Arg Arg Arg
            20

<210> SEQ ID NO 422
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
<223> OTHER INFORMATION: Beta-Ala
```

```
<400> SEQUENCE: 422

Xaa Cys Leu His Phe Arg Trp Cys Ala Ala Arg Arg Arg Arg Gln
1               5                   10                  15

Arg Arg Arg

<210> SEQ ID NO 423
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc

<400> SEQUENCE: 423

Xaa Cys Leu His Phe Arg Trp Cys Xaa Tyr Gly Arg Arg Arg Arg
1               5                   10                  15

Gln Arg Arg Arg
            20

<210> SEQ ID NO 424
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc

<400> SEQUENCE: 424

Xaa Cys Leu His Phe Arg Trp Cys Xaa Arg Arg Arg Arg Gln Arg
1               5                   10                  15

Arg Arg

<210> SEQ ID NO 425
<211> LENGTH: 21
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 425

Xaa Cys Leu His Phe Arg Trp Cys Xaa Xaa Tyr Gly Arg Arg Arg Arg
1               5                   10                  15

Arg Gln Arg Arg Arg
            20

<210> SEQ ID NO 426
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 426

Xaa Cys Leu His Phe Arg Trp Cys Xaa Xaa Arg Arg Arg Arg Gln
1               5                   10                  15

Arg Arg Arg

<210> SEQ ID NO 427
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
```

```
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala

<400> SEQUENCE: 427

Xaa Cys Leu His Phe Arg Trp Cys Ala Tyr Gly Arg Arg Arg Arg
1               5                   10                  15

Gln Arg Arg Arg Arg
            20

<210> SEQ ID NO 428
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala

<400> SEQUENCE: 428

Xaa Cys Leu His Phe Arg Trp Cys Ala Arg Arg Arg Arg Gln Arg
1               5                   10                  15

Arg Arg Arg

<210> SEQ ID NO 429
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
```

```
<222> LOCATION: (10)..(10)
<223> OTHER INFORMATION: Beta-Ala

<400> SEQUENCE: 429

Xaa Cys Leu His Phe Arg Trp Cys Ala Ala Tyr Gly Arg Arg Arg
1               5                   10                  15

Arg Gln Arg Arg Arg Arg
            20

<210> SEQ ID NO 430
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
<223> OTHER INFORMATION: Beta-Ala

<400> SEQUENCE: 430

Xaa Cys Leu His Phe Arg Trp Cys Ala Ala Arg Arg Arg Arg Gln
1               5                   10                  15

Arg Arg Arg Arg
            20

<210> SEQ ID NO 431
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc

<400> SEQUENCE: 431

Xaa Cys Leu His Phe Arg Trp Cys Xaa Tyr Gly Arg Arg Arg Arg
1               5                   10                  15

Gln Arg Arg Arg Arg
```

-continued

<210> SEQ ID NO 432
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc

<400> SEQUENCE: 432

Xaa Cys Leu His Phe Arg Trp Cys Xaa Arg Arg Arg Arg Gln Arg
1               5                   10                  15

Arg Arg Arg

<210> SEQ ID NO 433
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 433

Xaa Cys Leu His Phe Arg Trp Cys Xaa Xaa Tyr Gly Arg Arg Arg
1               5                   10                  15

Arg Gln Arg Arg Arg Arg
            20

<210> SEQ ID NO 434
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 434

Xaa Cys Leu His Phe Arg Trp Cys Xaa Xaa Arg Arg Arg Arg Gln
1               5                   10                  15

Arg Arg Arg Arg
            20

<210> SEQ ID NO 435
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala

<400> SEQUENCE: 435

Xaa Cys Xaa His Phe Arg Trp Cys Ala Tyr Gly Arg Arg Arg Arg
1               5                   10                  15

Gln Arg Arg Arg
            20

<210> SEQ ID NO 436
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Cha
<220> FEATURE:
```

```
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala

<400> SEQUENCE: 436

Xaa Cys Xaa His Phe Arg Trp Cys Ala Arg Arg Arg Arg Gln Arg
1               5                   10                  15

Arg Arg

<210> SEQ ID NO 437
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
<223> OTHER INFORMATION: Beta-Ala

<400> SEQUENCE: 437

Xaa Cys Xaa His Phe Arg Trp Cys Ala Ala Tyr Gly Arg Arg Arg
1               5                   10                  15

Arg Gln Arg Arg Arg
            20

<210> SEQ ID NO 438
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
```

<223> OTHER INFORMATION: Beta-Ala

<400> SEQUENCE: 438

Xaa Cys Xaa His Phe Arg Trp Cys Ala Ala Arg Arg Arg Arg Gln
1               5                   10                  15

Arg Arg Arg

<210> SEQ ID NO 439
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc

<400> SEQUENCE: 439

Xaa Cys Xaa His Phe Arg Trp Cys Xaa Tyr Gly Arg Arg Arg Arg
1               5                   10                  15

Gln Arg Arg Arg
            20

<210> SEQ ID NO 440
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc

<400> SEQUENCE: 440

Xaa Cys Xaa His Phe Arg Trp Cys Xaa Arg Arg Arg Arg Gln Arg
1               5                   10                  15

Arg Arg

<210> SEQ ID NO 441
<211> LENGTH: 21
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 441

Xaa Cys Xaa His Phe Arg Trp Cys Xaa Xaa Tyr Gly Arg Arg Arg
1               5                   10                  15

Arg Gln Arg Arg Arg
            20

<210> SEQ ID NO 442
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 442

Xaa Cys Xaa His Phe Arg Trp Cys Xaa Xaa Arg Arg Arg Arg Gln
1               5                   10                  15

Arg Arg Arg

<210> SEQ ID NO 443
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Nle
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala

<400> SEQUENCE: 443

Xaa Cys Xaa His Phe Arg Trp Cys Ala Tyr Gly Arg Arg Arg Arg
1               5                   10                  15

Gln Arg Arg Arg Arg
                20

<210> SEQ ID NO 444
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala

<400> SEQUENCE: 444

Xaa Cys Xaa His Phe Arg Trp Cys Ala Arg Arg Arg Arg Gln Arg
1               5                   10                  15

Arg Arg Arg

<210> SEQ ID NO 445
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
```

```
<221> NAME/KEY: MOD_RES
<222> LOCATION: (10)..(10)
<223> OTHER INFORMATION: Beta-Ala

<400> SEQUENCE: 445

Xaa Cys Xaa His Phe Arg Trp Cys Ala Ala Tyr Gly Arg Arg Arg
1               5                   10                  15

Arg Gln Arg Arg Arg Arg
            20

<210> SEQ ID NO 446
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
<223> OTHER INFORMATION: Beta-Ala

<400> SEQUENCE: 446

Xaa Cys Xaa His Phe Arg Trp Cys Ala Ala Arg Arg Arg Arg Gln
1               5                   10                  15

Arg Arg Arg Arg
            20

<210> SEQ ID NO 447
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc

<400> SEQUENCE: 447

Xaa Cys Xaa His Phe Arg Trp Cys Xaa Tyr Gly Arg Arg Arg Arg
1               5                   10                  15
```

Gln Arg Arg Arg Arg
            20

<210> SEQ ID NO 448
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc

<400> SEQUENCE: 448

Xaa Cys Xaa His Phe Arg Trp Cys Xaa Arg Arg Arg Arg Gln Arg
1               5                   10                  15

Arg Arg Arg

<210> SEQ ID NO 449
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 449

Xaa Cys Xaa His Phe Arg Trp Cys Xaa Xaa Tyr Gly Arg Arg Arg
1               5                   10                  15

Arg Gln Arg Arg Arg Arg
            20

<210> SEQ ID NO 450
<211> LENGTH: 20
<212> TYPE: PRT
<213> ORGANISM: Artificial Sequence
<220> FEATURE:
<223> OTHER INFORMATION: Description of Artificial Sequence: Synthetic

```
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 450

Xaa Cys Xaa His Phe Arg Trp Cys Xaa Xaa Arg Arg Arg Arg Arg Gln
1               5                   10                  15

Arg Arg Arg Arg
            20

<210> SEQ ID NO 451
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala

<400> SEQUENCE: 451

Xaa Cys His Phe Arg Trp Xaa Cys Ala Tyr Gly Arg Arg Arg Arg Arg
1               5                   10                  15

Gln Arg Arg Arg
            20

<210> SEQ ID NO 452
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
```

<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala

<400> SEQUENCE: 452

Xaa Cys His Phe Arg Trp Xaa Cys Ala Arg Arg Arg Arg Gln Arg
1               5                   10                  15

Arg Arg

<210> SEQ ID NO 453
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
<223> OTHER INFORMATION: Beta-Ala

<400> SEQUENCE: 453

Xaa Cys His Phe Arg Trp Xaa Cys Ala Ala Tyr Gly Arg Arg Arg
1               5                   10                  15

Arg Gln Arg Arg Arg
            20

<210> SEQ ID NO 454
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES

```
<222> LOCATION: (10)..(10)
<223> OTHER INFORMATION: Beta-Ala

<400> SEQUENCE: 454

Xaa Cys His Phe Arg Trp Xaa Cys Ala Ala Arg Arg Arg Arg Gln
1               5                   10                  15

Arg Arg Arg

<210> SEQ ID NO 455
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala

<400> SEQUENCE: 455

Xaa Cys His Phe Arg Trp Xaa Cys Ala Tyr Gly Arg Arg Arg Arg
1               5                   10                  15

Gln Arg Arg Arg Arg
                20

<210> SEQ ID NO 456
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala

<400> SEQUENCE: 456

Xaa Cys His Phe Arg Trp Xaa Cys Ala Arg Arg Arg Arg Gln Arg
1               5                   10                  15

Arg Arg Arg

<210> SEQ ID NO 457
<211> LENGTH: 22
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
<223> OTHER INFORMATION: Beta-Ala

<400> SEQUENCE: 457

Xaa Cys His Phe Arg Trp Xaa Cys Ala Ala Tyr Gly Arg Arg Arg
1               5                  10                 15

Arg Gln Arg Arg Arg Arg
            20

<210> SEQ ID NO 458
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
<223> OTHER INFORMATION: Beta-Ala

<400> SEQUENCE: 458

Xaa Cys His Phe Arg Trp Xaa Cys Ala Ala Arg Arg Arg Arg Arg Gln
1               5                  10                 15

Arg Arg Arg Arg
            20

<210> SEQ ID NO 459
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Doc

<400> SEQUENCE: 459

Xaa Cys His Phe Arg Trp Xaa Cys Xaa Tyr Gly Arg Arg Arg Arg
1               5                   10                  15

Gln Arg Arg Arg
            20

<210> SEQ ID NO 460
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Doc

<400> SEQUENCE: 460

Xaa Cys His Phe Arg Trp Xaa Cys Xaa Arg Arg Arg Arg Gln Arg
1               5                   10                  15

Arg Arg

<210> SEQ ID NO 461
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
```

```
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 461

Xaa Cys His Phe Arg Trp Xaa Cys Xaa Xaa Tyr Gly Arg Arg Arg Arg
1               5                  10                  15

Arg Gln Arg Arg Arg
            20

<210> SEQ ID NO 462
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 462

Xaa Cys His Phe Arg Trp Xaa Cys Xaa Xaa Arg Arg Arg Arg Arg Gln
1               5                  10                  15

Arg Arg Arg

<210> SEQ ID NO 463
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Doc

<400> SEQUENCE: 463

Xaa Cys His Phe Arg Trp Xaa Cys Xaa Tyr Gly Arg Arg Arg Arg Arg
1               5                  10                  15
```

```
Gln Arg Arg Arg Arg
        20

<210> SEQ ID NO 464
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Doc

<400> SEQUENCE: 464

Xaa Cys His Phe Arg Trp Xaa Cys Xaa Arg Arg Arg Arg Gln Arg
1               5                   10                  15

Arg Arg Arg

<210> SEQ ID NO 465
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 465

Xaa Cys His Phe Arg Trp Xaa Cys Xaa Xaa Tyr Gly Arg Arg Arg
1               5                   10                  15

Arg Gln Arg Arg Arg Arg
            20

<210> SEQ ID NO 466
<211> LENGTH: 20
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Doc
<220> FEATURE:
<221> NAME/KEY: MOD_RES
<222> LOCATION: (10)..(10)
<223> OTHER INFORMATION: Doc

<400> SEQUENCE: 466

Xaa Cys His Phe Arg Trp Xaa Cys Xaa Xaa Arg Arg Arg Arg Gln
1               5                  10                  15

Arg Arg Arg Arg
            20

<210> SEQ ID NO 467
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-4Br-Phe

<400> SEQUENCE: 467

Cys Glu His Phe Arg Trp Gly Cys Pro Pro Lys Asp
1               5                  10

<210> SEQ ID NO 468
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal

<400> SEQUENCE: 468

Cys Glu His Xaa Arg Trp Ala Cys Pro Pro Lys Asp
1               5                  10

<210> SEQ ID NO 469
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
```

```
<220> FEATURE:
<221> NAME/KEY: MOD_RES
<222> LOCATION: (6)..(6)
<223> OTHER INFORMATION: 2-Nal

<400> SEQUENCE: 469

Cys Glu His Xaa Arg Xaa Ala Cys Pro Pro Lys Asp
1               5                   10

<210> SEQ ID NO 470
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal

<400> SEQUENCE: 470

Cys Glu His Xaa Arg Xaa Ala Cys Pro Pro Lys Asp
1               5                   10

<210> SEQ ID NO 471
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal

<400> SEQUENCE: 471

Cys Glu His Xaa Arg Xaa Ala Cys Pro Pro Lys Asp
1               5                   10

<210> SEQ ID NO 472
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (7)..(7)
<223> OTHER INFORMATION: Beta-Ala

<400> SEQUENCE: 472

Cys Glu His Xaa Arg Xaa Ala Cys Pro Pro Lys Asp
1               5                   10
```

```
<210> SEQ ID NO 473
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (7)..(7)
<223> OTHER INFORMATION: Aib

<400> SEQUENCE: 473

Cys Glu His Xaa Arg Xaa Xaa Cys Pro Pro Lys Asp
1               5                   10

<210> SEQ ID NO 474
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe

<400> SEQUENCE: 474

Cys Ala His Phe Arg Trp Cys
1               5

<210> SEQ ID NO 475
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe

<400> SEQUENCE: 475

Cys Ala His Phe Arg Trp Cys
1               5

<210> SEQ ID NO 476
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-2-Nal

<400> SEQUENCE: 476

Cys Ala His Xaa Arg Trp Cys
1               5

<210> SEQ ID NO 477
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-2-Nal

<400> SEQUENCE: 477

Cys Ala His Xaa Arg Trp Cys
1               5

<210> SEQ ID NO 478
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe

<400> SEQUENCE: 478

Asp Ala His Phe Arg Trp Lys
1               5

<210> SEQ ID NO 479
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Orn
```

```
<400> SEQUENCE: 479

Asp Ala His Phe Arg Trp Xaa
1               5

<210> SEQ ID NO 480
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Dab

<400> SEQUENCE: 480

Asp Ala His Phe Arg Trp Xaa
1               5

<210> SEQ ID NO 481
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Dap

<400> SEQUENCE: 481

Asp Ala His Phe Arg Trp Xaa
1               5

<210> SEQ ID NO 482
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-2-Nal

<400> SEQUENCE: 482

Asp His Xaa Arg Trp Lys
1               5

<210> SEQ ID NO 483
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Phe

<400> SEQUENCE: 483

Asp His Phe Arg Trp Lys
1               5

<210> SEQ ID NO 484
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A3c
<220> FEATURE:
<221> NAME/KEY: MOD_RES
<222> LOCATION: (3)..(3)
<223> OTHER INFORMATION: D-Phe

<400> SEQUENCE: 484

Asp Xaa Phe Arg Trp Lys
1               5

<210> SEQ ID NO 485
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A5c
<220> FEATURE:
<221> NAME/KEY: MOD_RES
<222> LOCATION: (3)..(3)
<223> OTHER INFORMATION: D-Phe

<400> SEQUENCE: 485

Asp Xaa Phe Arg Trp Lys
1               5

<210> SEQ ID NO 486
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A6c
<220> FEATURE:
<221> NAME/KEY: MOD_RES
<222> LOCATION: (3)..(3)
<223> OTHER INFORMATION: D-Phe

<400> SEQUENCE: 486

Asp Xaa Phe Arg Trp Lys
1               5
```

```
<210> SEQ ID NO 487
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A3c
<220> FEATURE:
<221> NAME/KEY: MOD_RES
<222> LOCATION: (3)..(3)
<223> OTHER INFORMATION: D-2-Nal

<400> SEQUENCE: 487

Asp Xaa Xaa Arg Trp Lys
1               5

<210> SEQ ID NO 488
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A5c
<220> FEATURE:
<221> NAME/KEY: MOD_RES
<222> LOCATION: (3)..(3)
<223> OTHER INFORMATION: D-2-Nal

<400> SEQUENCE: 488

Asp Xaa Xaa Arg Trp Lys
1               5

<210> SEQ ID NO 489
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A6c
<220> FEATURE:
<221> NAME/KEY: MOD_RES
<222> LOCATION: (3)..(3)
<223> OTHER INFORMATION: D-2-Nal

<400> SEQUENCE: 489

Asp Xaa Xaa Arg Trp Lys
1               5

<210> SEQ ID NO 490
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Aic
```

```
<220> FEATURE:
<221> NAME/KEY: MOD_RES
<222> LOCATION: (3)..(3)
<223> OTHER INFORMATION: D-Phe

<400> SEQUENCE: 490

Asp Xaa Phe Arg Trp Lys
1               5

<210> SEQ ID NO 491
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Apc
<220> FEATURE:
<221> NAME/KEY: MOD_RES
<222> LOCATION: (3)..(3)
<223> OTHER INFORMATION: D-Phe

<400> SEQUENCE: 491

Asp Xaa Phe Arg Trp Lys
1               5

<210> SEQ ID NO 492
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Aic
<220> FEATURE:
<221> NAME/KEY: MOD_RES
<222> LOCATION: (3)..(3)
<223> OTHER INFORMATION: D-2-Nal

<400> SEQUENCE: 492

Asp Xaa Xaa Arg Trp Lys
1               5

<210> SEQ ID NO 493
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Apc
<220> FEATURE:
<221> NAME/KEY: MOD_RES
<222> LOCATION: (3)..(3)
<223> OTHER INFORMATION: D-2-Nal

<400> SEQUENCE: 493

Asp Xaa Xaa Arg Trp Lys
1               5

<210> SEQ ID NO 494
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Orn

<400> SEQUENCE: 494

Glu Ala His Phe Arg Trp Xaa
1               5

<210> SEQ ID NO 495
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Dab

<400> SEQUENCE: 495

Glu Ala His Phe Arg Trp Xaa
1               5

<210> SEQ ID NO 496
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Dap

<400> SEQUENCE: 496

Glu Ala His Phe Arg Trp Xaa
1               5

<210> SEQ ID NO 497
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe

<400> SEQUENCE: 497

Glu Ala His Phe Arg Trp Lys
1               5

<210> SEQ ID NO 498
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Phe
<220> FEATURE:
<221> NAME/KEY: MOD_RES
<222> LOCATION: (6)..(6)
<223> OTHER INFORMATION: Dap

<400> SEQUENCE: 498

Glu His Phe Arg Trp Xaa
1               5

<210> SEQ ID NO 499
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Phe

<400> SEQUENCE: 499

Glu His Phe Arg Trp Lys
1               5

<210> SEQ ID NO 500
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: D-Phe

<400> SEQUENCE: 500

Arg Gly Cys Glu His Phe Arg Trp Cys
1               5

<210> SEQ ID NO 501
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (6)..(6)
<223> OTHER INFORMATION: D-Phe

<400> SEQUENCE: 501

Xaa Gly Cys Glu His Phe Arg Trp Cys
1               5

<210> SEQ ID NO 502
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: D-Phe

<400> SEQUENCE: 502

Gly Gly Cys Glu His Phe Arg Trp Cys
1               5

<210> SEQ ID NO 503
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe

<400> SEQUENCE: 503

Xaa Gly Cys Ala His Phe Arg Trp Cys
1               5

<210> SEQ ID NO 504
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe
```

```
<400> SEQUENCE: 504

Gly Gly Cys Ala His Phe Arg Trp Cys
1               5

<210> SEQ ID NO 505
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe
<220> FEATURE:
<221> NAME/KEY: MOD_RES
<222> LOCATION: (9)..(9)
<223> OTHER INFORMATION: Pen

<400> SEQUENCE: 505

Xaa Gly Cys Ala His Phe Arg Trp Xaa
1               5

<210> SEQ ID NO 506
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe
<220> FEATURE:
<221> NAME/KEY: MOD_RES
<222> LOCATION: (9)..(9)
<223> OTHER INFORMATION: Pen

<400> SEQUENCE: 506

Gly Gly Cys Ala His Phe Arg Trp Xaa
1               5

<210> SEQ ID NO 507
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe
```

```
<400> SEQUENCE: 507

Ala Gly Cys Ala His Phe Arg Trp Cys
1               5

<210> SEQ ID NO 508
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe

<400> SEQUENCE: 508

Ala Gly Cys Ala His Phe Arg Trp Cys
1               5

<210> SEQ ID NO 509
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aib
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe

<400> SEQUENCE: 509

Xaa Gly Cys Ala His Phe Arg Trp Cys
1               5

<210> SEQ ID NO 510
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe

<400> SEQUENCE: 510

Val Gly Cys Ala His Phe Arg Trp Cys
1               5
```

<210> SEQ ID NO 511
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe

<400> SEQUENCE: 511

Ile Gly Cys Ala His Phe Arg Trp Cys
1               5

<210> SEQ ID NO 512
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe

<400> SEQUENCE: 512

Leu Gly Cys Ala His Phe Arg Trp Cys
1               5

<210> SEQ ID NO 513
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: D-2-Nal

<400> SEQUENCE: 513

Gly Gly Cys Glu His Xaa Arg Trp Cys
1               5

<210> SEQ ID NO 514
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (6)..(6)
<223> OTHER INFORMATION: D-2-Nal -continued

```
<400> SEQUENCE: 514

Xaa Gly Cys Glu His Xaa Arg Trp Cys
1               5

<210> SEQ ID NO 515
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (6)..(6)
<223> OTHER INFORMATION: D-Phe

<400> SEQUENCE: 515

Arg Gly Cys Glu His Phe Arg Trp Cys
1               5

<210> SEQ ID NO 516
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe

<400> SEQUENCE: 516

Arg Gly Cys Ala His Phe Arg Trp Cys
1               5

<210> SEQ ID NO 517
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe

<400> SEQUENCE: 517

Arg Gly Cys Ala His Phe Arg Trp Cys
1               5

<210> SEQ ID NO 518
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-2-Nal

<400> SEQUENCE: 518

Arg Gly Cys Ala His Xaa Arg Trp Cys
1               5

<210> SEQ ID NO 519
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-2-Nal

<400> SEQUENCE: 519

Arg Gly Cys Ala His Xaa Arg Trp Cys
1               5

<210> SEQ ID NO 520
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (6)..(6)
<223> OTHER INFORMATION: D-Phe

<400> SEQUENCE: 520

Ala Xaa Cys Glu His Phe Arg Trp Cys
1               5

<210> SEQ ID NO 521
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Nle
<220> FEATURE:
```

```
<221> NAME/KEY: MOD_RES
<222> LOCATION: (6)..(6)
<223> OTHER INFORMATION: D-Phe

<400> SEQUENCE: 521

Val Xaa Cys Glu His Phe Arg Trp Cys
1               5

<210> SEQ ID NO 522
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (6)..(6)
<223> OTHER INFORMATION: D-Phe

<400> SEQUENCE: 522

Gly Xaa Cys Glu His Phe Arg Trp Cys
1               5

<210> SEQ ID NO 523
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A6c
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe

<400> SEQUENCE: 523

Xaa Xaa Cys Ala His Phe Arg Trp Cys
1               5

<210> SEQ ID NO 524
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
```

```
<222> LOCATION: (6)..(6)
<223> OTHER INFORMATION: D-Phe

<400> SEQUENCE: 524

Gly Xaa Cys Ala His Phe Arg Trp Cys
1               5

<210> SEQ ID NO 525
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe

<400> SEQUENCE: 525

Ala Xaa Cys Ala His Phe Arg Trp Cys
1               5

<210> SEQ ID NO 526
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe

<400> SEQUENCE: 526

Ala Xaa Cys Ala His Phe Arg Trp Cys
1               5

<210> SEQ ID NO 527
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (4)..(4)
```

```
<223> OTHER INFORMATION: D-Ala
<220> FEATURE:
<221> NAME/KEY: MOD_RES
<222> LOCATION: (6)..(6)
<223> OTHER INFORMATION: D-Phe

<400> SEQUENCE: 527

Val Xaa Cys Ala His Phe Arg Trp Cys
1               5

<210> SEQ ID NO 528
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe

<400> SEQUENCE: 528

Leu Xaa Cys Ala His Phe Arg Trp Cys
1               5

<210> SEQ ID NO 529
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cha
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe

<400> SEQUENCE: 529

Xaa Xaa Cys Ala His Phe Arg Trp Cys
1               5

<210> SEQ ID NO 530
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aib
```

```
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe

<400> SEQUENCE: 530

Xaa Xaa Cys Ala His Phe Arg Trp Cys
1               5

<210> SEQ ID NO 531
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: D-Phe

<400> SEQUENCE: 531

Gly Arg Cys Glu His Phe Arg Trp Cys
1               5

<210> SEQ ID NO 532
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: D-2-Nal

<400> SEQUENCE: 532

Gly Arg Cys Glu His Xaa Arg Trp Cys
1               5

<210> SEQ ID NO 533
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe

<400> SEQUENCE: 533

Gly Arg Cys Ala His Phe Arg Trp Cys
1               5

<210> SEQ ID NO 534
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-2-Nal

<400> SEQUENCE: 534

Gly Arg Cys Ala His Xaa Arg Trp Cys
1               5

<210> SEQ ID NO 535
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Arg
<220> FEATURE:
<221> NAME/KEY: MOD_RES
<222> LOCATION: (6)..(6)
<223> OTHER INFORMATION: D-Phe

<400> SEQUENCE: 535

Gly Arg Cys Glu His Phe Arg Trp Cys
1               5

<210> SEQ ID NO 536
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Arg
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe

<400> SEQUENCE: 536

Gly Arg Cys Ala His Phe Arg Trp Cys
1               5

<210> SEQ ID NO 537
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Arg
```

```
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-2-Nal

<400> SEQUENCE: 537

Gly Arg Cys Ala His Xaa Arg Trp Cys
1               5

<210> SEQ ID NO 538
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (6)..(6)
<223> OTHER INFORMATION: D-Phe

<400> SEQUENCE: 538

Xaa Ala Cys Glu His Phe Arg Trp Cys
1               5

<210> SEQ ID NO 539
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe

<400> SEQUENCE: 539

Xaa Cys Ala His Phe Arg Trp Cys
1               5

<210> SEQ ID NO 540
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
```

```
<400> SEQUENCE: 540

Ala Cys Ala His Phe Arg Trp Cys
1               5

<210> SEQ ID NO 541
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe

<400> SEQUENCE: 541

Ala Cys Ala His Phe Arg Trp Cys
1               5

<210> SEQ ID NO 542
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aib
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe

<400> SEQUENCE: 542

Xaa Cys Ala His Phe Arg Trp Cys
1               5

<210> SEQ ID NO 543
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe

<400> SEQUENCE: 543

Val Cys Ala His Phe Arg Trp Cys
1               5
```

```
<210> SEQ ID NO 544
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Abu
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe

<400> SEQUENCE: 544

Xaa Cys Ala His Phe Arg Trp Cys
1               5

<210> SEQ ID NO 545
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe

<400> SEQUENCE: 545

Leu Cys Ala His Phe Arg Trp Cys
1               5

<210> SEQ ID NO 546
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe

<400> SEQUENCE: 546

Ile Cys Ala His Phe Arg Trp Cys
1               5

<210> SEQ ID NO 547
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: Cha
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe

<400> SEQUENCE: 547

Xaa Cys Ala His Phe Arg Trp Cys
1               5

<210> SEQ ID NO 548
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A6c
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe

<400> SEQUENCE: 548

Xaa Cys Ala His Phe Arg Trp Cys
1               5

<210> SEQ ID NO 549
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe

<400> SEQUENCE: 549

Phe Cys Ala His Phe Arg Trp Cys
1               5

<210> SEQ ID NO 550
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
```

```
<222> LOCATION: (5)..(5)
<223> OTHER INFORMATION: D-Phe

<400> SEQUENCE: 550

Gly Cys Ala His Phe Arg Trp Cys
1               5

<210> SEQ ID NO 551
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: D-Phe

<400> SEQUENCE: 551

Gly Cys Glu His Phe Arg Trp Cys
1               5

<210> SEQ ID NO 552
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe

<400> SEQUENCE: 552

Tyr Arg Cys Ala His Phe Arg Trp Cys
1               5

<210> SEQ ID NO 553
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 2-Nal
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe

<400> SEQUENCE: 553

Xaa Arg Cys Ala His Phe Arg Trp Cys
1               5

<210> SEQ ID NO 554
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 1-Nal
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe

<400> SEQUENCE: 554

Xaa Arg Cys Ala His Phe Arg Trp Cys
1               5

<210> SEQ ID NO 555
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe

<400> SEQUENCE: 555

Phe Arg Cys Ala His Phe Arg Trp Cys
1               5

<210> SEQ ID NO 556
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe

<400> SEQUENCE: 556

Trp Arg Cys Ala His Phe Arg Trp Cys
1               5

<210> SEQ ID NO 557
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pff
<220> FEATURE:
<221> NAME/KEY: MOD_RES
```

```
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe

<400> SEQUENCE: 557

Xaa Arg Cys Ala His Phe Arg Trp Cys
1               5

<210> SEQ ID NO 558
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe

<400> SEQUENCE: 558

His Arg Cys Ala His Phe Arg Trp Cys
1               5

<210> SEQ ID NO 559
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe

<400> SEQUENCE: 559

His Arg Cys Ala His Phe Arg Trp Cys
1               5

<210> SEQ ID NO 560
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe

<400> SEQUENCE: 560

Phe Arg Trp
1

<210> SEQ ID NO 561
<211> LENGTH: 3
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe

<400> SEQUENCE: 561

Phe Arg Trp
1

<210> SEQ ID NO 562
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe

<400> SEQUENCE: 562

Xaa Asp His Phe Arg Trp Lys
1               5

<210> SEQ ID NO 563
<211> LENGTH: 267
<212> TYPE: PRT
<213> ORGANISM: Homo sapiens

<400> SEQUENCE: 563

Met Pro Arg Ser Cys Cys Ser Arg Ser Gly Ala Leu Leu Leu Ala Leu
1               5                   10                  15

Leu Leu Gln Ala Ser Met Glu Val Arg Gly Trp Cys Leu Glu Ser Ser
            20                  25                  30

Gln Cys Gln Asp Leu Thr Thr Glu Ser Asn Leu Leu Glu Cys Ile Arg
        35                  40                  45

Ala Cys Lys Pro Asp Leu Ser Ala Glu Thr Pro Met Phe Pro Gly Asn
    50                  55                  60

Gly Asp Glu Gln Pro Leu Thr Glu Asn Pro Arg Lys Tyr Val Met Gly
65                  70                  75                  80

His Phe Arg Trp Asp Arg Phe Gly Arg Arg Asn Ser Ser Ser Ser Gly
                85                  90                  95

Ser Ser Gly Ala Gly Gln Lys Arg Glu Asp Val Ser Ala Gly Glu Asp
            100                 105                 110

Cys Gly Pro Leu Pro Glu Gly Gly Pro Glu Pro Arg Ser Asp Gly Ala
        115                 120                 125

Lys Pro Gly Pro Arg Glu Gly Lys Arg Ser Tyr Ser Met Glu His Phe
    130                 135                 140

Arg Trp Gly Lys Pro Val Gly Lys Lys Arg Pro Val Lys Val Tyr
145                 150                 155                 160

Pro Asn Gly Ala Glu Asp Glu Ser Ala Glu Ala Phe Pro Leu Glu Phe
                165                 170                 175

Lys Arg Glu Leu Thr Gly Gln Arg Leu Arg Glu Gly Asp Gly Pro Asp
            180                 185                 190
```

-continued

```
Gly Pro Ala Asp Asp Gly Ala Gly Ala Gln Ala Asp Leu Glu His Ser
            195                 200                 205
Leu Leu Val Ala Ala Glu Lys Lys Asp Glu Gly Pro Tyr Arg Met Glu
    210                 215                 220
His Phe Arg Trp Gly Ser Pro Pro Lys Asp Lys Arg Tyr Gly Gly Phe
225                 230                 235                 240
Met Thr Ser Glu Lys Ser Gln Thr Pro Leu Val Thr Leu Phe Lys Asn
                245                 250                 255
Ala Ile Ile Lys Asn Ala Tyr Lys Lys Gly Glu
            260                 265
```

<210> SEQ ID NO 564
<211> LENGTH: 8658
<212> TYPE: DNA
<213> ORGANISM: Homo sapiens

<400> SEQUENCE: 564

| | |
|---|---|
| ctgctcttca cagcatcacc ctctccccat ttaatggttt aggttaacag gactttttcc | 60 |
| ttgaggcttg ggacacggaa gggagcctcc cctaaaccag gcccttggag agcaggcccc | 120 |
| aggggagcag tgcaactcac cttcacaccc acaagacggc tcctgacttc tgctccctcc | 180 |
| tccctccccc aaagtggaac agagagaata tgattcccca cgacttccac atcacagttt | 240 |
| ccaaacaatg gggaaatcgg aggcctcccc gtgtgcagac ggtgatattt accgccaaat | 300 |
| gcgaaccagg cagatgccag ccccagcacg cacgcaggta acttcaccct cgcctcaacg | 360 |
| acctcagagg ctgcccggcc tgccccacac ggggtgcta agcctcccgc cgttctaag | 420 |
| cggagaccca acgccatcca taattaagtt cttcctgagg gcgagcggcc aggtgcgcct | 480 |
| tcggcaggac agtgctaatt ccagccccctt ccagcgcgt ctccccgcgc tcgtccccg | 540 |
| tctggaagcc cccctcccac gccccgcggc ccccttccc ctggcccggg gagctgctcc | 600 |
| ttgtgctgcc gggaaggtca agtcccgcgc ccaccagga gagctcggca agtatataag | 660 |
| gacagaggag cgcgggacca gcggcggcg aaggagggga agaagagccg cgaccgagag | 720 |
| aggccgccga gcgtccccgc cctcagagag cagcctcccg agacaggtaa gggcgcagcg | 780 |
| tgggggaccc gtgctctttc cccgggatcc cctgtccccg tcctcgcgat gcagtcggcc | 840 |
| ggctccggct ccgaaggcgg acctgggcgc ctctggctct ccgcggtccc gagttctcga | 900 |
| caaactttct gcgccgactg cggcatgaga agccgccagt agctgagctg gagggcccac | 960 |
| gtccggcccc tgggcggacg gccgcgaagc tgcaggcgct gtctccaggg agccggcggc | 1020 |
| ctcctctccc ccaggggctc gcggcggtcc ggaggctccg agagcttgct aggaggtctt | 1080 |
| gggacaaccc ggtctttttt tttttttttg agacggagtt tcgctcttgt tgcccatgct | 1140 |
| ggagagcaaa gggtgatct ctgctcaccg caaccttcgc ctcccgggtt caagcgattc | 1200 |
| tcctgcttca gcctcccgag tagctgggat tacaggcatg cgccaccacg cccggctaat | 1260 |
| ttttgtattt ttagtagtga cggagtttct ccatgttggt caggctggtc tcaaactccc | 1320 |
| gacaacaggt gatccgcccg ccttggcccc ccaaagttct ggcattacag gcgcgagcca | 1380 |
| ccgcccccgg ccagcccggt cttttagtat ctcttgctcc cagtttccag gataggtgtc | 1440 |
| acatcttgaa agtcaaattc catacacgct atcgcaaatt aatgttggaa acggggcagc | 1500 |
| agagaaaagg ataaaagtca taatgaacgc cctgccttcc ggattttttc ggattcagac | 1560 |
| ccctgaatcc ttgtttcctt gcccacctta gcgcacccga ggtggccgcg ctatgataat | 1620 |
| tacatgataa ctgggtcaat tacaatgcag aatagttggg tctcttctct ccaagaccta | 1680 |

```
gctgggtta aaaacaggtg gccggggcgg gagctgtcct agatcctgaa acgcactgtc  1740
tagtttcgga tgccctcaac agaaccgggg tggacggttt atggcgcaga tcctgggttg  1800
agggcacggg cagccatttg gaatgatcaa ggctcaggta aggggcgttt ccagcgaagg  1860
agagacagtc cacttggcat ttggattccc caaattcttc atgtttaaat ggggcaggga  1920
gggttcttac agaatggctg gaaggagcca aggaaaataa aagtgtgtgt ggattttttt  1980
tgtgtgtgtg tcagtttata aactctgcac agattatggc cactttaatg acttactgtt  2040
cctttgatgc ttttgttata ggactcgatg catgtatgtc atggtgtaag gacaaaactc  2100
ggcccctgtg ctcctctaat ctttacaaaa ggtcatggcc agcgtgcagt tttacagtaa  2160
caagcaaaat gatttgttga gctcatagag agcccctcac acctatgaag ttctaataag  2220
tgtagttcta ctataaagtt aatctcagga tgagcaaatt tcaagtttct attttccag  2280 agctttccat ttttggatta taatactttc cctacttaaa aaagcacaac atttgatatt  2340
tccccaataa tttgttgctt taaaaatgac acaaaggta ctatttgttc attgtagaga  2400
actgaaaata cacataagca aatacacata cacataagca aaatatacaa tacaaacaca  2460
agaccatctt tcagggaaga atctgaagtt ttagcaatag cagccatcta accagtttag  2520
caacagaata taagctctga gagggtggga gtgaatatgt taccacattg tacaacacag  2580
cacatagggc ataaggaggg gaaatgctct ctggggcttt ccaggaaggc ctgaagtcat  2640
tgcttctagc aaatgaaat cactccagag tagttatctt tgacaagaat tgaaatataa  2700
ttgagggaac tatcagacct gtaagatttt gttttttcct ttactaatat gttactttac  2760
atttgcattt ggtgacatac gtaactacca tttttctgtg actgtaacat ctgggcattt  2820
ttcagagcta aatgtgctat ggtcaacttg gagctttaat ctaattgcct ggtccaccaa  2880
gttctggctg tgtacttgaa tagatcactg gcagggtaca atgggaacag cctgtcccctt  2940 ggagccagga gaggacacca aggttgacca aagctcgttc agttgcccct ttagccgaag  3000
cgcacctggg ccagtcactg gctgccagtg ccatctaatg gctgctctga aaatgctcag  3060
ccttgcccgg caacccttca gaagctagca ccgtgcaggc ccagcgcctg gggaataggg  3120
cgagggtggg gtagagagaa ggaagtggcc tcctgaagta gaaatcagcg cttcagagga  3180 cttcactc caaagcctcc cctatataaa aaagatttgg cccacgcctc cccaaatgag  3240
agatttattt taggcaaact tattttaaaa tgccagcgtt cattaggagt gacaagacac  3300
ttagtcatcc acgctttaat gtgaattact tttctcatct aattacattt ctttctagca  3360
gctggctgag aagatcttct gaaatccaaa atgattgtag ggttggcggt gagctgatct  3420
ccggcctcga ggtggcttca gggggcccac ctggttaagg gaaatttggc agtgcgaggg  3480
tagtgctgga gagaggggtg ggtacagggg gctagggca ccatggatgc cccctccctta  3540 ctgtcccctg gtgtcttgac ctcagcttct gcccacaggc acttgctgga ttctccaaaa  3600
gtatctgcag tggctgttcc accaggaggt aattcccttc tggtctcttt ccctccaca  3660 tctgcatcct cttcaaatcc tgccatttca gaccacattt gagagctcta gaaacaaga  3720 catctgacac gtgacgtgtc cagaagatga gccagatttc aaagaactga gatctgcttt  3780
aaaaacgaag ctctccaaag ttactggagt ctgggtaata gtgatcacca gagtaatttg  3840
tgtgcaggac atcaaatcag gctgctcgaa atgctgccta aattggccag tggttttatt  3900
tgcttttctg tcaacctaat attcatagga aatagagttt cagaggaatg ataggatcct  3960
ggtggaataa aaagggaaaa gaccatcttg agcaggagtt tcagggtcct ccgttttcc  4020 caagttactt tcactcctga gatcttgcat gttagaacta cagcttaatg tagtgaaata  4080
```

```
ggaaagttct ctgttaggag cttagcctta ccttgtcatg gacattaaag taattgtctc   4140
tctttgggct tcaattttcc catctctcat gggaagggct gaaccaagca atccccaaaa   4200
tagcttccag ccttaacctt tttaggggtc tcgtttaaat agaagataac agggaaatgg   4260
tcacagttta cccaggtcca ttccctcctc cttatcacaa cttataccac cgctgtactg   4320
cacacctcct ttctcagcat tgctgctgtc cttaaaatgc ctttaactcc acaagagagt   4380
gtgttgttaa tgttggctca aggtccttcc tggtgagtgg ccaacattgt tttgctcctt   4440 gcagggtcc caccaatctt gtttgcttct gcagagcctc agcctgcctg gaagatgccg    4500
agatcgtgct gcagccgctc gggggccctg ttgctggcct tgctgcttca ggcctccatg   4560
gaagtgcgtg gctggtgcct ggagagcagc cagtgtcagg acctcaccac ggaaagcaac   4620
ctgctggtac gtgggccatg actgccatct tggcttagac attagatggg actggagctg   4680
ggaaagctca aaagaaaagg gtgtggggaa agggaaattc attcccagtg ataggcgtga   4740
ttcaatccag ggcaggagca aaactttgca gtgaagtaag aaatgggaga agaaatcagg   4800
gaaggaagca gcttcaggga gaggggttga gtccacaatt tctgcttggt tatccttact   4860
tcttgcccca tcttttatgg agaccttgaa ccctttaagc tagagatggt gctataagag   4920
caataatgga cccctcaatc tattctgtac tttacatctt tagcttccca aactattcct   4980
ttttaagaag ctcatatcac ttgccatttt cattccatat ttcttaccct tttatctact   5040
accggttgca aaaccagcca ggtagttctt caaatcatct ctggaagaag gaaaaaccag   5100
gggccctttt tttttttttct ttaattggtg ccaaatgtct catgtttatt ctggaggact   5160
ggccttctgc tgtgttcctc tacagtcttt ccagagcatg tgaaggcctt tgcatcaggc   5220
aggagctccc tccaggtcac cacagggtgt atgtatctgc ctgtgggggg tgtgtgtgtg   5280
tgtgtgttgg ggggcataaa tgagtaatga tgccaaatcc agagattaaa aggcacactg   5340
agaccaggcg agatggctca tggctgtaat cccagcactt ttagatgcta aggtgggagg   5400
attgcttgag cccagggatt caagacaagc ctgggcaaca tagtgagacc tccacttcta   5460
caaaaaataa aaaagttagc cagatgtggt ggcatgtgcc tgtagtccta gctacttggg   5520
aggttcactt gaggccagga gtctgacgac acagtaagct atgatcacac cattgcactc   5580
cagtctgggt aacagaatga gaccttgtct caaaacaaaa caaatgaaa caaacaaaca    5640 aacaaacccc catactgtta gtgtcagtga ccggaatttt aatcttgttg ccatcacctg   5700
gcaggtgctg agggtggaat gtacataact acattctgtg tattttgtca atgcagaagc   5760
tgagttaagg tgaagataga atgaggtcct caaagacaca gaccagtttt catgtgtaat   5820
ataaaataga aacaaagagc ccaggggatt ctgtgagttc cagtttggaa agacccaaga   5880
gtctcttgac ttgagacacc cacagcacag ctcaccaggg agggtgcact ggacacagtc   5940
aggacccatg ggttctagac ccagttttga ggtgtgggac cttgaccagg tcctatcacc   6000
tctctgagtc tcctgtttca ctatctgtcc acggagggg agtgtaaatt agttttttcc    6060
attgttaacg ttccacagag ttgtaattct gaacacctgg agtaggcaat gtccagctca   6120
acagagtggg taggatccott ttattttctc ctttgctatt cccaagaaag agagcagcca   6180
gtgagctttt catctttta tcactgaaaa ctcaaggctg cagcctatgc agccattttc    6240
ctaagctaat atgtaccaca atagagtcct ctagggacaa ggagcagaga cacaggttcc   6300
acagacggtg caatggaaat aacgctagct ttccacccct ccctccagtc agaatgagat   6360
tacagggaaa taagcttgcc ccagagctca ctggggatc tctcagaaat cagctcagaa    6420
```

```
gtcgtgaaag aaccaaggtg cagttttgga ggcttagtgc agagatggag ctggggtagg    6480
gcataaagta ggttttccat cactgaggta aggttgaggc attatttttt attttttgtt    6540
tatttattta tttttttgag acggagtctc gctctatcac ccaggctgga gtgcagtggc    6600
gcgatctccc ctcactgcaa gctccacctc ccaggttcac acaggttgaa gcattattaa    6660
aaatatgttt aaaaatatgg gccctagtag ccagacttct atcacctgga gagattatcc    6720
cccaaatttc agccccactc ccctcctgga cttgaattaa accatatgta tttattcaat    6780
attcttttta tttatttatt tatttttttg agacggagtc ttgctctgtt gccctggctg    6840
gagtgtggag tgcagtggtg tgatcttggc tcactgcaac ctctacctcc caggttcaag    6900
cggttctcct gcctcaggct ccagagtagc tgggattaca ggcgcccgcc accacaccca    6960
gcttatttat ttatttatac tagagatggt atttcaccat agttggccag gctggtcttg    7020
aactcctgac ctcatgtgat ctgcctgcct tggcctccca aagtgctggg attataggtg    7080
tgagccacca tgcccggccc tcaatattca ttaagtgcca acaactacca cccgtctgcc    7140
tttcttggag ccactccttt atgtcaggca tatgacagta agactttggt cctgttcaca    7200
aaagctaggg gtggctagat ggctagacaa accatggaat gggatgggaa gtgtgttgca    7260
gttgccagca gaagcatgaa ggggatggga caaaagaggc ggtggcaaga tcttagatgc    7320
ccacgagtgc caagaaagca ggtgggcaga cctgctctgt agggaggcct cgacgcttga    7380
cacgcccgac actgtgccct gtgtcctcgg cacgtggcga gggcggccag ggcctaggcg    7440
cagtgacggg cgcggcagcc gggccggggt gcggggcacg ggctgccctc atgccctcgc    7500
gtcttccccc aggagtgcat ccgggcctgc aagcccgacc tctcggccga gactcccatg    7560
ttcccgggaa atggcgacga gcagcctctg accgagaacc cccggaagta cgtcatgggc    7620
cacttccgct gggaccgatt cggccgccgc aacagcagca gcagcggcag cagcggcgca    7680
gggcagaagc gcgaggacgt ctcagcgggc gaagactgcg gcccgctgcc tgagggcggc    7740
cccgagcccc gcagcgatgg tgccaagccg ggcccgcgcg agggcaagcg ctcctactcc    7800
atggagcact tccgctgggg caagccggtg ggcaagaagc ggcgcccagt gaaggtgtac    7860
cctaacggcg ccgaggacga gtcggccgag gccttccccc tggagttcaa gagggagctg    7920
actggccagc gactccggga gggagatggc cccgacggcc ctgccgatga cggcgcaggg    7980
gcccaggccg acctggagca cagcctgctg gtggcggccg agaagaagga cgagggcccc    8040
tacaggatgg agcacttccg ctggggcagc ccgcccaagg acaagcgcta cggcggtttc    8100
atgacctccg agaagagcca gacgcccctg gtgacgctgt tcaaaaacgc catcatcaag    8160
aacgcctaca agaagggcga gtgagggcac agcgggcccc agggctaccc tcccccagga    8220
ggtcgacccc aaagcccctt gctctcccct gccctgctgc cgcctcccag cctgggggt     8280 cgtggcagat aatcagcctc ttaaagctgc ctgtagttag gaaataaaac ctttcaaatt    8340
tcacatccac ctctgacttt gaatgtaaac tgtgtgaata agtaaaaat acgtagccgt     8400 caaataacag cagcatggat cggaggagca cagtggtttc catgcggtag gatattcac     8460 aggacttagt gagcgtgaaa ggaaaatgtg cttcctgccc ccaccccaa atggatcttc     8520 gagggatcag atagtttggg tgaaggcaca gggtggctcc agcacctcta ggatggccgt    8580
attttccaca cactccactg agtgggagac tgctcagcta gcacacgtgt aaaggcagga    8640
ttcctgcaag agtgaccc                                                  8658

<210> SEQ ID NO 565
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 565

Arg Lys Lys Arg Arg Gln Arg Arg
1               5

<210> SEQ ID NO 566
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 566

Tyr Ala Arg Lys Ala Arg Arg Gln Ala Arg Arg
1               5                   10

<210> SEQ ID NO 567
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 567

Tyr Ala Arg Ala Ala Arg Arg Ala Ala Arg Arg
1               5                   10

<210> SEQ ID NO 568
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 568

Tyr Ala Arg Arg Arg Arg Arg Arg Arg Arg
1               5                   10

<210> SEQ ID NO 569
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 569

Tyr Ala Ala Ala Arg Arg Arg Arg Arg Arg Arg
1               5                   10

<210> SEQ ID NO 570
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 570

Tyr Ala Arg Ala Pro Arg Arg Ala Arg Arg
```

```
1               5                  10
```

<210> SEQ ID NO 571
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 571

```
Tyr Ala Arg Ala Pro Arg Arg Pro Arg Arg
1               5                  10
```

<210> SEQ ID NO 572
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 572

```
Arg Lys Gln Lys Arg Arg Arg Arg Arg
1               5
```

<210> SEQ ID NO 573
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 573

```
Arg Lys Lys Arg Gln Arg Arg Arg Arg
1               5
```

<210> SEQ ID NO 574
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 574

```
Arg Lys Lys Arg Arg Arg Gln Arg Arg
1               5
```

<210> SEQ ID NO 575
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 575

```
Arg Lys Lys Arg Arg Arg Arg Gln Arg
1               5
```

<210> SEQ ID NO 576
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 576

Arg Lys Lys Arg Arg Arg Arg Arg Gln
1               5

<210> SEQ ID NO 577
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 577

Arg Lys Lys Gln Arg Arg Arg Arg Arg
1               5

<210> SEQ ID NO 578
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 578

Arg Gln Lys Lys Arg Arg Arg Arg Arg
1               5

<210> SEQ ID NO 579
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 579

Arg Gln Arg Arg Arg Arg Arg Arg Arg
1               5

<210> SEQ ID NO 580
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 580

Arg Gln Arg Arg Arg Arg Arg Arg Arg Arg
1               5                   10

<210> SEQ ID NO 581
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 581

Arg Arg Gln Arg Arg Arg Arg Arg Arg
1               5

<210> SEQ ID NO 582

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 582

Arg Arg Gln Arg Arg Arg Arg Arg Arg
1               5                   10

<210> SEQ ID NO 583
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 583

Arg Arg Arg Gln Arg Arg Arg Arg Arg
1               5

<210> SEQ ID NO 584
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 584

Arg Arg Arg Gln Arg Arg Arg Arg Arg Arg
1               5                   10

<210> SEQ ID NO 585
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 585

Arg Arg Arg Arg Gln Arg Arg Arg Arg
1               5

<210> SEQ ID NO 586
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 586

Arg Arg Arg Arg Gln Arg Arg Arg Arg Arg
1               5                   10

<210> SEQ ID NO 587
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 587
```

Arg Arg Arg Arg Arg
1               5

<210> SEQ ID NO 588
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 588

Arg Arg Arg Arg Arg Gln Arg Arg Arg
1               5

<210> SEQ ID NO 589
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 589

Arg Arg Arg Arg Arg Gln Arg Arg Arg Arg
1               5                   10

<210> SEQ ID NO 590
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 590

Arg Arg Arg Arg Arg Arg
1               5

<210> SEQ ID NO 591
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 591

Arg Arg Arg Arg Arg Arg Gln Arg Arg Arg
1               5                   10

<210> SEQ ID NO 592
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 592

Arg Arg Arg Arg Arg Arg Arg
1               5

<210> SEQ ID NO 593
<211> LENGTH: 10
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 593

Arg Arg Arg Arg Arg Arg Arg Gln Arg Arg
1               5                   10

<210> SEQ ID NO 594
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 594

Arg Arg Arg Arg Arg Arg Arg Arg
1               5

<210> SEQ ID NO 595
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(7)
<223> OTHER INFORMATION: This region may encompass 1-7 residues

<400> SEQUENCE: 595

Arg Arg Arg Arg Arg Arg Arg Gln Arg
1               5

<210> SEQ ID NO 596
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 596

Arg Arg Arg Arg Arg Arg Arg Arg Arg
1               5

<210> SEQ ID NO 597
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 597

Arg Arg Arg Arg Arg Arg Arg Arg Arg Gln
1               5                   10

<210> SEQ ID NO 598
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
```

<223> OTHER INFORMATION: D-Arg

<400> SEQUENCE: 598

Arg Arg Arg Arg Arg
1               5

<210> SEQ ID NO 599
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: D-Arg

<400> SEQUENCE: 599

Arg Arg Arg Arg Arg Arg
1               5

<210> SEQ ID NO 600
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(7)
<223> OTHER INFORMATION: D-Arg

<400> SEQUENCE: 600

Arg Arg Arg Arg Arg Arg Arg
1               5

<210> SEQ ID NO 601
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(8)
<223> OTHER INFORMATION: D-Arg

<400> SEQUENCE: 601

Arg Arg Arg Arg Arg Arg Arg Arg
1               5

<210> SEQ ID NO 602
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(9)
<223> OTHER INFORMATION: D-Arg

<400> SEQUENCE: 602

Arg Arg Arg Arg Arg Arg Arg Arg Arg
1               5

<210> SEQ ID NO 603
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 603

Gln Arg Lys Lys Arg Arg Arg Arg Arg
1               5

<210> SEQ ID NO 604
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 604

Gln Arg Arg Arg Arg Arg Arg Arg Arg
1               5

<210> SEQ ID NO 605
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 605

Gln Arg Arg Arg Arg Arg Arg Arg Arg Arg
1               5                   10

<210> SEQ ID NO 606
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 606

Tyr Gly Arg Lys Lys Arg Arg Gln Arg Arg Arg
1               5                   10

<210> SEQ ID NO 607
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Doc

<400> SEQUENCE: 607

Tyr Gly Arg Lys Lys Arg Arg Gln Arg Arg Arg Xaa
1               5                   10

<210> SEQ ID NO 608
<211> LENGTH: 4
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Beta-Ala

<400> SEQUENCE: 608

Ala Ala Tyr Gly
1

<210> SEQ ID NO 609
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Doc
<220> FEATURE:
<221> NAME/KEY: MOD_RES
<222> LOCATION: (4)..(5)
<223> OTHER INFORMATION: Doc

<400> SEQUENCE: 609

Xaa Xaa Tyr Xaa Xaa Tyr Gly
1               5

<210> SEQ ID NO 610
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 610

Arg Lys Arg Arg Arg Gln Arg Arg Arg
1               5

<210> SEQ ID NO 611
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 611

Arg Arg Lys Arg Arg Gln Arg Arg Arg
1               5

<210> SEQ ID NO 612
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (3)..(9)
<223> OTHER INFORMATION: This region may encompass 1-7 residues

<400> SEQUENCE: 612

Arg Gln Arg Arg Arg Arg Arg Arg Arg
```

```
<210> SEQ ID NO 613
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(7)
<223> OTHER INFORMATION: This region may encompass 1-7 residues

<400> SEQUENCE: 613

Arg Arg Arg Arg Arg Arg Arg Gln Arg Arg Arg
1               5                   10

<210> SEQ ID NO 614
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-isomer of halogen substituted Phe or 2-Nal
<220> FEATURE:
<221> NAME/KEY: MOD_RES
<222> LOCATION: (6)..(6)
<223> OTHER INFORMATION: Bal, 1-Nal, 2-Nal or Trp
<220> FEATURE:
<221> NAME/KEY: MOD_RES
<222> LOCATION: (7)..(7)
<223> OTHER INFORMATION: Aib, Ala, Beta-Ala or Gly

<400> SEQUENCE: 614

Cys Glu His Xaa Arg Xaa Xaa Cys Pro Pro Lys Asp
1               5                   10
```

METHOD OF TREATING MELANOCORTIN-4 RECEPTOR PATHWAY-ASSOCIATED DISORDERS

CROSS REFERENCE TO RELATED APPLICATIONS

This application is a continuation of U.S. application Ser. No. 15/764,725, filed Mar. 29, 2018, which is a U.S. national phase application and claims the benefit of priority under 35 U.S.C. § 371 of International Application No. PCT/US2016/054457, filed Sep. 29, 2016, which claims benefit of U.S. Provisional Application No. 62/235,003, filed Sep. 30, 2015. The entire contents of each of the foregoing applications are hereby incorporated by reference.

SEQUENCE LISTING

The instant application contains a Sequence Listing which has been submitted electronically in ASCII format and is hereby incorporated by reference in its entirety. Said ASCII copy, created on Jun. 27, 2018 is named R2054-7005US_SL and is 294,812 bytes in size.

BACKGROUND OF THE INVENTION

Melanocortin 4 receptor (MC4R) is a heterotrimeric G-protein-coupled receptor, which transduces signals by activating adenylate cyclase. Expressed in hypothalamic nuclei and other neuronal and non-neuronal tissues, controlling feeding behavior and energy homeostasis, MC4R integrates an agonist (anorexigenic) signal provided by the α-melanocyte stimulating hormone (α-MSH), and an antagonist (orexigenic) signal provided by the agouti-related peptide (AGPR).

MC4R is a part of the leptin-melanocortin pathway, or POMC-MC4R pathway, which includes a number of proteins such as leptin, leptin receptors, pro-opiomelanocortin (POMC), prohormone convertases including PCSK1, and α-MSH, among others. AGPR binding to MC4R suppresses MC4R activity, while α-MSH binding stimulates the MC4R. Suppressed receptor activity generates an orexigenic signal, whereas stimulated receptor activity generates an anorexigenic signal. Signals from MC4R modulate feeding behavior through secondary effector neurons.

In humans, the hypothalamic POMC-MC4R pathway is part of the regulatory network of appetite and body weight. Monogenic defects in the pathway have been described to lead to severe early onset obesity. For example, patients with POMC loss of function mutations suffer from severe early onset obesity, hyperphagia, and adrenocorticotropic hormone (ACTH) deficiency. They also have low-pigmented skin and body hair. Prader Willi Syndrome (PWS) is thought to be caused by a loss of function of several genes on chromosome 15 in humans, in particular, at 15q11-q13, including one or more genes in the POMC-MC4R pathway. Patients with PWS suffer from severe hyperphagia that leads to severe obesity and other complications. There are currently no approved treatments for the obesity and hyperphagia associated with POMC-MC4R pathway genetic defect disorders such as PWS and POMC-null obesity. Deficiency of MSH, a cleavage product of POMC and the ligand of MC4R, is responsible for the early onset obesity and hyperphagia in these disorders associated with defects in the POMC-MC4R pathway. There is a need for a therapy, such as a MSH replacement therapy, that effectively treats the obesity and hyperphagia associated with POMC-MC4R pathway genetic defect disorders with fewer safety issues.

SUMMARY OF THE INVENTION

In an aspect, provided herein is a method of treating Prader Willi Syndrome (PWS) in a subject in need thereof, comprising:
administering an agonist of the melanocortin-4 receptor (MC4R) at a daily dosage of about 0.1 mg (e.g., 0.1 mg+/−5%) to about 10 mg (e.g., 10 mg+/−5%),
wherein the agonist is a MC4R agonist described herein, e.g., the agonist is

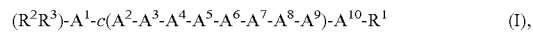

(I), wherein:
$A^1$ is Acc, HN—$(CH_2)_m$—C(O), L- or D-amino acid, or deleted;
$A^2$ is Cys, D-Cys, hCys, D-hCys, Pen, D-Pen, Asp, or Glu;
$A^3$ is Gly, Ala, β-Ala, Gaba, Aib, D-amino acid, or deleted;
$A^4$ is H is, 2-Pal, 3-Pal, 4-Pal, Taz, 2-Thi, 3-Thi, or ($X^1$, $X^2$, $X^3$, $X^4$, $X^5$)Phe;
$A^5$ is D-Phe, D-1-Nal, D-2-Nal, D-Trp, D-Bal, D-($X^1$, $X^2$, $X^3$, $X^4$, $X^5$)Phe, L-Phe or D-(Et)Tyr;
$A^6$ is Arg, hArg, Dab, Dap, Lys, Orn, or HN—CH$((CH_2)_n$—N($R^4R^5$))—C(O);
$A^7$ is Trp, 1-Nal, 2-Nal, Bal, Bip, D-Trp, D-2-Nal, D-Bal or D-Bip;
$A^8$ is Gly, D-Ala, Acc, Ala, 13-Ala, Gaba, Apn, Ahx, Aha, HN—$(CH_2)_s$—C(O), or deleted;
$A^9$ is Cys, D-Cys, hCys, D-hCys, Pen, D-Pen, Dab, Dap, Orn, or Lys;
$A^{10}$ is Acc, HN—$(CH_2)_t$—C(O), L- or D-amino acid, or deleted;
$R^1$ is OH or $NH_2$;
each of $R^2$ and $R^3$ is, independently for each occurrence, selected from the group consisting of H, $(C_1-C_{30})$alkyl, $(C_1-C_{30})$heteroalkyl, $(C_1-C_{30})$acyl, $(C_2-C_{30})$alkenyl, $(C_2-C_{30})$alkynyl, aryl$(C_1-C_{30})$alkyl, aryl$(C_1-C_{30})$acyl, substituted $(C_1-C_{30})$alkyl, substituted $(C_1-C_{30})$heteroalkyl, substituted $(C_1-C_{30})$acyl, substituted $(C_2-C_{30})$alkenyl, substituted $(C_2-C_{30})$alkynyl, substituted aryl$(C_1-C_{30})$alkyl, and substituted aryl$(C_1-C_{30})$acyl;
each of $R^4$ and $R^5$ is, independently for each occurrence, H, $(C_1-C_{40})$alkyl, $(C_1-C_{40})$heteroalkyl, $(C_1-C_{40})$acyl, $(C_2-C_{40})$alkenyl, $(C_2-C_{40})$alkynyl, aryl$(C_1-C_{40})$alkyl, aryl$(C_1-C_{40})$acyl, substituted $(C_1-C_{40})$alkyl, substituted $(C_1-C_{40})$heteroalkyl, substituted $(C_1-C_{40})$acyl, substituted $(C_2-C_{40})$alkenyl, substituted $(C_2-C_{40})$alkynyl, substituted aryl$(C_1-C_{40})$alkyl, substituted aryl$(C_1-C_{40})$acyl, $(C_1-C_{40})$alkylsulfonyl, or —C(NH)—$NH_2$;
m is, independently for each occurrence, 1, 2, 3, 4, 5, 6 or 7;
n is, independently for each occurrence, 1, 2, 3, 4 or 5;
s is, independently for each occurrence, 1, 2, 3, 4, 5, 6, or 7;
t is, independently for each occurrence, 1, 2, 3, 4, 5, 6, or 7;
X', $X^2$, $X^3$, $X^4$, and $X^8$ each is, independently for each occurrence, H, F, Cl, Br, I, $(C_{1-10})$alkyl, substituted $(C_{1-10})$alkyl, $(C_{2-10})$alkenyl, substituted $(C_{2-10})$alkenyl, $(C_{2-10})$alkynyl, substituted $(C_{2-10})$alkynyl, aryl, substituted aryl, OH, $NH_2$, $NO_2$, or CN,
thereby treating PWS.

In embodiments, the subject has or is identified as having a loss of function mutation in the 15q11-q13 region of chromosome 15.

In embodiments, the subject has or is identified as having a mutation (e.g., loss of function mutation) in the MAGEL2 gene.

In embodiments, the daily dosage is 0.1 mg to 10 mg. In embodiments, the daily dosage is about 0.1 mg to about 7.5 mg. In embodiments, the daily dosage is about 0.1 mg to about 5 mg. In embodiments, the daily dosage is about 0.1 mg to about 2.5 mg. In embodiments, the daily dosage is about 0.1 mg to about 2 mg. In embodiments, the daily dosage is about 0.1 mg to about 1 mg. In embodiments, the daily dosage is about 0.2 mg to about 10 mg. In embodiments, the daily dosage is about 0.2 mg to about 7.5 mg. In embodiments, the daily dosage is about 0.2 mg to about 5 mg. In embodiments, the daily dosage is about 0.2 mg to about 2.5 mg. In embodiments, the daily dosage is about 0.2 mg to about 2 mg. In embodiments, the daily dosage is about 0.2 mg to about 1.5 mg. In embodiments, the daily dosage is about 0.2 mg to about 1 mg. In embodiments, the daily dosage is about 0.3 mg to about 10 mg. In embodiments, the daily dosage is about 0.3 mg to about 7.5 mg. In embodiments, the daily dosage is about 0.3 mg to about 5 mg. In embodiments, the daily dosage is about 0.3 mg to about 2.5 mg. In embodiments, the daily dosage is about 0.3 mg to about 2 mg. In embodiments, the daily dosage is about 0.3 mg to about 1.5 mg. In embodiments, the daily dosage is about 0.3 mg to about 1 mg. In embodiments, the daily dosage is about 0.25 mg (e.g., 0.25 mg) to about 0.5 mg (e.g., 0.5 mg). In embodiments, the daily dosage is about 0.5 mg (e.g., 0.5 mg) to about 0.75 mg (e.g., 0.75 mg). In embodiments, the daily dosage is about 0.25 mg (e.g., 0.25 mg). In embodiments, the daily dosage is about 0.5 mg (e.g., 0.5 mg). In embodiments, the daily dosage is about 0.75 mg (e.g., 0.75 mg) to about 1.25 mg (1.25 mg). In embodiments, the daily dosage is about 1 mg (e.g., 1 mg). In embodiments, the daily dosage is about 1.25 mg (e.g., 1.25 mg) to about 2 mg (e.g., 2 mg). In embodiments, the daily dosage is about 1.5 mg (e.g., 1.5 mg). In embodiments, the daily dosage is about 2 mg (e.g., 2 mg).

In embodiments, the method comprises administering the agonist in a unit dosage suitable for injection, e.g., subcutaneous injection, to the subject.

In embodiments, the unit dosage comprises about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or 2 mg of the agonist.

In embodiments, the unit dosage is disposed within a delivery device, e.g., a syringe (e.g., prefilled syringe), an implantable device, a needleness hypodermic injection device, an infusion pump (e.g., implantable infusion pump), or an osmotic delivery system.

In embodiments, the agonist is administered subcutaneously, e.g., by subcutaneous injection.

In embodiments, the agonist is administered daily over a period of at least 3 weeks, e.g., at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 weeks or more, or at least 1, 2, 3, 4, 5, 6, 7, 8, 9, 10, 11, or 12 months or more, or at least 1, 2, 3, 4 years or more.

In embodiments, the subject is obese, e.g., severely obese.

In embodiments, the subject has early onset severe obesity.

In embodiments, the subject is hyperphagic.

In embodiments, the subject has a body mass index (BMI) greater than 25 kg/m$^2$ (e.g., ≥25, 30, 31, 32, 33, 34, 35, 36, 37, 38, 39, 40, 41, 42, 43, 44, 45, 46, 47, 48, 49, 50 kg/m$^2$ or greater) prior to administration of the agonist, e.g., at the time the agonist is prescribed, or at the time of the first administration.

In embodiments, the subject has a body mass index (BMI) greater than 35 kg/m$^2$ (e.g., ≥36, 37, 38, 39, 40, 41, 42, 43, 44, 45, 46, 47, 48, 49, 50 kg/m$^2$ or greater) prior to administration of the agonist, e.g., at the time the agonist is prescribed, or at the time of the first administration.

In embodiments, the subject has a body mass index (BMI) greater than 40 kg/m$^2$ (e.g., ≥41, 42, 43, 44, 45, 46, 47, 48, 49, 50, 51, 52, 53, 54, 55 kg/m$^2$ or greater) prior to administration of the agonist, e.g., at the time the agonist is prescribed, or at the time of the first administration.

In embodiments, the subject has a body mass index (BMI) greater than 45 kg/m$^2$ (e.g., ≥46, 47, 48, 49, 50, 51, 52, 53, 54, 55 kg/m$^2$ or greater) prior to administration of the agonist, e.g., at the time the agonist is prescribed, or at the time of the first administration.

In embodiments, the subject has a BMI higher than the 85-95th percentile prior to administration of the agonist, e.g., at the time the agonist is prescribed, or at the time of the first administration.

In embodiments, the subject has failed one or more previous therapies, e.g., exercise, diet, or behavioral therapies, prior to administration of the agonist, e.g., at the time the agonist is prescribed, or at the time of the first administration.

In embodiments, the subject has a lower body weight after administration of the agonist than before administration of the agonist.

In embodiments, administration of the agonist results in a reduction of weight in the subject compared to the weight of the subject before treatment of about 1 kg to 3 kg after 1 week of treatment, or about 1 kg to 6 kg after 2 weeks of treatment, or about 2 kg to 12 kg after 4 weeks of treatment, or about 4 kg to 24 kg after 8 weeks of treatment, or about 8 kg to 48 kg after 16 weeks of treatment.

In embodiments, administration of the agonist results in weight loss in the subject at a rate of about 1-2 kg/week, e.g., about 2 kg/week, e.g., over a period of 1-2 weeks of treatment or longer, 2-4 weeks of treatment or longer, 4-8 weeks of treatment or longer, 8-16 weeks of treatment or longer, 16-32 weeks or longer, or 32-64 weeks or longer.

In embodiments, administration of the agonist results in a reduction in hunger level (e.g., a lower score on the Likert hunger scale, e.g., a lower score by at least 1, 2, 3, 4, 5, 6, 7, 8, 9 or 10 points) in the subject compared to the hunger level of the subject before treatment, e.g., results in abolishment of hunger (e.g., a score of 0 on the Likert hunger scale) in the subject, e.g., after 1-2 weeks of treatment or longer, 2-4 weeks of treatment or longer, 4-8 weeks of treatment or longer, or 8-16 weeks of treatment or longer.

In embodiments, administration of the agonist results in no detectable/significant decrease in resting energy expenditure (REE) in the subject, e.g., over a period of 24 hours, one week, or 30 days or longer, e.g., as compared to a control REE (e.g., the REE in the subject prior to treatment or a predetermined REE, e.g., in subjects of similar pre-treatment BMI, e.g., when expressed as REE per kg of lean body mass).

In embodiments, administration of the agonist results in an increase in resting energy expenditure (REE) in the subject, e.g., over a period of 24 hours, one week, or 30 days, or longer e.g., as compared to a control REE (e.g., the REE in the subject prior to treatment or compared to a predetermined REE, e.g., in subjects of similar pre-treatment BMI, when expressed as REE per kg of lean body mass, e.g., after a similar level of weight loss has been attained by fasting).

In embodiments, administration of the agonist results in a reduction in food intake by the subject compared to a control (e.g., the food intake of the subject prior to treatment), e.g., wherein the food intake is daily food intake or food intake over a period of 24 hours, or one week.

In embodiments, administration of the agonist results in a reduction in food intake of at least 100 kilocalories, e.g., at least 100, 125, 150, 175, 200, 225, 250, 275, 300, 325, 350, 375, 400, 425, 450, 475, 500, 525, 550, 575, 600, 1000 kilocalories or more, compared to a control (e.g., the food intake of the subject prior to treatment or a predetermined food intake level), e.g., wherein the food intake is daily food intake or food intake over a period of 24, hours, or one week.

In embodiments, administration of the agonist results in a reduction in food intake of at least 5 kcal/kg/day, e.g., 5, 10, 20, 30, 40, 50, 60, 70, 80, or 90 or more kcal/kg/day. In embodiments, the reduction in food intake is relative to the food intake at baseline. In embodiments, the baseline food intake is at least 100 kcal/kg/day, e.g., for a pediatric subject at about 1 year of age. In embodiments, the baseline food intake is at least 40 kcal/kg/day, e.g., for a pediatric subject, e.g., in late adolescence.

In embodiments, administration of the agonist results in a reduction in waist circumference of the subject compared to a control (e.g., the waist circumference of the subject prior to treatment), as measured 1, 2, 3, 4, 5, 6, 7, 8, 9, 10 weeks or more after initiation of treatment.

In embodiments, administration of the agonist results in a reduction in waist circumference of at least 2 cm (e.g., at least 2, 3, 4, 5, 6, 7, 8, 9, 10 cm or more) in the subject compared to a control (e.g., the waist circumference of the subject prior to treatment), as measured 1, 2, 3, 4, 5, 6, 7, 8, 9, 10 weeks or more after initiation of treatment.

In embodiments, administration of the agonist results in no detectable increase in blood pressure (e.g., diastolic and/or systolic blood pressure) of the subject compared to the blood pressure of the subject prior to treatment, as measured 1, 2, 3, 4, 5, 6, 7, 8, 9, 10 weeks or more after initiation of treatment.

In embodiments, administration of the agonist results in a reduction in blood pressure (e.g., diastolic and/or systolic blood pressure) of the subject compared to the blood pressure of the subject prior to treatment, as measured 1, 2, 3, 4, 5, 6, 7, 8, 9, 10 weeks or more after initiation of treatment.

In embodiments, administration of the agonist results in a reduction in systolic blood of the subject of at least 3 mmHg (e.g., at least 3, 3.5, 4, 4.5, 5, 5.5, 6, 6.5, 7 mmHg or more) compared to the blood pressure of the subject prior to treatment, as measured 1, 2, 3, 4, 5, 6, 7, 8, 9, 10 weeks or more after initiation of treatment.

In embodiments, administration of the agonist results in a reduction in diastolic blood pressure of the subject of at least 4 mmHg (e.g., at least 4, 7, 7.5, 8, 8.5, 9, 9.5, 10 mmHg or more) compared to the blood pressure of the subject prior to treatment, as measured 1, 2, 3, 4, 5, 6, 7, 8, 9, 10 weeks or more after initiation of treatment.

In embodiments, the subject is a mammal, e.g., a human.

In embodiments, the agonist is Ac-Arg-c(Cys-D-Ala-His-D-Phe-Arg-Trp-Cys)-NH$_2$ (SEQ ID NO: 140).

In embodiments, the method further comprises acquiring knowledge of the genotype of the subject, e.g., acquiring knowledge of the genotype the 15q11-q13 region of chromosome 15 or of the MAGEL2 gene.

In embodiments, the agonist is administered in response to the detection of a predetermined sequence, e.g., a mutation, in 15q11-q13 region of chromosome 15 or in the MAGEL2 gene.

In embodiments, the knowledge is acquired directly, e.g., from a sample (e.g., a blood, serum, urine, or tissue (e.g., biopsy) sample) from the subject.

In embodiments, the predetermined sequence, e.g., mutation, is detected in a nucleic acid by a method chosen from one or more of: a nucleic acid hybridization assay, an amplification-based assay, a PCR-RFLP assay, real-time PCR, sequencing, screening analysis, FISH, spectral karyotyping or MFISH, comparative genomic hybridization, in situ hybridization, SSP, HPLC or mass-spectrometric genotyping.

In embodiments, the predetermined sequence, e.g., mutation, is detected in the subject.

In embodiments, the predetermined sequence, e.g., mutation, is detected in a nucleic acid molecule or a polypeptide in a sample from the subject.

In embodiments, the sample comprises cells from a blood, serum, urine, or tissue (e.g., biopsy) from the subject.

In embodiments, the knowledge is acquired from another party, e.g., wherein the party is the subject, a caregiver, a physician, an endocrinologist, a hospital, clinic, third-party payor, insurance company or government office.

In embodiments, the method comprises:
responsive to a determination of the presence or absence the predetermined sequence, e.g., mutation, in the subject, one or more of:
(1) identifying or selecting the subject as having Prader Willi Syndrome (PWS); and/or
(2) identifying or selecting the subject as likely or unlikely to respond to the agonist.

In embodiments, the presence of the predetermined sequence, e.g., mutation, is detected in the subject, and responsive to that determination, the method comprises identifying the subject as having Prader Willi Syndrome (PWS).

In embodiments, the presence of the predetermined sequence, e.g., mutation, is detected in the subject, and responsive to that determination, the method comprises identifying the subject as likely to respond to the agonist.

In embodiments, the subject has or is identified as having PWS.

In an aspect, provided herein is a method of treating a disorder in a subject in need thereof, comprising:
administering an agonist of the melanocortin-4 receptor (MC4R) at a daily dosage of about 0.1 mg (e.g., 0.1 mg+/−5%) to about 10 mg (e.g., 10 mg+/−5%), wherein the disorder is chosen from:
(i) Prader Willi Syndrome (PWS);
(ii) a disorder characterized by one or more mutations (e.g., loss of function mutations) in the POMC gene;
(iii) a disorder characterized by one or more mutations (e.g., loss of function mutations) in the PCSK1 gene;
(iv) a disorder characterized by one or more mutations (e.g., loss of function mutations) in the MAGEL2 gene;
(v) a disorder characterized by one or more mutations (e.g., loss of function mutations) in the leptin receptor gene;
(vi) a disorder characterized by one or more mutations (e.g., loss of function mutations) in the leptin gene;
(vii) a disorder characterized by one or more mutations (e.g., loss of function mutations) in the 5-HT2c receptor gene;

(viii) a disorder characterized by one or more mutations (e.g., loss of function mutations) in the nescient helix loop helix 2 (NhHL2) gene;
(ix) a disorder characterized by one or more mutations (e.g., loss of function mutations) in the pro-hormone convertase gene;
(x) a disorder characterized by one or more mutations (e.g., loss of function mutations) in the carboxypeptidase E (CPE) gene;
(xi) a disorder characterized by one or more mutations (e.g., loss of function mutations) in the single-minded 1 (SIM1) gene;
(xii) a disorder characterized by a hypermethylated POMC gene (e.g., hypermethylated at a POMC intron, e.g., at a CpG island of the POMC gene, e.g., comprising one or more methylated cytosines, e.g., a 5'methyl cytosine); or
(xiii) a disorder characterized by a defect in the POMC-MC4R pathway other than:
  (a) a heterozygous POMC mutation characterized by the presence of one functional POMC allele and one non-functional POMC allele,
  (b) a heterozygous leptin mutation characterized by the presence of one functional leptin allele and one non-functional leptin allele,
  (c) a melanocortin-4 receptor (MC4R) mutation (e.g., loss of function mutation), or
  (d) a pro-hormone convertase mutation (e.g., loss of function mutation);
wherein the agonist is a MC4R agonist described herein, e.g., the agonist is

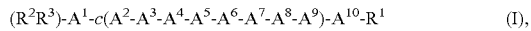

(I), wherein:
$A^1$ is Acc, HN—$(CH_2)_m$—C(O), L- or D-amino acid, or deleted;
$A^2$ is Cys, D-Cys, hCys, D-hCys, Pen, D-Pen, Asp, or Glu;
$A^3$ is Gly, Ala, β-Ala, Gaba, Aib, D-amino acid, or deleted;
$A^4$ is His, 2-Pal, 3-Pal, 4-Pal, Taz, 2-Thi, 3-Thi, or ($X^1$, $X^2$, $X^3$, $X^4$, $X^5$)Phe;
$A^5$ is D-Phe, D-1-Nal, D-2-Nal, D-Trp, D-Bal, D-($X^1$, $X^2$, $X^3$, $X^4$, $X^5$)Phe, L-Phe or D-(Et)Tyr;
$A^6$ is Arg, hArg, Dab, Dap, Lys, Orn, or HN—CH(($CH_2$)$_n$—N($R^4R^5$))—C(O);
$A^7$ is Trp, 1-Nal, 2-Nal, Bal, Bip, D-Trp, D-2-Nal, D-Bal or D-Bip;
$A^8$ is Gly, D-Ala, Acc, Ala, 13-Ala, Gaba, Apn, Ahx, Aha, HN—$(CH_2)_s$—C(O), or deleted;
$A^9$ is Cys, D-Cys, hCys, D-hCys, Pen, D-Pen, Dab, Dap, Orn, or Lys;
$A^{10}$ is Acc, HN—$(CH_2)_r$—C(O), L- or D-amino acid, or deleted;
$R^1$ is OH or $NH_2$;
each of $R^2$ and $R^3$ is, independently for each occurrence, selected from the group consisting of H, ($C_1$-$C_{30}$)alkyl, ($C_1$-$C_{30}$)heteroalkyl, ($C_1$-$C_{30}$)acyl, ($C_2$-$C_{30}$)alkenyl, ($C_2$-$C_{30}$)alkynyl, aryl($C_1$-$C_{30}$)alkyl, aryl($C_1$-$C_{30}$)acyl, substituted ($C_1$-$C_{30}$)alkyl, substituted ($C_1$-$C_{30}$)heteroalkyl, substituted ($C_1$-$C_{30}$)acyl, substituted ($C_2$-$C_{30}$)alkenyl, substituted ($C_2$-$C_{30}$)alkynyl, substituted aryl ($C_1$-$C_{30}$)alkyl, and substituted aryl($C_1$-$C_{30}$)acyl;
each of $R^4$ and $R^5$ is, independently for each occurrence, H, ($C_1$-$C_{40}$)alkyl, ($C_1$-$C_{40}$)heteroalkyl, ($C_1$-$C_{40}$)acyl, ($C_2$-$C_{40}$)alkenyl, ($C_2$-$C_{40}$)alkynyl, aryl($C_1$-$C_{40}$)alkyl, aryl($C_1$-$C_{40}$)acyl, substituted ($C_1$-$C_{40}$)alkyl, substituted ($C_1$-$C_{40}$)heteroalkyl, substituted ($C_1$-$C_{40}$)acyl, substituted ($C_2$-$C_{40}$)alkenyl, substituted ($C_2$-$C_{40}$)alkynyl, substituted aryl($C_1$-$C_{40}$)alkyl, substituted aryl($C_1$-$C_{40}$) acyl, ($C_1$-$C_{40}$)alkylsulfonyl, or —C(NH)—$NH_2$;
m is, independently for each occurrence, 1, 2, 3, 4, 5, 6 or 7;
n is, independently for each occurrence, 1, 2, 3, 4 or 5;
s is, independently for each occurrence, 1, 2, 3, 4, 5, 6, or 7;
t is, independently for each occurrence, 1, 2, 3, 4, 5, 6, or 7;
X', $X^2$, $X^3$, $X^4$, and $X^8$ each is, independently for each occurrence, H, F, Cl, Br, I, ($C_{1-10}$)alkyl, substituted ($C_{1-10}$)alkyl, ($C_{2-10}$)alkenyl, substituted ($C_{2-10}$)alkenyl, ($C_{2-10}$)alkynyl, substituted ($C_2$-10)alkynyl, aryl, substituted aryl, OH, $NH_2$, $NO_2$, or CN.

In embodiments, the subject comprises one or more mutations, e.g., from one or more genes described herein.

In embodiments, the disorder is Prader Willi Syndrome (PWS).

In embodiments, the subject has or is identified as having a loss of function mutation in the paternal allele of the 15q11-q13 region of chromosome 15.

In embodiments, the subject has or is identified as having a mutation, e.g., loss of function mutation, in the MAGEL2 gene.

In embodiments, the disorder is characterized by one or more mutations (e.g., loss of function mutations) in the POMC gene.

In embodiments, the subject is or is identified as being a heterozygous carrier of the mutation(s), e.g., having one functional POMC allele and one non-functional POMC allele.

In embodiments, the subject is or is identified as being a compound heterozygous carrier of the mutation(s), e.g., having two distinct non-functional POMC alleles, e.g., having a POMC null genotype.

In embodiments, the subject is or is identified as being a homozygous carrier of the mutation(s), e.g., having a homozygous POMC null genotype.

In embodiments, the disorder is characterized by one or more mutations (e.g., loss of function mutations) in the PCSK1 gene.

In embodiments, the subject is or is identified as being a heterozygous carrier of the mutation(s), e.g., having one functional PCSK1 allele and one non-functional PCSK1 allele.

In embodiments, the subject is or is identified as being a compound heterozygous carrier of the mutation(s), e.g., having two non-functional PCSK1 alleles, e.g., having a PCSK1 null genotype.

In embodiments, the subject is or is identified as being a homozygous carrier of the mutation(s), e.g., having a homozygous PCSK1 null genotype.

In embodiments, the disorder is characterized by one or mutations (e.g., loss of function mutations) in the MAGEL2 gene.

In embodiments, the subject is or is identified as being a heterozygous carrier of the mutation(s), e.g., having one functional MAGEL2 allele and one non-functional MAGEL2 allele, including the subjects where the remaining functional allele is silenced by maternal imprinting, as result of which the subject is a functional MAGEL2 null patient.

In embodiments, the subject is or is identified as being a compound heterozygous carrier of the mutation(s), e.g., having two mutated non-functional MAGEL2 alleles, e.g., having a MAGEL2 null genotype.

In embodiments, the subject is or is identified as being a homozygous carrier of the mutation(s), e.g., having a MAGEL2 null genotype.

In embodiments, the disorder is characterized by one or mutations (e.g., loss of function mutations) in the leptin receptor gene.

In embodiments, the subject is or is identified as being a heterozygous carrier of the mutation(s), e.g., having one functional leptin receptor allele and one non-functional leptin receptor allele.

In embodiments, the subject is or is identified as being a compound heterozygous carrier of the mutation(s), e.g., having two non-functional leptin receptor alleles, e.g., having a leptin receptor null genotype.

In embodiments, the subject is or is identified as being a homozygous carrier of the mutation(s), e.g., having a leptin receptor null genotype.

In embodiments, the disorder is characterized by one or mutations (e.g., loss of function mutations) in the leptin gene.

In embodiments, the subject is or is identified as being a heterozygous carrier of the mutation(s), e.g., having one functional leptin allele and one non-functional leptin allele.

In embodiments, the subject is or is identified as being a compound heterozygous carrier of the mutation(s), e.g., having two non-functional leptin alleles, e.g., having a leptin null genotype.

In embodiments, the subject is or is identified as being a homozygous carrier of the mutation(s), e.g., having a leptin null genotype.

In embodiments, the disorder is characterized by one or mutations (e.g., loss of function mutations) in the 5-HT2c receptor gene.

In embodiments, the subject is or is identified as being a heterozygous carrier of the mutation(s), e.g., having one functional 5-HT2c receptor allele and one non-functional 5-HT2c receptor allele.

In embodiments, the subject is or is identified as being a compound heterozygous carrier of the mutation(s), e.g., having two non-functional 5-HT2c receptor alleles, e.g., having a 5-HT2c receptor null genotype.

In embodiments, the subject is or is identified as being a homozygous carrier of the mutation(s), e.g., having a 5-HT2c receptor null genotype.

In embodiments, the disorder is characterized by one or mutations (e.g., loss of function mutations) in the nescient helix loop helix 2 (NhHL2) gene.

In embodiments, the subject is or is identified as being a heterozygous carrier of the mutation(s), e.g., having one functional NhHL2 allele and one non-functional NhHL2 receptor allele.

In embodiments, the subject is or is identified as being a compound heterozygous carrier of the mutation(s), e.g., having two non-functional NhHL2 alleles, e.g., having a NhHL2 null genotype.

In embodiments, the subject is or is identified as being a homozygous carrier of the mutation(s), e.g., having a NhHL2 null genotype.

In embodiments, the disorder is characterized by one or mutations (e.g., loss of function mutations) in the pro-hormone convertase gene.

In embodiments, the subject is or is identified as being a heterozygous carrier of the mutation(s), e.g., having one functional pro-hormone convertase allele and one non-functional pro-hormone convertase allele.

In embodiments, the subject is or is identified as being a compound heterozygous carrier of the mutation(s), e.g., having two non-functional pro-hormone convertase alleles, e.g., having a pro-hormone convertase null genotype.

In embodiments, the subject is or is identified as being a homozygous carrier of the mutation(s), e.g., having a pro-hormone convertase null genotype.

In embodiments, the disorder is characterized by one or mutations (e.g., loss of function mutations) in the carboxypeptidase E (CPE) gene.

In embodiments, the subject is or is identified as being a heterozygous carrier of the mutation(s), e.g., having one functional CPE allele and one non-functional CPE allele.

In embodiments, the subject is or is identified as being a compound heterozygous carrier of the mutation(s), e.g., having two non-functional CPE alleles, e.g., having a CPE null genotype.

In embodiments, the subject is or is identified as being a homozygous carrier of the mutation(s), e.g., having a CPE null genotype.

In embodiments, the disorder is characterized by one or mutations (e.g., loss of function mutations) in the single-minded 1 (SIM1) gene.

In embodiments, the subject is or is identified as being a heterozygous carrier of the mutation(s), e.g., having one functional SIM1 allele and one non-functional SIM1 allele.

In embodiments, the subject is or is identified as being a compound heterozygous carrier of the mutation(s), e.g., having two non-functional SIM1 alleles, e.g., having a SIM1 null genotype.

In embodiments, the subject is or is identified as being a homozygous carrier of the mutation(s), e.g., having a SIM1 null genotype.

In embodiments, the disorder is characterized by a hypermethylated POMC gene (e.g., hypermethylated at a POMC intron, e.g., at a CpG island of the POMC gene, e.g., comprising a methylated cytosine, e.g., a 5'methyl cytosine).

In embodiments, the disorder is characterized by a defect in the POMC-MC4R pathway other than:
(a) a heterozygous POMC mutation characterized by the presence of one functional POMC allele and one non-functional POMC allele,
(b) a heterozygous leptin mutation characterized by the presence of one functional leptin allele and one non-functional leptin allele,
(c) a heterozygous melanocortin-4 receptor (MC4R) mutation characterized by the presence of one functional MC4R allele and one non-functional MC4R allele, or
(d) a pro-hormone convertase mutation (e.g., loss of function mutation).

In embodiments, the daily dosage is 0.1 mg to 10 mg. In embodiments, the daily dosage is about 0.1 mg to about 7.5 mg. In embodiments, the daily dosage is about 0.1 mg to about 5 mg. In embodiments, the daily dosage is about 0.1 mg to about 2.5 mg. In embodiments, the daily dosage is about 0.1 mg to about 2 mg. In embodiments, the daily dosage is about 0.1 mg to about 1 mg. In embodiments, the daily dosage is about 0.2 mg to about 10 mg. In embodiments, the daily dosage is about 0.2 mg to about 7.5 mg. In embodiments, the daily dosage is about 0.2 mg to about 5 mg. In embodiments, the daily dosage is about 0.2 mg to about 2.5 mg. In embodiments, the daily dosage is about 0.2 mg to about 2 mg. In embodiments, the daily dosage is about 0.2 mg to about 1.5 mg. In embodiments, the daily dosage is about 0.2 mg to about 1 mg. In embodiments, the daily dosage is about 0.3 mg to about 10 mg. In embodiments, the daily dosage is about 0.3 mg to about 7.5 mg. In embodiments, the daily dosage is about 0.3 mg to about 5 mg. In embodiments, the daily dosage is about 0.3 mg to about 2.5 mg. In embodiments, the daily dosage is about 0.3 mg to about 2 mg. In embodiments, the daily dosage is about 0.3 mg to about 1.5 mg. In embodiments, the daily dosage is about 0.3 mg to about 1 mg. In embodiments, the daily dosage is about 0.25 mg (e.g., 0.25 mg) to about 0.5 mg (e.g., 0.5 mg). In embodiments, the daily dosage is about 0.5 mg (e.g., 0.5 mg) to about 0.75 mg (e.g., 0.75 mg). In embodiments, the daily dosage is about 0.25 mg (e.g., 0.25 mg). In embodiments, the daily dosage is about 0.5 mg (e.g., 0.5 mg). In embodiments, the daily dosage is about 0.75 mg (e.g., 0.75 mg) to about 1.25 mg (1.25 mg). In embodiments, the daily dosage is about 1 mg (e.g., 1 mg). In embodiments, the daily dosage is about 1.25 mg (e.g., 1.25 mg) to about 2 mg (e.g., 2 mg). In embodiments, the daily dosage is about 1.5 mg (e.g., 1.5 mg). In embodiments, the daily dosage is about 2 mg (e.g., 2 mg).

In embodiments, the method comprises administering the agonist in a unit dosage suitable for injection, e.g., subcutaneous injection, to the subject.

In embodiments, the unit dosage comprises about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or 2 mg of the agonist.

In embodiments, the unit dosage is disposed within a delivery device, e.g., a syringe (e.g., prefilled syringe), an implantable device, a needleness hypodermic injection device, an infusion pump (e.g., implantable infusion pump), or an osmotic delivery system.

In embodiments, the agonist is administered subcutaneously, e.g., by subcutaneous injection.

In embodiments, the agonist is administered daily over a period of at least 3 weeks, e.g., at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 weeks or more, or at least 1, 2, 3, 4, 5, 6, 7, 8, 9, 10, 11, or 12 months or more, or at least 1, 2, 3, 4 years or more.

In embodiments, the subject is obese, e.g., severely obese.

In embodiments, the subject has early onset severe obesity.

In embodiments, the subject is hyperphagic.

In embodiments, the subject has a body mass index (BMI) greater than 25 kg/m$^2$ (e.g., ≥25, 30, 31, 32, 33, 34, 35, 36, 37, 38, 39, 40, 41, 42, 43, 44, 45, 46, 47, 48, 49, 50 kg/m$^2$ or greater) prior to administration of the agonist, e.g., at the time the agonist is prescribed, or at the time of the first administration.

In embodiments, the subject has a body mass index (BMI) greater than 35 kg/m$^2$ (e.g., ≥36, 37, 38, 39, 40, 41, 42, 43, 44, 45, 46, 47, 48, 49, 50 kg/m$^2$ or greater) prior to administration of the agonist, e.g., at the time the agonist is prescribed, or at the time of the first administration.

In embodiments, the subject has a body mass index (BMI) greater than 40 kg/m$^2$ (e.g., ≥41, 42, 43, 44, 45, 46, 47, 48, 49, 50, 51, 52, 53, 54, 55 kg/m$^2$ or greater) prior to administration of the agonist, e.g., at the time the agonist is prescribed, or at the time of the first administration.

In embodiments, the subject has a body mass index (BMI) greater than 45 kg/m$^2$ (e.g., ≥46, 47, 48, 49, 50, 51, 52, 53, 54, 55 kg/m$^2$ or greater) prior to administration of the agonist, e.g., at the time the agonist is prescribed, or at the time of the first administration.

In embodiments, the subject has a BMI higher than the 85-95th percentile prior to administration of the agonist, e.g., at the time the agonist is prescribed, or at the time of the first administration.

In embodiments, the subject has failed one or more previous therapies, e.g., exercise, diet, or behavioral therapies, prior to administration of the agonist, e.g., at the time the agonist is prescribed, or at the time of the first administration.

In embodiments, the subject has a lower body weight after administration of the agonist than before administration of the agonist.

In embodiments, administration of the agonist results in a reduction of weight in the subject compared to the weight of the subject before treatment of about 1 kg to 3 kg after 1 week of treatment, or about 1 kg to 6 kg after 2 weeks of treatment, or about 2 kg to 12 kg after 4 weeks of treatment, or about 4 kg to 24 kg after 8 weeks of treatment, or about 8 kg to 48 kg after 16 weeks of treatment.

In embodiments, administration of the agonist results in weight loss in the subject at a rate of about 1-2 kg/week, e.g., about 2 kg/week, e.g., over a period of 1-2 weeks of treatment or longer, 2-4 weeks of treatment or longer, 4-8 weeks of treatment or longer, 8-16 weeks of treatment or longer, 16-32 weeks or longer, or 32-64 weeks or longer.

In embodiments, administration of the agonist results in a reduction in hunger level (e.g., a lower score on the Likert hunger scale, e.g., a lower score by at least 1, 2, 3, 4, 5, 6, 7, 8, 9 or 10 points) in the subject compared to the hunger level of the subject before treatment, e.g., results in abolishment of hunger (e.g., a score of 0 on the Likert hunger scale) in the subject, e.g., after 1-2 weeks of treatment or longer, 2-4 weeks of treatment or longer, 4-8 weeks of treatment or longer, or 8-16 weeks of treatment or longer.

In embodiments, administration of the agonist results in no detectable/significant decrease in resting energy expenditure (REE) in the subject, e.g., over a period of 24 hours, one week, or 30 days or longer, e.g., as compared to a control REE (e.g., the REE in the subject prior to treatment or a predetermined REE, e.g., in subjects of similar pre-treatment BMI, e.g., when expressed as REE per kg of lean body mass).

In embodiments, administration of the agonist results in an increase in resting energy expenditure (REE) in the subject, e.g., over a period of 24 hours, one week, or 30 days, or longer e.g., as compared to a control REE (e.g., the REE in the subject prior to treatment or compared to a predetermined REE, e.g., in subjects of similar pre-treatment BMI, when expressed as REE per kg of lean body mass, e.g., after a similar level of weight loss has been attained by fasting).

In embodiments, administration of the agonist results in a reduction in food intake by the subject compared to a control (e.g., the food intake of the subject prior to treatment), e.g., wherein the food intake is daily food intake or food intake over a period of 24 hours, or one week.

In embodiments, administration of the agonist results in a reduction in food intake of at least 100 kilocalories, e.g., at least 100, 125, 150, 175, 200, 225, 250, 275, 300, 325, 350, 375, 400, 425, 450, 475, 500, 525, 550, 575, 600, 1000 kilocalories or more, compared to a control (e.g., the food intake of the subject prior to treatment or a predetermined food intake level), e.g., wherein the food intake is daily food intake or food intake over a period of 24, hours, or one week.

In embodiments, administration of the agonist results in a reduction in food intake of at least 5 kcal/kg/day, e.g., 5, 10, 20, 30, 40, 50, 60, 70, 80, or 90 or more kcal/kg/day. In embodiments, the reduction in food intake is relative to the food intake at baseline. In embodiments, the baseline food intake is at least 100 kcal/kg/day, e.g., for a pediatric subject at about 1 year of age. In embodiments, the baseline food intake is at least 40 kcal/kg/day, e.g., for a pediatric subject, e.g., in late adolescence.

In embodiments, administration of the agonist results in a reduction in waist circumference of the subject compared to a control (e.g., the waist circumference of the subject prior to treatment), as measured 1, 2, 3, 4, 5, 6, 7, 8, 9, 10 weeks or more after initiation of treatment.

In embodiments, administration of the agonist results in a reduction in waist circumference of at least 2 cm (e.g., at least 2, 3, 4, 5, 6, 7, 8, 9, 10 cm or more) in the subject compared to a control (e.g., the waist circumference of the subject prior to treatment), as measured 1, 2, 3, 4, 5, 6, 7, 8, 9, 10 weeks or more after initiation of treatment.

In embodiments, administration of the agonist results in no detectable increase in blood pressure (e.g., diastolic and/or systolic blood pressure) of the subject compared to the blood pressure of the subject prior to treatment, as measured 1, 2, 3, 4, 5, 6, 7, 8, 9, 10 weeks or more after initiation of treatment.

In embodiments, administration of the agonist results in a reduction in blood pressure (e.g., diastolic and/or systolic blood pressure) of the subject compared to the blood pressure of the subject prior to treatment, as measured 1, 2, 3, 4, 5, 6, 7, 8, 9, 10 weeks or more after initiation of treatment.

In embodiments, administration of the agonist results in a reduction in systolic blood of the subject of at least 3 mmHg (e.g., at least 3, 3.5, 4, 4.5, 5, 5.5, 6, 6.5, 7 mmHg or more) compared to the blood pressure of the subject prior to treatment, as measured 1, 2, 3, 4, 5, 6, 7, 8, 9, 10 weeks or more after initiation of treatment.

In embodiments, administration of the agonist results in a reduction in diastolic blood pressure of the subject of at least 4 mmHg (e.g., at least 4, 7, 7.5, 8, 8.5, 9, 9.5, 10 mmHg or more) compared to the blood pressure of the subject prior to treatment, as measured 1, 2, 3, 4, 5, 6, 7, 8, 9, 10 weeks or more after initiation of treatment.

In embodiments, the subject is a mammal, e.g., a human.

In embodiments, the agonist is Ac-Arg-c(Cys-D-Ala-His-D-Phe-Arg-Trp-Cys)-NH$_2$ (SEQ ID NO: 140).

In embodiments, the method comprises acquiring knowledge of the genotype of the subject, e.g., acquiring knowledge of the genotype of, e.g., of a mutation in:
the POMC gene;
the PCSK1 gene;
the MAGEL2 gene;
the leptin receptor gene;
the leptin gene;
the 5-HT2c receptor gene;
the nescient helix loop helix 2 (NhHL2) gene;
the pro-hormone convertase gene;
the carboxypeptidase E (CPE) gene;
the single-minded 1 (SIM1) gene; or
a POMC-MC4R pathway gene.

In embodiments, the agonist is administered in response to the detection of a predetermined sequence, e.g., a mutation, in a gene described herein.

In embodiments, the method comprises acquiring knowledge of the state of methylation of the POMC gene (e.g., hypermethylated at a POMC intron, e.g., at a CpG island of the POMC gene, e.g., comprising a methylated cytosine, e.g., a 5'methyl cytosine).

In embodiments, the agonist is administered in response to the detection of hypermethylation.

In embodiments, the knowledge is acquired directly, e.g., from a sample (e.g., a blood, serum, urine, or tissue (e.g., biopsy) sample) from the subject.

In embodiments, the predetermined sequence, e.g., mutation, is detected in a nucleic acid by a method chosen from one or more of: a nucleic acid hybridization assay, an amplification-based assay, a PCR-RFLP assay, real-time PCR, sequencing, screening analysis, FISH, spectral karyotyping or MFISH, comparative genomic hybridization, in situ hybridization, SSP, HPLC or mass-spectrometric genotyping.

In embodiments, the predetermined sequence, e.g., mutation, is detected in the subject.

In embodiments, the predetermined sequence, e.g., mutation, is detected in a nucleic acid molecule or a polypeptide in a sample from the subject.

In embodiments, the state of methylation, e.g., hypermethylation, e.g., methylated cytosine, is detected by a method chosen from one or more of: mass spectrometry, methylation-specific PCR, sequencing of bisulfite treated DNA, HpaII tiny fragment Enrichment by Ligation-mediated PCR Assay, ChIP-on-chip assay, restriction landmark genomic scanning, methylated DNA immunoprecipitation, molecular break light assay for DNA adenine methyltransferase activity, methyl sensitive Southern blotting, or high resolution melt analysis.

In embodiments, the hypermethylation, e.g., methylated cytosine, is detected in the subject.

In embodiments, the hypermethylation, e.g., methylated cytosine, is detected in a nucleic acid molecule in a sample from the subject.

In embodiments, the sample comprises cells from a blood, serum, urine, or tissue (e.g., biopsy) from the subject.

In embodiments, the knowledge is acquired from another party, e.g., wherein the party is the subject, a caregiver, a physician, an endocrinologist, a hospital, clinic, third-party payor, insurance company or government office.

In embodiments, the detection of the predetermined sequence arises from a collaboration with another party.

In embodiments, the method comprises:
responsive to a determination of the presence or absence of (a) the predetermined sequence, e.g., mutation, and/or (b) hypermethylation in the subject, one or more of:
(1) identifying or selecting the subject as having Prader Willi Syndrome (PWS);
(2) identifying or selecting the subject as having a disorder characterized by one or more mutations in the POMC gene, e.g., POMC deficiency;
(3) identifying or selecting the subject as having a disorder characterized by one or more mutations in the PCSK1 gene, e.g., PCSK1 deficiency;
(4) identifying or selecting the subject as having a disorder characterized by one or more mutations in the MAGEL2 gene, e.g., MAGEL2 deficiency;
(5) identifying or selecting the subject as having a disorder characterized by one or more mutations in the leptin receptor gene, e.g., leptin receptor deficiency;
(6) identifying or selecting the subject as having a disorder characterized by one or more mutations in the leptin gene, e.g., leptin deficiency;
(7) identifying or selecting the subject as having a disorder characterized by one or more mutations in the 5-HT2c receptor gene, e.g., 5-HT2c receptor deficiency;
(8) identifying or selecting the subject as having a disorder characterized by one or more mutations in the NhHL2 gene, e.g., NhHL2 deficiency;
(9) identifying or selecting the subject as having a disorder characterized by one or more mutations in the pro-hormone convertase gene, e.g., pro-hormone convertase deficiency;

(10) identifying or selecting the subject as having a disorder characterized by one or more mutations in the CPE gene, e.g., CPE deficiency;
(11) identifying or selecting the subject as having a disorder characterized by one or more mutations in the SIM1 gene, e.g., SIM1 deficiency;
(12) identifying or selecting the subject as having a disorder characterized by a hypermethylated POMC gene, e.g., POMC deficiency;
(13) identifying or selecting the subject has having a disorder characterized by one or more mutations in a POMC-MC4R pathway gene, e.g., POMC-MC4R pathway deficiency; and/or
(14) identifying or selecting the subject as likely or unlikely to respond to the agonist.

In embodiments, the presence of the predetermined sequence, e.g., mutation (e.g., mutation in MAGEL2 and/or mutation in the paternal allele of the 15q11-q13 region of chromosome 15) is detected in the subject, and responsive to that determination, the method comprises identifying the subject as having Prader Willi Syndrome (PWS).

In embodiments, the presence of the predetermined sequence, e.g., mutation (e.g., mutation in the POMC gene) is detected in the subject, and responsive to that determination, the method comprises identifying the subject as having a disorder characterized by one or more mutations in the POMC gene, e.g., POMC deficiency.

In embodiments, the presence of the predetermined sequence, e.g., mutation (e.g., mutation in the PCSK1 gene) is detected in the subject, and responsive to that determination, the method comprises identifying the subject as having a disorder characterized by one or more mutations in the PCSK1 gene, e.g., PCSK1 deficiency.

In embodiments, the presence of the predetermined sequence, e.g., mutation (e.g., mutation in the leptin receptor gene) is detected in the subject, and responsive to that determination, the method comprises identifying the subject as having a disorder characterized by one or more mutations in the leptin receptor gene, e.g., leptin receptor deficiency.

In embodiments, the presence of the predetermined sequence, e.g., mutation (e.g., mutation in the leptin gene) is detected in the subject, and responsive to that determination, the method comprises identifying the subject as having a disorder characterized by one or more mutations in the leptin gene, e.g., leptin deficiency.

In embodiments, the presence of the predetermined sequence, e.g., mutation (e.g., mutation in the 5-HT2c receptor gene) is detected in the subject, and responsive to that determination, the method comprises identifying the subject as having a disorder characterized by one or more mutations in the 5-HT2c receptor gene, e.g., 5-HT2c receptor deficiency.

In embodiments, the presence of the predetermined sequence, e.g., mutation (e.g., mutation in the NhHL2 gene) is detected in the subject, and responsive to that determination, the method comprises identifying the subject as having a disorder characterized by one or more mutations in the NhHL2 gene, e.g., NhHL2 deficiency.

In embodiments, the presence of the predetermined sequence, e.g., mutation (e.g., mutation in the pro-hormone convertase gene) is detected in the subject, and responsive to that determination, the method comprises identifying the subject as having a disorder characterized by one or more mutations in the pro-hormone convertase gene, e.g., pro-hormone convertase deficiency.

In embodiments, the presence of the predetermined sequence, e.g., mutation (e.g., mutation in the CPE gene) is detected in the subject, and responsive to that determination, the method comprises identifying the subject as having a disorder characterized by one or more mutations in the CPE gene, e.g., CPE deficiency.

In embodiments, the presence of the predetermined sequence, e.g., mutation (e.g., mutation in the SIM1 gene) is detected in the subject, and responsive to that determination, the method comprises identifying the subject as having a disorder characterized by one or more mutations in the SIM1 gene, e.g., SIM1 deficiency.

In embodiments, the presence of the predetermined sequence, e.g., mutation (e.g., mutation in a gene described herein) is detected in the subject, and responsive to that determination, the method comprises identifying the subject as having a disorder characterized by one or more mutations in a POMC-MC4R pathway gene, e.g., POMC-MC4R pathway deficiency.

In embodiments, the presence of the hypermethylation in the POMC gene is detected in the subject, and responsive to that determination, the method comprises identifying the subject as having a disorder characterized by a hypermethylated POMC gene, e.g., POMC deficiency.

In embodiments, the presence of the predetermined sequence, e.g., mutation, or the hypermethylation, is detected in the subject, and responsive to that determination, the method comprises identifying the subject as likely to respond to the agonist.

In embodiments, the subject has or is identified as having PWS or a disorder characterized by one or more mutations in the POMC, PCSK1, MAGEL2, leptin receptor, leptin, 5-HT2c receptor, NhHL2, pro-hormone convertase, CPE, SIM1, or other POMC-MC4R pathway gene, e.g., POMC-MC4R pathway deficiency.

In an aspect, provided herein is a method of treating a disorder chosen from:
(i) a disorder characterized by one or more mutations (e.g., loss of function mutations) in the PCSK1 gene;
(ii) a disorder characterized by one or more mutations (e.g., loss of function mutations) in the MAGEL2 gene;
(iii) a disorder characterized by one or more mutations (e.g., loss of function mutations) in the leptin receptor gene;
(iv) a disorder characterized by one or more mutations (e.g., loss of function mutations) in the 5-HT2c receptor gene;
(v) a disorder characterized by one or more mutations (e.g., loss of function mutations) in the nescient helix loop helix 2 (NhHL2) gene;
(vi) a disorder characterized by one or more mutations (e.g., loss of function mutations) in the carboxypeptidase E (CPE) gene;
(vii) a disorder characterized by one or more mutations (e.g., loss of function mutations) in the single-minded 1 (SIM1) gene;
(viii) a disorder characterized by a hypermethylated POMC gene (e.g., hypermethylated at a POMC intron, e.g., at a CpG island of the POMC gene, e.g., comprising a methylated cytosine, e.g., a 5'methyl cytosine);
(ix) a disorder characterized by a defect in the POMC-MC4R pathway other than:
(a) a POMC mutation, e.g., a heterozygous POMC mutation characterized by the presence of one functional POMC allele and one non-functional POMC allele, (b) a leptin mutation, e.g., a heterozygous leptin mutation characterized by the presence of one functional leptin allele and one non-functional leptin allele,
(c) a melanocortin-4 receptor (MC4R) mutation, or
(d) a prohormone convertase mutation;
(x) a disorder characterized by a homozygous POMC mutation (e.g., loss of function mutation), e.g., characterized by a POMC null genotype;
(xi) a disorder characterized by a compound heterozygous POMC mutation (e.g., characterized by the presence of two non-functional alleles) e.g., characterized by a POMC null genotype;
(xii) a disorder characterized by a homozygous leptin mutation (e.g., loss of function mutation), e.g., characterized by a leptin null genotype;
(xiii) a disorder characterized by a compound heterozygous leptin mutation (e.g., characterized by the presence of two non-functional alleles) e.g., characterized by a leptin null genotype,
in a subject in need thereof, comprising administering an agonist of the melanocortin-4 receptor (MC4R),
wherein the agonist is a MC4R agonist described herein, e.g., the agonist is

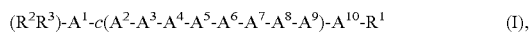

$$(R^2R^3)\text{-}A^1\text{-}c(A^2\text{-}A^3\text{-}A^4\text{-}A^5\text{-}A^6\text{-}A^7\text{-}A^8\text{-}A^9)\text{-}A^{10}\text{-}R^1 \qquad (I),$$

wherein:
$A^1$ is Acc, HN—(CH$_2$)$_m$—C(O), L- or D-amino acid, or deleted;
$A^2$ is Cys, D-Cys, hCys, D-hCys, Pen, D-Pen, Asp, or Glu;
$A^3$ is Gly, Ala, β-Ala, Gaba, Aib, D-amino acid, or deleted;
$A^4$ is His, 2-Pal, 3-Pal, 4-Pal, Taz, 2-Thi, 3-Thi, or (X$^1$, X$^2$, X$^3$, X$^4$, X$^5$)Phe;
$A^5$ is D-Phe, D-1-Nal, D-2-Nal, D-Trp, D-Bal, D-(X$^1$, X$^2$, X$^3$, X$^4$, X$^5$)Phe, L-Phe or D-(Et)Tyr;
$A^6$ is Arg, hArg, Dab, Dap, Lys, Orn, or HN—CH((CH$_2$)$_n$—N(R$^4$R$^5$))—C(O);
$A^7$ is Trp, 1-Nal, 2-Nal, Bal, Bip, D-Trp, D-2-Nal, D-Bal or D-Bip;
$A^8$ is Gly, D-Ala, Acc, Ala, β-Ala, Gaba, Apn, Ahx, Aha, HN—(CH$_2$)$_s$—C(O), or deleted;
$A^9$ is Cys, D-Cys, hCys, D-hCys, Pen, D-Pen, Dab, Dap, Orn, or Lys;
$A^{10}$ is Acc, HN—(CH$_2$)$_r$—C(O), L- or D-amino acid, or deleted;
$R^1$ is OH or NH$_2$;
each of $R^2$ and $R^3$ is, independently for each occurrence, selected from the group consisting of H, (C$_1$-C$_{30}$)alkyl, (C$_1$-C$_{30}$)heteroalkyl, (C$_1$-C$_{30}$)acyl, (C$_2$-C$_{30}$)alkenyl, (C$_2$-C$_{30}$)alkynyl, aryl(C$_1$-C$_{30}$)alkyl, aryl(C$_1$-C$_{30}$)acyl, substituted (C$_1$-C$_{30}$)alkyl, substituted (C$_1$-C$_{30}$)heteroalkyl, substituted (C$_1$-C$_{30}$)acyl, substituted (C$_2$-C$_{30}$) alkenyl, substituted (C$_2$-C$_{30}$)alkynyl, substituted aryl (C$_1$-C$_{30}$)alkyl, and substituted aryl(C$_1$-C$_{30}$)acyl;
each of $R^4$ and $R^5$ is, independently for each occurrence, H, (C$_1$-C$_{40}$)alkyl, (C$_1$-C$_{40}$)heteroalkyl, (C$_1$-C$_{40}$)acyl, (C$_2$-C$_{40}$)alkenyl, (C$_2$-C$_{40}$)alkynyl, aryl(C$_1$-C$_{40}$)alkyl, aryl(C$_1$-C$_{40}$)acyl, substituted (C$_1$-C$_{40}$)alkyl, substituted (C$_1$-C$_{40}$)heteroalkyl, substituted (C$_1$-C$_{40}$)acyl, substituted (C$_2$-C$_{40}$)alkenyl, substituted (C$_2$-C$_{40}$)alkynyl, substituted aryl(C$_1$-C$_{40}$)alkyl, substituted aryl(C$_1$-C$_{40}$) acyl, (C$_1$-C$_{40}$)alkylsulfonyl, or —C(NH)—NH$_2$;
m is, independently for each occurrence, 1, 2, 3, 4, 5, 6 or 7;
n is, independently for each occurrence, 1, 2, 3, 4 or 5;
s is, independently for each occurrence, 1, 2, 3, 4, 5, 6, or 7;
t is, independently for each occurrence, 1, 2, 3, 4, 5, 6, or 7;
X', X$^2$, X$^3$, X$^4$, and X$^8$ each is, independently for each occurrence, H, F, Cl, Br, I, (C$_{1-10}$)alkyl, substituted (C$_{1-10}$)alkyl, (C$_{2-10}$)alkenyl, substituted (C$_{2-10}$)alkenyl, (C$_{2-10}$)alkynyl, substituted (C$_{2-10}$)alkynyl, aryl, substituted aryl, OH, NH$_2$, NO$_2$, or CN.

In embodiments, the disorder is characterized by a homozygous POMC mutation (e.g., loss of mutation), e.g., characterized by a POMC null genotype.

In embodiments, the disorder is characterized by a compound heterozygous POMC mutation (e.g., characterized by the presence of two non-functional alleles) e.g., characterized by a POMC null genotype.

In embodiments, the mutations are mutations described herein, e.g., p.Lys51Term g.A6851>T and p.Arg145ProfsX12 g.7134delG.

In embodiments, the disorder is characterized by one or more mutations (e.g., loss of function mutations) in the PCSK1 gene.

In embodiments, the subject is or is identified as being a heterozygous carrier of the mutation(s), e.g., having one functional PCSK1 allele and one non-functional PCSK1 allele.

In embodiments, the subject is or is identified as being a compound heterozygous carrier of the mutation(s), e.g., having two non-functional PCSK1 alleles, e.g., having a PCSK1 null genotype.

In embodiments, the subject is or is identified as being a homozygous carrier of the mutation(s), e.g., having a PCSK1 null genotype.

In embodiments, the disorder is characterized by one or mutations (e.g., loss of function mutations) in the MAGEL2 gene.

In embodiments, the subject is or is identified as being a heterozygous carrier of the mutation(s), e.g., having one functional MAGEL2 allele and one non-functional MAGEL2 allele.

In embodiments, the subject is or is identified as being a compound heterozygous carrier of the mutation(s), e.g., having two non-functional MAGEL2 alleles, e.g., having a MAGEL2 null genotype.

In embodiments, the subject is or is identified as being a homozygous carrier of the mutation(s), e.g., having a MAGEL2 null genotype.

In embodiments, the disorder is characterized by one or mutations (e.g., loss of function mutations) in the leptin receptor gene.

In embodiments, the subject is or is identified as being a heterozygous carrier of the mutation(s), e.g., having one functional leptin receptor allele and one non-functional leptin receptor allele.

In embodiments, the subject is or is identified as being a compound heterozygous carrier of the mutation(s), e.g., having two non-functional leptin receptor alleles, e.g., having a leptin receptor null genotype.

In embodiments, the subject is or is identified as being a homozygous carrier of the mutation(s), e.g., having a leptin receptor null genotype.

In embodiments, the disorder is characterized by a homozygous leptin mutation (e.g., loss of mutation), e.g., characterized by a leptin null genotype.

In embodiments, the disorder is characterized by a compound heterozygous leptin mutation (e.g., characterized by the presence of two non-functional alleles) e.g., characterized by a leptin null genotype.

In embodiments, the disorder is characterized by one or mutations (e.g., loss of function mutations) in the 5-HT2c receptor gene.

In embodiments, the subject is or is identified as being a heterozygous carrier of the mutation(s), e.g., having one functional 5-HT2c receptor allele and one non-functional 5-HT2c receptor allele.

In embodiments, the subject is or is identified as being a compound heterozygous carrier of the mutation(s), e.g., having two non-functional 5-HT2c receptor alleles, e.g., having a 5-HT2c receptor null genotype.

In embodiments, the subject is or is identified as being a homozygous carrier of the mutation(s), e.g., having a 5-HT2c receptor null genotype.

In embodiments, the disorder is characterized by one or mutations (e.g., loss of function mutations) in the nescient helix loop helix 2 (NhHL2) gene.

In embodiments, the subject is or is identified as being a heterozygous carrier of the mutation(s), e.g., having one functional NhHL2 allele and one non-functional NhHL2 receptor allele.

In embodiments, the subject is or is identified as being a compound heterozygous carrier of the mutation(s), e.g., having two non-functional NhHL2 alleles, e.g., having a NhHL2 null genotype.

In embodiments, the subject is or is identified as being a homozygous carrier of the mutation(s), e.g., having a NhHL2 null genotype.

In embodiments, the disorder is characterized by one or mutations (e.g., loss of function mutations) in the carboxypeptidase E (CPE) gene.

In embodiments, the subject is or is identified as being a heterozygous carrier of the mutation(s), e.g., having one functional CPE allele and one non-functional CPE allele.

In embodiments, the subject is or is identified as being a compound heterozygous carrier of the mutation(s), e.g., having two non-functional CPE alleles, e.g., having a CPE null genotype.

In embodiments, the subject is or is identified as being a homozygous carrier of the mutation(s), e.g., having a CPE null genotype.

In embodiments, the disorder is characterized by one or mutations (e.g., loss of function mutations) in the single-minded 1 (SIM1) gene.

In embodiments, the subject is or is identified as being a heterozygous carrier of the mutation(s), e.g., having one functional SIM1 allele and one non-functional SIM1 allele.

In embodiments, the subject is or is identified as being a compound heterozygous carrier of the mutation(s), e.g., having two non-functional SIM1 alleles, e.g., having a SIM1 null genotype.

In embodiments, the subject is or is identified as being a homozygous carrier of the mutation(s), e.g., having a SIM1 null genotype.

In embodiments, the disorder is characterized by a hypermethylated POMC gene (e.g., hypermethylated at a POMC intron, e.g., at a CpG island of the POMC gene, e.g., comprising a methylated cytosine, e.g., a 5'methyl cytosine).

In embodiments, the subject has or is identified as having a hypermethylated CpG island in the POMC gene, e.g., at the intron2-exon3 boundary of the POMC gene.

In embodiments, the disorder is characterized by a defect in the POMC-MC4R pathway other than a POMC mutation, e.g., a heterozygous POMC mutation characterized by the presence of one functional POMC allele and one non-functional POMC allele.

In embodiments, the disorder is characterized by a defect in the POMC-MC4R pathway other than a leptin mutation, e.g., a heterozygous leptin mutation characterized by the presence of one functional leptin allele and one non-functional leptin allele.

In embodiments, the disorder is characterized by a defect in the POMC-MC4R pathway other than a MC4R mutation, e.g., a heterozygous melanocortin-4 receptor (MC4R) mutation characterized by the presence of one functional MC4R allele and one non-functional MC4R allele.

In embodiments, the disorder is characterized by a defect in the POMC-MC4R pathway other than a pro-hormone convertase mutation.

In embodiments, the method comprises administering the agonist in a unit dosage suitable for injection, e.g., subcutaneous injection, to the subject.

In embodiments, the unit dosage comprises about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or 2 mg of the agonist.

In embodiments, the unit dosage is disposed within a delivery device, e.g., a syringe (e.g., prefilled syringe), an implantable device, a needleness hypodermic injection device, an infusion pump (e.g., implantable infusion pump), or an osmotic delivery system.

In embodiments, the agonist is administered subcutaneously, e.g., by subcutaneous injection.

In embodiments, the agonist is administered daily over a period of at least 3 weeks, e.g., at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 weeks or more, or at least 1, 2, 3, 4, 5, 6, 7, 8, 9, 10, 11, or 12 months or more, or at least 1, 2, 3, 4 years or more.

In embodiments, the subject is obese, e.g., severely obese.

In embodiments, the subject has early onset severe obesity.

In embodiments, the subject is hyperphagic.

In embodiments, the subject has a body mass index (BMI) greater than 25 kg/m$^2$ (e.g., ≥25, 30, 31, 32, 33, 34, 35, 36, 37, 38, 39, 40, 41, 42, 43, 44, 45, 46, 47, 48, 49, 50 kg/m$^2$ or greater) prior to administration of the agonist, e.g., at the time the agonist is prescribed, or at the time of the first administration.

In embodiments, the subject has a body mass index (BMI) greater than 35 kg/m$^2$ (e.g., ≥36, 37, 38, 39, 40, 41, 42, 43, 44, 45, 46, 47, 48, 49, 50 kg/m$^2$ or greater) prior to administration of the agonist, e.g., at the time the agonist is prescribed, or at the time of the first administration.

In embodiments, the subject has a body mass index (BMI) greater than 40 kg/m$^2$ (e.g., ≥41, 42, 43, 44, 45, 46, 47, 48, 49, 50, 51, 52, 53, 54, 55 kg/m$^2$ or greater) prior to administration of the agonist, e.g., at the time the agonist is prescribed, or at the time of the first administration.

In embodiments, the subject has a body mass index (BMI) greater than 45 kg/m$^2$ (e.g., ≥46, 47, 48, 49, 50, 51, 52, 53, 54, 55 kg/m$^2$ or greater) prior to administration of the agonist, e.g., at the time the agonist is prescribed, or at the time of the first administration.

In embodiments, the subject has a BMI higher than the 85-95th percentile prior to administration of the agonist, e.g., at the time the agonist is prescribed, or at the time of the first administration.

In embodiments, the subject has failed one or more previous therapies, e.g., exercise, diet, or behavioral therapies, prior to administration of the agonist, e.g., at the time the agonist is prescribed, or at the time of the first administration.

In embodiments, the subject has a lower body weight after administration of the agonist than before administration of the agonist.

In embodiments, administration of the agonist results in a reduction of weight in the subject compared to the weight of the subject before treatment of about 1 kg to 3 kg after 1 week of treatment, or about 1 kg to 6 kg after 2 weeks of treatment, or about 2 kg to 12 kg after 4 weeks of treatment, or about 4 kg to 24 kg after 8 weeks of treatment, or about 8 kg to 48 kg after 16 weeks of treatment.

In embodiments, administration of the agonist results in weight loss in the subject at a rate of about 1-2 kg/week, e.g., about 2 kg/week, e.g., over a period of 1-2 weeks of treatment or longer, 2-4 weeks of treatment or longer, 4-8 weeks of treatment or longer, 8-16 weeks of treatment or longer, 16-32 weeks or longer, or 32-64 weeks or longer.

In embodiments, administration of the agonist results in a reduction in hunger level (e.g., a lower score on the Likert hunger scale, e.g., a lower score by at least 1, 2, 3, 4, 5, 6, 7, 8, 9 or 10 points) in the subject compared to the hunger level of the subject before treatment, e.g., results in abolishment of hunger (e.g., a score of 0 on the Likert hunger scale) in the subject, e.g., after 1-2 weeks of treatment or longer, 2-4 weeks of treatment or longer, 4-8 weeks of treatment or longer, or 8-16 weeks of treatment or longer.

In embodiments, administration of the agonist results in no detectable/significant decrease in resting energy expenditure (REE) in the subject, e.g., over a period of 24 hours, one week, or 30 days or longer, e.g., as compared to a control REE (e.g., the REE in the subject prior to treatment or a predetermined REE, e.g., in subjects of similar pre-treatment BMI, e.g., when expressed as REE per kg of lean body mass).

In embodiments, administration of the agonist results in an increase in resting energy expenditure (REE) in the subject, e.g., over a period of 24 hours, one week, or 30 days, or longer e.g., as compared to a control REE (e.g., the REE in the subject prior to treatment or compared to a predetermined REE, e.g., in subjects of similar pre-treatment BMI, when expressed as REE per kg of lean body mass, e.g., after a similar level of weight loss has been attained by fasting).

In embodiments, administration of the agonist results in a reduction in food intake by the subject compared to a control (e.g., the food intake of the subject prior to treatment), e.g., wherein the food intake is daily food intake or food intake over a period of 24 hours, or one week.

In embodiments, administration of the agonist results in a reduction in food intake of at least 100 kilocalories, e.g., at least 100, 125, 150, 175, 200, 225, 250, 275, 300, 325, 350, 375, 400, 425, 450, 475, 500, 525, 550, 575, 600, 1000 kilocalories or more, compared to a control (e.g., the food intake of the subject prior to treatment or a predetermined food intake level), e.g., wherein the food intake is daily food intake or food intake over a period of 24, hours, or one week.

In embodiments, administration of the agonist results in a reduction in food intake of at least 5 kcal/kg/day, e.g., 5, 10, 20, 30, 40, 50, 60, 70, 80, or 90 or more kcal/kg/day. In embodiments, the reduction in food intake is relative to the food intake at baseline. In embodiments, the baseline food intake is at least 100 kcal/kg/day, e.g., for a pediatric subject at about 1 year of age. In embodiments, the baseline food intake is at least 40 kcal/kg/day, e.g., for a pediatric subject, e.g., in late adolescence.

In embodiments, administration of the agonist results in a reduction in waist circumference of the subject compared to a control (e.g., the waist circumference of the subject prior to treatment), as measured 1, 2, 3, 4, 5, 6, 7, 8, 9, 10 weeks or more after initiation of treatment.

In embodiments, administration of the agonist results in a reduction in waist circumference of at least 2 cm (e.g., at least 2, 3, 4, 5, 6, 7, 8, 9, 10 cm or more) in the subject compared to a control (e.g., the waist circumference of the subject prior to treatment), as measured 1, 2, 3, 4, 5, 6, 7, 8, 9, 10 weeks or more after initiation of treatment.

In embodiments, administration of the agonist results in no detectable increase in blood pressure (e.g., diastolic and/or systolic blood pressure) of the subject compared to the blood pressure of the subject prior to treatment, as measured 1, 2, 3, 4, 5, 6, 7, 8, 9, 10 weeks or more after initiation of treatment.

In embodiments, administration of the agonist results in a reduction in blood pressure (e.g., diastolic and/or systolic blood pressure) of the subject compared to the blood pressure of the subject prior to treatment, as measured 1, 2, 3, 4, 5, 6, 7, 8, 9, 10 weeks or more after initiation of treatment.

In embodiments, administration of the agonist results in a reduction in systolic blood of the subject of at least 3 mmHg (e.g., at least 3, 3.5, 4, 4.5, 5, 5.5, 6, 6.5, 7 mmHg or more) compared to the blood pressure of the subject prior to treatment, as measured 1, 2, 3, 4, 5, 6, 7, 8, 9, 10 weeks or more after initiation of treatment.

In embodiments, administration of the agonist results in a reduction in diastolic blood pressure of the subject of at least 4 mmHg (e.g., at least 4, 7, 7.5, 8, 8.5, 9, 9.5, 10 mmHg or more) compared to the blood pressure of the subject prior to treatment, as measured 1, 2, 3, 4, 5, 6, 7, 8, 9, 10 weeks or more after initiation of treatment.

In embodiments, the subject is a mammal, e.g., a human.

In embodiments, the agonist is Ac-Arg-c(Cys-D-Ala-His-D-Phe-Arg-Trp-Cys)-NH$_2$ (SEQ ID NO: 140).

In embodiments, the method comprises acquiring knowledge of the genotype of the subject, e.g., acquiring knowledge of the genotype of, e.g., of a mutation in:
the POMC gene;
the PCSK1 gene;
the MAGEL2 gene;
the leptin receptor gene;
the leptin gene;
the 5-HT2c receptor gene;
the nescient helix loop helix 2 (NhHL2) gene;
the carboxypeptidase E (CPE) gene; or
the single-minded 1 (SIM1) gene.

In embodiments, the agonist is administered in response to the detection of a predetermined sequence, e.g., a mutation, in a gene described herein.

In embodiments, the method comprises acquiring knowledge of the state of methylation of the POMC gene (e.g., hypermethylated at a POMC intron, e.g., at a CpG island of the POMC gene, e.g., comprising a methylated cytosine, e.g., a 5'methyl cytosine).

In embodiments, the agonist is administered in response to the detection of hypermethylation.

In embodiments, the knowledge is acquired directly, e.g., from a sample (e.g., a blood, serum, urine, or tissue (e.g., biopsy) sample) from the subject.

In embodiments, the predetermined sequence, e.g., mutation, is detected in a nucleic acid by a method chosen from one or more of: a nucleic acid hybridization assay, an amplification-based assay, a PCR-RFLP assay, real-time PCR, sequencing, screening analysis, FISH, spectral karyotyping or MFISH, comparative genomic hybridization, in situ hybridization, SSP, HPLC or mass-spectrometric genotyping.

In embodiments, the predetermined sequence, e.g., mutation, is detected in the subject.

In embodiments, the predetermined sequence, e.g., mutation, is detected in a nucleic acid molecule or a polypeptide in a sample from the subject.

In embodiments, the state of methylation, e.g., hypermethylation, e.g., methylated cytosine, is detected by a method chosen from one or more of: mass spectrometry, methylation-specific PCR, sequencing of bisulfite treated DNA, HpaII tiny fragment Enrichment by Ligation-mediated PCR Assay, ChIP-on-chip assay, restriction landmark genomic scanning, methylated DNA immunoprecipitation, molecular break light assay for DNA adenine methyltransferase activity, methyl sensitive Southern blotting, or high resolution melt analysis.

In embodiments, the hypermethylation, e.g., methylated cytosine, is detected in the subject.

In embodiments, the hypermethylation, e.g., methylated cytosine, is detected in a nucleic acid molecule in a sample from the subject.

In embodiments, the sample comprises cells from a blood, serum, urine, or tissue (e.g., biopsy) from the subject.

In embodiments, the knowledge is acquired from another party, e.g., wherein the party is the subject, a caregiver, a physician, an endocrinologist, a hospital, clinic, third-party payor, insurance company or government office.

In embodiments, the detection of the predetermined sequence arises from a collaboration with another party.

In embodiments, the detection of the hypermethylation arises from a collaboration with another party.

In embodiments, the method comprises:
responsive to a determination of the presence or absence of (a) the predetermined sequence, e.g., mutation, and/or (b) hypermethylation in the subject, one or more of:
(1) identifying or selecting the subject as having a disorder characterized by one or more mutations in the PCSK1 gene, e.g., PCSK1 deficiency;
(2) identifying or selecting the subject as having a disorder characterized by one or more mutations in the MAGEL2 gene, e.g., MAGEL2 deficiency;
(3) identifying or selecting the subject as having a disorder characterized by one or more mutations in the leptin receptor gene, e.g., leptin receptor deficiency;
(4) identifying or selecting the subject as having a disorder characterized by one or more mutations in the 5-HT2c receptor gene, e.g., 5-HT2c receptor deficiency;
(5) identifying or selecting the subject as having a disorder characterized by one or more mutations in the NhHL2 gene, e.g., NhHL2 deficiency;
(6) identifying or selecting the subject as having a disorder characterized by one or more mutations in the CPE gene, e.g., CPE deficiency;
(7) identifying or selecting the subject as having a disorder characterized by one or more mutations in the SIM1 gene, e.g., SIM1 deficiency;
(8) identifying or selecting the subject as having a disorder characterized by a hypermethylated POMC gene, e.g., POMC deficiency;
(9) identifying or selecting the subject has having a disorder characterized by one or more mutations in a POMC-MC4R pathway gene, e.g., POMC-MC4R pathway deficiency;
(10) identifying or selecting the subject as having a disorder characterized by a defect in the POMC-MC4R pathway other than a POMC mutation;
(11) identifying or selecting the subject as having a disorder characterized by a defect in the POMC-MC4R pathway other than a leptin mutation; (12) identifying or selecting the subject as having a disorder characterized by a defect in the POMC-MC4R pathway other than a MC4R mutation;
(13) identifying or selecting the subject as having a disorder characterized by a defect in the POMC-MC4R pathway other than a prohormone convertase mutation;
(14) identifying or selecting the subject as having a disorder characterized by a homozygous POMC mutation;
(15) identifying or selecting the subject as having a disorder characterized by a compound heterozygous POMC mutation;
(16) identifying or selecting the subject as having a disorder characterized by a homozygous leptin mutation;
(17) identifying or selecting the subject as having a disorder characterized by a compound heterozygous leptin mutation; and/or
(18) identifying or selecting the subject as likely or unlikely to respond to the agonist.

In embodiments, the presence of the predetermined sequence, e.g., mutation (e.g., mutation in MAGEL2) is detected in the subject, and responsive to that determination, the method comprises identifying the subject as having Prader Willi Syndrome (PWS).

In embodiments, the presence of the predetermined sequence, e.g., mutation (e.g., mutation in the PCSK1 gene) is detected in the subject, and responsive to that determination, the method comprises identifying the subject as having a disorder characterized by one or more mutations in the PCSK1 gene, e.g., PCSK1 deficiency.

In embodiments, the presence of the predetermined sequence, e.g., mutation (e.g., mutation in the leptin receptor gene) is detected in the subject, and responsive to that determination, the method comprises identifying the subject as having a disorder characterized by one or more mutations in the leptin receptor gene, e.g., leptin receptor deficiency.

In embodiments, the presence of the predetermined sequence, e.g., mutation (e.g., mutation in the 5-HT2c receptor gene) is detected in the subject, and responsive to that determination, the method comprises identifying the subject as having a disorder characterized by one or more mutations in the 5-HT2c receptor gene, e.g., 5-HT2c receptor deficiency.

In embodiments, the presence of the predetermined sequence, e.g., mutation (e.g., mutation in the NhHL2 gene) is detected in the subject, and responsive to that determination, the method comprises identifying the subject as having a disorder characterized by one or more mutations in the NhHL2 gene, e.g., NhHL2 deficiency.

In embodiments, the presence of the predetermined sequence, e.g., mutation (e.g., mutation in the CPE gene) is detected in the subject, and responsive to that determination, the method comprises identifying the subject as having a disorder characterized by one or more mutations in the CPE gene, e.g., CPE deficiency.

In embodiments, the presence of the predetermined sequence, e.g., mutation (e.g., mutation in the SIM1 gene) is detected in the subject, and responsive to that determination, the method comprises identifying the subject as having a disorder characterized by one or more mutations in the SIM1 gene, e.g., SIM1 deficiency.

In embodiments, the presence of the predetermined sequence, e.g., mutation (e.g., mutation in a gene described herein) is detected in the subject, and responsive to that determination, the method comprises identifying the subject as having a disorder characterized by one or more mutations in a POMC-MC4R pathway gene, e.g., POMC-MC4R pathway deficiency.

In embodiments, the presence of the hypermethylation in the POMC gene is detected in the subject, and responsive to that determination, the method comprises identifying the subject as having a disorder characterized by a hypermethylated POMC gene, e.g., POMC deficiency.

In embodiments, the presence of the predetermined sequence, e.g., mutation (e.g., homozygous POMC mutation) is detected in the subject, and responsive to that determination, the method comprises identifying the subject as having a disorder characterized by a homozygous POMC mutation, e.g., POMC deficiency.

In embodiments, the presence of the predetermined sequence, e.g., mutation (e.g., compound heterozygous POMC mutation) is detected in the subject, and responsive to that determination, the method comprises identifying the subject as having a disorder characterized by a compound heterozygous POMC mutation, e.g., POMC deficiency.

In embodiments, the presence of the predetermined sequence, e.g., mutation (e.g., homozygous leptin mutation) is detected in the subject, and responsive to that determination, the method comprises identifying the subject as having a disorder characterized by a homozygous leptin mutation, e.g., leptin deficiency.

In embodiments, the presence of the predetermined sequence, e.g., mutation (e.g., compound heterozygous leptin mutation) is detected in the subject, and responsive to that determination, the method comprises identifying the subject as having a disorder characterized by a compound heterozygous leptin mutation, e.g., leptin deficiency.

In embodiments, the presence of the predetermined sequence, e.g., mutation, or the hypermethylation, is detected in the subject, and responsive to that determination, the method comprises identifying the subject as likely to respond to the agonist.

In embodiments, the subject has or is identified as having a disorder characterized by one or more mutations in the PCSK1, MAGEL2, leptin receptor, 5-HT2c receptor, NhHL2, pro-hormone convertase, CPE, SIM1, or other POMC-MC4R pathway gene, e.g., POMC-MC4R pathway deficiency.

In embodiments, the subject has or is identified as having a disorder characterized by a homozygous or compound heterozygous mutation in one or more of the POMC or leptin gene, e.g., POMC deficiency or leptin deficiency.

In as aspect, provided herein is a unit dosage of an agonist described herein, wherein the unit dosage contains 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or 2 mg of the agonist.

In embodiments, the unit dosage contains 0.5 mg of agonist.

In embodiments, the unit dosage contains 1.0 mg of agonist.

In embodiments, the unit dosage contains 1.5 mg of agonist.

In embodiments, the unit dosage is suitable for injection, e.g., subcutaneous injection.

In embodiments, the unit dosage is disposed in a delivery device suitable for injection, e.g., subcutaneous injection.

In embodiments, the unit dosage is disposed in a syringe or pen-type injector suitable for injection, e.g., subcutaneous injection.

In embodiments, the agonist is Ac-Arg-c(Cys-D-Ala-His-D-Phe-Arg-Trp-Cys)-NH$_2$ (SEQ ID NO: 140).

In an aspect, provided herein is a method of evaluating a subject, comprising: acquiring information that identifies the subject as having or not having a predetermined sequence, e.g., mutation, in the 15q11-q13 region of chromosome 15 or in the MAGEL2 gene,
    wherein identification of the subject as having the mutation identifies the patient as more likely to have improved symptoms following treatment with a MC4R agonist (e.g., a MC4R agonist described herein), and identification of the subject as not having a mutation in the 15q11-q13 region of chromosome 15 or in the MAGEL2 gene identifies the patient as being less likely to have improved symptoms following treatment with a MC4R agonist, e.g., a MC4R agonist described herein.

In another aspect, provided herein is a method of evaluating a subject, comprising:
    acquiring information that identifies the subject as having or not having a predetermined sequence, e.g., mutation, in one or more of:
    the POMC gene;
    the PCSK1 gene;
    the MAGEL2 gene;
    the leptin receptor gene;
    the leptin gene;
    the 5-HT2c receptor gene;
    the nescient helix loop helix 2 (NhHL2) gene;
    the carboxypeptidase E (CPE) gene; or
    the single-minded 1 (SIM1) gene;
wherein identification of the subject as having the predetermined sequence, e.g., mutation, identifies the patient as more likely to have improved symptoms following treatment with a MC4R agonist (e.g., a MC4R agonist described herein), and identification of the subject as not having the predetermined sequence, e.g., mutation, identifies the patient as being less likely to have improved symptoms following treatment with a MC4R agonist, e.g., a MC4R agonist described herein.

In accordance with any method described herein, in embodiments, the improved symptoms comprise one or more of:
    (a) a decrease in body weight;
    (b) a decrease in waist circumference;
    (c) a decrease in hunger level;
    (d) a decrease in food intake level; and/or
    (e) a lack of decrease or an increase in resting energy expenditure.

In embodiments, the mutation is a loss of function mutation.

In embodiments, the mutation is a homozygous mutation, e.g., homozygous loss of function mutation.

In embodiments, the mutation is a heterozygous mutation.

In embodiments, the heterozygous mutation is a compound heterozygous mutation (e.g., characterized by the presence of two non-functional alleles).

In embodiments, the heterozygous mutation is characterized by the presence of one functional allele and one non-functional allele.

In embodiments, the method further comprises providing a report to another party, e.g., wherein the party is the subject, a caregiver, a physician, an oncologist, a hospital, clinic, third-party payor, insurance company or government office.

In embodiments, said report is in electronic, web-based, or paper form.

In embodiments, the report identifies the presence or absence of the mutation in the subject, and optionally includes an identifier for the subject from which the information was obtained.

In embodiments, the report comprises:
  information on the genotype (e.g., presence or absence of the predetermined sequence, e.g., mutation) of the subject;
  information on prognosis or suggested therapeutic options, e.g., MC4R agonists;
  information on the likely effectiveness of a therapeutic option, e.g., MC4R agonist, the acceptability of a therapeutic option, or the advisability of applying the therapeutic option to the subject; and/or
  information, or a recommendation on, the administration of the therapeutic option (e.g., MC4R agonist).

In embodiments, the agonist is Ac-Arg-c(Cys-D-Ala-His-D-Phe-Arg-Trp-Cys)-NH$_2$ (SEQ ID NO: 140).

In an aspect, provided herein is a method of selecting a subject having Prader Willi Syndrome (PWS), comprising:
  acquiring knowledge of the genotype of the subject, e.g., acquiring knowledge of the genotype of the paternal allele of the 15q11-q13 region of chromosome 15 or of the MAGEL2 gene;
  wherein the acquiring step comprises determining the presence or absence of a predetermined sequence, e.g., mutation in the paternal allele of the 15q11-q13 region of chromosome 15 or in the MAGEL2 gene; and
  wherein the presence of the predetermined sequence, e.g., mutation, identifies the subject as having PWS.

In an aspect, provided herein is a method of selecting a subject having a POMC-MC4R pathway deficiency, comprising:
  (i) acquiring knowledge of the genotype of the subject, e.g., acquiring knowledge of the genotype of, e.g., of a mutation in:
    the POMC gene;
    the PCSK1 gene;
    the MAGEL2 gene;
    the leptin receptor gene;
    the leptin gene;
    the 5-HT2c receptor gene;
    the nescient helix loop helix 2 (NhHL2) gene;
  the carboxypeptidase E (CPE) gene; or
  the single-minded 1 (SIM1) gene;
    wherein the presence of the mutation identifies the subject as having a POMC-MC4R pathway deficiency; or
    (ii) acquiring knowledge of the state of methylation of the POMC gene (e.g., hypermethylated at a POMC intron, e.g., at a CpG island of the POMC gene, e.g., comprising a methylated cytosine, e.g., a 5'methyl cytosine),
wherein the presence of the hypermethylation at the POMC intron identifies the subject as having a POMC-MC4R pathway deficiency.

In accordance with any method described herein, in embodiments, the method further comprises administering an agonist of the melanocortin-4 receptor (MC4R) to the subject, e.g., an agonist described herein, e.g., setmelanotide.

In embodiments, the mutation is a loss of function mutation.

In embodiments, the mutation is a homozygous mutation, e.g., homozygous loss of function mutation.

In embodiments, the mutation is a heterozygous mutation.

In embodiments, the heterozygous mutation is a compound heterozygous mutation (e.g., characterized by the presence of two distinct non-functional alleles).

In embodiments, the heterozygous mutation is characterized by the presence of one functional allele and one non-functional allele.

In embodiments, the agonist is Ac-Arg-c(Cys-D-Ala-His-D-Phe-Arg-Trp-Cys)-NH$_2$ (SEQ ID NO: 140).

Also provided herein is a use of a MC4R agonist, e.g., a MC4R agonist described herein, in the treatment of or in the manufacture of a medicament for the treatment of Prader Willi Syndrome (PWS), wherein the MC4R agonist is administered at a daily dosage of about 0.1 mg (e.g., 0.1 mg+/−5%) to about 10 mg (e.g., 10 mg+/−5%).

Also provided herein is a use of a MC4R agonist, e.g., a MC4R agonist described herein, in the treatment of or in the manufacture of a medicament for the treatment of a disorder chosen from:
  (i) Prader Willi Syndrome (PWS);
  (ii) a disorder characterized by one or more mutations (e.g., loss of function mutations) in the POMC gene;
  (iii) a disorder characterized by one or more mutations (e.g., loss of function mutations) in the PCSK1 gene;
  (iv) a disorder characterized by one or more mutations (e.g., loss of function mutations) in the MAGEL2 gene;
  (v) a disorder characterized by one or more mutations (e.g., loss of function mutations) in the leptin receptor gene;
  (vi) a disorder characterized by one or more mutations (e.g., loss of function mutations) in the leptin gene;
  (vii) a disorder characterized by one or more mutations (e.g., loss of function mutations) in the 5-HT2c receptor gene;
  (viii) a disorder characterized by one or more mutations (e.g., loss of function mutations) in the nescient helix loop helix 2 (NhHL2) gene;
  (ix) a disorder characterized by one or more mutations (e.g., loss of function mutations) in the pro-hormone convertase gene;
  (x) a disorder characterized by one or more mutations (e.g., loss of function mutations) in the carboxypeptidase E (CPE) gene;
  (xi) a disorder characterized by one or more mutations (e.g., loss of function mutations) in the single-minded 1 (SIM1) gene;
  (xii) a disorder characterized by a hypermethylated POMC gene (e.g., hypermethylated at a POMC intron, e.g., at a CpG island of the POMC gene, e.g., comprising one or more methylated cytosines, e.g., a 5'methyl cytosine); or
  (xiii) a disorder characterized by a defect in the POMC-MC4R pathway other than:
    (a) a heterozygous POMC mutation characterized by the presence of one functional POMC allele and one non-functional POMC allele,
    (b) a heterozygous leptin mutation characterized by the presence of one functional leptin allele and one non-functional leptin allele,
    (c) a melanocortin-4 receptor (MC4R) mutation (e.g., loss of function mutation), or
    (d) a pro-hormone convertase mutation (e.g., loss of function mutation).

optionally wherein the agonist is administered at a daily dosage of about 0.1 mg (e.g., 0.1 mg+/−5%) to about 10 mg (e.g., 10 mg+/−5%).

Additional embodiments in accordance with any method described herein include those that follow.

In embodiments, the MC4R agonist is a compound of Formula I, wherein:
- $A^1$ is $A^6c$, Arg, D-Arg, Cha, D-Cha, hCha, Chg, D-Chg, Gaba, Ile, Leu, hLeu, Met, β-hMet, 2-Nal, D-2-Nal, Nip, Nle, Oic, Phe, D-Phe, hPhe, hPro, Val, or deleted;
- $A^2$ is Asp, Cys, D-Cys, hCys, D-hCys, Glu, Pen, or D-Pen;
- $A^3$ is D-Abu, Aib, Ala, β-Ala, D-Ala, D-Cha, Gaba, D-Glu, Gly, D-Ile, D-Leu, D-Tle, D-Val, or deleted;
- $A^4$ is H is or 3-Pal;
- $A^5$ is D-Bal, D-1-Nal, D-2-Nal, D-Phe, D-Trp, or D-(Et)Tyr;
- $A^6$ is Arg, or hArg;
- $A^7$ is Bal, Bip, 1-Nal, 2-Nal, Trp, D-Trp;
- $A^8$ is $A^6c$, D-Ala, Aha, Ahx, Ala, β-Ala, Apn, Gaba, Gly or deleted;
- $A^9$ is Cys, D-Cys, hCys, D-hCys, Lys, Pen, or D-Pen;
- $A^{10}$ is Thr, or deleted, wherein at least one of $A^3$ or $A^8$ is deleted, but not both, or pharmaceutically acceptable salts thereof.

In embodiments, the MC4R agonist is not an adrenocorticotropic hormone (ACTH).

In embodiments, the MC4R agonist is not melanotan-II (MT-II) (Ac-Nle-cyclo[Asp-His-D-Phe-Arg-Trp-Lys]-$NH_2$) (SEQ ID NO: 562).

In embodiments, the MC4R agonist comprises 8 amino acids or more.

In embodiments, the MC4R agonist is Ac-Arg-c(Cys-D-Ala-His-D-Phe-Arg-Trp-Cys)-$NH_2$ (SEQ ID NO: 140) or a pharmaceutically acceptable salt thereof.

In embodiments, the MC4R agonist is Hydantoin(C(O)-(Arg-Gly))-c(Cys-Glu-His-D-Phe-Arg-Trp-Cys)-$NH_2$ (SEQ ID NO: 500) or a pharmaceutically acceptable salt thereof.

In embodiments, the MC4R agonist is a tripeptide D-Phe-Arg-Trp (SEQ ID NO: 560) or a pharmaceutical salt thereof.

In embodiments, the MC4R agonist is a peptide that includes D-Phe-Arg-Trp (SEQ ID NO: 560) or a pharmaceutical salt thereof.

In embodiments, the MC4R agonist is a peptide that includes an acetylated tripeptide Ac-D-Phe-Arg-Trp-$NH_2$ (SEQ ID NO: 561) or a pharmaceutical salt thereof.

In embodiments, the MC4R agonist is c[Hydantoin(C(O)-(Glu-D-Ala))-His-D-Phe-Arg-Trp-Dap]-$NH_2$ (SEQ ID NO: 496) or a pharmaceutically acceptable salt thereof.

In embodiments, the MC4R agonist is Hydantoin(C(O)-(Nle-Gly))-c(Cys-Glu-His-D-Phe-Arg-Trp-Cys)-$NH_2$ (SEQ ID NO: 501) or a pharmaceutically acceptable salt thereof.

In embodiments, the MC4R agonist is Hydantoin(C(O)-(Gly-Gly))-c(Cys-D-Ala-His-D-Phe-Arg-Trp-Pen)-$NH_2$ SEQ ID NO: 506) or a pharmaceutically acceptable salt thereof.

In embodiments, the MC4R agonist is Hydantoin(C(O)-(Ala-Gly))-c(Cys-D-Ala-His-D-Phe-Arg-Trp-Cys)-$NH_2$ (SEQ ID NO: 507) or a pharmaceutically acceptable salt thereof.

In embodiments, the MC4R agonist is Hydantoin(C(O)-(D-Arg-Gly))-c(Cys-Glu-His-D-Phe-Arg-Trp-Cys)-$NH_2$ (SEQ ID NO: 515) or a pharmaceutically acceptable salt thereof.

In embodiments, the MC4R agonist is Hydantoin(C(O)-(Gly-D-Arg))-c(Cys-Glu-His-D-Phe-Arg-Trp-Cys)-$NH_2$ (SEQ ID NO: 535) or a pharmaceutically acceptable salt thereof.

In embodiments, the MC4R agonist is Hydantoin(C(O)-(Gly-Arg))-c(Cys-Glu-His-D-Phe-Arg-Trp-Cys)-$NH_2$ (SEQ ID NO: 531) or a pharmaceutically acceptable salt thereof.

In embodiments, the MC4R agonist is Ac-c(Cys-Glu-His-D-2-Nal-Arg-Trp-Ala-Cys)-(Pro)$_2$-Lys-Asp-$NH_2$ (SEQ ID NO: 468) or a pharmaceutically acceptable salt thereof.

In embodiments, the MC4R agonist is Ac-c(Cys-Glu-His-D-2-Nal-Arg-1-Nal-Ala-Cys)-(Pro)$_2$-Lys-Asp-$NH_2$ (SEQ ID NO: 470) or a pharmaceutically acceptable salt thereof.

In embodiments, the MC4R agonist is Ac-c(Cys-Glu-His-D-2-Nal-Arg-Bal-Ala-Cys)-(Pro)$_2$-Lys-Asp-$NH_2$ (SEQ ID NO: 471) or a pharmaceutically acceptable salt thereof.

In embodiments, the MC4R agonist is Ac-c(Cys-Glu-His-D-2-Nal-Arg-2-Nal-β-Ala-Cys)-(Pro)$_2$-Lys-Asp-$NH_2$ (SEQ ID NO: 472) or a pharmaceutically acceptable salt thereof.

In embodiments, the MC4R agonist is Ac-c(Cys-Glu-His-D-2-Nal-Arg-2-Nal-Aib-Cys)-(Pro)$_2$-Lys-Asp-$NH_2$ (SEQ ID NO: 473) or a pharmaceutically acceptable salt thereof.

In embodiments, the MC4R agonist is c[Hydantoin(C(O)-(Asp-Aic))-D-2-Nal-Arg-Trp-Lys]-$NH_2$ (SEQ ID NO: 492) or a pharmaceutically acceptable salt thereof.

In embodiments, the MC4R agonist is c[Hydantoin(C(O)-(Asp-A6c))-D-2-Nal-Arg-Trp-Lys]-$NH_2$ (SEQ ID NO: 489) or a pharmaceutically acceptable salt thereof.

In embodiments, the MC4R agonist is Ac-Arg-c(Cys-D-Ala-His-D-2-Nal-Arg-Trp-Cys)-$NH_2$ (SEQ ID NO: 139) or a pharmaceutically acceptable salt thereof.

In embodiments, the MC4R agonist is Ac-hCha-c(Asp-His-D-Phe-Arg-Trp-Gaba-Lys)-$NH_2$ (SEQ ID NO: 36) or a pharmaceutically acceptable salt thereof.

In embodiments, the MC4R agonist is D-Phe-c(Cys-His-D-Phe-Arg-Bip-β-Ala-D-Cys)-Thr-NH2 (SEQ ID NO: 81) or a pharmaceutically acceptable salt thereof.

In embodiments, the MC4R agonist is D-Phe-c(Cys-His-D-Phe-hArg-Bip-β-Ala-D-Cys)-Thr-NH2 (SEQ ID NO: 83) or a pharmaceutically acceptable salt thereof.

In embodiments, the MC4R agonist is D-Phe-c(Cys-His-D-(Et)Tyr-hArg-Bip-β-Ala-D-Cys)-Thr-NH2 (SEQ ID NO: 84) or a pharmaceutically acceptable salt thereof.

In embodiments, the MC4R agonist is D-Phe-c(Cys-His-D-(Et)Tyr-hArg-Trp-β-Ala-D-Cys)-Thr-NH2 (SEQ ID NO: 82) or a pharmaceutically acceptable salt thereof.

In embodiments, the MC4R agonist is any MC4R agonist described in US 2014/0329743 A1, incorporated herein by reference.

In embodiments, the MC4R agonist is any MC4R agonist described in WO2014/144260 A1, incorporated herein by reference.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting. Headings, sub-headings or numbered or lettered elements, e.g., (a), (b), (i) etc, are presented merely for ease of reading. The use of headings or numbered or lettered elements in this document does not require the steps or elements be performed in alphabetical order or that the steps or elements are necessarily discrete from one another. Other features, objects, and advantages of the invention will be apparent from the description and drawings, and from the claims.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A is an enlarged version of the inset in FIG. 1B and shows cumulative food intake through 3 hours post-dosing. FIG. 1B shows cumulative food intake through overnight.

FIGS. 3A and 3D are graphs that show food intake as a function of time in wild-type mice and db/db mice at varying concentrations of setmelanotide.

DETAILED DESCRIPTION OF THE INVENTION

Figure 1A:
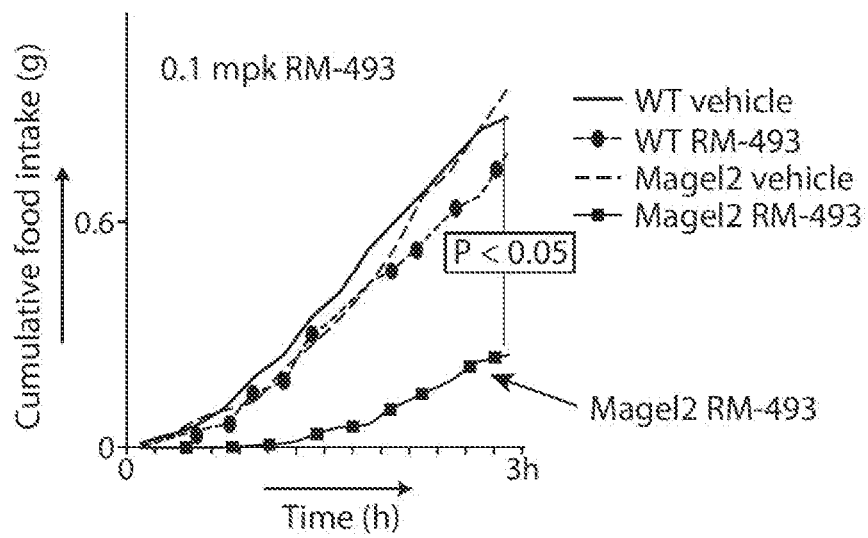
FIGS. 1A and 1B are graphs that show the effects on cumulative food intake suppression following treatment with setmelanotide (RM-493 at 0.1 mg/kg (mpk)) versus vehicle in Magel2-null (Magel2) and wildtype (WT) mice.

The present disclosure is based at least in part on the discovery that targeting defects in the POMC-MC4R pathway, e.g., targeting defects upstream of MC4R, by using a MC4R agonist as replacement therapy led to significant weight loss, decrease in hunger, and/or reveal an increase in energy expenditure in obese subjects. The disclosure is also based in part on the discovery that obese subjects having a defect (e.g., genetic defect) in one or more genes upstream of MC4R in the POMC-MC4R pathway are likely to exhibit a significantly greater response (e.g., in decreasing body weight and/or hunger and/or increasing energy expenditure) to an MC4R agonist than obese subjects not having such a defect. For example, as described herein, subjects having a non-functional Magel2 gene (e.g., Magel2-null obesity) may be much more responsive (e.g., in decreasing food intake) following exposure to an MC4R agonist than obese subjects not having such a genetic disorder (e.g., wild-type obese).

Also, as described herein, subjects having a non-functional POMC gene (e.g., POMC null obesity) exhibited a significantly greater response (e.g., in decreasing body weight and/or hunger and/or increasing energy expenditure) to an MC4R agonist than obese subjects not having such a genetic disorder (e.g., wild-type obese). In particular, the MC4R agonist led to a weight loss of about 2-2.5 kg per week over the course of 26 weeks of treatment (a total weight loss of about 36 kg after 26 weeks, corresponding to about 23% of the initial body weight). This weight loss in the POMC deficient subject is over 2-fold greater compared to that observed in wild-type obese subjects (which exhibited a weight loss after MC4R agonist treatment of about 0.6-0.9 kg per week over 2-4 weeks). Also, the greater weight loss seen in the POMC deficient subject persisted over a long period of time and did not appear to desensitize.

The dramatic weight loss and duration of weight loss observed in the POMC deficient subject is not only significantly greater than that observed for wild-type obese subjects treated with the MC4R agonist, but also significantly greater than the weight loss seen in obese subjects treated with currently marketed therapies. In clinical studies, marketed therapies such as Belviq® (Lorcaserin HCl tablets), Qsymia® (Phentermine and Topiramate extended release capsules), Contrave® (Naltrexone HCl and Bupropion HCl extended release tablets), and Saxenda® (Liraglutide injection) at prescribed doses caused less than 5 kg placebo adjusted weight loss in obese subjects after one year of treatment. The hyperresponsiveness of POMC-MC4R pathway deficient subjects (e.g., POMC deficient subjects) to an MC4R agonist, e.g., an MC4R agonist described herein, is surprising, as it is believed that weight loss in obese subjects reaches a limit at around 5% as subjects appear to become desensitized and adapt to the therapy effects, ascribed to physiological and compensatory changes that include a decrease in energy expenditure as the subject loses weight. Surprisingly, this limit in continued weight loss was not observed in the POMC deficient subject, who continued to lose weight well beyond 5% even after 13-26 weeks of treatment.

Without being bound by theory, a MC4R agonist, such as setmelanotide, can act to replace a missing MC4R signaling step in subjects having a genetic defect in the POMC-MC4R pathway (e.g., genetic disorders such as PWS and POMC-null obesity). As such, it is believed that a MC4R agonist, such as setmelanotide, can lead to even greater efficacy in these patient populations than those with general (e.g., wild-type) obesity. Accordingly, the methods and compositions described herein provide an optimized approach to restore MC4R pathway function in subjects with genetic disorders (e.g., genetic deficiencies in one or more genes of the POMC-MC4R pathway) such as PWS, POMC-null, and PCSK-null obesity, thereby decreasing the extreme hyperphagia and obesity seen in these subjects. Provided herein are methods to treat subjects having a genetic defect in one or more genes of the POMC-MC4R pathway as well as methods to identify/select subjects that have such defects and/or that are likely to respond to a MC4R agonist (e.g., more likely to respond to a MC4R agonist than wild-type obese subjects).

Definitions

As used herein "about" and "approximately" generally mean an acceptable degree of error for the quantity measured given the nature or precision of the measurements. Exemplary degrees of error are within 20 percent (%), typically, within 10%, and more typically, within 5% of a given value or range of values.

"Acquire" or "acquiring" as the terms are used herein, refer to obtaining possession of a physical entity, or a value, e.g., a numerical value, or knowledge of (e.g., knowledge of the sequence or mutational state of) a genotype or a nucleic acid or polypeptide, by "directly acquiring" or "indirectly acquiring" the physical entity, value, or knowledge. "Directly acquiring" means performing a physical process (e.g., performing a synthetic or analytical method) to obtain the physical entity, value, or knowledge. "Indirectly acquiring" refers to receiving the physical entity, value, or knowledge from another party or source (e.g., a third party laboratory that directly acquired the physical entity, value, or knowledge). Directly acquiring a physical entity includes performing a process that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Directly acquiring a value or knowledge includes performing a process that includes a physical change in a sample or another substance. Examples include performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent.

As used herein, the term "obese" refers to a subject having a body mass index (BMI) within the ranges defined as "obese" by the Center for Desease Control (see, e.g., URL.cdc.gov/obesity/defining.html and www.cdc.gov/obesity/childhood/defining.html, last accessed on Aug. 19, 2015) or as defined by "Clinical Guidelines on the Identification, Evaluation, and Treatment of Overweight and Obesity in Adults" from the National Institutes of Health. BMI is obtained by dividing a subject's weight, e.g., in kilograms (kg) by the square of the subject's height, e.g., in meter (m). For example, an adult who has a BMI of 30 kg/m$^2$ or higher is considered obese. For example, an adult with a BMI of 25.0 to 29.9 kg/m$^2$ is considered overweight; an adult with a BMI of 18.5 to 24.9 kg/m$^2$ is considered to have a normal or healthy weight range; and an adult with a BMI of less than 18.5 kg/m$^2$ is considered to be underweight. For example, an adult having a height of 5 feet, 9 inches with a body weight of 203 pounds or more is considered obese. For children and teens, obese refers to a subject having a BMI at or above the 85th to 95th percentile for children and teens of the same age and sex.

A "severely obese" subject or a subject having "severe obesity" refers to a subject having a BMI of 35 kg/m$^2$ or higher, e.g., 40 kg/m$^2$ or higher. For example, a severely obese subject is over 100% over the ideal (normal, healthy) body weight.

As used herein "early onset", e.g., as in early onset obesity, refers to an onset (e.g., first occurrence of one or more symptoms of a disorder, e.g., a disorder described herein, e.g., obesity, PWS, POMC-null obesity) that occurs in a subject before adulthood, e.g., during childhood, e.g., when the subject is less 18 years of age or younger (e.g., 18, 17, 16, 15, 14, 13, 12, 11, 10, 9, 8, 7, 6, 5, 4, 3, 2, or 1 year of age or younger, or during adolescence, e.g., when the child is younger than 12 years of age or when the child is younger than 6 years of age).

As used herein, the term "metabolic syndrome" refers to a group of symptoms that occur together and increase the risk for coronary artery disease, stroke, and type 2 diabetes. According to the American Heart Association and the National Heart, Lung, and Blood Institute, metabolic syndrome also referred to as Syndrome X) is present if a subject has three or more of the following signs:

1) Blood pressure equal to or higher than 130/85 mmHg;
2) Fasting blood sugar (glucose) equal to or higher than 100 mg/dL;
3) Large waist circumference (length around the waist):
   Men—40 inches or more;
   Women—35 inches or more;
4) Low HDL cholesterol:
   Men—under 40 mg/dL;
   Women—under 50 mg/dL;
5) Triglycerides equal to or higher than 150 mg/dL.

Metabolic syndrome can be diagnosed by testing subject's blood pressure, blood glucose level, HDL cholesterol level, LDL cholesterol level, total cholesterol level, and triglyceride level.

As used herein, the term "agonist" refers to any chemical compound, either naturally occurring or synthetic, that, upon interacting with (e.g., binding to) its target, e.g., MC4R, raises the signaling activity of MC4R above its basal level. An agonist can be a superagonist (i.e. a compound that is capable of producing a greater maximal response than the endogenous agonist for the target receptor, and thus has an efficacy of more than 100%), a full agonist (i.e. a compound that elicits a maximal response following receptor occupation and activation) or a partial agonist (i.e. a compounds that can activate receptors but are unable to elicit the maximal response of the receptor system).

As used herein "treating" includes achieving one or more of the following results: reducing the body weight (as measured, for example, by a body mass index (BMI) and/or body weight), e.g., compared to a control (e.g., body weight before treatment or a predetermined body weight); reducing the waist circumference, e.g., compared to a control (e.g., waist circumference before treatment or a predetermined waist circumference); reducing the hunger level, e.g., compared to a control (e.g., hunger level before treatment or a predetermined hunger level); increasing the resting energy expenditure (REE), e.g., compared to a control (e.g., REE before treatment or a predetermined REE); decreasing the food intake, e.g., compared to a control level (e.g., before treatment or a predetermined food intake); ameliorating or improving a clinical symptom or indicators associated with a disorder described herein such as obesity, PWS, POMC-null obesity, e.g., type-II diabetes, pre-diabetic condition, blood level of haemoglobin A1C (Hb1Ac) above 6%, hyperinsulimenia, hyperlipidemia, insulin insensitivity, or glucose intolerance; delaying, inhibiting or preventing the progression of obesity and/or obesity related indications; or partially or totally delaying, inhibiting or preventing the onset or development of obesity or a obesity related indication. Delaying, inhibiting or preventing the progression of the obesity includes for example, delaying, inhibiting or preventing the progression of a subject having normal weight to obesity. In embodiments, a control is a value of a parameter measured before treatment by a MC4R agonist described herein or a predetermined value. The term "treating" further includes partially or totally reducing the risk for coronary artery disease, stroke, and type 2 diabetes associated with the metabolic syndrome as well as ameliorating or improving a clinical symptom or signs of metabolic syndrome associated with metabolic syndrome, such as any one or more of the five indicators listed above. For example, the term "treating" includes delaying, inhibiting or preventing the progression of parameters associated with the metabolic syndrome, including insulin resistance, glucose clearance and parameters of cardiovascular disease including heart rate and blood pressure.

As used herein "inhibition" or "inhibits" can include a reduction in a certain parameter, such as a parameter described herein. For example, inhibition of a parameter, e.g., activity, can be at least 5%, 10%, 20%, 30%, 40%, or more is included by this term. Thus, inhibition need not be 100%.

"Prophylactic treatment" refers to treatment before onset of obesity to prevent, inhibit or reduce its occurrence.

As used herein, the term "subject" refers to a mammal, e.g., a human. Subject can also refer to an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

As used herein, the term "mutation" can refer to an altered nucleic acid sequence of a gene or fragment thereof compared to a wild-type sequence. For example, a mutation can include a point mutation, frame-shift mutation, missense mutation, inversion, deletion, insertion, truncation, chromosomal translocation. In embodiments, a mutation can result in the gene or fragment thereof coding for a non-functional protein, a protein with reduced activity (or a partially functional protein), or a protein with altered activity. For example, a "loss of function" mutation refers to a mutation that results in the gene or fragment thereof coding for a non-functional protein, which has substantially reduced activity compared to its wild-type counterpart (e.g., a non-functional protein has less than 10%, 9%, 8%, 7%, 6%, 5%, 4%, 3%, 2%, 1% or less activity than its wild-type counterpart). For example, "partial loss of function" mutation refers to a mutation that results in the gene or fragment thereof coding for a partially functional protein, which has reduced activity compared to its wild-type counterpart (e.g., a partially functional protein has less than 50% and greater than 10% of the activity of its wild-type counterpart).

As used herein "heterozygous" refers to the presence of two different alleles (having different nucleic acid sequences) for a given gene in a subject. In some embodiments, "heterozygous mutation" can refer to the presence of a mutation on one allele for a given gene and the lack of a mutation on the other allele of the same gene in a subject (e.g., one mutant allele and one wild type allele for a given gene). In other embodiments, a "heterozygous mutation" can be a "compound heterozygous" mutation, which refers to the presence of a mutation (e.g., loss of function mutation or partial loss of function mutation) on one allele for a given gene and a different (e.g., loss of function mutation or partial loss of function mutation) on the other allele for the same gene (e.g., two different alleles that are both mutated, e.g., non-functional or partially functional). In embodiments, where a compound heterozygous mutation includes two non-functional alleles, the genotype can be a null genotype or functionally deficient genotype.

As used herein "homozygous" refers to the presence of two identical alleles for a given gene. In some embodiments, a "homozygous mutation" refers to the presence of two mutant alleles for a given gene, where the two mutant alleles are identical.

As used herein "null genotype" refers to the presence of two non-functional alleles of a gene in a subject.

As used herein "unit dosage" refers to a physically discrete unit suited as unitary doses for a subject to be treated. Each unit contains a predetermined quantity of active compound calculated to produce the desired therapeutic effect in association with the required pharmaceutical carrier.

As used herein "dosage" refers to a quantity or amount of a therapeutic agent. In some embodiments, a dosage is the amount administered to the subject in a single administration, e.g., in a single injection, a single infusion, or single administration of one or more unit dosages. In embodiments, a dosage is the amount administered to the subject in multiple administrations, e.g., multiple injections, multiple infusions, or multiple administrations of one or more unit dosages. In other embodiments, a dosage can refer to the total amount administered to the subject in a certain time period, e.g., per day. In such examples, the dosage is typically referred to as "daily dosage" or dosage in terms of quantity per day.

As used herein "hunger" or "hunger level" refers to a subject's appetite, desire to consume food, or perceived need for food. In embodiments, the hunger or hunger level of a subject can be quantified by using a scale to obtain a hunger score. In embodiments, the scale for hunger assigns a higher score for a subject that more frequently (e.g., often or always) feels unbearable hunger and a lower score for a subject that less frequently (e.g., sometimes or never) feels unbearable hunger. See, e.g., Sibilia. Psychologicol Topics 19 (2010), 2, 341-354. For example, a Likert scale for hunger can be used that assigns scores from 0 to 10 points (0=no hunger; 10-severe hunger). In other examples, a Likert scale for hunger can be used that assigns scores from 1 to 4 points, where a subject who never feels unbearable hunger is assigned a score of 1, where a subject who sometimes feels unbearable hunger is assigned a score of 2, where a subject who often feels unbearable hunger is assigned a score of 3, and where a subject who always feels unbearable hunger is assigned a score of 4. See i.d.

POMC-MC4R Pathway

The melanocortin system, which includes melanocortins (MCs), agouti, agouti-related proteins, and their receptors, integrate hormonal, metabolic, and neural signals in order to control energy homeostasis and regulate appetite, energy expenditure, and body weight. The MCs, which include alpha-melanocyte-stimulating hormone (α-MSH), β-MSH, γ-MSH, and ACTH, are a family of peptide hormones that are derived from a precursor protein called pro-opiomelanocortin (POMC). Activation of MC4 receptor (MC4R) in the POMC-MC4R pathway increases energy expenditure and decreases food intake. See, e.g., Fan et al. Nature 1997; 385:165-68. The POMC-MC4R pathway includes a number of proteins, such as melanocortins (MCs), MC4 receptor (MC4R), POMC, Proprotein Convertase Subtilisin/Kexin Type 1 (PCSK1, also called PC1/3), MAGE-like-2 (MAGEL2), leptin receptor (leptin-R), leptin, 5-hydroxytryptamine (serotonin) receptor 2C, G protein-coupled (5-HT2c receptor), nescient helix loop helix 2 (NhHL2, also called NSCL2), pro-hormone convertase, carboxypeptidase E (CPE), and single-minded 1 (Sim1), that together contribute to the regulation of energy homeostasis, e.g., by regulating appetite and energy expenditure. MC4R and other components of the POMC-MC4R pathway have a significant role in weight regulation. A mutation of the MC4R gene was reported to result in early-onset and severe obesity. It is believed that other genetic defects in the POMC-MC4R pathway likely also lead to early-onset and severe obesity.

MC4R hMC4R is a protein encoded by a genomic sequence having GenBank accession number CH471077.2.

Mutations in the MC4R receptor are an associated cause of severe childhood obesity. The carrier prevalence for MC4R mutations in a juvenile-onset obese population has been noted to be around 2.5% with a highest prevalence of 6% among severely obese children. Humans with MC4R mutations show a more or less similar phenotype as has been described for mice with mutations in the MC4R gene. MC4R deficient patients show hyperphagia, hyperinsulinaemia, increased fat mass, accompanied by lean body mass, bone mineral density and linear growth rate increases, with no changes in cortisol levels, gonadotropin, thyroid and sex steroid levels. In contrast to MC4R deletion, hyperphagia and hyperinsulinaemia tends to subside with age in human subjects. Similar to the MC4R knockout mice, the phenotype in heterozygote carriers is intermediate in comparison to homozygote carriers. The exhibited hyperphagia observed upon a test meal is less severe than that observed in people with a leptin deficiency. The severity of MC4R dysfunction seen in assays in vitro can predict the amount of food ingested at a test meal by the subject harboring that particular mutation and correlates with the onset and severity of the obese phenotype. At east 90 different MC4R mutations have been associated with obesity and additional mutations in the MC4R are likely to be discovered, leading to a similar obesity phenotype.

Examples of the MC4R mutations that cause obesity in humans are described, e.g., in Farooqi et al., *The Journal of Clinical Investigation*, July 2000, vol. 106 (2), pp. 271-279 and Vaisse et al., *The Journal of Clinical Investigation*, July 2000, vol. 106 (2), pp. 253-262, the relevant portions of which are incorporated herein by reference).

Additional mutations that potentially cause obesity in humans include, R18H, R18L, S36Y, P48S, V50M, F51L, E61K, 169T, D90N, S94R, G98R, I121T, A154D, Y157S, W174C, G181D, F202L, A219 V, I226T, G231S, G238D, N240S, C271R, S295P, P299L, E308K, 1317V, L325F, and 750DelGA, as described in Xiang et al., "Pharmacological characterization of 30 human melanocortin-4 receptor polymorphisms with the endogenous proopiomelanocortin-derived agonists, synthetic agonists, and the endogenous agouti-related protein antagonist." Biochemistry, 2010 Jun. 8; 49(22):4583-600, the relevant portions of which are incorporated herein by reference.

Further examples of mutations that potentially cause obesity in humans are those listed in Online Mendelian Inheritance in Man (OMIM), a database of human genes and genetic disorders, under the accession number 155541 (MC4R) (more precisely, accession nos. 155541.0001-155541.0023) at the URL http://omim.org/entry/155541. Representative examples include 4-BP DEL, NT631; 4-BP INS, NT732; TYR35TER; ASP37VAL; SER58CYS; ILE102SER; ASN274SER; 1-BP INS, 112A; 4-BP DEL, 211CTCT; ILE125LYS; ALA175THR; ILE316SER; TYR287TER; ASN97ASP; 15-BP DEL (delta88-92 codons); and SER127LEU. The relevant portions of the OMIM database are incorporated herein by reference.

Additional exemplary mutations in MC4R are described in Lee. Annals Acad. Med. 38.1(2009):34-44.

In example embodiments, the MC4R mutation results in retention of the MC4R signaling activity.

Mutations in the genomic sequence encoding MC4R can be detected by the methods that are known to a person of ordinary skill in the art. For example, the genomic sequence can be cloned using nucleotide primers, such as e.g., the primers described in Farooqi et al., The Journal of Clinical Investigation, July 2000, vol. 106 (2), pp. 271-279 and Vaisse et al., The Journal of Clinical Investigation, July 2000, vol. 106 (2), pp. 253-262, and the cloned sequence analyzed using commercially available sequencers and software.

Activity of MC4R can be measured by the methods known to a person of ordinary skill in the art. For example, cells can be transiently transfected with the cloned MC4R DNA, the transfected cells contacted by an agonist of MC4R (e.g. α-MSH), and the intracellular level of cAMP, the secondary messenger of MC4R, measured by an electrochemiluminescence assay described, e.g., in Roubert et al., Journal of Endocrinology (2010) 207, pp. 177-183. A reduction in MC4R signaling can be ascertained by comparing the intracellular level of cAMP produced in response to a given agonist by a wild type MC4R to that produced by a mutant MC4R.

POMC

POMC is a component of the POMC-MC4R pathway that acts upstream of the MC4R. POMC is a precursor protein that is cleaved by pro-hormone convertases to generate multiple peptide hormones (e.g., alpha-MSH, ACTH, beta-endorphin, and enkephalin). Convertases that process POMC polypeptides include prohormone convertase 1 (PC1, also called PC1/3 or PCSK1), prohormone convertase 2 (PC2), carboxypeptidase E (CPE), peptidyl α-amidating monooxygenase (PAM), N-acetyltransferase (N-AT), and prolylcarboxypeptidase (PRCP).

The POMC gene is located on human chromosome 2p23.3, and the gene sequence is provided in GenBank Accession No. NG_008997.1, incorporated herein by reference. An exemplary nucleic acid sequence of human POMC mRNA transcript variant X1 is provided in GenBank Accession No. XM_011532917.1, incorporated herein by reference. An exemplary amino acid sequence of human POMC isoform X1 is provided in GenBank Accession No. XP_011531219.1, incorporated herein by reference. An exemplary nucleic acid sequence of human POMC mRNA transcript variant 1 is provided in GenBank Accession No. NM_001035256.1, incorporated herein by reference. An exemplary amino acid sequence of human POMC pre-proprotein is provided in GenBank Accession No. NP_001030333.1. An exemplary nucleic acid sequence of human POMC mRNA transcript variant 2 is provided in GenBank Accession No. NM_000939.2, incorporated herein by reference. An exemplary amino acid sequence of human POMC pre-proprotein is provided in GenBank Accession No. NP_000930.1.

POMC neurons, which express POMC, provide an anorexigenic effect, where secretion of POMC neuropeptides from the POMC neurons decreases body weight and food intake. Loss of function mutations of the POMC gene have been reported to result in obesity, red hair, and adrenal insufficiency. For example, defects in POMC (e.g., loss of function mutation(s) or hypermethylation) have been associated with obesity and ACTH deficiency. See, e.g., Mendiratta et al. Intl. J. Ped. Endocrinol. 2011:5; and Kuehnen et al. PLOS Genetics. 8.3(2012):e1002543. A homozygous codon 231 cytosine to adenosine (c.231C>A) change in POMC has been reported to result in a premature termination codon, causing loss of function of POMC, which was associated with extreme weight gain, congenital adrenal insufficienty, and hypoglycemia. See, e.g., Mendiratta et al. Intl. J. Ped. Endocrinol. 2011:5. In embodiments, exemplary mutations in POMC are described in Lee. Annals Acad. Med. 38.1(2009):34-44.

In embodiments, exemplary mutations in POMC are described in Table 1 below. In embodiments, homozygous and/or heterozygous (e.g., compound heterozygous) mutations from Table 1 are contemplated.

TABLE 1

Examples of loss of function POMC heterozygote (POMC+/−) Variants*

| Variants* | Reference | Function |
|---|---|---|
| Cys28Phe | J Clin Endo 2008; 93; 4494 | |
| Leu37Phe | J Clin Endo 2008; 93; 4494 | |
| | Cell Met. 2006; 3; 135 | |
| His143GLu | Cell Met. 2006; 3; 135 | Alpha-MSH loss of function |
| Phe144Leu | Ped Res. 2008; 63; 2; 211 | Alpha-MSH loss of function |
| Tyr221Cys | Cell Met. 2006; 3; 135 | Beta-MSH loss of function |
| | Cell Met. 2006; 3; 135 | |
| | Cell met. 2006; 3; 141 | |
| Pro231Leu | Clin Chem 2005; 51(8); 1358 | Beta-MSH likely loss of function |
| Arg236Gly | Hum Mol Gen. 2002; 11; 1997 | Beta-endorphin loss of function |
| | Hum Mol Gen. 2002; 11; 1997 | |
| Glu244X | Clin Chem 2005; 51(8); 1358 | |

*Amino acid numbering corresponds to that of the protein including the signal peptide, as described in Takahashi, et al. 1981 Febs Letters 135(1)97.
X indicates early termination.

In certain embodiments, e.g., as referred to in Table 1, the POMC amino acid sequence is that described in Takahashi, et al. 1981 Febs Letters 135(1)97, copied below (where the 26-amino acid signal peptide is underlined).

(SEQ ID NO: 563)

<u>MPRSCCSRSG ALLLALLLQA SMEVRG</u> WCLE SSQCQDLTTE

SNLLECIRAC KPDLSAETPM FPGNGDEQPL TENPRKYVMG

HFRWDRFGRR NSSSSGSSGA GQKREDVSAG EDCGPLPEGG

PEPRSDGAKP GPREGKRSYS MEHFRWGKPV GKKRRPVKVY

PNGAEDESAE AFPLEFKREL TGQRLREGDG PDGPADDGAG

AQADLEHSLL VAAEKKDEGP YRMEHFRWGS PPKDKRYGGF

MTSEKSQTPL VTLFKNAIIK NAYKKGE

In certain embodiments, e.g., as referred to in Table 1, the POMC gene nucleotide sequence is that described in Takahashi et al. Nucl Acids Res. 1983, 11(19)6847, e.g., provided in GenBank Accession No. V01510.1 and copied below.

(SEQ ID NO: 564)

```
   1 ctgctcttca cagcatcacc ctctccccat ttaatggttt aggttaacag gactttttcc
  61 ttgaggcttg ggacacggaa gggagcctcc cctaaaccag gcccttggag agcaggcccc
 121 aggggagcag tgcaactcac cttcacaccc acaagacggc tcctgacttc tgctccctcc
 181 tccctcccc aaagtggaac agagagaata tgattcccca cgacttccac atcacagttt
 241 ccaaacaatg gggaaatcgg aggcctcccc gtgtgcagac ggtgatattt accgccaaat
 301 gcgaaccagg cagatgccag ccccagcacg cacgcaggta acttcaccct cgcctcaacg
 361 acctcagagg ctgcccggcc tgccccacac gggggtgcta agcctcccgc ccgttctaag
 421 cggagaccca acgccatcca taattaagtt cttcctgagg gcgagcggcc aggtgcgcct
 481 tcggcaggac agtgctaatt ccagcccctt tccagcgcgt ctccccgcgc tcgtccccg
 541 tctggaagcc cccctcccac gccccgcggc ccccttccc ctggcccggg agctgctcc
 601 ttgtgctgcc gggaaggtca aagtcccgcg cccaccagga gagctcggca agtatataag
 661 gacagaggag cgcgggacca agcggcggcg aaggagggga agaagagccg cgaccgagag
 721 aggccgccga gcgtccccgc cctcagagag cagcctcccg agacaggtaa gggcgcagcg
 781 tgggggaccc gtgctctttc cccgggatcc cctgtcccg tcctcgcgat gcagtcggcc
 841 ggctccggct ccgaaggcgg acctgggcgc ctctggctct ccgcggtccc gagttctcga
 901 caaactttct gcgccgactg cggcatgaga agccgccagt agctgagctg gagggcccac
 961 gtccggcccc tgggcggacg gccgcgaagc tgcaggcgct gtctccaggg agccggcggc
1021 ctcctctccc caggggctc gcggcggtcc ggaggctccg agagcttgct aggaggtctt
1081 gggacaaccc ggtcttttt tttttttttg agacggagtt tcgctcttgt tgcccatgct
1141 ggagagcaaa ggggtgatct ctgctcaccg caaccttcgc ctcccgggtt caagcgattc
1201 tcctgcttca gcctcccgag tagctgggat tacaggcatg cgccaccacg cccggctaat
1261 ttttgtattt ttagtagtga cggagtttct ccatgttggt caggctggtc tcaaactccc
1321 gacaacaggt gatccgcccg ccttggcccc caaagttct ggcattacag gcgcgagcca
1381 ccgccccgg ccagcccggt cttttagtat ctcttgctcc cagtttccag gataggtgtc
```

-continued

```
1441 acatcttgaa agtcaaattc catacacgct atcgcaaatt aatgttggaa acggggcagc
1501 agagaaaagg ataaaagtca taatgaacgc cctgccttcc ggattttttc ggattcagac
1561 ccctgaatcc ttgtttcctt gcccaccttg gcgcacccga ggtggccgcg ctatgataat
1621 tacatgataa ctgggtcaat tacaatgcag aatagttggg tctcttctct ccaagaccta
1681 gctggggtta aaacaggtg gccggggcgg gagctgtcct agatcctgaa acgcactgtc
1741 tagtttcgga tgccctcaac agaaccgggg tggacggttt atggcgcaga tcctgggttg
1801 agggcacggg cagccatttg aatgatcaa ggctcaggta aggggcgttt ccagcgaagg
1861 agagacagtc cacttggcat ttggattccc caaattcttc atgtttaaat ggggcaggga
1921 gggttcttac agaatggctg aaggagcca aggaaaataa aagtgtgtgt ggatttttt
1981 tgtgtgtgtg tcagtttata aactctgcac agattatggc cactttaatg acttactgtt
2041 cctttgatgc ttttgttata ggactcgatg catgtatgtc atggtgtaag acaaaactc
2101 ggccctgtg ctcctctaat ctttacaaaa ggtcatggcc agcgtgcagt ttacagtaa
2161 caagcaaaat gatttgttga gctcatagag agcccctcac acctatgaag ttctaataag
2221 tgtagttcta ctataaagtt aatctcagga tgagcaaatt tcaagtttct atttttccag
2281 agctttccat ttttggatta taatactttc cctacttaaa aaagcacaac atttgatatt
2341 tccccaataa tttgttgctt taaaaatgac acaaaaggta ctatttgttc attgtagaga
2401 actgaaaata cacataagca aatacacata cacataagca aaatatacaa tacaaacaca
2461 agaccatctt tcagggaaga atctgaagtt ttagcaatag cagccatcta accagtttag
2521 caacagaata taagctctga gagggtggga gtgaatatgt taccacattg tacaacacag
2581 cacatagggc ataaggaggg gaaatgctct ctggggcttt ccaggaaggc ctgaagtcat
2641 tgcttctagc aaatggaaat cactccagag tagttatctt tgacaagaat tgaaatataa
2701 ttgagggaac tatcagacct gtaagatttt gttttttcct ttactaatat gttactttac
2761 atttgcattt ggtgacatac gtaactacca tttttctgtg actgtaacat ctgggcattt
2821 ttcagagcta aatgtgctat ggtcaacttg gagctttaat ctaattgcct ggtccaccaa
2881 gttctggctg tgtacttgaa tagatcactg gcagggtaca atgggaacag cctgtcccctt
2941 ggagccagga aggacacca aggttgacca aagctcgttc agttgcccct ttagccgaag
3001 cgcacctggg ccagtcactg gctgccagtg ccatctaatg gctgctctga aaatgctcag
3061 ccttgcccgg caacccttca gaagctagca ccgtgcaggc ccagcgcctg gggaataggg
3121 cgagggtggg gtagagagaa ggaagtggcc tcctgaagta gaaatcagcg cttcagagga
3181 ctttcacttc caaagcctcc cctatataaa aaagatttgg cccacgcctc cccaaatgag
3241 agatttattt taggcaaact tattttaaaa tgccagcgtt cattaggagt gacaagacac
3301 ttagtcatcc acgctttaat gtgaattact tttctcatct aattacattt ctttctagca
3361 gctggctgag aagatcttct gaaatccaaa atgattgtag ggttggcggt gagctgatct
3421 ccggcctcga ggtggcttca gggggcccac ctggttaagg gaaatttggc agtgcgaggg
3481 tagtgctgga gagaggggtg ggtacagggg gctaggggca ccatggatgc cccctcctta
3541 ctgtcccctg gtgtcttgac ctcagcttct gcccacaggc acttgctgga ttctccaaaa
3601 gtatctgcag tggctgttcc accaggaggt aattcccttc tggtctcttt ccctccaca
3661 tctgcatcct cttcaaatcc tgccatttca gaccacattt gagagctcta gagaacaaga
3721 catctgacac gtgacgtgtc cagaagatga gccagatttc aaagaactga gatctgcttt
3781 aaaaacgaag ctctccaaag ttactggagt ctgggtaata gtgatcacca gagtaatttg
```

-continued

```
3841 tgtgcaggac atcaaatcag gctgctcgaa atgctgccta aattggccag tggttttatt
3901 tgcttttctg tcaacctaat attcatagga aatagagttt cagaggaatg ataggatcct
3961 ggtggaataa aaagggaaaa gaccatcttg agcaggagtt tcagggtcct ccgttttttcc
4021 caagttactt tcactcctga gatcttgcat gttagaacta cagcttaatg tagtgaaata
4081 ggaaagttct ctgttaggag cttagcctta ccttgtcatg gacattaaag taattgtctc
4141 tctttgggct tcaattttcc catctctcat gggaagggct gaaccaagca atccccaaaa
4201 tagcttccag ccttaacctt tttaggggtc tcgtttaaat agaagataac agggaaatgg
4261 tcacagttta cccaggtcca ttccctcctc cttatcacaa cttataccac cgctgtactg
4321 cacacctcct ttctcagcat tgctgctgtc cttaaaatgc ctttaactcc acaagagagt
4381 gtgttgttaa tgttggctca aggtccttcc tggtgagtgg ccaacattgt tttgctcctt
4441 gcagggtcc caccaatctt gtttgcttct gcagagcctc agcctgcctg gaagatgccg
4501 agatcgtgct gcagccgctc gggggccctg ttgctggcct tgctgcttca ggcctccatg
4561 gaagtgcgtg gctggtgcct ggagagcagc cagtgtcagg acctcaccac ggaaagcaac
4621 ctgctggtac gtgggccatg actgccatct tggcttagac attagatggg actggagctg
4681 ggaaagctca aagaaaagg gtgtggggaa agggaaattc attcccagtg ataggcgtga
4741 ttcaatccag ggcaggagca aaactttgca gtgaagtaag aaatgggaga agaaatcagg
4801 gaaggaagca gcttcaggga gaggggttga gtccacaatt tctgcttggt tatccttact
4861 tcttgcccca tcttttatgg agaccttgaa ccctttaagc tagagatggt gctataagag
4921 caataatgga cccctcaatc tattctgtac tttacatctt tagcttccca aactattcct
4981 ttttaagaag ctcatatcac ttgccatttt cattccatat ttcttaccct tttatctact
5041 accggttgca aaaccagcca ggtagttctt caaatcatct ctggaagaag gaaaaccag
5101 gggccctttt tttttttttct ttaattggtg ccaaatgtct catgtttatt ctggaggact
5161 ggccttctgc tgtgttcctc tacagtcttt ccagagcatg tgaaggcctt tgcatcaggc
5221 aggagctccc tccaggtcac cacagggtgt atgtatctgc ctgtggggg tgtgtgtgtg
5281 tgtgtgttgg ggggcataaa tgagtaatga tgccaaatcc agagattaaa aggcacactg
5341 agaccaggcg agatggctca tggctgtaat cccagcactt ttagatgcta aggtgggagg
5401 attgcttgag cccagggatt caagacaagc ctgggcaaca tagtgagacc tccacttcta
5461 caaaaataa aaaagttagc cagatgtggt ggcatgtgcc tgtagtccta gctacttggg
5521 aggttcactt gaggccagga gtctgacgac acagtaagct atgatcacac cattgcactc
5581 cagtctgggt aacagaatga gaccttgtct caaaacaaaa caaaatgaaa caaacaaaca
5641 aacaaacccc catactgtta gtgtcagtga ccggaatttt aatcttgttg ccatcacctg
5701 gcaggtgctg agggtggaat gtacataact acattctgtg tattttgtca atgcagaagc
5761 tgagttaagg tgaagataga atgaggtcct caaagacaca gaccagtttt catgtgtaat
5821 ataaaataga aacaaagagc ccaggggatt ctgtgagttc cagtttggaa agacccaaga
5881 gtctcttgac ttgagacacc cacagcacag ctcaccaggg agggtgcact ggacacagtc
5941 aggacccatg ggttctagac ccagttttga ggtgtgggac cttgaccagg tcctatcacc
6001 tctctgagtc tcctgtttca ctatctgtcc acgggagggg agtgtaaatt agttttttcc
6061 attgttaacg ttcacagag ttgtaattct gaacacctgg agtaggcaat gtccagctca
6121 acagagtggg taggatcctt ttattttctc ctttgctatt cccaagaaag agagcagcca
6181 gtgagctttt catcttttta tcactgaaaa ctcaaggctg cagcctatgc agccattttc
6241 ctaagctaat atgtaccaca atagagtcct ctagggacaa ggagcagaga cacaggttcc
```

-continued

```
6301 acagacggtg caatggaaat aacgctagct ttccacccct ccctccagtc agaatgagat
6361 tacagggaaa taagcttgcc ccagagctca ctggggatc tctcagaaat cagctcagaa
6421 gtcgtgaaag aaccaaggtg cagttttgga ggcttagtgc agagatggag ctggggtagg
6481 gcataaagta ggttttccat cactgaggta aggttgaggc attatttttt atttttgtt
6541 tatttattta ttttttgag acggagtctc gctctatcac ccaggctgga gtgcagtggc
6601 gcgatctccc ctcactgcaa gctccacctc ccaggttcac acaggttgaa gcattattaa
6661 aaatatgttt aaaaatatgg gccctagtag ccagacttct atcacctgga gagattatcc
6721 cccaaatttc agcccactc ccctcctgga cttgaattaa accatatgta tttattcaat
6781 attcttttta tttatttatt tattttttg agacggagtc ttgctctgtt gccctggctg
6841 gagtgtggag tgcagtggtg tgatcttggc tcactgcaac ctctacctcc caggttcaag
6901 cggttctcct gcctcaggct ccagagtagc tgggattaca ggcgcccgcc accacaccca
6961 gcttatttat ttatttatac tagagatggt atttcaccat agttggccag ctggtcttg
7021 aactcctgac ctcatgtgat ctgcctgcct tggcctccca aagtgctggg attataggtg
7081 tgagccacca tgcccggccc tcaatattca ttaagtgcca caactacca cccgtctgcc
7141 tttcttggag ccactccttt atgtcaggca tatgacagta agactttggt cctgttcaca
7201 aaagctaggg gtggctagat ggctagacaa accatggaat gggatgggaa gtgtgttgca
7261 gttgccagca gaagcatgaa ggggatggga caaagaggc ggtggcaaga tcttagatgc
7321 ccacgagtgc caagaaagca ggtgggcaga cctgctctgt agggaggcct cgacgcttga
7381 cacgcccgac actgtgccct gtgtcctcgg cacgtggcga gggcggccag ggcctaggcg
7441 cagtgacggg cgcggcagcc gggccggggt gcggggcacg ggctgccctc atgccctcgc
7501 gtcttccccc aggagtgcat ccgggcctgc aagcccgacc tctcggccga gactcccatg
7561 ttcccgggaa atggcgacga gcagcctctg accgagaacc cccggaagta cgtcatgggc
7621 cacttccgct gggaccgatt cggccgccgc aacagcagca gcgcggcag cagcggcgca
7681 gggcagaagc gcgaggacgt ctcagcgggc gaagactgcg gcccgctgcc tgagggcggc
7741 cccgagcccc gcagcgatgg tgccaagccg ggcccgcgcg agggcaagcg ctcctactcc
7801 atggagcact ccgctgggg caagccggtg ggcaagaagc ggcgcccagt gaaggtgtac
7861 cctaacggcg ccgaggacga gtcggccgag gccttccccc tggagttcaa gagggagctg
7921 actggccagc gactccggga gggagatggc cccgacggcc ctgccgatga cggcgcaggg
7981 gcccaggcca cctggagca cagcctgctg gtggcggccg agaagaagga cgagggcccc
8041 tacaggatgg agcacttccg ctgggcagc ccgcccaagg acaagcgcta cggcggtttc
8101 atgacctccg agaagagcca gacgcccctg gtgacgctgt tcaaaaacgc catcatcaag
8161 aacgcctaca gaagggcga gtgagggcac agcgggcccc agggctaccc tcccccagga
8221 ggtcgacccc aaagcccctt gctctcccct gccctgctgc cgcctcccag cctgggggt
8281 cgtggcagat aatcagcctc ttaaagctgc ctgtagttag gaaataaaac ctttcaaatt
8341 tcacatccac ctctgacttt gaatgtaaac tgtgtgaata agtaaaaat acgtagccgt
8401 caaataacag cagcatggat cggaggagca cagtggtttc catgcggtag gatatttcac
8461 aggacttagt gagcgtgaaa ggaaaatgtg cttcctgccc ccaccccaa atggatcttc
8521 gagggatcag atagtttggg tgaaggcaca gggtggctcc agcacctcta ggatggccgt
8581 attttccaca cactccactg agtgggagac tgctcagcta gcacacgtgt aaaggcagga
8641 ttcctgcaag agtgaccc
```

In some embodiments, exemplary mutations in POMC, e.g., that lead to homozygous POMC deficiency, are described, e.g., in the references in Table 2, each of which are incorporated herein by reference.

TABLE 2

| Reference |
| --- |
| Aslan et al. International Journal of Obesity (2014) 38, 148-151 |
| Krude et al. J Clin Endocrinol Metab 88: 4633-4640, 2003) |
| Krude et al. Nature genetics volume 19 (June) 1998; 155-157. |
| Darcan S et al. Transient Salt Wasting in POMC-deficiency. Exp Clin Endocrinol Diabetes 2010; 118: 281-283 |
| Mendiratta et al. International Journal of Pediatric Endocrinology 2011, 2011: 5 |
| Farooqi et al. Diabetes 2006; 55(9): 2549-2553 |
| Clement et al. JCEM 2008; 93(12): 4955-4962. |
| Krude H, Grüters A: Implications of Proopiomelanocortin (POMC) mutations in humans: the POMC deficiency syndrome. Trends in Endocrinology and Metabolism 2000, 11(1): 15-22. |
| Hung et al. J Ped Endocrinol Metabol 2012; 25(1-2): 175-179 |
| Ozen et al. J Ped Endocrinol Metabol 2015; 28(5-6): 691-694 |
| Cirillo G, et al., Br J Dermatol. 2012; 167: 1393-5 |
| Samuels J Clin End Met, 2013, 98(2); 736-742 |

Additionally, hypermethylation of the POMC gene has been associated with childhood obesity. See, e.g., Kuehnen et al. PLOS Genetics. 8.3(2012):e1002543. A hypermethylation variant at a CpG island at the intron2-exon3 boundary of the POMC gene was significantly associated with obesity compared to normal-weight children. See i.d. It is believed that exon3 of POMC is involved in binding to the transcription enhancer P300, and hypermethylation in exon3 reduces expression of the POMC transcript. See i.d.

In yet other embodiments, an exemplary mutation in POMC includes one or more mutations described in one or more of the following: Aslan, Int J Obes (Lond). 2014 January; 38(1):148-51; Krude, Nature 1998; 19; 155-157; Krude, J clin Res Metab 2003, 88(10); 4633-4640; Samuels, J Clin Endocrin Metab, 2013; 98(2); 736-742; Clement, J Clin Endocrin Metab., 2008; 93(12); 4955-4962; Creemers, J Clin Endocr Metab, 2008, 93(11); 4494-4499; Cirillo, British Assoc Derm, 2012, 167; 1390-1400; ESPE poster Barcelona 2015, R Marina et al.; Farooqi, Diabetes 2006; 55; 2549-2553; Mendiratta, Int J Pediatr Endocrinol. 2011; 2011:5; A Meloni, et al., ESPE Poster Barcelona 2015; Hinney, J Clin Endocrin Metab, 1998, 10; 3737-3741; Lee, Cell Metabol., 2006; 3; 135-140 (PLOF); Dubern, Pediatric Res. 2008; 63(2); 211-216; Philippe et al. Int. J. Obes. 39.2.(2015):295-302; Bieberman, 2006; 3; 141-146; or Buono, Clin Chem, 2005; 51(8); 1358-1364; Challis, Hum. Mol. Genet. 11(17): 1997; Hum. Mol. Genet. 11(17): 1998, each of which is hereby incorporated by reference in its entirety.

PCSK1

Proprotein convertase subtilisin/kexin type 1 (PCSK1, also called PC1/3) is an enzyme that acts upstream of the MC4R in the POMC-MC4R pathway by processing (cleaving) prohormones such as POMC into their mature forms.

A heterozygous nonsense variant in PCSK1 (p.Arg80*), which encodes a propeptide truncated to less than two out of the 14 exons, has been reported to be associated with obesity in humans. See, e.g., Philippe et al. Intl. J. Obesity 39.2 (2015): 295-302.

The PCSK1 gene is located at cytogenetic location 5q15-q21 in humans. The human PCSK1 gene sequence is provided in GenBank Accession No. NG_021161.1, incorporated herein by reference. An exemplary nucleic acid sequence of human PCSK1 transcript variant 1 is provided in GenBank Accession No. NM_000439.4 (see, e.g., Hsiao et al. Gene 533 (1), 32-37 (2014)), incorporated herein by reference. An exemplary amino acid sequence of human PCSK1 isoform 1 is provided in GenBank Accession No. NP_000430.3, incorporated herein by reference. An exemplary nucleic acid sequence of human PCSK1 transcript variant 2 is provided in GenBank Accession No. NM_001177875.1, incorporated herein by reference. An exemplary amino acid sequence of human PCSK isoform 2 is provided in GenBank Accession No. NP_001171346.1, incorporated herein by reference.

In some embodiments, exemplary mutations in PCSK1, e.g., that lead to homozygous PCSK1 deficiency, are described, e.g., in the references in Table 3, each of which are incorporated herein by reference.

TABLE 3

| Reference |
| --- |
| Jackson et al (Cambridge). Nature Genetics 1997: 16 (June): 303-306 |
| O Rahilly et al. NEJM 1995: 333: 1386-1390 |
| Jackson et al. J. Clin. Invest. 112: 1550-1560 (2003). doi: 10.1172/JCI200318784 |
| Farooqi et al. J Clin Endocrinol Metab. 92: 3369-3373, 2007 |
| Martin et al. Gastroenterology 2013; 145: 138-148 |
| Yourshaw et al. J Pediatr Gastroenterol Nutr. 2013 December; 57(6): 759-767 |
| Frank et al (Farooqi). Molecular Genetics and Metabolism 110 (2013) 191-194 |
| Wilschanski et al. PLOS One October 2014; DOI: 10.1371/Journal.pone.0108878 |

In some embodiments, exemplary mutations in PCSK1, e.g., that lead to heterozygous PCSK1 deficiency, are described, e.g., in the references in Table 4, each of which are incorporated herein by reference.

TABLE 4

| Examples of loss of function PCSK1 heterozygote (PCSK1+/−) variants | Ref | Function |
| --- | --- | --- |
| Met125Ile Thr175Met Asn180Ser Tyr181His Gly262Arg Ser325Asn Thr558Ala | Diabetes 2012, Vol 61: 383 | All loss of function |
| Asn221Asp Gln665E-S690Thr | Nature genetics 2008, 40(8): 943 | Impacts PCSK1 Ca2+ binding |

In yet other embodiments, an exemplary mutation in PCSK1 includes one or more mutations described in one or more of the following: Martin, Gastroenterology 145:138-48, 2013; Creemers, Diabetes 61:383, 2012; Jackson, Nature Gen.: Jul. 16, 1997,p. 303; Martin, Gastroenterology 145: 138-48, 2013; Blanco et al. Endocrinology 156:3625-37, 2015; Jackson, J. Clin. Investigation 112:1550-51, 2003; Benzinou, Nat. Genetics 8:943, 2008; Yourshaw, Gastroenterology 57 (6): 759, 2013; Faroqi, J. Clin. Endocrinol. and Metab. 92:3369-73, 2007; Pickett, PLOS One 8: e55065, 2013; Bohours-Nouet, EXPE Poster at Barcelona 2015 PWS meeting; Graeme et al., Mol. Gen. Metabol. 110:191-94, 2013; Blanco et al. Endocrinology 155:3434-47, 2014;

Wilschansky PLOS ONE 9:108878, 2014; Frank, Mol. Gen Metabol. 2013; and Harter J. Pediatr. Gastroentrol Nutr. 2015, each of which is hereby incorporated by reference in its entirety.

MAGEL2

MAGEL2 (Melanoma Antigen (MAGE) Family L2, or MAGE-like protein 2) is believed to be involved in ubiquitin ligase activity of zinc finger-containing E3 ubiquitin-protein ligases and possibly in regulation of the circadian clock. MAGEL2 is a member of the MAGE family of proteins that are involved in pathways that modulate protein degradation, protein modification, transcription, and cytoskeletal rearrangements. See, e.g., Mercer et al. PLOS Genetics 9.1 (2013):e1003207.

In mice, MAGEL2 is expressed in the hypothalamus, including in the arcuate nucleus, which controls energy homeostasis. Mice lacking expression of the MAGEL2 gene (MAGEL2 null mice) have been reported to have poor weight gain early on followed by increased adiposity and weight gain. See, e.g., Mercer et al. PLOS Genetics 9.1 (2013): e1003207. Adult mice lacking MAGEL2 (MAGEL2 null mice) have been reported to exhibit defective anorexigenic responses to leptin and defective responses of POMC neurons to leptin. See, e.g., Pravdivyi et al. Hum. Mol. Genet. 2015, 1-8. Mice lacking MAGEL2 (MAGEL2 null mice) also had lower levels of alpha-MSH in the paraventricular hypothalamic nucleus. See i.d. In embodiments, exemplary MAGEL2 mutations, e.g., loss of function MAGEL2 mutations, are described in Schaaf et al Nat Genet. 2013 November; 45(11):1405-8. doi: 10.1038/ng.2776. Epub 2013 Sep. 29; and Soden et al. Sci Transl Med. 2014 Dec. 3; 6 (265):265ra168, each of which are incorporated herein by reference.

MAGEL2 is one of a number of genes inactivated in Prader Willi Syndrome (PWS). Inactivating mutations in MAGEL2 have been found in children having features of PWS. See i.d. A heterozygous c.1652delT (p.Val551fs) mutation in MAGEL2 (NM_019066.4) was reported in a 13 year old human subject. See, e.g., Schaaf et al. Nat. Genet. 45.11(2013):1405-09. A heterozygous c.1802delC (p.Pro601fs) mutation was also reported in an 8-year old human subject. See i.d. Also, a heterozygous c.3181_3182delAT (p.Ile1061fs) mutation was reported in a 5-year old human subject. See i.d. A c.3124C>T (p.Gln1024*) mutation was also reported in a 19-year old human subject. See i.d. PWS is described in greater detail below.

The human MAGEL2 gene sequence is NG_016776.1, incorporated herein by reference. An exemplary nucleic acid sequence of the human MAGEL2 transcript is NM_019066.4, incorporated herein by reference. An exemplary amino acid sequence of human MAGEL2 is NP_061939.3, incorporated herein by reference.

Leptin and Leptin-R

Leptin is a hormone produced by adipocytes that acts to inhibit hunger in order to regulate energy homeostasis—food intake, body weight, and glucose homeostasis. Leptin acts upstream of the MC4R in the POMC-MC4 pathway by binding to the leptin receptor (leptin-R, also called LEP-R, OB-R, or CD295). POMC neurons are involved in mediated leptin activity in the brain, and one effect of leptin binding to leptin-R is the stimulation of POMC expression. See, e.g., Varela et al. EMBO Reports 13.12(2012):1079-86. It has been reported that deletion of leptin-R in POMC neurons leads to obesity, an effect partly rescuable by overexpression of leptin-R in these leptin-R null mice. See i.d. Mutations of leptin (Lep ob/ob) or leptin-R (Lep db/db) have been reported to be associated with impaired glucose homeostasis and increased body weight in mice. See i.d. In addition, a fa/fa rat has been described to be leptin-R deficient. See, e.g., Cettour-Rose et al. Endocrinology: 2002; 143(6); 2277-2283.

Examples of mutant (e.g., non-functional) versions of leptin in humans have been described that have been associated with obesity. A homozygous frame-shift mutation that deleted a guanine nucleotide in codon 133 of the leptin gene was associated with severe obesity in some severely obese children. See, e.g., Montague et al. Nature 387.6636(1997): 903-8. A homozygous transversion (c.298G→T) in leptin led to an aspartate to tyrosine change at amino acid position 100 (p.D100Y) and was associated with early-onset extreme obesity (see, e.g., Wabitsch et al. N. Engl. J. Med. 372.1 (2015): 47-54). Homozygous Gln223Arg and homozygous Lys656Asn mutations in leptin-R have been associated with obesity in humans. See, e.g., Masuo et al. Hypertens. Res. 31.6(2008):1093-100. Additional exemplary mutations in leptin/leptin-R are described in Lee. Annals Acad. Med. 38.1(2009):34-44.

In some embodiments, exemplary mutations in leptin receptor (LEPR), e.g., that lead to homozygous leptin receptor deficiency, are described, e.g., in the references in Table 5, each of which are incorporated herein by reference.

TABLE 5

| Reference |
| --- |
| Farooqi et al., New Engl J Med, 356: 237-247; 2007 |
| Clement et al., Nature 392: 398-401, 1998. |
| Montague et al., Nature 387: 903-908, 1997 |
| Farooqi et al., J. Clin. Invest. 110: 1093-1103, 2002 |
| Gibson et al., J. Clin. Endocr. Metab. 89: 4821-4826, 2004 |
| Wabitsch et al., New Eng. J. Med. 372: 48-54, 2015. |
| Saeed et al., Obesity 2014; 22; 1112-1117 |
| Huvenne et al., J Clin Endocrinol Metab. 2015 Vol 100; issue 5: E757-766 |

In some embodiments, exemplary mutations in leptin receptor, e.g., that lead to homozygous leptin receptor deficiency, are described, e.g., in the references in Table 6, each of which are incorporated herein by reference

TABLE 6

| Examples of loss of function LEPR homozygote (LEPR−/−) variants | Ref | Function |
| --- | --- | --- |
| c.2396-1 G>T | Obesity 2014; 22(4); 1112 | Exon 15 splicing defect |
| c.1675 G>A | Obesity 2014; 22(4); 1112 | Nonsense mutation |
| p.Cys604Gly | J Clin Endocrinol Metab; | Likely LEPR loss |
| p.Leu786Pro | 2015; 100(5): E757 | of function |
| p.His800__Asn831del | | |
| p.Tyr422His | | |
| p.Thr711NfsX18 | | |
| P.535-1G>A | | |
| p.166CfsX7 | | |
| 4-bp del codon 22 | N Eng J Med. 2007; | Impaired LEPR |
| 11-bp del codon 70 | 356(3): 237 | signaling |
| 66-bp del codon 514 | | |
| Trp31X | | |
| Ala409Glu | | |
| Trp664Arg | | |
| His684Pro | | |
| 1-bp del codon 15/ | | |
| Arg612His | | |

Exemplary nucleic acid sequences of human leptin transcript are provided in NM_000230.2 and BC060830.1, incorporated herein by reference. Exemplary amino acid sequences of human leptin precursor are provided in NP_000221.1, AAH69452.1, AAH69527.1, AAH69323.1, AAH60830.1, incorporated herein by reference. Exemplary nucleic acid sequences of human leptin receptor are provided in GenBank Accession Nos. U66497.1, U66496.1, U66495.1, U43168.1, NM_001198689.1, NM_001198688.1, NM_001198687.1, NM_001003679.3, NM_002303.5, NM_001003680.3, incorporated herein by reference. Exemplary amino acid sequences of human leptin receptor are provided in GenBank Accession Nos. P48357.2, AAB09673.1, AAC23650.1, AAB07497.1, AAB07496.1, AAB07495.1, AAA93015.1, incorporated herein by reference.

In yet other embodiments, an exemplary mutation in LEPR includes one or more of the mutations described in one or more of the following: Faroqui et al., N Engl J Med 356:237-24, 2007; Gill et al., Obesity 22:576-84, 2014; Kimber et al., Endocrinol. 149:6043-52, 2008; Huvenne et al. J. Clin. Endo Metab. 100:E757-66, 2015; and Mammes et al., Eur. J. Clin. Inv. 31:398-4004, 2015, each of which is hereby incorporated by reference in its entirety.

5HT2c Receptor

The 5-hydroxytryptamine (serotonin) receptor 2C, G protein-coupled (5-HT2c receptor) is a G protein-coupled receptor (GPCR) that binds to the neurotransmitter serotonin. The 5HT2c receptor is involved in regulating feeding, among other physiological functions. The 5HT2c receptor acts upstream of the MC4R in the POMC-MC4R pathway. Stimulation of the 5-HT2c receptor results in an increase in POMC in the anterior pituitary lobe. By binding to serotonin receptors, including 5HT2c receptor, serotonin increases POMC activity and reduces feeding behavior. See, e.g., Roepke et al. Am. J. Physiol. Endocrinol. Metab. 302.11 (2012):E1399-406. 5HT2c receptor agonists have been reported to reduce feeding in rats and mice. See, e.g., Bickerdike. Curr. Top. Med. Chem. 3.8 (2003): 885-97. Alternative splicing of the 5-HT2C receptor is regulated by the snoRNA, SNORD115. SNORD115 is inactivated in PWS. Without wishing to be bound by theory, it is believed that 5HT2c polymorphisms are associated with obesity.

The human 5-HT2c receptor gene sequence is provided in GenBank Accession No. NG_012082.2 (see, e.g., Jahnsen J A et al. Eur. J. Pharmacol. 684 (1-3), 44-50 (2012)), incorporated herein by reference. Exemplary nucleic acid sequences of human 5-HT2c receptor are provided in GenBank Accession Nos. NM_001256761.2, NM_001256760.2, NM_000868.3, incorporated herein by reference. Exemplary amino acid sequences of human 5-HT2c receptor are provided in GenBank Accession Nos. NP_001243690.1, NP_001243689.1, NP_000859.1, incorporated herein by reference.

NhLH2

NhLH2 is a neuronal transcription factor that acts upstream of MC4R in the POMC-MC4R pathway. NhLH2 is a member of the basic helix-loop-helix (bHLH) family of transcription factors. NhLH2 is expressed in a number of differentiated adult neurons, including POMC neurons and MC4R neurons. Expression of NhLH2 can be regulated by food intake and leptin levels. See, e.g., Good et al. Trends Endocrinol. Metab. 24.8(2013):385-90. Based on NhLH2 knockout mouse studies, in which deletion of the gene resulted in adult-onset obesity, NhLH2 has been reported to mediate body weight control and fertility. See, e.g., Good et al. Nat. Genet. 15(1997):397-401. In embodiments, exemplary mutations, e.g., that lead to heterozygous NhLH2 deficiency, are described, e.g., in Rayyan et al. Gene. 2013; 512(1):134-42, incorporated herein by reference.

NhLH2 binds to the leptin-regulated transcription factor Signal transducer and activator-3 (Stat-3) to regulate PCSK1 in response to leptin or food intake. In NhLH2 knockout mice, there are lower levels of PCSK1 than in wild type mice. This results in reduced levels of PCSK1 processed peptide, e.g., mature POMC. See, e.g., Good et al. Trends Endocrinol. Metab. 24.8 (2013): 385-90.

Exemplary nucleic acid sequences of human NhLH2 are provided in GenBank Accession Nos. XM_006710666.2, XR_946659.1, NM_001111061.1, NM_005599.3 (see, e.g., Al Rayyan et al. Gene 512 (1), 134-142 (2013)), incorporated herein by reference. Exemplary amino acid sequences of human NhLH2 are provided in GenBank Accession Nos. XP006710729.1, NP_001104531.1, NP_005590.1, incorporated herein by reference.

Pro-Hormone Convertase

Pro-hormone convertase are serine proteases that process precursors of peptide hormones and neuropeptides. There are multiple types pro-hormone convertases: PCSK1 (also called PC1, PC3, and PC1/3), PCSK2 (also called PC2), PCSK3 (also called furin, pace, and PC1), PCSK4 (also called PC4), PCSK5 (also called PC5, PC6, and PC5/6), PCSK6 (also called PACE4), PCSK7 (also called PC7, PC8), PCSK8 (also called Site 1 protease, SIP, SKI), and PCSK9 (also called NARC-1). Pro-hormone convertases are responsible for cleaving POMC to generate alpha-MSH. For example, PC1 cleaves POMC to generate pro-ACTH, which is then cleaved by PC2 to generate ACTH1-17. See, e.g., Pritchard et al. J. Endocrinol. 172 (2002): 411-21.

It is believed that defective POMC processing can lead to obesity. A patient having compound heterozygous mutations in the PC1 gene had extreme childhood obesity, abnormal glucose homeostasis, hypocorticolism, and hypogonadotrophic hypogonadism. See i.d. Another obese patient was reported to have defective POMC processing. See i.d.

Exemplary sequences of PCSK1 are described above. Exemplary nucleic acid sequences of human PCSK2 are provided in GenBank Accession Nos. NM_002594.4 (see, e.g., van Wamelen et al. J. Neuropathol. Exp. Neurol. 72 (12), 1126-1134 (2013)), NM_001201529.2, NM_001201528.1, incorporated herein by reference. Exemplary amino acid sequences of human PCSK2 are provided in GenBank Accession Nos. NP_001188458.1, NP_001188457.1, NP_002585.2, incorporated herein by reference. Exemplary nucleic acid sequences of human PCSK3 are provided in GenBank Accession Nos. NM_001289824.1, NM_001289823.1, NM_002569.3, incorporated herein by reference. Exemplary amino acid sequences of human PCSK3 are provided in GenBank Accession Nos. NP_001276753.1 (see, e.g., Dahms et al. ACS Chem. Biol. 9 (5), 1113-1118 (2014)), NP_001276752.1, NP_002560.1, incorporated herein by reference. An exemplary nucleic acid sequence of human PCSK4 is provided in GenBank Accession No. NM_017573.4 (see, e.g., Seidah et al. J. Biol. Chem. 288 (30), 21473-21481 (2013)), incorporated herein by reference. An exemplary amino acid sequence of human PCSK4 is provided in GenBank Accession No. NP_060043.2, incorporated herein by reference. The human PCSK5 gene sequence is provided in GenBank Accession No. NG_029445.1, incorporated herein by reference. Exemplary nucleic acid sequences of human PCSK5 are provided in GenBank Accession Nos. NR_120409.1, NM_006200.5, NM_001190482.1 (see, e.g., Mbikay et al. Genomics 26 (1), 123-129 (1995)), incorporated herein by reference. Exemplary amino acid sequences of human PCSK5 are provided in GenBank Accession Nos. NP_001177411.1, NP_006191.2, incorporated herein by reference. The human PCSK6 gene sequence is provided in GenBank Accession No. NG_030047.3, incorporated herein by reference. Exemplary nucleic acid sequences of human PCSK6 are provided in GenBank Accession nos. NM_138325.3, NM_001291309.1, NM_138323.2, NM_138324.2, NM_138322.3, NM_138319.3, NM_002570.4 (see, e.g., Tsuji et al. J. Biochem. 122 (2), 438-452 (1997)), incorporated herein by reference. An exemplary nucleic acid sequence of human PCSK7 is provided in GenBank Accession no. NM_004716.3 (see, e.g., Stickel et al. Hum. Mol. Genet. 23 (14), 3883-3890 (2014)), incorporated herein by reference. An exemplary amino acid sequence of human PCSK7 is provided in GenBank Accession No. NP_004707.2, incorporated herein by reference. The human PCSK8 gene sequence is provided in GenBank Accession No. NG_033017.1, incorporated herein by reference. An exemplary nucleic acid sequence of human PCSK8 is provided in GenBank Accession No. NM_003791.3 (see, e.g., Weiss et al. J. Invest. Dermatol. 134 (1), 168-175 (2014)), incorporated herein by reference. An exemplary amino acid sequence of human PCSK8 is provided in GenBank Accession no. NP_003782.1, incorporated herein by reference. The human PCSK9 gene sequence is provided in GenBank Accession No. NG_009061.1, incorporated herein by reference. Exemplary nucleic acid sequences of human PCSK9 are provided in GenBank Accession No. XM_011541193.1, NR_110451.1, and NM_174936.3 (see, e.g., Brouwers et al. Clin. Sci. 126 (9), 679-684 (2014)), incorporated herein by reference. Exemplary amino acid sequences of human PCSK9 are provided in GenBank Accession no. XP_011539495.1 and NP_777596.2, incorporated herein by reference.

In some embodiments, exemplary mutations in a prohormone convertase, e.g., PCSK1, e.g., that lead to homozygous deficiency, are described, e.g., in the references in Table 3, each of which are incorporated herein by reference.

In some embodiments, exemplary mutations in a prohormone convertase, e.g., PCSK1, e.g., that lead to heterozygous deficiency, are described, e.g., in the references in Table 4, each of which are incorporated herein by reference.

CPE

Carboxypeptidase E (CPE), also called carboxypeptidase H (CPH) or convertase, is an enzyme that catalyzes the release of C-terminal lysine or arginine residues from polypeptides. CPE is involved in the processing of many neuropeptides and peptide hormones. For example, CPE acts downstream of the pro-hormone convertases, which generate intermediate peptide precursors, to further process polypeptides to remove C-terminal basic residues in order to generate mature peptides. For example, CPE is involved in processing POMC. Mutations in CPE have been associated with obesity. For example, morbidly obese female patient was described to have a truncating mutation of the CPE gene (c.76_98del; p.E26RfsX68). See, e.g., Alsters et al. PloS ONE. 10.6(2015):e0131417. In embodiments, exemplary mutations in CPE, e.g., that lead to homozygous CPE deficiency, are described, e.g., in Alsters et al. PloS One. 10.6(2015):e0131417, incorporated herein by reference.

An exemplary nucleic acid sequence of CPE is provided in GenBank Accession No. NM_001873.2 (Skalka et al. Oncogene 32 (23), 2836-2847 (2013)), incorporated herein by reference. An exemplary amino acid sequence of CPE is provided in GenBank Accession No. NP_001864.1, incorporated herein by reference.

Sim1

Single-minded 1 (Sim1) is a transcription factor involved in the development of the paraventricular nucleus of the hypothalamus, which regulates body weight, energy expenditure, and appetite. Sim1 acts on the MC4R in the POMC-MC4R pathway. Loss of function of Sim1 (e.g., in Sim1+/− and Sim1−/−mice) have been reported to cause hyperphagia, obesity, and increased susceptibility to diet-induced obesity. See, e.g., Xi et al. PLOS One. 7.4(2012):e36453. Also, Sim1 neuron ablation in mice led to obesity caused by increased food intake and reduced energy expenditure. See i.d. In embodiments, exemplary mutations in Sim1, e.g., that lead to heterozygous Sim1 deficiency, are described, e.g., in Bonnefond et al. J. Clin. Invest. 123.7 (2013): 3037-41, incorporated herein by reference.

The human SIM1 gene sequence is provided in GenBank Accession No. NG_008230.1, incorporated herein by reference. Exemplary nucleic acid sequences of human SIM1 are provided in GenBank Accession Nos. XM_011536073.1 (see, e.g., Ramachandrappa et al. J. Clin. Invest. 123 (7), 3042-3050 (2013)), XM_011536072.1, XM_005267100.2, NM_005068.2, incorporated herein by reference. Exemplary amino acid sequences of human SIM1 are provided in GenBank Accession no. XP_011534375.1, XP_011534374.1, XP_005267157.1, NP_005059.2, incorporated herein by reference.

BBS1-20

BBS1-BBS20 are 20 genes that are associated with Bardet-Biedl syndrome. Mutation(s) in one or more of the BBS genes have been associated with obesity, blindness and loss of hearing. Mice lacking the BBS1 gene in the nervous system have been shown to develop obesity. See, e.g., Guo et al. PLOS Genetics 12.2 (2016): e1005890. Also, heterozygous carriers of mutations in BBS genes have been described to have a greater propensity for obesity than control subjects. See, e.g., Gupta et al. J. Endocrinol. 203 (2009):327-36.

In embodiments of any method described herein, the method comprises treating a subject having one or more mutations in one or more of the genes BBS1-BBS20. In embodiments, a method described herein comprises use of a MC4R agonist described herein to treat a subject having one or more mutations in one or more of the genes, BBS1-BBS20. Exemplary mutations include non-coding variants in one or more of the BBS genes, e.g., BBS2, BBS4, and/or BBS6. For example, SNPs in BBS6 and BBS4 have been shown by some reports to be associated with adult and childhood obesity. See, e.g., Gupta et al. J. Endocrinol. 203 (2009): 327-36.

ALMS1

Alström syndrome (ALMS) is an autosomal recessive disease associated with blindness, deafness, diabetes, and obesity, hyperinsulinemia, and altered glucose metabolism that can lead to the development of type 2 diabetes at a young age in afflicted subjects. ALMS is caused by mutations in ALMS1, a gene that has been mapped to chormosome 2p13. The progression from early onset obesity toward the impaired fasting glucose or impaired glucose tolerance and overt diabetes is believed to occur mostly because of a progressive failure of β-cell insulin secretion without any further worsening of insulin resistance with age, even in the presence of weight reduction (Bettini et al. Pediatr. Diabetes 13:59-67, 2012). The identification of ALMS1 as a ciliary protein explains several of the observed phenotypes and their similarity to other ciliopathies including the Bardet-Biedl syndrome.

Nucleic acid sequences linked to Alström syndrome, variants of the nucleic acid sequence, the protein produced by that nucleic acid sequence and screening methods for testing individuals to determine if they are carriers of Alström syndrome, are disclosed in, e.g., U.S. Pat. No. 7,196,171.

In embodiments of any method described herein, the method comprises treating a subject having one or more mutations in one or more alleles of the ALMS1 gene. In embodiments, a method described herein comprises use of a MC4R agonist described herein to treat a subject having one or more mutations in the gene.

Nucleic acid sequences linked to Alstrom syndrome, variants of the nucleic acid sequence, the protein produced by that nucleic acid sequence and screening methods for testing individuals to determine if they are carriers of Alstrom syndrome, are disclosed in, e.g., U.S. Pat. No. 7,196,171.

Pseudo Hypoparathyroidism (GNAS1)

In pseudohypoparathyroidism the body is unable to respond to parathyroid hormone and is among other clinical symptoms associated with obesity and short stature. The principal symptoms are low calcium levels and high blood phosphate levels. Afflicted individuals have cataracts, dental problems, seizures, numbness, and/or tetany (muscle twitches and hand and foot spasms). Symptoms are typically initially observed in childhood. People with this disorder are also resistant to other hormones, such as thyroid-stimulating hormone and gonadotropins. Type 1A is also associated with a group of symptoms referred to as Albrightis hereditary osteodystrophy, which includes short stature, a round face, obesity, and short hand bones. Pseudohypoparathyroidism type 1A is caused by a mutation in the GNAS gene and is inherited in an autosomal dominant manner. The GNAS1 gene is described in, e.g., US20060147936.

In embodiments of any method described herein, the method comprises treating a subject having one or more mutations in one or more alleles of the GNAS1 gene. In embodiments, a method described herein comprises use of a MC4R agonist described herein to treat a subject having one or more mutations in the gene.

Additional Genes

Additional genes useful in the methods disclosed herein include BDNF, MCH1R, MCH, NTRK2, SIM1 (*J Clin Invest.* 2013; 123 (7): 3042-3050. doi:10.1172/JCI68016), ENPP1, COH1, CNR1, NPC1, c-MAF, PTER, FTO, TMEM18 (childhood), SDCCAG8, TNKS/MSRA, GNPDA2 (childhood), NEGr1, INSIG2, KCTD15, NROB2, and 16p11.2 deletions (including the SH2B1 gene).

In embodiments of any method described herein, the method comprises treating a subject having one or more mutations in one or more of one or more of these genes. In embodiments, a method described herein comprises use of a MC4R agonist described herein to treat a subject having mutations in one of more of these genes.

Disorders

In accordance with the methods and compositions described herein, in some embodiments, a MC4R agonist, e.g., MC4R agonist described herein, e.g., setmelanotide, is used to treat a disorder, such as a metabolic disorder, e.g., obesity, hyperphagia, or metabolic syndrome.

In embodiments, a MC4R agonist, e.g., MC4R agonist described herein, e.g., setmelanotide, is used to treat a genetic disorder caused by a deficiency in one or more components of the POMC-MC4R pathway. In embodiments, a MC4R agonist, e.g., MC4R agonist described herein, e.g., setmelanotide, is used to treat a genetic disorder such as Prader-Willi Syndrome (PWS) or POMC-null obesity. In embodiments, a MC4R agonist, e.g., MC4R agonist described herein, e.g., setmelanotide, is used to treat a genetic disorder associated with a defect in one or more of the following genes: POMC, PCSK1, MAGEL2, Leptin-R, leptin, 5-HT2c receptor, NhHL2, pro-hormone convertase, CPE, MC4R, or Sim1. In embodiments, a MC4R agonist, e.g., MC4R agonist described herein, e.g., setmelanotide, is used to treat a genetic disorder associated with hypermethylation of the POMC gene, e.g., at a POMC intron.

In embodiments, the genetic disorder is associated with obesity, e.g., severe obesity, and/or hyperphagia.

Prader Willi Syndrome (PWS)

Prader Willi Syndrome (PWS) is a rare genetic disease with a prevalence ranging from approximately one in 8,000 to one in 25,000 patients in the U.S. A hallmark of PWS is severe hyperphagia—an overriding physiological drive to eat—leading to severe obesity and other complications. Obesity is one of the greatest health threats to PWS patients, and hyperphagia impairs the ability of PWS patients to live independently, requiring costly and constant supervision to prevent overeating. Without supervision, these patients are likely to die prematurely as a result of choking, stomach rupture, or from complications caused by morbid obesity. Currently, there are no approved treatments for the obesity and hyperphagia associated with PWS.

Symptoms of PWS include infantile hypotonia with failure to thrive, rapid weight gain and overeating during childhood, as well as intellectual disability, developmental delay, short stature, hypogonadism. Diagnostic criteria for PWS are described, e.g., in Holm et al. Pediatrics 91(1993): 398-402.

It is believed that the genetics underlying PWS involve a loss of function of several genes on chromosome 15 in humans, in particular, at 15q11-q13. See, e.g., Schaaf et al. Nat. Genet. 45.11 (2013): 1405-09. Protein coding genes in this section of the chromosome include MKRN3, MAGEL2, NDN, NPAP1, and SNURF-SNRPN. See i.d. Examples of a MAGEL2 null deficiency are described, e.g., in Schaaf et al.; and in Soden et al. Sci Transl Med. 2014 Dec. 3; 6(265): 265ra168, incorporated herein by reference. About 70% of PWS patients have large deletion (about 4 Mb) in the paternal 15q11-q13 chromosomal region. See, e.g., Bervini et al. Front. Neuroendocrinol. 34(2014):107-119. About 25% of PWS patients have maternal uniparental disomy. See i.d. Mice lacking MAGEL2 gene expression have impaired POMC neurons and develop some of the same symptoms exhibited by humans with PWS. It is believed that a defect in the MAGEL2 gene (which is found on chromosome 15 in humans) may impair the function of pro-opiomelanocortin (POMC) neurons, which are key components of the MC4 pathway that normally promote satiety by activating downstream MC4 receptors. This impairment can create a block in the MC4 pathway.

Without wishing to be bound by theory, it is believed that the MC4R agonists described herein, e.g., setmelanotide, may reestablish weight and appetite control in PWS subjects by bypassing the defective POMC neurons and activating the MC4 pathways below the block in the pathway. For example, the melanocortin receptor agonists described herein, e.g., setmelanotide, can act as a replacement therapy for MSH.

POMC-Null Obesity

Also described as POMC deficiency syndrome, patients with POMC-null obesity have homozygous loss-of-function in the pro-opiomelanocortin (POMC) genes, which results in early-onset, severe obesity. Patients with POMC-null mutations have severe obesity, with BMIs exceeding 40 and uncontrolled appetite (severe hyperphagia) beginning in childhood. This genetic disorder may also be associated with hormonal deficiencies, such as hypoadrenalism, and red hair and fair skin are common. The disorder may also lead to early death. POMC-null obesity is a very rare genetic disorder, and there are no approved treatments for the obesity and hyperphagia associated with this condition. There are an estimated 50 to 500 POMC null patients worldwide.

Bardet-Biedl Syndrome (BBS)

In embodiments, a MC4R agonist described herein is used to treat Bardet-Biedl syndrome (BBS). BBS is a genetically heterogeneous disorder. BBS is a form of Laurence-Moon-Beidl syndrome and is characterized by obesity, retinopathy, learning disability, polydactyly, and hypogenitalism. See, e.g., Green et al. New Engl. J. Med. 321(1989):1002-9. Without wishing to be bound by theory, it is believed that BBS is characterized by one or more mutation(s) in one or more of 20 genes (BBS1-BBS20). Most of the BBS genes encode proteins thought to be important for the function, formation, and stability of cilia. It is believed that eight BBS proteins (BBS1, BBS2, BBS4, BBS5, BBS7, BBS8, BBS9, and BBS18) form a complex called the BBSome that mediates trafficking to the ciliary membrane. BBS6, BBS10, and BBS12 are believed to form a complex with the CCT/TRIC family of group II chaperonins.

Mutation(s) in the BBS gene(s) are thought to lead to defective cilia, e.g, neuronal cilia, or dysfunctional ciliary regulation. Ciliary dysfunction is believed to cause impaired leptin signaling and hyperleptinemia. The role of primary cilia and cilia proteins in energy homeostasis and obesity-related disorders is described, e.g., in., Gupta et al. J. Endocrinol. 203(2009):327-36; and Oh et al. Cell Metab. 21.1(2015):21-31. Patients with BBS have been found to have hyperleptinemia that is suggestive of leptin resistance, with triglycerides, leptin, diastolic BP-Z, and intra-abdominal fat mass significantly greater in BBS patients than in controls. See, e.g., Feuillan et al. J. Clin. Endocrinol. Metab. 96.3 (2011). Obesity in BBS mutant mice, for example, is thought to be caused by leptin resistance and defects in leptin receptor trafficking. See, e.g., Berbari et al. Proc. Natl. Acad. Sci. USA 110.19 (2013): 7796-7801. BBS2, BB4, and BB6 mutant mice have been shown to be hyperleptinemic and failed to reduce their food intake in response to leptin. See, e.g., Berbari et al. Proc. Natl. Acad. Sci. USA 110.19 (2013):7796-7801.

Alström Syndrome

Alström syndrome (ALMS) is an autosomal recessive disease with clinical symptoms that include severe obesity, hyperinsulinemia, and altered glucose metabolism that can lead to the development of type 2 diabetes at a young age in afflicted subjects. ALMS is caused by mutations in ALMS1, a gene that has been mapped to chormosome 2p13.

The progression from early onset obesity toward the impaired fasting glucose or impaired glucose tolerance and overt diabetes is believed to occur mostly because of a progressive failure of β-cell insulin secretion without any further worsening of insulin resistance with age, even in the presence of weight reduction (Bettini et al. Pediatr. Diabetes 13:59-67, 2012).

Outcomes

In embodiments, methods described herein result in one or more outcomes, including a reduction of weight (e.g., body weight), a reduction in hunger level, no detectable decrease in energy expenditure (e.g., resting energy expenditure), an increase in energy expenditure (e.g., resting energy expenditure), a reduction in daily/weekly/monthly food intake, a reduction in waist circumference, no detectable increase in blood pressure, or a reduction in blood pressure in a subject, e.g., relative to a control.

In embodiments, the control is the measurement of the parameter in the subject prior to administration of (treatment with) a MC4R agonist. In embodiments, the control is a predetermined value, e.g., the value of the parameter in an average obese human population, e.g., of like age and gender as the subject; or the value of the parameter measured in the subject at a previous time point (e.g., at a previous visit, e.g., to a physician, medical facility or laboratory).

In embodiments, the outcome (e.g., the reduction, increase, no detectable decrease, or no detectable increase in a given parameter) is measured in the subject 1, 2, 3, 4, 5, 6, 7, 8, 9, weeks or more after initation of treatment with a MC4R agonist. In other embodiments, the outcome (e.g., the reduction, increase, no detectable decrease, or no detectable increase in a given parameter) is measured in the subject over a period of time (e.g., over a period of 1-2 weeks, 2-4 weeks, 4-6 weeks, 6-8 weeks, 8-12 weeks, or 12-16 weeks) during a course of treatment.

In embodiments, methods described herein result in a reduction of weight (e.g., body weight) in the subject compared to a control (e.g., weight of the subject before treatment or a predetermined value, e.g., average weight of an obese human population of like age and gender as the subject not subjected to therapeutic intervention, or the weight of the subject at a previous measurement, e.g., at a previous visit). In embodiments, the reduction is about 1 kg to 3 kg after 1 week of treatment, about 1 kg to 6 kg after 2 weeks of treatment, about 2 kg to 12 kg after 4 weeks of treatment, about 4 kg to 24 kg after 8 weeks of treatment, or about 8 kg to 48 kg after 16 weeks of treatment. In embodiments, the reduction is at a rate of loss of about 1-2 kg/week, e.g., about 2 kg/week, e.g., over a period of 1-2 weeks of treatment or longer, 2-4 weeks of treatment or longer, 4-8 weeks of treatment or longer, 8-16 weeks of treatment, or 16-32 weeks of treatment, or longer.

Measurement of weight, e.g., body weight, can be performed using standard methods in the art.

In embodiments, methods described herein result in a reduction in hunger level in the subject compared to a control (e.g., hunger level of the subject before treatment or a predetermined hunger level, e.g., average hunger level of an obese human population of like age and gender as the subject or the hunger level of the subject at a previous measurement, e.g., at a previous visit). In embodiments, the methods described herein result in abolishment of hunger in the subject.

In embodiments, hunger is measured by a scale, such as a Likert hunger scale, which ranges from 0 to 10 and is described herein. In embodiments, methods described herein result in a reduction in hunger score in the subject compared to a control (e.g., hunger level of the subject before treatment or a predetermined hunger level, e.g., average hunger level of an obese human population of like age and gender as the subject or the hunger level of the subject at a previous measurement, e.g., at a previous visit). In embodiments, methods described herein result in a lower score on the Likert hunger scale, e.g., a lower score by at least 1, 2, 3, 4, 5, 6, 7, 8, 9 or 10 points, compared to the control (e.g., hunger level of the subject before treatment or a predetermined hunger level, e.g., average hunger level of an obese human population of like age and gender as the subject or the hunger level of the subject at a previous measurement, e.g., at a previous visit). In embodiments, methods described herein result in a score of 0 on the Likert hunger scale after treatment.

In embodiments, the reduction in hunger level is measured/observed after 1 to 2 weeks of treatment or longer, 2-4 weeks of treatment or longer, 4-8 weeks of treatment or longer, or 8-16 weeks of treatment or longer.

REE is a measure of the basal metabolic rate of the subject and can be determined using methods such as those described in Chen et al. J. Clin. Endocrinol. Metab. 100.4 (2015):1639-45. In embodiments, the REE can be determined by placing the subject in a whole-room indirect calorimeter (also called a metabolic chamber) at a certain time after treatment (e.g., after 3, 4, 5, 6, 7 days, or 1, 2, 3, 4, or more weeks). In embodiments, the REE is measured in 30-minute measurements periods, and in some cases, REE values from several 30-minute periods are averaged to generate an average REE. In embodiments, the REE can be determined after a 10-12 hour fasting period, at thermoneutrality (e.g., around 25° C.), where the subject is awake without psychological or physical stress. In embodiments, REE is measured in units of energy per unit time (e.g., kcal/h or kcal/day). In embodiments, the REE is measured relative to kg lean body mass in a subject (e.g., REE/kg lean mass), e.g., as described in the Examples.

In embodiments, methods described herein result in no change or no decrease in energy expenditure, e.g., resting energy expenditure (REE), in the subject over an hourly, daily (e.g., in 24 hours), weekly (e.g., in 7 days), or monthly (e.g., in 30 days) period compared to a control REE (e.g., the REE in the subject prior to treatment or a predetermined REE, e.g., average REE of an obese human population of like age and gender and normalized for weight as the subject or the REE of the subject at a previous measurement, e.g., previous visit), e.g., as measured after 3, 4, 5, 6, 7 days, or 1, 2, 3, 4, or more weeks of treatment.

In embodiments, methods described herein result in no detectable change or no detectable decrease in energy expenditure, e.g., resting energy expenditure (REE) per kg lean body mass, in the subject over an hourly, daily (e.g., in 24 hours), weekly (e.g., in 7 days), or monthly (e.g., in 30 days) period compared to the control REE (e.g., the REE in the subject prior to treatment or a predetermined REE, e.g., average REE of an obese human population of like age and gender as the subject or the REE of the subject at a previous measurement, e.g., previous visit), e.g., as measured after 3, 4, 5, 6, 7 days, or 1, 2, 3, 4, or more weeks of treatment.

In embodiments, methods described herein result in an increase in energy expenditure, e.g., resting energy expenditure (REE), in the subject over a hourly, daily (e.g., in 24 hours), weekly (e.g., in 7 days), or monthly (e.g., in 30 days) period compared to a control REE (e.g., the REE in the subject prior to treatment or a predetermined REE, e.g., average REE of an obese human population of like age and gender and normalized for weight as the subject or the REE of the subject at a previous measurement, e.g., previous visit), e.g., as measured after 3, 4, 5, 6, 7 days, or 1, 2, 3, 4, or more weeks of treatment.

In embodiments, the increase in REE in the subject is at least 20 kcal/day (e.g., at least 20, 30, 40, 50, 60, 70, 80, 90, 100, 110, 120, 130, 140, 150 kcal/day or more), e.g., as measured after 3, 4, 5, 6, 7 days, or 1, 2, 3, 4, or more weeks of treatment.

In embodiments, the increase in REE in the subject is at least 2% (e.g., at least 2%, 3%, 4%, 5%, 6%, 7%, 8%, 9%, 10%, 11%, 12%, 13%, 14%, 15% or more), e.g., as measured after 3, 4, 5, 6, 7 days, or 1, 2, 3, 4, or more weeks of treatment, compared to the REE in the subject prior to treatment.

In embodiments, the REE in the subject (e.g., adult subject) after treatment with a MC4R agonist (e.g., after 3, 4, 5, 6, 7 days, or 1, 2, 3, 4, or more weeks of treatment) is at least 1800 kcal/day (e.g., at least 1800, 1825, 1850, 1875, 1900, 1925, 1950, 1975, 2000, 2025, 2050, 2100, 2150, 2200, 2250, 2300, 2400 kcal/day, or more), e.g., for an adult subject. In embodiments, the REE in the subject (e.g., pediatric subject) after treatment with a MC4R agonist (e.g., after 3, 4, 5, 6, 7 days, or 1, 2, 3, 4, or more weeks of treatment) is at least 200 kcal/day (e.g., at least 200, 225, 250, 275, 300, 325, 350, 375, 400, 450, 500 kcal/day or more), e.g., for pediatric patients.

In embodiments, methods described herein result in a reduction in food intake by the subject compared to a control (e.g., the food intake of the subject prior to treatment or a predetermined food intake level, e.g., the food intake of an average human obese population or the food intake of the subject at a previous measurement, e.g., at a previous visit), e.g., where the food intake is measured as daily food intake or food intake over a period of 24 hours, or one week. In embodiments, the reduction is at least 100 kilocalories, e.g., at least 100, 125, 150, 175, 200, 225, 250, 275, 300, 325, 350, 375, 400, 425, 450, 475, 500, 525, 550, 575, 600, 1000 kilocalories or more, e.g., for daily food intake or food intake over a period of 24 hours, or one week, or 30 days or for longer time periods, e.g., for an adult subject. In embodiments, mean food intake can decrease from a baseline at or above about 100 kcal/kg/day to about 90, 80, 70, 60, 50, 40, 30, 20 or 10 kcal/kg/day or lower after treatment with a MC4R agonist, e.g., setmelanotide, e.g., in a pediatric subject at about 1 year of age. In embodiments, mean food intake can decrease from a baseline at or above about 40 kcal/kg/day to about 35, 30, 20 or 10 kcal/kg/day or lower after treatment with a MC4R agonist, e.g., setmelanotide, e.g., in a pediatric subject in late adolescence.

Food intake can be determined by standard methods, e.g., as described in Rutishauser. Pub. Health Nutr. 8.7A(2005): 1100-07.

In embodiments, methods described herein result in a reduction in waist circumference of the subject compared to a control (e.g., the waist circumference of the subject prior to treatment or the waist circumference of the subject at a previous measurement, e.g., previous visit), as measured 1, 2, 3, 4, 5, 6, 7, 8, 9, 10 weeks or more after initiation of treatment.

In embodiments, the reduction in waist circumference is at least 2 cm (e.g., at least 2, 3, 4, 5, 6, 7, 8, 9, 10 cm or more) in the subject (e.g., adult subject) compared to a control (e.g., the waist circumference of the subject prior to treatment or a predetermined waist circumference, e.g., the waist circumference of an average obese human population of like age and gender or the waist circumference of the subject at a previous measurement, e.g., previous visit), as measured 1, 2, 3, 4, 5, 6, 7, 8, 9, 10 weeks or more after initiation of treatment.

In embodiments, the waist circumference is measured using standard methods. In embodiments, the waist circumference is the largest circumference around a subject's mid-section, e.g., around a subject's abdomen. In other embodiments, the waist circumference is measured around the natural waist (e.g., in between the lowest rib and the top of the hip bone), the umbilicus, or at the narrowest point of the midsection.

In embodiments, methods described herein result in no detectable increase in blood pressure (e.g., diastolic and/or systolic blood pressure) of the subject compared to a control blood pressure (e.g., the blood pressure of the subject prior to treatment or a predetermined blood pressure, e.g., the blood pressure of an average obese human population of like age and gender or the blood pressure of the subject at a previous measurement, e.g., previous visit), as measured 1, 2, 3, 4, 5, 6, 7, 8, 9, 10 weeks or more after initiation of treatment.

In embodiments, methods described herein result in a reduction in blood pressure (e.g., diastolic and/or systolic blood pressure) of the subject a control blood pressure (e.g., the blood pressure of the subject prior to treatment or a predetermined blood pressure, e.g., the blood pressure of an average obese human population of like age and gender or the blood pressure of the subject at a previous measurement, e.g., previous visit), as measured 1, 2, 3, 4, 5, 6, 7, 8, 9, 10 weeks or more after initiation of treatment.

In embodiments, the reduction in blood pressure, e.g., systolic blood pressure, is at least 3 mmHg (e.g., at least 3, 3.5, 4, 4.5, 5, 5.5, 6, 6.5, 7 mmHg or more) compared to the blood pressure of the subject prior to treatment, as measured 1, 2, 3, 4, 5, 6, 7, 8, 9, 10 weeks or more after initiation of treatment.

In embodiments, the reduction in blood pressure, e.g., diastolic blood pressure, is at least 4 mmHg (e.g., at least 4, 7, 7.5, 8, 8.5, 9, 9.5, 10 mmHg or more) compared to the blood pressure of the subject prior to treatment, as measured 1, 2, 3, 4, 5, 6, 7, 8, 9, 10 weeks or more after initiation of treatment.

In embodiments, the methods described herein do not result in an adverse effect on heart rate or blood pressure.

Subject

In accordance with any method described herein, in certain embodiments, the subject is obese, e.g., prior to administration of an agonist described herein, e.g., at the time the agonist is prescribed, or at the time of the first administration of the agonist. In embodiments, the subject is a severely obese, pediatric or adult patient e.g., prior to administration of an agonist described herein, e.g., at the time the agonist is prescribed or at the time of the first administration of the agonist. In embodiments, the subject is hyperphagic, e.g., prior to administration of an agonist described herein, e.g., at the time the agonist is prescribed, or at the time of the first administration of the agonist.

In embodiments, the subject (e.g., adult subject) has a body mass index (BMI) greater than 25 kg/m$^2$ or 30 kg/m$^2$ (e.g., ≥25, 26, 27, 28, 29, 30, 31, 32, 33, 34, 35, 36, 37, 38, 39, 40, 41, 42, 43, 44, 45, 46, 47, 48, 49, 50 kg/m$^2$ or greater) prior to administration of the agonist, e.g., at the time the agonist is prescribed, or at the time of the first administration.

In embodiments, the subject (e.g., pediatric subject) has a body mass index (BMI) higher than 85-95 percentile prior to administration of the agonist, e.g., at the time the agonist is prescribed, or at the time of the first administration.

In embodiments, the subject has a body weight of at least about 5 kg, e.g., at least about 5 kg, 10 kg, 20 kg, 30, 40, 50, 60, 70, 80, 90, 100, 110, 120, 130, 140,145, 150, 155, 160, 165, 170, 175, 180, 185, 190, 200, 205, 210, 215, 220 kg or greater, e.g., prior to administration of the agonist, e.g., at the time the agonist is prescribed, or at the time of the first administration. In embodiments, the subject has a body weight of a least 20 kg, at least 60 kg, or at least 100 kg, e.g., prior to administration of the agonist, e.g., at the time the agonist is prescribed, or at the time of the first administration.

In embodiments, the subject is an adult, e.g., 18 years of age or older, e.g., 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, or older.

In embodiments, the subject is a pediatric subject, e.g., less 18 years of age or younger (e.g., 18, 17, 16, 15, 14, 13, 12, 11, 10, 9, 8, 7, 6, 5, 4, 3, 2, or 1 year of age or younger.

In embodiments, the subject has or is identified as having a defect, e.g., genetic defect, or a mutation, in one or more genes of the POMC-MC4R pathway. In embodiments, the subject has or is identified as having one or more mutations in the POMC, PCSK1, MAGEL2, leptin receptor, leptin, 5-HT2c receptor, NhHL2, pro-hormone convertase, CPE, MC4R, or Sim1 genes or other genes that impair functioning of the POMC-MC4R pathway. In embodiments, the subject has or is identified as having a hypermethylated POMC gene (e.g., hypermethylated at a POMC intron, e.g., at a CpG island of the POMC gene, e.g., comprising a methylated cytosine, e.g., a 5'methyl cytosine).

In embodiments, the subject has Prader Willi Syndrome.

In embodiments, the subject has or is identified as having a loss of function mutation in the 15q11-q13 region of chromosome 15, e.g., in the paternal allele.

In embodiments, the subject has or is identified as having a mutation (e.g., loss of function mutation) in the MAGEL2 gene.

In embodiments, the subject has or is identified as having a POMC-null, PCSK1-null genotype, MAGEL2-null genotype, leptin receptor-null genotype, leptin-null genotype, 5-HT2c receptor-null genotype, NhHL2-null genotype, pro-hormone convertase-null genotype, CPE-null genotype, MC4R-null genotype, and/or SIM1-null genotype. For example, the subject has or is identified as having a POMC-null, PCSK1-null obesity, MAGEL2-null obesity, leptin receptor-null obesity, leptin-null obesity, 5-HT2c receptor-null obesity, NhHL2-null obesity, pro-hormone convertase-null genotype, CPE-null obesity, MC4R-null obesity, and/or SIM1-null obesity.

In embodiments, the subject has or is identified as having a POMC mutation described herein, e.g., a POMC mutation described in Table 1. In embodiments, the subject has or is identified as having a mutation in the POMC amino acid sequence chosen from one or more of: Cys28Phe, Leu37Phe, His143Glu, Phe144Leu, Tyr221Cys, Pro231Leu, Arg236Gly, or Glu244X, where the amino acid sequence numbering is described in Takahashi, et al. 1981 Febs Letters 135(1)97 (and shown as SEQ ID NO: 563) and corresponds to that of the protein containing the signal peptide, and where X corresponds to early termination.

In embodiments, the subject has or is identified as having a POMC mutation (e.g., homozygous POMC mutation) described in a reference in Table 2. In embodiments, the subject has or is identified as having a POMC mutation (e.g., heterozygous POMC mutation) described in a reference in Table 1.

In embodiments, the POMC mutation is a homozygous mutation. In embodiments, the POMC mutation is a heterozygous mutation (e.g., compound heterozygous mutation). In embodiments, the POMC mutation is a loss of function mutation. In embodiments, the POMC mutation is a partial loss of function mutation.

In embodiments, the subject has or is identified as having a hypermethylation in the POMC gene, e.g., a hypermethylation in exon3 of the POMC gene, or a hypermethylation at the intron2-exon3 boundary of the POMC gene, e.g., a hypermethylation at a CpG island at the intron2-exon3 boundary of the POMC gene.

In embodiments, the subject has or is identified as having a PCSK1 mutation described herein, e.g., a heterozygous nonsense variant (p.Arg80*), a PCSK1 mutation (e.g., homozygous mutation) described in a reference of Table 3, or a PCSK1 mutation (e.g., heterozygous mutation) described in a reference of Table 4. In embodiments, the subject has or is identified as having a mutation in the PCSK1 amino acid sequence chosen from: Met125Ile, Thr175Met, Asn180Ser, Tyr181His, Gly262Arg, Ser325Asn, Thr558Ala, Asn221Asp, Gln665E, or S690Thr.

In embodiments, the PCSK1 mutation is a homozygous mutation. In embodiments, the PCSK1 mutation is a heterozygous mutation (e.g., compound heterozygous mutation). In embodiments, the PCSK1 mutation is a loss of function mutation. In embodiments, the PCSK1 mutation is a partial loss of function mutation.

In embodiments, the subject has or is identified as having a MAGEL2 mutation described herein, e.g., c.1652delT (p.Val551fs), c.1802delC (p.Pro601fs), c.3181_3182delAT (p.Ile1061fs), c.3124C>T (p.Gln1024*), or a mutation described in Schaaf et al. Nat. Genet. 45.11(2013):1405-09 or Soden et al. Sci Transl Med. 2014 Dec. 3; 6(265): 265ra168. In embodiments, the MAGEL2 mutation is a homozygous mutation. In embodiments, the MAGEL2 mutation is a heterozygous mutation (e.g., compound heterozygous mutation). In embodiments, the MAGEL2 mutation is a loss of function mutation. In embodiments, the MAGEL2 mutation causes a decrease in function/activity.

In embodiments, the subject has or is identified as having a leptin or leptin-R mutation described herein. In embodiments, the subject has or is identified as having a leptin mutation described herein, e.g., homozygous frame-shift mutation that deletes a guanine nucleotide in codon 133 of the leptin gene, or a homozygous transversion (c.298G→T) that leads to an aspartate to tyrosine change at amino acid position 100 (p.D100Y). In embodiments, the subject has or is identified as having a leptin-R mutation described herein, e.g., a Gln223Arg or a Lys656Asn mutation, or a mutation (e.g., homozygous mutation) described in a reference of Table 5. In embodiments, the subject has or is identified as having a leptin-R mutation (e.g., homozygous leptin-R mutation) described in Table 6. In some embodiments, the subject has or is identified as having a leptin-R mutation chosen from: c.2396-1 G>T, c.1675 G>A, p.Cys604Gly, p.Leu786Pro, p.His800_Asn831del, p.Tyr422His, p.Thr711NfsX18, P.535-1G>A, p.166CfsX7, 4-bp del codon 22, 11-bp del codon 70, 66-bp del codon 514, Trp31X, Ala409Glu, Trp664Arg, His684Pro, 1-bp del codon 15, or Arg612His.

In embodiments, the leptin or leptin-R mutation is a homozygous mutation. In embodiments, the leptin or leptin-R mutation is a heterozygous mutation (e.g., compound heterozygous mutation). In embodiments, the leptin or leptin-R mutation is a loss of function mutation. In embodiments, the leptin or leptin-R mutation is a partial loss of function mutation.

In embodiments, the subject has or is identified as having a 5-HT2c receptor mutation described herein. In embodiments, the 5-HT2c receptor mutation is a homozygous mutation. In embodiments, the 5-HT2c receptor mutation is a heterozygous mutation (e.g., compound heterozygous mutation). In embodiments, the 5-HT2c receptor mutation is a loss of function mutation. In embodiments, the 5-HT2c receptor mutation is a partial loss of function mutation.

In embodiments, the subject has or is identified as having a NhLH2 mutation described herein, e.g., described in Good et al. Nat. Genet. 15(1997):397-401. In embodiments, the NhLH2 mutation is a homozygous mutation. In embodiments, the NhLH2 mutation is a heterozygous mutation (e.g., compound heterozygous mutation). In embodiments, the NhLH2 mutation is a loss of function mutation. In embodiments, the NhLH2 mutation is a partial loss of function mutation.

In embodiments, the subject has or is identified as having a pro-hormone convertase mutation described herein, e.g., as described in Pritchard et al. J. Endocrinol. 172(2002):411-21, or as described in a reference of Table 3 or Table 4. In embodiments, the pro-hormone convertase mutation is a homozygous mutation. In embodiments, the pro-hormone convertase mutation is a heterozygous mutation (e.g., compound heterozygous mutation). In embodiments, the pro-hormone convertase mutation is a loss of function mutation. In embodiments, the pro-hormone convertase mutation is a partial loss of function mutation.

In embodiments, the subject has or is identified as having a CPE mutation described herein, e.g., (c.76_98del; p.E26RfsX68), or as described in Alsters et al. PloS ONE. 10.6 (2015): e0131417. In embodiments, the CPE mutation is a homozygous mutation. In embodiments, the CPE mutation is a heterozygous mutation (e.g., compound heterozygous mutation). In embodiments, the CPE mutation is a loss of function mutation. In embodiments, the CPE mutation is a partial loss of function mutation.

In embodiments, the subject has or is identified as having a SIM1 mutation described herein, e.g., as described in Bonnefond et al. J. Clin. Invest. 123.7(2013):3037-41. In embodiments, the SIM1mutation is a homozygous mutation. In embodiments, the SIM1mutation is a heterozygous mutation (e.g., compound heterozygous mutation). In embodiments, the SIM1 mutation is a loss of function mutation. In embodiments, the SIM1 mutation is a partial loss of function mutation.

In embodiments, methods herein can comprise identifying or selecting a subject having a defect e.g., genetic defect, or a mutation, in one or more genes of the POMC-MC4R pathway. In embodiments, methods herein can comprise acquiring knowledge of the genotype, predetermined sequence, or mutation. In embodiments, the methods herein can comprise acquiring knowledge of the genotype of, e.g., of a mutation in one or more of POMC, PCSK1, MAGEL2, leptin receptor, leptin, 5-HT2c receptor, NhHL2, pro-hormone convertase, CPE, MC4R, Sim1, and/or other POMC-MC4R pathway genes. In embodiments, the agonist is administered in response to acquiring knowledge, e.g., detection or identification, of a predetermined sequence, e.g., a mutation, in a gene described herein, one or more of POMC, PCSK1, MAGEL2, leptin receptor, leptin, 5-HT2c receptor, NhHL2, pro-hormone convertase, CPE, MC4R, Sim1, or other POMC-MC4R pathway genes.

In embodiments, methods herein can comprise acquiring knowledge of the state of methylation of the POMC gene (e.g., hypermethylated at a POMC intron, e.g., at a CpG island of the POMC gene, e.g., comprising a methylated cytosine, e.g., a 5'methyl cytosine). In embodiments, the agonist is administered in response to the detection of hypermethylation.

In embodiments, methods herein can comprise acquiring knowledge of the genotype of the subject, e.g., acquiring knowledge of the genotype the 15q11-q13 region of chromosome 15 (e.g., in the paternal allele) or of the MAGEL2 gene. In embodiments, the agonist is administered in response to the detection of a predetermined sequence, e.g., a mutation, in 15q11-q13 region of chromosome 15 (e.g., in the paternal allele) or in the MAGEL2 gene.

In embodiments, identification or selection of a subject as having a certain genotype or predetermined sequence, e.g., mutation, in a gene, can comprise acquiring knowledge of the certain genotype or predetermined sequence, e.g., mutation. Knowledge of the sort can be acquired in a number of ways, as described in detail in the Definitions section.

In some embodiments, a sequence is acquired, e.g., by obtaining possession of a nucleotide sequence, by "directly acquiring" or "indirectly acquiring" the sequence. "Directly acquiring a sequence" means performing a process (e.g., performing a synthetic or analytical method) to obtain the sequence, such as performing a sequencing method (e.g., a Next Generation Sequencing (NGS) method). "Indirectly acquiring a sequence" refers to receiving information or knowledge of, or receiving, the sequence from another party or source (e.g., a third party laboratory that directly acquired the sequence). The sequence acquired need not be a full sequence, e.g., sequencing of at least one nucleotide, or obtaining information or knowledge, that identifies a genotype or predetermined sequence, e.g., mutation, disclosed herein as being present in a subject constitutes acquiring a sequence.

In embodiments, the sequence can be directly acquired. Directly acquiring a sequence includes performing a process that includes a physical change in a physical substance, e.g., a starting material, such as a tissue sample, e.g., a blood sample or tissue biopsy, or analysis of an isolated nucleic acid (e.g., DNA or RNA) sample. Exemplary changes include making a physical entity from two or more starting materials, shearing or fragmenting a substance, such as a genomic DNA fragment; separating or purifying a substance (e.g., isolating a nucleic acid sample from a tissue); combining two or more separate entities into a mixture, performing a chemical reaction that includes breaking or forming a covalent or non-covalent bond. Directly acquiring a value includes performing a process that includes a physical change in a sample or another substance as described above.

In some embodiments, acquiring knowledge of the certain genotype or predetermined sequence, e.g., mutation, can comprise acquiring a sample, e.g., from which the genotype or predetermined sequence, e.g., mutation, is determined. "Acquiring a sample" as the term is used herein, refers to obtaining possession of a sample, e.g., a tissue sample or nucleic acid sample, by "directly acquiring" or "indirectly acquiring" the sample. "Directly acquiring a sample" means performing a process (e.g., performing a physical method such as a surgery or extraction) to obtain the sample. "Indirectly acquiring a sample" refers to receiving the sample from another party or source (e.g., a third party laboratory that directly acquired the sample). Directly acquiring a sample includes performing a process that includes a physical change in a physical substance, e.g., a starting material, such as a tissue, e.g., a tissue in a human patient or a tissue that has was previously isolated from a patient. Exemplary changes include making a physical entity from a starting material, dissecting or scraping a tissue; separating or purifying a substance (e.g., a sample tissue or a nucleic acid sample); combining two or more separate entities into a mixture; performing a chemical reaction that includes breaking or forming a covalent or non-covalent bond. Directly acquiring a sample includes performing a process that includes a physical change in a sample or another substance, e.g., as described above.

In some aspects, provided herein is also a method of evaluating a subject, e.g., for likely responsiveness to a MC4R agonist, e.g., a MC4R agonist described herein, e.g., setmelanotide. In some embodiments, the method comprises acquiring information about the genotype of the subject. In embodiments, the method comprises acquiring information about the presence or absence of a defect, e.g., genetic defect, in one or more genes of the POMC-MC4R pathway in the subject.

In embodiments, the subject can be identified as having a defect, e.g., genetic defect, e.g., mutation, in one or more genes of the POMC-MC4R pathway, using methods described herein.

In embodiments, the identification of the subject having a defect, e.g., genetic defect, e.g., mutation, indicates that the subject is likely to respond (e.g., with an improvement in one or more symptoms) to a MC4R agonist, e.g., a MC4R agonist described herein, e.g., setmelanotide. In embodiments, an improvement in a symptom can include an outcome described herein. For example, an improvement in a symptom can include a reduction of weight (e.g., body weight), a reduction in hunger level, no detectable decrease in energy expenditure (e.g., resting energy expenditure), an increase in energy expenditure (e.g., resting energy expenditure), a reduction in daily/weekly/monthly food intake, or a reduction in waist circumference, e.g., relative to a control.

In embodiments, the identification of the subject having the defect, e.g., genetic defect, e.g., mutation, indicates that the subject is more likely to respond to (or is likely to have a greater response to) a MC4R agonist, e.g., a MC4R agonist described herein, e.g., setmelanotide, than a subject (e.g., obese subject, e.g., of like age and/or pre-treatment weight) lacking a genetic defect in the POMC-MC4R pathway, e.g., a wild-type obese subject. In embodiments, a subject that is more likely to respond is more likely to have one or more improved symptoms, such as symptoms described herein, e.g., compared to a control, e.g., a subject (e.g., obese subject, e.g., of like age and/or pre-treatment weight) lacking a genetic defect in the POMC-MC4R pathway, e.g., a wild-type obese subject. In embodiments, a subject that is likely to have a greater response is likely to have a greater improvement in symptoms, e.g., symptoms described herein, e.g., greater weight loss, greater decrease in waist circumference, greater increase in resting energy expenditure, greater decrease in food intake, greater decrease in hunger level, e.g., compared to a control, e.g., a subject (e.g., obese subject, e.g., of like age and/or pre-treatment weight) lacking a genetic defect in the POMC-MC4R pathway, e.g., a wild-type obese subject.

In embodiments, methods described herein further comprise providing a report that identifies the presence or absence of the genetic defect and in some cases an identifier for the subject. In embodiments, the report provides a recommendation on potential therapeutic options, likely effectiveness of a therapeutic option, and/or recommendations/instructions for administration of the therapeutic option (e.g., MC4R agonist, e.g., MC4R agonist described herein, e.g., setmelanotide).

MC4R Agonists

Examples of naturally occurring MC4R agonists include α-MSH, β-MSH, γ-MSH and adenocorticitropic hormone (ACTH) or a functional fragment thereof. Examples of synthetic MC4R agonists are described in detail below.

In an example embodiment, an agonist employed by the methods of the present invention can be any known agonist of MC4R. In some example embodiment, the MC4R agonist is not an adrenocorticotropic hormone (ACTH) or a fragment thereof.

In an example embodiment, an MC4R agonist is any of the peptides disclosed in International Application published as WO2005/000339, incorporated herein by reference. Specifically, examples include peptides of the following structural formula:

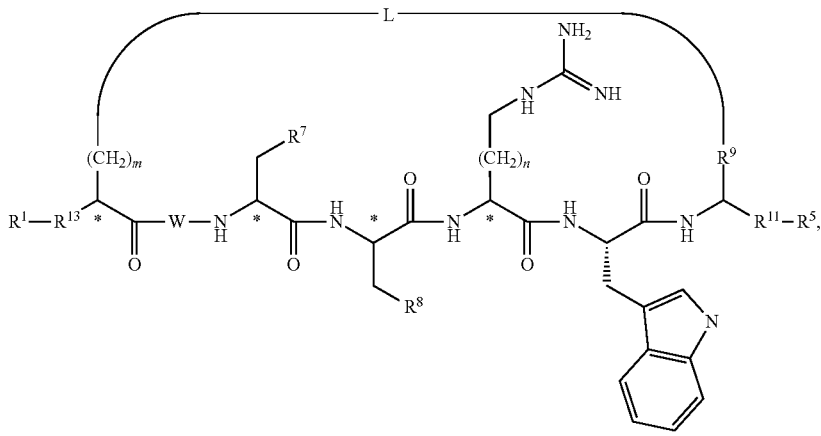

wherein

W is Glu, Gln, Asp, Asn, Ala, Gly, Thr, Ser, Pro, Met, Ile, Val, Arg, His, Tyr, Trp, Phe, Lys, Leu, Cya, or is absent;

$R^1$ is —H, —C(O)CH$_3$, —C(O)(CH$_2$)$_{1-4}$CH$_3$, —C(O)(CH$_2$)$_{1-4}$NHC(NH)NH$_2$, Tyr-ßArg-, Ac-Tyr-ß-hArg-, gluconoyl-Tyr-Arg-, Ac-diaminobutyryl-, Ac-diaminopropionyl-, N-propionyl-, N-butyryl-, N-valeryl-, N-methyl-Tyr-Arg-, N-glutaryl-Tyr-Arg-, N-succinyl-Tyr-Arg-, $R^6$—SO$_2$NHC(O)CH$_2$CH$_2$C(O)—, $R^6$—SO$_2$NHC(O)CH$_2$CH$_2$C(O)Arg-, $R^6$—SO$_2$NHCH$_2$CH$_2$CH$_2$C(O)—, C$_3$-C$_7$ cycloalkylcarbonyl, pheylsulfonyl, C$_8$-C$_{14}$ bicyclic arylsulfonyl, phenyl-(CH$_2$)$_q$C(O)—, C$_8$-C$_{14}$ bicyclic aryl-(CH$_2$)$_q$C(O)—,

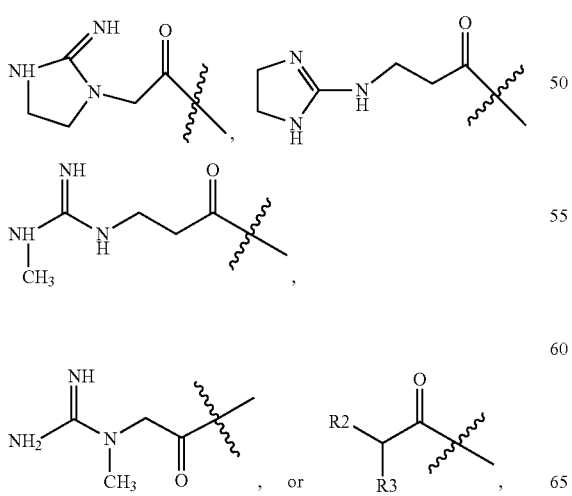

wherein $R^2$ is —H, —NH$_2$, —NHC(O)CH$_3$, —NHC(O)(CH$_2$)$_{1-4}$CH$_3$, —NH-TyrC(O)CH$_3$, $R^6$SO$_2$NH—, Ac-Cya-NH—, Tyr-NH—, HO—(C$_6$H$_5$)—CH$_2$CH$_2$C(O)NH—, or CH$_3$—(C$_6$H$_5$)—C(O)CH$_2$CH$_2$C(O)NH—;

$R^3$ is C$_1$-C$_4$ straight or branched alkyl, NH$_2$—CH$_2$—(CH$_2$)$_q$—, HO—CH$_2$—, (CH$_3$)$_2$CHNH(CH$_2$)$_4$—, $R^6$(CH$_2$)$_q$—, $R^6$SO$_2$NH—, Ser, Ile,

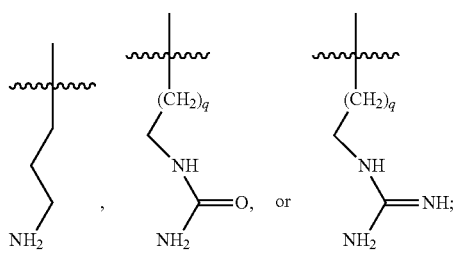

q is 0, 1, 2, or 3;

$R^6$ is a phenyl or C$_8$-C$_{14}$ bicyclic aryl;

m is 1 or 2;

n is 1, 2, 3, or 4;

$R^9$ is (CH$_2$)$_p$ or (CH$_3$)$_2$C—;

p is 1 or 2;

$R_{10}$ is NH— or is absent;

$R^7$ is a 5- or 6-membered heteroaryl or a 5- or 6-membered heteroaryl ring optionally substituted with $R^4$;

$R^4$ is H, C$_1$-C$_4$ straight or branched alkyl, phenyl, benzyl, or (C$_6$H$_5$)—CH$_2$—O—CH$_2$—;

$R^8$ is phenyl, a phenyl ring optionally substituted with X, or cyclohexyl;

X is H, Cl, F, Br, methyl, or methoxy;

$R^{11}$ is —C(O) or —CH$_2$;

$R^5$ is —NH$_2$, —OH, glycinol, NH$_2$-Pro-Ser-, NH$_2$-Pro-Lys-, HO-Ser-, HO-Pro-Ser-, HO-Lys-, Ser alcohol, -Ser-Pro alcohol, -Lys-Pro alcohol, HOCH$_2$CH$_2$—O—CH$_2$CH$_2$NH—, NH$_2$-Phe-Arg-, NH$_2$-Glu-, NH$_2$CH$_2$RCH$_2$NH—, RHN—, RO— where R is a C$_1$-C$_4$ straight or branched alkyl; and L is —S—S— or —S—CH$_2$—S—.

Other examples of MC4R agonists include peptides of the following structural formula:

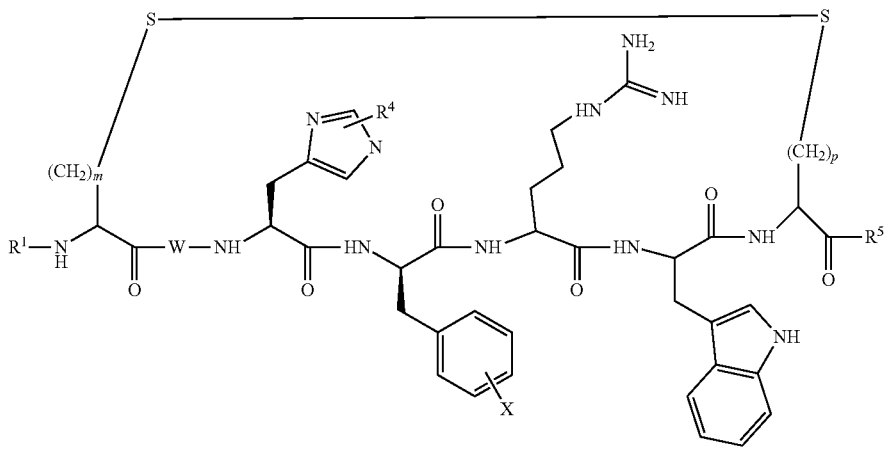

wherein:

W is a single bond, Glu, Gln, Asp, Asn, Ala, Gly, Thr, Ser, Pro, Met, Ile, Val, Arg, His, Tyr, Trp, or Phe;

$R^1$ is —H, —C(O)CH$_3$, —C(O)(CH$_2$)$_{1-4}$CH$_3$, —C(O)(CH$_2$)$_{1-4}$—NHC(NH)NH$_2$, Tyr-ßArg, gluconoyl-Tyr-Arg, Ac-Dab, Ac-Dap, N-succinyl-Tyr-Arg, N-propionyl, N-valeryl, N-glutaryl-Tyr-Arg, N-butyryl,

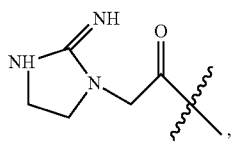

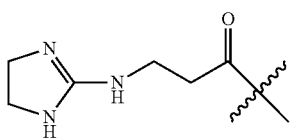

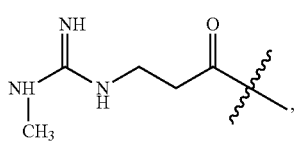

-continued

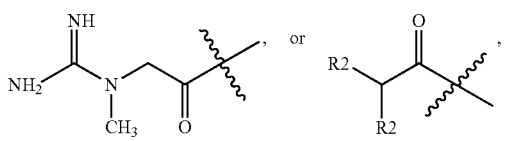

wherein $R^2$ is —H, —NH$_2$, —NHC(O)CH$_3$, —NHC(O)(CH$_2$)$_{1-4}$CH$_3$, or —NH-TyrC(O)CH$_3$;

$R^3$ is C$_1$-C$_4$ straight or branched alkyl, Ser, Ile,

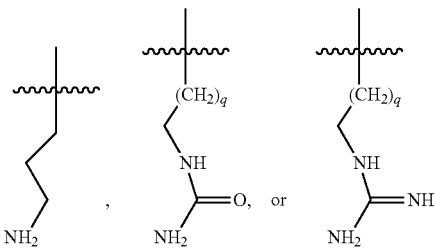

q is 0, 1, 2, or 3;

m is 1 or 2;

p is 1 or 2;

$R^4$ is H or C$_1$-C$_4$ straight or branched alkyl;

X is H, C$_1$, F, Br, methyl, or methoxy; and $R^5$ is —NH$_2$, —OH, glycinol, -Ser-Pro-NH$_2$, -Lys-Pro-NH$_2$, -Ser-OH, -Ser-Pro-OH, -Lys-Pro-OH-Arg-Phe-NH$_2$, -Glu-NH$_2$, —NHR, or —OR, where R is a C$_1$-C$_4$ straight or branched alkyl.

In yet another example embodiment, the MC4R agonist can be represented by the following structural formula:

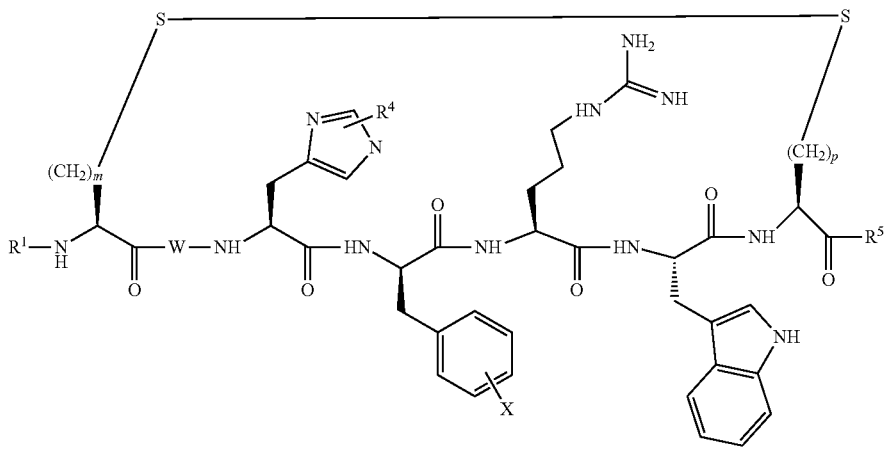

wherein

W is Glu, Gln, Asp, Ala, Gly, Thr, Ser, Pro, Met, Ile, Val, Arg, His, Tyr, Trp, Phe, Lys, Leu, Cya, or is absent;

$R^1$ is —H, —C(O)CH$_3$, —C(O)(CH$_2$)$_{1-4}$CH$_3$, —C(O)(CH$_2$)$_{1-4}$NHC(NH)NH$_2$, Tyr-ß-Arg-, Ac-Tyr-ß-hArg-, gluconoyl-Tyr-Arg-, Ac-diaminobutyryl-, Ac-diaminopropionyl-, N-propionyl-, N-butyryl-, N-valeryl-, N-methyl-Tyr-Arg-, N-glutaryl-Tyr-Arg-, N-succinyl-Tyr-Arg-, $R^6$—SO$_2$NHC(O)CH$_2$CH$_2$C(O)—, $R^6$—SO$_2$NHC(O)CH$_2$CH$_2$C(O)Arg-, $R^6$—SO$_2$NHCH$_2$CH$_2$CH$_2$C(O)—, C$_3$-C$_7$ cycloalkylcarbonyl, phenylsulfonyl, C$_8$-C$_{14}$ bicyclic arylsulfonyl, phenyl-(CH$_2$)$_q$C(O)—, C$_8$-C$_{14}$ bicyclic aryl-(CH$_2$)$_q$C(O)—,

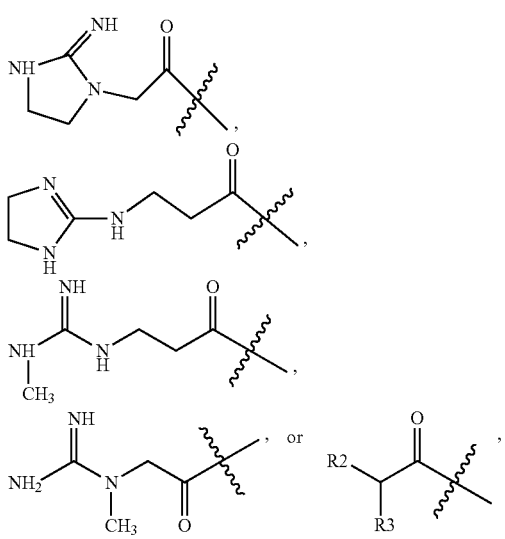

wherein $R^2$ is —H, —NH$_2$, —NHC(O)CH$_3$, —NHC(O)(CH$_2$)$_{1-4}$CH$_3$, —NH-TyrC(O)CH$_3$, $R^6$SO$_2$NH—, Ac-Cya-NH—, Tyr-NH—, HO—(C$_6$H$_5$)—CH$_2$CH$_2$C(O)NH—, or CH$_3$—(C$_6$H$_5$)—C(O)CH$_2$CH$_2$C(O)NH—;

$R^3$ is C$_1$-C$_4$ straight or branched alkyl, NH$_2$—CH$_2$—(CH$_2$)$_q$—, HO—CH$_2$—, (CH$_3$)$_2$CHNH(CH$_2$)$_4$—, $R^6$(CH$_2$)$_q$—, $R^6$SO$_2$NH—, Ser, Ile,

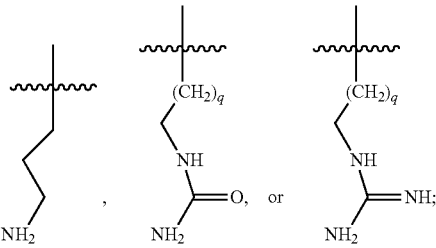

q is 0, 1, 2, or 3;
$R^6$ is a phenyl or C$_8$-C$_{14}$ bicyclic aryl;
m is 1 or 2;
p is 1 or 2;
$R^4$ is H, C$_1$-C$_4$ straight or branched alkyl, phenyl, benzyl, or (C$_6$H$_5$)—CH$_2$—O—CH$_2$—;
X is H, C$_1$, F, Br, methyl, or methoxy; and
$R^5$ is —NH$_2$, —OH, glycinol, NH$_2$-Pro-Ser-, NH$_2$-Pro-Lys-, HO-Ser-, HO-Pro-Ser-, HO-Lys-, -Ser alcohol, -Ser-Pro alcohol, -Lys-Pro alcohol, HOCH$_2$CH$_2$—O—CH$_2$CH$_2$NH—, NH$_2$-Phe-Arg-, NH$_2$-Glu-, NH$_2$CH$_2$RCH$_2$NH—, or RO— where R is a C$_1$-C$_4$ straight or branched alkyl.

Additional examples of MC4R agonists useful to practice the present invention are found in WO2011104378; WO2011104379; WO201060901; WO200887189, WO200887188, WO200887187, WO200887186; US20110065652; WO2010144341; WO2010144344; WO201065799; WO201065800; WO201065801; WO201065802; WO201037081; WO2009152079; WO2009151383; US20100311648; US20100280079; WO201081666; WO201034500; WO200910299; WO2008116665; WO201052256; WO201052255; WO201126015; US20100120783; WO201096854; US20100190793; WO201025142; and WO201015972. Further examples of MC4R agonists useful to practice the present invention are found in U.S. Pat. Nos. 8,263,608; 8,247,530; 8,114,844; and 7,968,548. The entire teachings of these publications are incorporated herein by reference.

In one example embodiment, the agonist of MC4R is a tripeptide D-Phe-Arg-Trp (SEQ ID NO: 560) or a pharmaceutical salt thereof. In another example, the agonist is any peptide that includes SEQ ID NO: 560 or a pharmaceutical salt thereof. In yet another example, the MC4R agonist is an acetylated tripeptide Ac-D-Phe-Arg-Trp-NH$_2$ (SEQ ID NO: 561) or a pharmaceutical salt thereof.

In an example embodiment, the agonists of MC4R are those of Formula (I) or a pharmaceutically acceptable salt, hydrate, solvate or a prodrug thereof (see International Patent Application Publication Number WO 2007/008704, incorporated herein by reference in its entirety):

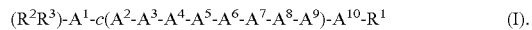

$$(R^2R^3)\text{-}A^1\text{-}c(A^2\text{-}A^3\text{-}A^4\text{-}A^5\text{-}A^6\text{-}A^7\text{-}A^8\text{-}A^9)\text{-}A^{10}\text{-}R^1 \qquad (I).$$

In Formula (I):
- $A^1$ is Acc, HN—(CH$_2$)$_m$—C(O), L- or D-amino acid, or deleted;
- $A^2$ is Cys, D-Cys, hCys, D-hCys, Pen, D-Pen, Asp, or Glu;
- $A^3$ is Gly, Ala, β-Ala, Gaba, Aib, D-amino acid, or deleted;
- $A^4$ is His, 2-Pal, 3-Pal, 4-Pal, Taz, 2-Thi, 3-Thi, or (X$^1$, X$^2$, X$^3$, X$^4$, X$^5$)Phe;
- $A^5$ is D-Phe, D-1-Nal, D-2-Nal, D-Trp, D-Bal, D-(X$^1$, X$^2$, X$^3$, X$^4$, X$^5$)Phe, L-Phe or D-(Et)Tyr;
- $A^6$ is Arg, hArg, Dab, Dap, Lys, Orn, or HN—CH((CH$_2$)$_n$—N(R$^4$R$^5$))—C(O);
- $A^7$ is Trp, 1-Nal, 2-Nal, Bal, Bip, D-Trp, D-2-Nal, D-Bal or D-Bip;
- $A^8$ is Gly, D-Ala, Acc, Ala, 13-Ala, Gaba, Apn, Ahx, Aha, HN—(CH$_2$)$_s$—C(O), or deleted;
- $A^9$ is Cys, D-Cys, hCys, D-hCys, Pen, D-Pen, Dab, Dap, Orn, or Lys;
- $A^{10}$ is Acc, HN—(CH$_2$)$_t$—C(O), L- or D-amino acid, or deleted;
- $R^1$ is OH or NH$_2$;
- each of $R^2$ and $R^3$ is, independently for each occurrence, selected from the group consisting of H, (C$_1$-C$_{30}$)alkyl, (C$_1$-C$_{30}$)heteroalkyl, (C$_1$-C$_{30}$)acyl, (C$_2$-C$_{30}$)alkenyl, (C$_2$-C$_{30}$)alkynyl, aryl(C$_1$-C$_{30}$)alkyl, aryl(C$_1$-C$_{30}$)acyl, substituted (C$_1$-C$_{30}$)alkyl, substituted (C$_1$-C$_{30}$)heteroalkyl, substituted (C$_1$-C$_{30}$)acyl, substituted (C$_2$-C$_{30}$)alkenyl, substituted (C$_2$-C$_{30}$)alkynyl, substituted aryl (C$_1$-C$_{30}$)alkyl, and substituted aryl(C$_1$-C$_{30}$)acyl;
- each of $R^4$ and $R^5$ is, independently for each occurrence, H, (C$_1$-C$_{40}$)alkyl, (C$_1$-C$_{40}$)heteroalkyl, (C$_1$-C$_{40}$)acyl, (C$_2$-C$_{40}$)alkenyl, (C$_2$-C$_{40}$)alkynyl, aryl(C$_1$-C$_{40}$)alkyl, aryl(C$_1$-C$_{40}$)acyl, substituted (C$_1$-C$_{40}$)alkyl, substituted (C$_1$-C$_{40}$)heteroalkyl, substituted (C$_1$-C$_{40}$)acyl, substituted (C$_2$-C$_{40}$)alkenyl, substituted (C$_2$-C$_{40}$)alkynyl, substituted aryl(C$_1$-C$_{40}$)alkyl, substituted aryl(C$_1$-C$_{40}$) acyl, (C$_1$-C$_{40}$)alkylsulfonyl, or —C(NH)—NH$_2$;
- m is, independently for each occurrence, 1, 2, 3, 4, 5, 6 or 7;
- n is, independently for each occurrence, 1, 2, 3, 4 or 5;
- s is, independently for each occurrence, 1, 2, 3, 4, 5, 6, or 7;
- t is, independently for each occurrence, 1, 2, 3, 4, 5, 6, or 7;
- X', X$^2$, X$^3$, X$^4$, and X$^8$ each is, independently for each occurrence, H, F, C$_1$, Br, I, (C$_{1\text{-}10}$)alkyl, substituted (C$_{1\text{-}10}$)alkyl, (C$_{2\text{-}10}$)alkenyl, substituted (C$_{2\text{-}10}$)alkenyl, (C$_{2\text{-}10}$)alkynyl, substituted (C$_{2\text{-}10}$)alkynyl, aryl, substituted aryl, OH, NH$_2$, NO$_2$, or CN.

In exemplary embodiments of the agonists of Formula (I):
(I) when $R^4$ is (C$_1$-C$_{40}$)acyl, aryl(C$_1$-C$_{40}$)acyl, substituted (C$_1$-C$_{40}$)acyl, substituted aryl(C$_1$-C$_{40}$)acyl, (C$_1$-C$_{40}$) alkylsulfonyl, or —C(NH)—NH$_2$, then $R^5$ is H or (C$_1$-C$_{40}$)alkyl, (C$_1$-C$_{40}$)heteroalkyl, (C$_2$-C$_{40}$)alkenyl, (C$_2$-C$_{40}$)alkynyl, aryl(C$_1$-C$_{40}$)alkyl, substituted (C$_1$-C$_{40}$)alkyl, substituted (C$_1$-C$_{40}$)heteroalkyl, substituted (C$_2$-C$_{40}$)alkenyl, substituted (C$_2$-C$_{40}$)alkynyl, or substituted aryl(C$_1$-C$_{40}$)alkyl;
(II) when $R^2$ is (C$_1$-C$_{30}$)acyl, aryl(C$_1$-C$_{30}$)acyl, substituted (C$_1$-C$_{30}$)acyl, or substituted aryl(C$_1$-C$_{30}$)acyl, then $R^3$ is H, (C$_1$-C$_{30}$)alkyl, (C$_1$-C$_{30}$)heteroalkyl, (C$_2$-C$_{30}$)alkenyl, (C$_2$-C$_{30}$)alkynyl, aryl(C$_1$-C$_{30}$)alkyl, substituted (C$_1$-C$_{30}$)alkyl, substituted (C$_1$-C$_{30}$)heteroalkyl, substituted (C$_2$-C$_{30}$)alkenyl, substituted (C$_2$-C$_{30}$)alkynyl, or substituted aryl(C$_1$-C$_{30}$)alkyl;
(III) either $A^3$ or $A^8$ or both must be present in said compound;
(IV) when $A^2$ is Cys, D-Cys, hCys, D-hCys, Pen, or D-Pen, then $A^9$ is Cys, D-Cys, hCys, D-hCys, Pen, or D-Pen;
(V) when $A^2$ is Asp or Glu, then $A^9$ is Dab, Dap, Orn, or Lys;
(VI) when $A^8$ is Ala or Gly, then $A^1$ is not Nle; and
(VII) when $A^1$ is deleted, then $R^2$ and $R^3$ cannot both be H.

In an example embodiment, the agonists employed by the methods described herein are the compounds of Formula I, wherein:
- $A^1$ is A$^6$c, Arg, D-Arg, Cha, D-Cha, hCha, Chg, D-Chg, Gaba, Ile, Leu, hLeu, Met, B-hMet, 2-Nal, D-2-Nal, Nip, Nle, Oic, Phe, D-Phe, hPhe, hPro, Val, or deleted;
- $A^2$ is Asp, Cys, D-Cys, hCys, D-hCys, Glu, Pen, or D-Pen;
- $A^3$ is D-Abu, Aib, Ala, β-Ala, D-Ala, D-Cha, Gaba, D-Glu, Gly, D-Ile, D-Leu, D-Tle, D-Val, or deleted;
- $A^4$ is His or 3-Pal;
- $A^5$ is D-Bal, D-1-Nal, D-2-Nal, D-Phe, D-Trp, or D-(Et) Tyr;
- $A^6$ is Arg, or hArg;
- $A^7$ is Bal, Bip, 1-Nal, 2-Nal, Trp, D-Trp;
- $A^8$ is A6c, D-Ala, Aha, Ahx, Ala, β-Ala, Apn, Gaba, Gly or deleted;
- $A^9$ is Cys, D-Cys, hCys, D-hCys, Lys, Pen, or D-Pen;
- $A^{10}$ is Thr, or deleted, wherein at least one of $A^3$ or $A^8$ is deleted, but not both, or pharmaceutically acceptable salts thereof.

In an example embodiments, agonists of Formula (I) useful in practicing the invention described herein are compounds of the following formula or a pharmaceutically acceptable salt thereof:

SEQ ID NO: 1
Ac-Nle-c(Asp-His-D-Phe-Arg-Trp-β-Ala-Lys)-NH$_2$;

SEQ ID NO: 2
Ac-Nle-c(Asp-His-D-Phe-Arg-Trp-A6c-Lys)-NH$_2$;

SEQ ID NO: 3
Ac-Nle-c(Cys-His-D-Phe-Arg-Trp-Ahx-Cys)-NH$_2$;

```
                                            SEQ ID NO: 4
D-Phe-c(Cys-His-D-Phe-Arg-Trp-Ala-D-Cys)-Thr- NH2;

SEQ ID NO: 5
D-Phe-c(Cys-His-D-Phe-Arg-Trp-β-Ala-D-Cys)-Thr-NH2;

SEQ ID NO: 6
D-Phe-c(Cys-His-D-Phe-Arg-Trp-Gaba-D-Cys)-Thr-NH2;

SEQ ID NO: 7
Ac-Nle-c(Cys-His-D-Phe-Arg-Trp-Apn-Cys)-NH2;

SEQ ID NO: 8
Ac-Nle-c(Asp-His-D-Phe-Arg-Trp-Apn-Lys)-NH2;

SEQ ID NO: 9
Ac-A6c-c(Asp-His-D-Phe-Arg-Trp-Gaba-Lys)-NH2;

SEQ ID NO: 10
Ac-D-2-Nal-c(Asp-His-D-Phe-Arg-Trp-Gaba-Lys)-NH2;

SEQ ID NO: 11
Ac-Cha-c(Asp-His-D-Phe-Arg-Trp-Gaba-Lys)-NH2;

SEQ ID NO: 12
Ac-Nle-c(Asp-His-D-Phe-Arg-Trp-Gaba-Lys)-NH2;

SEQ ID NO: 13
Ac-Nle-c(Cys-D-Ala-His-D-Phe-Arg-Trp-Cys)-NH2;

SEQ ID NO: 14
Ac-Nle-c(Cys-β-Ala-His-D-Phe-Arg-Trp-Cys)-NH2;

SEQ ID NO: 15
Ac-Nle-c(Cys-Gaba-His-D-Phe-Arg-Trp-Cys)-NH2;

SEQ ID NO: 16
Ac-Nle-c(Cys-Aib-His-D-Phe-Arg-Trp-Cys)-NH2;

SEQ ID NO: 17
Ac-Nle-c(Cys-Gly-His-D-Phe-Arg-Trp-Cys)-NH2;

SEQ ID NO: 18
Ac-Nle-c(D-Cys-Ala-His-D-Phe-Arg-Trp-Cys)-NH2;

SEQ ID NO: 19
Ac-Nle-c(D-Cys-D-Ala-His-D-Phe-Arg-Trp-Cys)-NH2;

SEQ ID NO: 20
Ac-Nle-c(D-Cys-β-Ala-His-D-Phe-Arg-Trp-Cys)-NH2;

SEQ ID NO: 21
Ac-Nle-c(D-Cys-Gaba-His-D-Phe-Arg-Trp-Cys)-NH2;

SEQ ID NO: 22
Ac-Nle-c(D-Cys-Aib-His-D-Phe-Arg-Trp-Cys)-NH2;

SEQ ID NO: 23
Ac-Nle-c(D-Cys-Gly-His-D-Phe-Arg-Trp-Cys)-NH2;

SEQ ID NO: 24
Ac-Nle-c(Cys-D-Ala-His-D-Phe-Arg-Trp-D-Cys)-NH2;

SEQ ID NO: 25
Ac-Nle-c(Cys-β-Ala-His-D-Phe-Arg-Trp-D-Cys)- NH2;

SEQ ID NO: 26
Ac-Nle-c(Cys-Gaba-His-D-Phe-Arg-Trp-D-Cys)- NH2;

SEQ ID NO: 27
Ac-Nle-c(Cys-Aib-His-D-Phe-Arg-Trp-D-Cys)- NH2;

SEQ ID NO: 28
Ac-Nle-c(Cys-Gly-His-D-Phe-Arg-Trp-D-Cys)-NH2;

SEQ ID NO: 29
Ac-Nle-c(D-Cys-Ala-His-D-Phe-Arg-Trp-D-Cys)- NH2;

SEQ ID NO: 30
Ac-Nle-c(D-Cys-D-Ala-His-D-Phe-Arg-Trp-D-Cys)- NH2;
```

-continued

```
                                    SEQ ID NO: 31
Ac-Nle-c(D-Cys-β-Ala-His-D-Phe-Arg-Trp-D-Cys)-NH₂;

SEQ ID NO: 32
Ac-Nle-c(D-Cys-Gaba-His-D-Phe-Arg-Trp-D-Cys)-NH₂;

SEQ ID NO: 33
Ac-Nle-c(D-Cys-Aib-His-D-Phe-Arg-Trp-D-Cys)-NH₂;

SEQ ID NO: 34
Ac-Oic-c(Asp-His-D-Phe-Arg-Trp-Gaba-Lys)-NH₂;

SEQ ID NO: 35
Ac-Chg-c(Asp-His-D-Phe-Arg-Trp-Gaba-Lys)-NH₂;

SEQ ID NO: 36
Ac-hCha-c(Asp-His-D-Phe-Arg-Trp-Gaba-Lys)-NH₂;

SEQ ID NO: 37
Ac-D-Cha-c(Asp-His-D-Phe-Arg-Trp-Gaba-Lys)-NH₂;

SEQ ID NO: 38
Ac-D-hCha-c(Asp-His-D-Phe-Arg-Trp-Gaba-Lys)-NH₂;

SEQ ID NO: 39
Ac-Nip-c(Asp-His-D-Phe-Arg-Trp-Gaba-Lys)-NH₂;

SEQ ID NO: 40
Ac-hPro-c(Asp-His-D-Phe-Arg-Trp-Gaba-Lys)-NH₂;

SEQ ID NO: 41
Ac-hLeu-c(Asp-His-D-Phe-Arg-Trp-Gaba-Lys)-NH₂;

SEQ ID NO: 42
Ac-Phe-c(Asp-His-D-Phe-Arg-Trp-Gaba-Lys)-NH₂;

SEQ ID NO: 43
Ac-D-Phe-c(Asp-His-D-Phe-Arg-Trp-Gaba-Lys)-NH₂;

SEQ ID NO: 44
Ac-D-Chg-c(Asp-His-D-Phe-Arg-Trp-Gaba-Lys)-NH₂;

SEQ ID NO: 45
n-butanoyl-Cha-c(Asp-His-D-Phe-Arg-Trp-Gaba-Lys)-NH₂;

SEQ ID NO: 46
n-butyryl-Cha-c(Asp-His-D-Phe-Arg-Trp-Gaba-Lys)-NH₂;

SEQ ID NO: 47
Ac-hPhe-c(Asp-His-D-Phe-Arg-Trp-Gaba-Lys)-NH₂;

SEQ ID NO: 48
Ac-β-hMet-c(Asp-His-D-Phe-Arg-Trp-Gaba-Lys)-NH₂;

SEQ ID NO: 49
Ac-Gaba-c(Asp-His-D-Phe-Arg-Trp-Gaba-Lys)-NH₂;

SEQ ID NO: 50
Ac-Cha-c(Asp-His-D-Phe-Arg-D-Trp-Ala-Lys)-NH₂;
f1
                                    SEQ ID NO: 51
Ac-hCha-c(Asp-His-D-Phe-Arg-D-Trp-Ala-Lys)-NH₂;

SEQ ID NO: 52
Ac-Leu-c(Asp-His-D-Phe-Arg-D-Trp-Ala-Lys)-NH₂;

SEQ ID NO: 53
Ac-hLeu-c(Asp-His-D-Phe-Arg-D-Trp-Ala-Lys)-NH₂;

SEQ ID NO: 54
Ac-Phe-c(Asp-His-D-Phe-Arg-D-Trp-Ala-Lys)-NH₂;

SEQ ID NO: 55
Ac-Nle-c(Asp-His-D-Phe-Arg-D-Trp-D-Ala-Lys)-NH₂;

SEQ ID NO: 56
Ac-Nle-c(Asp-His-D-Phe-Arg-D-Trp-β-Ala-Lys)-NH₂;
```

```
                                                      SEQ ID NO: 57
Ac-Nle-c(Asp-His-D-Phe-Arg-D-Trp-Gaba-Lys)-NH2;

SEQ ID NO: 58
Ac-Nle-c(Asp-His-D-Phe-Arg-D-Trp-Aha-Lys)-NH2;

SEQ ID NO: 59
Ac-Nle-c(Asp-His-D-Phe-Arg-D-Trp-Apn-Lys)-NH2;

SEQ ID NO: 60
Ac-Nle-c(Cys-His-D-Phe-Arg-D-Trp-Apn-Cys)-NH2;

SEQ ID NO: 61
Ac-Nle-c(Cys-His-D-Phe-Arg-D-Trp-Gaba-Cys)-NH2;

SEQ ID NO: 62
Ac-Nle-c(Cys-His-D-Phe-Arg-D-Trp-Ahx-Cys)-NH2;

SEQ ID NO: 63
Ac-Nle-c(Cys-His-D-Phe-Arg-D-Trp-β-Ala-Cys)-NH2;

SEQ ID NO: 64
Ac-Nle-c(Cys-His-D-Phe-Arg-D-Trp-D-Ala-Cys)-NH2;

SEQ ID NO: 65
Ac-Nle-c(Cys-D-Ala-His-D-2-Nal-Arg-Trp-Cys)-NH2;

SEQ ID NO: 66
Ac-Nle-c(Cys-D-Ala-His-D-2-Nal-Arg-2-Nal-Cys)-NH2;

SEQ ID NO: 67
Ac-Nle-c(Cys-D-Ala-His-D-2-Nal-Arg-1-Nal-Cys)-NH2;

SEQ ID NO: 68
n-butanoyl-Nle-c(Cys-D-Ala-His-D-Phe-Arg-2-Nal-Cys)-NH2;

SEQ ID NO: 69
n-butanoyl-Nle-c(Cys-D-Ala-His-D-Phe-Arg-Trp-Cys)-NH2;

SEQ ID NO: 70
Ac-Nle-c(Cys-D-Ala-His-D-Phe-Arg-2-Nal-Cys)-NH2;

SEQ ID NO: 71
Ac-Nle-c(Cys-D-Ala-His-D-Phe-Arg-1-Nal-Cys)-NH2;

SEQ ID NO: 72
Ac-Nle-c(Cys-D-Ala-His-D-Phe-Arg-Bal-Cys)-NH2;

SEQ ID NO: 73
Ac-Nle-c(Cys-D-Glu-His-D-Phe-Arg-Trp-Cys)-NH2;

SEQ ID NO: 74
Ac-Nle-c(Asp-His-D-Phe-Arg-Trp-D-Ala-Lys)-NH2;

SEQ ID NO: 75
Ac-Nle-c(Cys-D-Ala-His-D-2-Nal-Arg-Bal-Cys)-NH2;

SEQ ID NO: 76
Ac-Nle-c(Pen-D-Ala-His-D-Phe-Arg-Trp-Cys)-NH2;

SEQ ID NO: 77
Ac-Nle-c(Cys-D-Ala-His-D-Phe-Arg-Trp-Pen)-NH2;

SEQ ID NO: 78
Ac-Nle-c(Pen-D-Ala-His-D-Phe-Arg-Trp-Pen)-NH2;

SEQ ID NO: 79
D-Phe-c(Cys-His-D-Phe-hArg-Trp-β-Ala-D-Cys)-Thr-NH2;

SEQ ID NO: 80
D-Phe-c(Cys-His-D-(Et)Tyr-Arg-Trp-β-Ala-D-Cys)-Thr-NH2;

SEQ ID NO: 81
D-Phe-c(Cys-His-D-Phe-Arg-Bip-β-Ala-D-Cys)-Thr-NH2;

SEQ ID NO: 82
D-Phe-c(Cys-His-D-(Et)Tyr-hArg-Trp-β-Ala-D-Cys)-Thr-NH2;

SEQ ID NO: 83
D-Phe-c(Cys-His-D-Phe-hArg-Bip-β-Ala-D-Cys)-Thr-NH2;
```

-continued

```
                                                 SEQ ID NO: 84
D-Phe-c(Cys-His-D-(Et)Tyr-hArg-Bip-β-Ala-D-Cys)-Thr- NH₂;

SEQ ID NO: 85
Nle-c(Cys-His-D-Phe-Arg-Trp-Apn-Cys)- NH₂;

SEQ ID NO: 86
Ac-Nle-c(Asp-D-Ala-His-D-Phe-Arg-Trp-Lys)- NH₂;

SEQ ID NO: 87
Ac-Nle-c(Asp-D-Ala-His-D-Phe-Arg-Bal-Lys)- NH₂;

SEQ ID NO: 88
Ac-Nle-c(Cys-D-Ala-His-D-Phe-Arg-Trp-Pen)-OH;

SEQ ID NO: 89
Ac-Nle-c(Cys-D-Abu-His-D-Phe-Arg-Trp-Cys)- NH₂;

SEQ ID NO: 90
Ac-Nle-c(Cys-D-Val-His-D-Phe-Arg-Trp-Cys)- NH₂;

SEQ ID NO: 91
Ac-Nle-c(Cys-D-Ile-His-D-Phe-Arg-Trp-Cys)- NH₂;

SEQ ID NO: 92
Ac-Nle-c(Cys-D-Leu-His-D-Phe-Arg-Trp-Cys)- NH₂;

SEQ ID NO: 93
Ac-Nle-c(Cys-D-Tle-His-D-Phe-Arg-Trp-Cys)- NH₂;

SEQ ID NO: 94
Ac-Nle-c(Cys-D-Cha-His-D-Phe-Arg-Trp-Cys)- NH₂;

SEQ ID NO: 95
Ac-Nle-c(Pen-His-D-Phe-Arg-Trp-Gaba-Cys)- NH₂;

SEQ ID NO: 96
Ac-Nle-c(Cys-His-D-Phe-Arg-Trp-Gaba-Pen)- NH₂;

SEQ ID NO: 97
Ac-Nle-c(Pen-His-D-Phe-Arg-Trp-Gaba-Pen)- NH₂;

SEQ ID NO: 98
Ac-Leu-c(Cys-His-D-Phe-Arg-Trp-Gaba-Cys)- NH₂;

SEQ ID NO: 99
Ac-Cha-c(Cys-His-D-Phe-Arg-Trp-Gaba-Cys)- NH₂;

SEQ ID NO: 100
Ac-Ile-c(Cys-His-D-Phe-Arg-Trp -Gaba-Cys)- NH₂;

SEQ ID NO: 101
Ac-Phe-c(Cys-His-D-Phe-Arg- Trp-Gaba-Cys)- NH₂;

SEQ ID NO: 102
Ac-Val-c(Cys-His-D-Phe-Arg-Trp-Gaba-Cys)- NH₂;

SEQ ID NO: 103
Ac-2-Nal-c(Cys-His-D-Phe-Arg-Trp-Gaba-Cys)- NH₂;

SEQ ID NO: 104
Nle-c(Cys-His-D-Phe-Arg-Trp-Gaba-Cys)- NH₂;

SEQ ID NO: 105
Phe-c(Cys-His-D-Phe-Arg-Trp-Gaba-Cys)- NH₂;

SEQ ID NO: 106
Ac-Nle-c(Cys-3-Pal-D-Phe-Arg-Trp-Gaba-Cys)- NH₂;

SEQ ID NO: 107
Ac-Nle-c(Cys-D-Ala-His-D-Phe-Arg-Trp-Cys)-OH;

SEQ ID NO: 108
Ac-Nle-c(Cys-His-Phe-Arg-D-Trp-Gaba-Cys)- NH₂;

SEQ ID NO: 109
Ac-Nle-c(Asp-His-D-2-Nal-Arg-Trp-Ala-Lys)- NH₂;

SEQ ID NO: 110
Ac-Nle-c(Asp-His-D-2-Nal-Arg-Trp-β-Ala-Lys)- NH₂;
```

```
                                                    SEQ ID NO: 111
Ac-Nle-c(Cys-His-D-2-Nal-Arg-Trp-Gaba-Cys)-NH2;

SEQ ID NO: 112
Ac-Nle-c(Cys-His-D-2-Nal-Arg-Trp-Ahx-Cys)-NH2;

SEQ ID NO: 113
Ac-hPhe-c(Asp-His-D-2-Nal-Arg-Trp-Gaba-Lys)-NH2;

SEQ ID NO: 114
Ac-Cha-c(Asp-His-D-2-Nal-Arg-Trp-Gaba-Lys)-NH2;

SEQ ID NO: 115
Ac-Nle-c(Asp-His-D-Phe-Arg-Trp-β-Ala-Lys)-OH;

SEQ ID NO: 116
Ac-Nle-c(Cys-His-D-Phe-Arg-Trp-Ahx-Cys)-OH;

SEQ ID NO: 117
D-Phe-c(Cys-His-D-Phe-Arg-Trp-Ala-D-Cys)-Thr-OH;

SEQ ID NO: 118
D-Phe-c(Cys-His-D-Phe-Arg-Trp-β-Ala-D-Cys)-Thr-OH;

SEQ ID NO: 119
D-Phe-c(Cys-His-D-Phe-Arg-Trp-Gaba-D-Cys)-Thr-OH;

SEQ ID NO: 120
Ac-Nle-c(Cys-His-D-Phe-Arg-Trp-Apn-Cys)-OH;

SEQ ID NO: 121
Ac-Nle-c(Asp-His-D-Phe-Arg-Trp-Apn-Lys)-OH;

SEQ ID NO: 122
Ac-Cha-c(Asp-His-D-Phe-Arg-Trp-Gaba-Lys)-OH;

SEQ ID NO: 123
Ac-Nle-c(Asp-His-D-Phe-Arg-Trp-Gaba-Lys)-OH;

SEQ ID NO: 124
Ac-Chg-c(Asp-His-D-Phe-Arg-Trp-Gaba-Lys)-OH;

SEQ ID NO: 125
Ac-D-Cha-c(Asp-His-D-Phe-Arg-Trp-Gaba-Lys)-OH;

SEQ ID NO: 126
Ac-hCha-c(Asp-His-D-Phe-Arg-Trp-Gaba-Lys)-OH;

SEQ ID NO: 127
Ac-D-Chg-c(Asp-His-D-Phe-Arg-Trp-Gaba-Lys)-OH;

SEQ ID NO: 128
Ac-hPhe-c(Asp-His-D-Phe-Arg-Trp-Gaba-Lys)-OH;

SEQ ID NO: 129
Ac-Nle-c(Cys-His-D-Phe-Arg-D-Trp-Gaba-Cys)-OH;

SEQ ID NO: 130
Ac-Nle-c(Cys-His-D-Phe-Arg-D-Trp-Ahx-Cys)-OH;

SEQ ID NO: 131
Ac-Nle-c(Cys-His-D-Phe-Arg-D-Trp-β-Ala-Cys)-OH;

SEQ ID NO: 132
Ac-Nle-c(Cys-His-D-Phe-Arg-D-Trp-D-Ala-Cys)-OH;

SEQ ID NO: 133
Ac-Nle-c(Cys-D-Ala-His-D-2-Nal-Arg-Trp-Cys)-OH;

SEQ ID NO: 134
Ac-Nle-c(Cys-D-Ala-His-D-2-Nal-Arg-2-Nal-Cys)-OH;

SEQ ID NO: 135
Ac-Nle-c(Cys-D-Ala-His-D-2-Nal-Arg-1-Nal-Cys)-OH;

SEQ ID NO: 136
Ac-Nle-c(Cys-D-Ala-His-D-2-Nal-Arg-Bal-Cys)-OH;

SEQ ID NO: 137
Ac-Nle-c(Pen-D-Ala-His-D-Phe-Arg-Trp-Cys)-OH;
```

```
Ac-Nle-c(Cys-His-D-Phe-Arg-Trp-Gaba-Pen)-OH;                       SEQ ID NO: 138

Ac-Arg-c(Cys-D-Ala-His-D-2-Nal-Arg-Trp-Cys)- NH2;                  SEQ ID NO: 139

Ac-Arg-c(Cys-D-Ala-His-D-Phe-Arg-Trp-Cys)- NH2;                    SEQ ID NO: 140

Ac-D-Arg-c(Cys-D-Ala-His-D-Phe-Arg-Trp-Cys)- NH2;                  SEQ ID NO: 141

Ac-D-Arg-c(Cys-D-Ala-His-D-Phe-Arg-Trp-Pen)- NH2;                  SEQ ID NO: 142

Ac-D-Arg-c(Cys-His-D-Phe-Arg-Trp-Gaba-Pen)- NH2;                   SEQ ID NO: 143

Ac-Arg-c(Cys-His-D-Phe-Arg-Trp-Gaba-Pen)- NH2;                     SEQ ID NO: 144

Ac-Arg-c(Cys-D-Ala-His-D-Phe-Arg-Trp-Pen)- NH2;                    SEQ ID NO: 145

Ac-D-Arg-c(Asp-His-D-Phe-Arg-Trp-Ala-Lys)- NH2;                    SEQ ID NO: 146
or

Ac-Arg-c(Asp-His-D-Phe-Arg-Trp-Ala-Lys)- NH2;                      SEQ ID NO: 147
``` or pharmaceutically acceptable salts thereof.

In embodiments, the MC4R agonist is setmelanotide (also called RM-493), having the sequence of Ac-Arg-c(Cys-D-Ala-His-D-Phe-Arg-Trp-Cys)-NH$_2$ (SEQ ID NO: 140). Setmelanotide is a peptide that retains the specificity and functionality of the naturally occurring hormone that activates MC4R and has not been shown to adversely affect blood pressure in clinical trials. See, e.g., Chen et al. J. Clin. Endocrinol. Metab. 2015; 100(4):1639-45. The structure of setmelanotide is shown below.

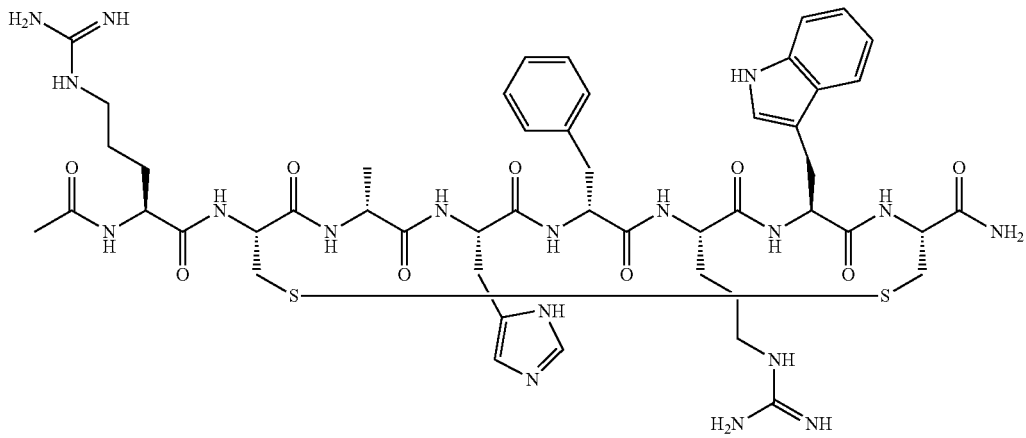 [SMILES: CC(=O)N[C@@H](CCCNC(=N)N)C(=O)N[C@H]1CSSC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2cnc[nH]2)NC(=O)[C@@H](C)NC1=O]

Setmelanotide is an 8 amino acid cyclic peptide that is efficient in activating MC4R. See, e.g., U.S. Pat. No. 8,039,435B2, incorporated herein by reference. Setmelanotide has been generally well-tolerated with little, if any, signs of increased blood pressure and only infrequent effects on sexual activity.

In an example embodiment, an agonist of MC4R receptor useful for practicing methods described herein is any of the compounds described by Formula (II) or a pharmaceutically acceptable salt, hydrate, solvate or a prodrug thereof (see International Patent Application Publication Number WO 2007/008704 incorporated herein by reference in its entirety):

$$(R^2R^3)-A^1-c(A^2-A^3-A^4-A^5-A^6-A^7-A^8-A^9)-NH_2 \quad (II)$$

In formula (II):
$A^1$ is Nle or deleted;
$A^2$ is Cys or Asp;
$A^3$ is Glu or D-Ala;
$A^4$ is His;
$A^5$ is D-Phe;
$A^6$ is Arg;
$A^7$ is Trp, 2-Nal or Bal;
$A^8$ is Gly, Ala, D-Ala, β-Ala, Gaba or Apn;
$A^9$ is Cys or Lys;
each of $R^2$ and $R^3$ is independently selected from the group consisting of H or (C$_1$-C$_6$)acyl.

In exemplary embodiments of Formula (II):
(I) when $R^2$ is $(C_1-C_6)$acyl, then $R^3$ is H; and
(II) when $A^2$ is Cys, then $A^9$ is Cys.

In alternative example embodiments of the present invention, the compounds useful for practicing the methods disclosed herein are:

Ac-Nle-c(Cys-D-Ala-His-D-Phe-Arg-Trp-Gly-Cys)-NH$_2$;  (SEQ ID NO: 148)

Ac-Nle-c(Cys-D-Ala-His-D-Phe-Arg-Trp-D-Ala-Cys)-NH$_2$;  (SEQ ID NO: 149)

Ac-Nle-c(Cys-D-Ala-His-D-Phe-Arg-Trp-β-Ala-Cys)-NH$_2$;  (SEQ ID NO: 150)

Ac-Nle-c(Cys-D-Ala-His-D-Phe-Arg-Trp-Gaba-Cys)-NH$_2$;  (SEQ ID NO: 151)

Ac-Nle-c(Cys-D-Ala-His-D-Phe-Arg-Trp-Apn-Cys)-NH$_2$;  (SEQ ID NO: 152)

Ac-c(Cys-Glu-His-D-Phe-Arg-Trp-Ala-Cys)-NH$_2$;  (SEQ ID NO: 153)

Ac-c(Cys-Glu-His-D-Phe-Arg-2-Nal-Ala-Cys)-NH$_2$  (SEQ ID NO: 154)

Ac-c(Cys-D-Ala-His-D-Phe-Arg-Trp-Ala-Cys)-NH$_2$;  (SEQ ID NO: 155)

Ac-c(Cys-D-Ala-His-D-Phe-Arg-2-Nal-Ala-Cys)-NH$_2$;  (SEQ ID NO: 156)

Ac-Nle-c(Cys-D-Ala-His-D-Phe-Arg-Trp-Ala-Cys)-NH$_2$;  (SEQ ID NO: 157)

or

Ac-Nle-c(Asp-D-Ala-His-D-Phe-Arg-Bal-Ala-Lys)-NH$_2$;  (SEQ ID NO: 158)

or a pharmaceutically acceptable salt thereof.

In an exemplary embodiment, the agonists of MC4R useful for practicing the methods described herein is any of the compounds of Formula (III), or a pharmaceutically acceptable salt, hydrate, solvate or a prodrug thereof (see International Application Publication Number WO 2007/008684, incorporated herein by reference in its entirety):

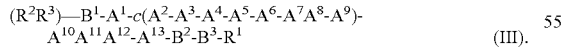

$(R^2R^3)$—$B^1$-$A^1$-$c(A^2$-$A^3$-$A^4$-$A^5$-$A^6$-$A^7A^8$-$A^9)$-$A^{10}A^{11}A^{12}$-$A^{13}$-$B^2$-$B^3$-$R^1$     (III)

In Formula (III):
$B^1$ is a peptide moiety which contains 5, 6, 7, 8, 9, 10, 11, 12, 13, 14, or 15 amino acids, wherein at least 5 amino acids are independently selected from the group consisting of L-Arg, D-Arg, L-hArg and D-hArg, or $B^1$ is optionally deleted;
$A^1$ is Acc, HN—$(CH_2)_m$—C(O), L- or D-amino acid or deleted;
$A^2$ is Cys, D-Cys, hCys, D-hCys, Pen, D-Pen, Asp or Glu;
$A^3$ is Gly, Glu, Ala, β-Ala, Gaba, Aib, D-amino acid or deleted;
$A^4$ is His, 2-Pal, 3-Pal, 4-Pal, Taz, 2-Thi, 3-Thi or (X', $X^2$, $X^3$, $X^4$, $X^5$)Phe;
$A^5$ is D-Phe, D-1-Nal, D-2-Nal, D-Trp, D-Bal, D-($X^1$, $X^2$, $X^3$, $X^4$, $X^5$)Phe, D-(Et)Tyr, D-Dip, D-Bip or D-Bpa;
$A^6$ is Arg, hArg, Dab, Dap, Lys, Orn or HN—CH$((CH_2)_n$—N$(R^4R^5))$—C(O);
$A^7$ is Trp, 1-Nal, 2-Nal, Bal, Bip, Dip, Bpa, D-Trp, D-1-Nal, D-2-Nal, D-Bal, D-Bip, D-Dip or D-Bpa;
$A^8$ is Gly, D-Ala, Acc, Ala, β-Ala, Gaba, Apn, Ahx, Aha, HN—$(CH_2)_s$—C(O) or deleted;
$A^9$ is Cys, D-Cys, hCys, D-hCys, Pen, D-Pen, Dab, Dap, Orn or Lys;
$A^{10}$ is Acc, HN—$(CH_2)$; —C(O), Pro, hPro, 3-Hyp, 4-Hyp, Thr, an L- or D-amino acid or deleted;
$A^{11}$ is Pro, hPro, 3-Hyp, 4-Hyp or deleted;
$A^{12}$ is Lys, Dab, Dap, Arg, hArg or deleted;
$A^{13}$ is Asp, Glu or deleted;
$B^2$ is a peptide moiety containing 1, 2, 3, 4, or 5 amino acids or deleted,
$B^3$ is a peptide moiety which contains 5, 6, 7, 8, 9, 10, 11, 12, 13, 14 or 15 amino acids wherein at least 5 amino acids are independently selected from the group consisting of L-Arg, D-Arg, L-hArg and D-hArg, or is deleted;
$R^1$ is OH or NH$_2$;
$R^2$ and $R^3$ each is, independently for each occurrence, selected from the group consisting of H, $(C_1-C_{30})$alkyl, $(C_1-C_{30})$heteroalkyl, $(C_1-C_{30})$acyl, $(C_2-C_{30})$alkenyl, $(C_2-C_{30})$alkynyl, aryl$(C_1-C_{30})$alkyl, aryl$(C_1-C_{30})$acyl, substituted $(C_1-C_{30})$alkyl, substituted $(C_1-C_{30})$heteroalkyl, substituted $(C_1-C_{30})$acyl, substituted $(C_2-C_{30})$alkenyl, substituted $(C_2-C_{30})$alkynyl, substituted aryl$(C_1-C_{30})$alkyl and substituted aryl$(C_1-C_{30})$acyl;
$R^4$ and $R^5$ each is, independently for each occurrence, H, $(C_1-C_{40})$alkyl, $(C_1-C_{40})$heteroalkyl, $(C_1-C_{40})$acyl, $(C_2-C_{40})$alkenyl, $(C_2-C_{40})$alkynyl, aryl$(C_1-C_{40})$alkyl, aryl$(C_1-C_{40})$acyl, substituted $(C_1-C_{40})$alkyl, substituted $(C_1-C_{40})$heteroalkyl, substituted $(C_1-C_{40})$acyl, substituted $(C_2-C_{40})$alkenyl, substituted $(C_2-C_{40})$alkynyl, substituted aryl$(C_1-C_{40})$alkyl, substituted aryl$(C_1-C_{40})$acyl, $(C_1-C_{40})$alkylsulfonyl or C(NH)—NH$_2$;
n is, independently for each occurrence, 1, 2, 3, 4 or 5;
m is, independently for each occurrence, 1, 2, 3, 4, 5, 6 or 7;
s is, independently for each occurrence, 1, 2, 3, 4, 5, 6 or 7;
t is, independently for each occurrence, 1, 2, 3, 4, 5, 6 or 7;
$X^1$, $X^2$, $X^3$, $X^4$ and $X^5$ each is, independently for each occurrence, H, F, Cl, Br, I, $(C_{1-10})$alkyl, substituted $(C_{1-10})$alkyl, $(C_{2-10})$alkenyl, substituted $(C_{2-10})$alkenyl, $(C_{2-10})$alkynyl, substituted $(C_{2-10})$alkynyl, aryl, substituted aryl, OH, NH$_2$, NO$_2$ or CN.

In an example embodiments of Formula (III):
(I) when $R^4$ is $(C_1-C_{40})$acyl, aryl$(C_1-C_{40})$acyl, substituted $(C_1-C_{40})$acyl, substituted aryl$(C_1-C_{40})$acyl, $(C_1-C_{40})$alkylsulfonyl or C(NH)—NH$_2$, then $R^5$ is H, $(C_1-C_{40})$alkyl, $(C_1-C_{40})$heteroalkyl, $(C_2-C_{40})$alkenyl, $(C_2-C_{40})$alkynyl, aryl$(C_1-C_{40})$alkyl, substituted $(C_1-C_{40})$alkyl, substituted $(C_1-C_{40})$heteroalkyl, substituted $(C_2-C_{40})$alkenyl, substituted $(C_2-C_{40})$alkynyl or substituted aryl $(C_1-C_{40})$alkyl;
(II) when $R^2$ is $(C_1-C_{30})$acyl, aryl$(C_1-C_{30})$acyl, substituted $(C_1-C_{30})$acyl or substituted aryl$(C_1-C_{30})$acyl, then $R^3$ is H, $(C_1-C_{30})$alkyl, $(C_1-C_{30})$heteroalkyl, $(C_2-C_{30})$alkenyl, $(C_2-C_{30})$alkynyl, aryl$(C_1-C_{30})$alkyl, substituted $(C_1-C_{30})$alkyl, substituted $(C_1-C_{30})$heteroalkyl, substituted (C$_2$-C$_{30}$)alkenyl, substituted (C$_2$-C$_{30}$)alkynyl or substituted aryl(C$_1$-C$_{30}$)alkyl;

(III) neither B$^1$ nor B$^2$ contains one or more of the following amino acid sequences: Arg-(Lys)$_2$-(Arg)$_2$-Gln-(Arg)$_3$ (SEQ ID NO: 565), Tyr-Ala-Arg-Lys-Ala-(Arg)$_2$-Gln-Ala-(Arg)$_2$ (SEQ ID NO: 566), Tyr-Ala-Arg-(Ala)$_2$-(Arg)$_2$-(Ala)$_2$-(Arg)$_2$ (SEQ ID NO: 567), Tyr-Ala-(Arg)$_9$ (SEQ ID NO: 568), Tyr-(Ala)$_3$-(Arg)$_7$ (SEQ ID NO: 569), Tyr-Ala-Arg-Ala-Pro-(Arg)$_2$-Ala-(Arg)$_3$ (SEQ ID NO: 570) or Tyr-Ala-Arg-Ala-Pro-(Arg)$_2$-Pro-(Arg)$_2$ (SEQ ID NO: 571);

(IV) either B$^1$ or B$^2$ or both must be present in said compound;

(V) when A$^2$ is Cys, D-Cys, hCys, D-hCys, Pen or D-Pen, then A$^9$ is Cys, D-Cys, hCys, D-hCys, Pen or D-Pen; and (VI) when A$^2$ is Asp or Glu, then A$^9$ is Dab, Dap, Orn or Lys.

In exemplary embodiments, in Formula (III);

B$^1$ is Arg-Lys-Gln-Lys-(Arg)$_5$ (SEQ ID NO: 572), Arg-(Lys)$_2$-Arg-Gln-(Arg)$_4$ (SEQ ID NO: 573), Arg-(Lys)$_2$-(Arg)$_3$-Gln-(Arg)$_2$ (SEQ ID NO: 574), Arg-(Lys)$_2$-(Arg)$_4$-Gln-Arg (SEQ ID NO: 575), Arg-(Lys)$_2$-(Arg)$_5$-Gln (SEQ ID NO: 576), Arg-(Lys)$_2$-Gln-(Arg)$_5$ (SEQ ID NO: 577), Arg-Gln-(Lys)$_2$-(Arg)$_5$ (SEQ ID NO: 578), Arg-Gln-(Arg)$_7$ (SEQ ID NO: 579), Arg-Gln-(Arg); (SEQ ID NO: 580), (Arg)$_2$-Gln-(Arg)$_6$ (SEQ ID NO: 581), (Arg)$_2$-Gln-(Arg)$_7$ (SEQ ID NO: 582), (Arg)$_3$-Gln-(Arg)$_5$ (SEQ ID NO: 583), (Arg)$_3$-Gln-(Arg)$_6$ (SEQ ID NO: 584), (Arg)$_4$-Gln-(Arg)$_4$ (SEQ ID NO: 585), (Arg)$_4$-Gln-(Arg)$_5$ (SEQ ID NO: 587), (Arg) 5 (SEQ ID NO: 587), (Arg)$_5$-Gln-(Arg)$_3$ (SEQ ID NO: 588), (Arg)$_5$-Gln-(Arg)$_4$ (SEQ ID NO: 589), (Arg)$_6$ (SEQ ID NO: 590), (Arg)$_6$-Gln-(Arg)$_3$ (SEQ ID NO: 591), (Arg)$_7$ (SEQ ID NO: 592), (Arg)$_7$-Gln-(Arg)$_2$ (SEQ ID NO: 593), (Arg)$_8$ (SEQ ID NO: 594), (Arg) s-Gln-Arg (SEQ ID NO: 595), (Arg)$_9$ (SEQ ID NO: 596), (Arg)$_9$-Gln (SEQ ID NO: 597), (D-Arg)$_5$ (SEQ ID NO: 598), (D-Arg)$_6$ (SEQ ID NO: 599), (D-Arg)$_7$ (SEQ ID NO: 600), (D-Arg)$_8$ (SEQ ID NO: 601), (D-Arg)$_9$ (SEQ ID NO: 602), Gln-Arg-(Lys)$_2$-(Arg)$_5$ (SEQ ID NO: 603), Gln-(Arg)$_8$ (SEQ ID NO: 604), Gln-(Arg)$_9$ (SEQ ID NO: 605), Tyr-Gly-Arg-(Lys)$_2$-(Arg)$_2$-Gln-(Arg)$_3$ (SEQ ID NO: 606), Tyr-Gly-Arg-(Lys)$_2$-(Arg)$_2$-Gln-(Arg)$_3$-Doc (SEQ ID NO: 607); or deleted;

B$^2$ is β-Ala, β-Ala-Gly, β-Ala-Tyr, β-Ala-Tyr-Gly, (β-Ala)$_2$, (β-Ala)$_2$-Gly, (β-Ala)$_2$-Tyr, (β-Ala)$_2$-Tyr-Gly (SEQ ID NO: 608), Doc, Doc-Gly, Doc-Tyr, Doc-Tyr-Gly, (Doc)$_2$, (Doc)$_2$-Gly, (Doc)$_2$-Tyr-(Doc)$_2$-Tyr-Gly (SEQ ID NO: 609), or deleted;

B$^3$ is Arg-Lys-Gln-Lys-(Arg)$_5$ (SEQ ID NO: 572), Arg-Lys-(Arg)$_3$-Gln-(Arg)$_3$ (SEQ ID NO: 610), Arg-(Lys)$_2$-Arg-Gln-(Arg)$_4$ (SEQ ID NO: 573), Arg-(Lys)$_2$-Gln-(Arg)$_5$ (SEQ ID NO: 577), Arg-(Lys)$_2$-(Arg)$_2$-Gln-(Arg)$_3$ (SEQ ID NO: 565), Arg-(Lys)$_2$-(Arg)$_3$-Gln-(Arg)$_2$ (SEQ ID NO: 574), Arg-(Lys)$_2$-(Arg)$_4$-Gln-Arg (SEQ ID NO: 575), Arg-(Lys)$_2$-(Arg)$_5$-Gln (SEQ ID NO: 576), Arg-Gln-(Lys)$_2$-(Arg)$_5$ (SEQ ID NO: 578), Arg-Gln-(Arg)$_7$ (SEQ ID NO: 579), Arg-Gln-(Arg)$_5$ (SEQ ID NO: 612), (Arg)$_2$-Lys-(Arg)$_2$-Gln-(Arg)$_3$ (SEQ ID NO: 611), (Arg)$_2$-Gln-(Arg)$_6$ (SEQ ID NO: 581), (Arg)$_2$-Gln-(Arg)$_7$ (SEQ ID NO: 582), (Arg)$_3$-Gln-(Arg)$_5$ (SEQ ID NO: 583), (Arg)$_3$-Gln-(Arg)$_6$ (SEQ ID NO: 584), (Arg)$_4$-Gln-(Arg)$_4$ (SEQ ID NO: 585), (Arg)$_4$-Gln-(Arg)$_5$ (SEQ ID NO: 586), (Arg)$_5$ (SEQ ID NO: 587), (Arg) s-Gln-(Arg)$_3$ (SEQ ID NO: 613), (Arg)$_5$-Gln-(Arg)$_4$ (SEQ ID NO: 589), (Arg)$_6$ (SEQ ID NO: 590), (Arg)$_6$-Gln-(Arg)$_3$ (SEQ ID NO: 591), (Arg)$_7$ (SEQ ID NO: 592), (Arg)$_7$-Gln-(Arg)$_2$ (SEQ ID NO: 593), (Arg): (SEQ ID NO: 594), (Arg) s-Gln-Arg (SEQ ID NO: 595), (Arg)$_9$ (SEQ ID NO: 596), (Arg)$_9$-Gln (SEQ ID NO: 597), (D-Arg)$_5$ (SEQ ID NO: 598), (D-Arg)$_6$ (SEQ ID NO: 599), (D-Arg)$_7$ (SEQ ID NO: 600), (D-Arg): (SEQ ID NO: 601), (D-Arg)$_9$ (SEQ ID NO: 602), Gln-Arg-(Lys)$_2$-(Arg)$_5$ (SEQ ID NO: 603), Gln-(Arg)$_8$ (SEQ ID NO: 604), Gln-(Arg)$_9$ (SEQ ID NO: 605), or deleted; A$^1$ is A6c, Cha, hCha, Chg, D-Chg, hChg, Gaba, hLeu, Met, β-hMet, D-2-Nal, Nip, Nle, Oic, Phe, D-Phe, hPhe, hPro, or deleted;

A$^1$ is A6c, Cha, hCha, Chg, D-Chg, hChg, Gaba, hLeu, Met, β-hMet, D-2-Nal, Nip, Nle, Oic, Phe, D-Phe, hPhe, hPro, or deleted;

A$^2$ is Cys;

A$^3$ is D-Abu, Aib, Ala, β-Ala, D-Ala, D-Cha, Gaba, Glu, Gly, D-Ile, D-Leu, D-Met, D-Nle, D-Phe, D-Tle, D-Trp, D-Tyr, D-Val, or deleted;

A$^4$ is H;

A$^5$ is D-Bal, D-1-Nal, D-2-Nal, D-Phe, D-(X$^1$, X$^2$, X$^3$, X$^4$, X$^5$)Phe, D-Trp, or D-(Et)Tyr;

A$^6$ is Arg or hArg;

A$^7$ is Bal, Bip, 1-Nal, 2-Nal, Trp, or D-Trp;

A$^8$ is A5c, A6c, Aha, Ahx, Ala, β-Ala, Apn, Gaba, Gly, or deleted;

A$^9$ is Cys, D-Cys, hCys, D-hCys, Lys, Pen, or D-Pen;

A$^{10}$ is Pro, Thr or deleted;

A$^{11}$ is Pro or deleted;

A$^{12}$ is arg, Lys, or deleted;

A$^{13}$ is Asp or deleted;

each of R$^2$ and R$^3$ is, independently, H or acyl;

or pharmaceutically acceptable salts thereof.

In exemplary embodiments, the MC4R agonists useful for practicing the methods of the present invention are at least one of the following compounds:

(SEQ ID NO: 159)
Tyr-Gly-Arg-(Lys)$_2$-(Arg)$_2$-Gln-(Arg)$_3$-Nle-c(Asp-His-D-2-Nal-Arg-Trp-Lys)-NH$_2$;

(SEQ ID NO: 160)
Tyr-Gly-Arg-(Lys)$_2$-(Arg)$_2$-Gln-(Arg)$_3$-Doc-Nle-c(Asp-His-D-2-Nal-Arg-Trp-Lys)-NH$_2$;

(SEQ ID NO: 161)
Nle-c(Asp-His-D-2-Nal-Arg-Trp-Lys)-β-Ala-Tyr-Gly-Arg-(Lys)$_2$-(Arg)$_2$-Gln-(Arg)$_3$-NH$_2$;

-continued

```
                                                          (SEQ ID NO: 162)
Ac-Nle-c(Asp-His-D-2-Nal-Arg-Trp-Lys)-β-Ala-Tyr-Gly-Arg-(Lys)₂-(Arg)₂-Gln- (Arg)₃-NH₂;

(SEQ ID NO: 163)
Nle-c(Asp-His-D-2-Nal-Arg-Trp-Lys)-(Doc)₂-Tyr-Gly-Arg-(Lys)₂-(Arg)₂-Gln- (Arg)₃-NH₂;

(SEQ ID NO: 164)
Ac-Nle-c(Asp-His-D-2-Nal-Arg-Trp-Lys)-(Pro)₂-Lys-Asp-Tyr-Gly-Arg-(Lys)₂-

(Arg)₂-Gln-(Arg)₃-NH₂;

(SEQ ID NO: 165)
Ac-c(Cys-Glu-His-D-2-Nal-Arg-Trp-Gly-Cys)-(Pro)₂-Lys-Asp-Tyr-Gly-Arg-(Lys)₂-

(Arg)₂-Gln-(Arg)₃-NH₂;

(SEQ ID NO: 166)
Ac-Nle-c(Asp-His-D-2-Nal-Arg-Trp-Lys)-(β-Ala)₂-Tyr-Gly-Arg-(Lys)₂-(Arg)₂-Gln- (Arg)₃-NH₂;

(SEQ ID NO: 167)
Ac-Nle-c(Asp-His-D-2-Nal-Arg-Trp-Lys)-(Pro)₂-Lys-Asp-Doc-Tyr-Gly-Arg-(Lys)₂-

(Arg)₂-Gln-(Arg)₃-NH₂;

(SEQ ID NO: 168)
Ac-c(Cys-Glu-His-D-2-Nal-Arg-Trp-Gly-Cys)-(Pro)₂-Lys-Asp-Doc-Tyr-Gly-Arg- (Lys)₂-(Arg)₂-Gln-(Arg)₃-NH₂;

(SEQ ID NO: 169)
Ac-c(Cys-Glu-His-D-2-Nal-Arg-Trp-Ala-Cys)-(Pro)₂-Lys-Asp-3-Ala-Tyr-Gly-Arg- (Lys)₂-(Arg)₂-Gln-(Arg)₃-NH₂;

(SEQ ID NO: 170)
Ac-c(Cys-Glu-His-D-2-Nal-Arg-Trp-Ala-Cys)-(Pro)₂-Lys-Asp-Doc-Tyr-Gly-Arg- (Lys)₂-(Arg)₂-Gln-(Arg)₃-NH₂;

(SEQ ID NO: 171)
Ac-Nle-c(Asp-His-D-2-Nal-Arg-Trp-Lys)-(Doc)₂-Tyr-Gly-Arg-(Lys)₂-(Arg)₂-Gln- (Arg)₃-NH₂;

(SEQ ID NO: 172)
Ac-c(Cys-Glu-His-D-2-Nal-Arg-2-Nal-Ala-Cys)-(Pro)₂-Lys-Asp-β-Ala-Tyr-Gly-Arg- (Lys)₂-(Arg)₂-Gln-(Arg)₃-NH₂;

(SEQ ID NO: 173)
Ac-c(Cys-Glu-His-D-2-Nal-Arg-Bal-Ala-Cys)-(Pro)₂-Lys-Asp-β-Ala-(Arg)₅-Gln- (Arg)₃-NH₂;

(SEQ ID NO: 174)
Ac-c(Cys-Glu-His-D-2-Nal-Arg-Bal-Ala-Cys)-(Pro)₂-Lys-Asp-β-Ala-Gly-(Arg)₅-

Gln-(Arg)₃-NH₂;

(SEQ ID NO: 175)
Ac-c(Cys-Glu-His-D-2-Nal-Arg-Bal-Ala-Cys)-(Pro)₂-Lys-Asp-β-Ala-Tyr-Gly- (Arg)₅-Gln-(Arg)₃-NH₂;

(SEQ ID NO: 176)
Ac-c(Cys-Glu-His-D-2-Nal-Arg-Trp-Ala-Cys)-(Pro)₂-Lys-Asp-β-Ala-Tyr-Gly-Arg- (Lys)₂-Arg-Gln-(Arg)₄-NH₂;

(SEQ ID NO: 177)
Ac-c(Cys-Glu-His-D-2-Nal-Arg-Trp-Ala-Cys)-(Pro)₂-Lys-Asp-β-Ala-Tyr-Gly-Arg- (Lys)₂-Gln-(Arg)₅-NH₂;
```

-continued (SEQ ID NO: 178)
Ac-c(Cys-Glu-His-D-2-Nal-Arg-Trp-Ala-Cys)-(Pro)$_2$-Lys-Asp-β-Ala-Tyr-Gly-Arg-Lys-Gln-Lys-(Arg)$_5$-NH$_2$;

(SEQ ID NO: 179)
Ac-c(Cys-Glu-His-D-2-Nal-Arg-Trp-Ala-Cys)-(Pro)$_2$-Lys-Asp-β-Ala-Tyr-Gly-Arg-(Lys)$_2$-(Arg)$_4$-Gln-Arg-NH$_2$;

(SEQ ID NO: 180)
Ac-c(Cys-Glu-His-D-2-Nal-Arg-Bal-Ala-Cys)-(Pro)$_2$-Lys-Asp-β-Ala-Tyr-Aib-Arg-(Lys)$_2$-(Arg)$_2$-Gln-(Arg)$_3$-NH$_2$;

(SEQ ID NO: 181)
Ac-c(Cys-Glu-His-D-2-Nal-Arg-1-Nal-Ala-Cys)-(Pro)$_2$-Arg-Asp-β-Ala-(Arg)$_5$-Gln-(Arg)$_3$-NH$_2$;

(SEQ ID NO: 182)
Ac-c(Cys-Glu-His-D-2-Nal-Arg-1-Nal-Ala-Cys)-(Pro)$_2$-Lys-Asp-β-Ala-(Arg)$_5$-Gln-(Arg)$_3$-NH$_2$;

(SEQ ID NO: 183)
Ac-c(Cys-Glu-His-D-2-Nal-Arg-1-Nal-Ala-Cys)-(Pro)$_2$-Lys-Asp-β-Ala-(Arg)$_6$-Gln-(Arg)$_3$-NH$_2$;

(SEQ ID NO: 184)
Ac-c(Cys-Glu-His-D-2-Nal-Arg-2-Nal-Ala-Cys)-(Pro)$_2$-Arg-Asp-β-Ala-(Arg)$_5$-Gln-(Arg)$_3$-NH$_2$;

(SEQ ID NO: 185)
Ac-c(Cys-Glu-His-D-2-Nal-Arg-2-Nal-Ala-Cys)-(Pro)$_2$-Lys-Asp-β-Ala-(Arg)$_5$-Gln-(Arg)$_3$-NH$_2$;

(SEQ ID NO: 186)
Ac-c(Cys-Glu-His-D-2-Nal-Arg-2-Nal-Ala-Cys)-(Pro)$_2$-Lys-Asp-β-Ala-(Arg)$_6$-Gln-(Arg)$_3$-NH$_2$;

(SEQ ID NO: 187)
Ac-c(Cys-Glu-His-D-2-Nal-Arg-Bal-Ala-Cys)-(Pro)$_2$-Arg-Asp-β-Ala-(Arg)$_6$-Gln-(Arg)$_3$-NH$_2$;

(SEQ ID NO: 188)
Ac-c(Cys-Glu-His-D-2-Nal-Arg-Bal-Ala-Cys)-(Pro)$_2$-Arg-Asp-β-Ala-(Arg)$_5$-Gln-(Arg)$_3$-NH$_2$;

(SEQ ID NO: 189)
Ac-c(Cys-Glu-His-D-2-Nal-Arg-Bal-Ala-Cys)-(Pro)$_2$-Lys-Asp-β-Ala-(Arg)$_6$-Gln-(Arg)$_3$-NH$_2$;

(SEQ ID NO: 190)
Ac-c(Cys-Glu-His-D-2-Nal-Arg-Trp-Ala-Cys)-(Pro)$_2$-Lys-Asp-β-Ala-Tyr-Gly-Arg-(Lys)$_2$-(Arg)$_3$-Gln-(Arg)$_2$-NH$_2$;

(SEQ ID NO: 191)
Ac-c(Cys-Glu-His-D-2-Nal-Arg-Trp-Ala-Cys)-(Pro)$_2$-Lys-Asp-β-Ala-Tyr-Gly-Arg-Gln-(Lys)$_2$-(Arg)$_5$-NH$_2$;

(SEQ ID NO: 192)
Ac-c(Cys-Glu-His-D-2-Nal-Arg-Trp-Ala-Cys)-(Pro)$_2$-Lys-Asp-β-Ala-Tyr-Gly-Arg-(Lys)$_2$-(Arg)$_5$-Gln-NH$_2$;

(SEQ ID NO: 193)
Ac-c(Cys-Glu-His-D-2-Nal-Arg-1-Nal-Ala-Cys)-(Pro)$_2$-Lys-Asp-β-Ala-Tyr-Gly-Arg-(Lys)$_2$-(Arg)$_2$-Gln-(Arg)$_3$-NH$_2$;

```
                                                    (SEQ ID NO: 194)
Ac-c(Cys-Glu-His-D-2-Nal-Arg-Bal-Ala-Cys)-(Pro)₂-Lys-Asp-β-Ala-Tyr-Gly-Arg-
(Lys)₂-(Arg)₂-Gln-(Arg)₃-NH₂;

(SEQ ID NO: 195)
Ac-c(Cys-Glu-His-D-2-Nal-Arg-1-Nal-Ala-Cys)-(Pro)₂-Lys-Asp-β-Ala-(Arg)₂-Lys-
(Arg)₂-Gln-(Arg)₃-NH₂;

(SEQ ID NO: 196)
Ac-c(Cys-Glu-His-D-2-Nal-Arg-1-Nal-Ala-Cys)-(Pro)₂-Lys-Asp-β-Ala-Arg-Lys-
(Arg)₃-Gln-(Arg)₃-NH₂;

(SEQ ID NO: 197)
Ac-c(Cys-Glu-His-D-2-Nal-Arg-2-Nal-Ala-Cys)-(Pro)₂-Lys-Asp-β-Ala-(Arg)₂-Lys-
(Arg)₂-Gln-(Arg)₃-NH₂;

(SEQ ID NO: 198)
Ac-c(Cys-Glu-His-D-2-Nal-Arg-2-Nal-Ala-Cys)-(Pro)₂-Lys-Asp-β-Ala-Tyr-Gly-
(Arg)₂-Lys-(Arg)₂-Gln-(Arg)₃-NH₂;

(SEQ ID NO: 199)
Ac-c(Cys-Glu-His-D-2-Nal-Arg-2-Nal-Ala-Cys)-(Pro)₂-Lys-Asp-f3-Ala-Gly-(Arg)₂-
Lys-(Arg)₂-Gln-(Arg)₃-NH₂;

(SEQ ID NO: 200)
Ac-c(Cys-Glu-His-D-2-Nal-Arg-2-Nal-Ala-Cys)-(Pro)₂-Lys-Asp-f3-Ala-Gly-Arg-
Lys-(Arg)₃-Gln-(Arg)₃-NH₂;

(SEQ ID NO: 201)
Ac-c(Cys-Glu-His-D-2-Nal-Arg-1-Nal-Ala-Cys)-(Pro)₂-Lys-Asp-β-Ala-Tyr-Gly-
(Arg)₂-Lys-(Arg)₂-Gln-(Arg)₃-NH₂;

(SEQ ID NO: 202)
Ac-c(Cys-Glu-His-D-2-Nal-Arg-1-Nal-Ala-Cys)-(Pro)₂-Lys-Asp-β-Ala-Tyr-Gly-Arg-
Lys-(Arg)₃-Gln-(Arg)₃-NH₂;

(SEQ ID NO: 203)
Ac-c(Cys-Glu-His-D-2-Nal-Arg-1-Nal-Ala-Cys)-(Pro)₂-Lys-Asp-β-Ala-Gly-(Arg)₂-
Lys-(Arg)₂-Gln-(Arg)₃-NH₂;

(SEQ ID NO: 204)
Ac-c(Cys-Glu-His-D-2-Nal-Arg-1-Nal-Ala-Cys)-(Pro)₂-Lys-Asp-β-Ala-Gly-Arg-
Lys-(Arg)₃-Gln-(Arg)₃-NH₂;

(SEQ ID NO: 205)
Ac-c(Cys-Glu-His-D-2-Nal-Arg-2-Nal-Ala-Cys)-(Pro)₂-Lys-Asp-β-Ala-(Arg)₂-Lys-
(Arg)₂-Gln-(Arg)₃-NH₂;

(SEQ ID NO: 206)
Ac-c(Cys-Glu-His-D-2-Nal-Arg-2-Nal-Ala-Cys)-(Pro)₂-Lys-Asp-β-Ala-Arg-Lys-
(Arg)₃-Gln-(Arg)₃-NH₂;

(SEQ ID NO: 207)
Ac-c(Cys-Glu-His-D-2-Nal-Arg-2-Nal-Ala-Cys)-(Pro)₂-Lys-Asp-β-Ala-Tyr-Gly-Arg-
Lys-(Arg)₃-Gln-(Arg)₃-NH₂;

(SEQ ID NO: 208)
Ac-c(Cys-Glu-His-D-2-Nal-Arg-Bal-Ala-Cys)-(Pro)₂-Lys-Asp-β-Ala-(Arg)₂-Lys-
(Arg)₂-Gln-(Arg)₃-NH₂;

(SEQ ID NO: 209)
Ac-c(Cys-Glu-His-D-2-Nal-Arg-Bal-Ala-Cys)-(Pro)₂-Lys-Asp-β-Ala-Arg-Lys-
(Arg)₃-Gln-(Arg)₃-NH₂;
```

-continued (SEQ ID NO: 210)
Ac-c(Cys-Glu-His-D-2-Nal-Arg-Bal-Ala-Cys)-(Pro)$_2$-Lys-Asp-β-Ala-Tyr-Gly-(Arg)$_2$-Lys-(Arg)$_2$-Gln-(Arg)$_3$-NH$_2$;

(SEQ ID NO: 211)
Ac-c(Cys-Glu-His-D-2-Nal-Arg-Bal-Ala-Cys)-(Pro)$_2$-Lys-Asp-β-Ala-Tyr-Gly-Arg-Lys-(Arg)$_3$-Gln-(Arg)$_3$-NH$_2$;

(SEQ ID NO: 212)
Ac-c(Cys-Glu-His-D-2-Nal-Arg-Bal-Ala-Cys)-(Pro)$_2$-Lys-Asp-β-Ala-Gly-(Arg)$_2$-Lys-(Arg)$_2$-Gln-(Arg)$_3$-NH$_2$;

(SEQ ID NO: 213)
Ac-c(Cys-Glu-His-D-2-Nal-Arg-Bal-Ala-Cys)-(Pro)$_2$-Lys-Asp-β-Ala-Gly-Arg-Lys-(Arg)$_3$-Gln-(Arg)$_3$-NH$_2$;

(SEQ ID NO: 214)
Ac-c(Cys-Glu-His-D-2-Nal-Arg-Trp-Ala-Cys)-(Pro)$_2$-Lys-Asp-β-Ala-(Arg)$_5$-Gln-(Arg)$_3$-NH$_2$;

(SEQ ID NO: 215)
Ac-c(Cys-Glu-His-D-2-Nal-Arg-Trp-Ala-Cys)-(Pro)$_2$-Arg-Asp-β-Ala-(Arg)$_5$-Gln-(Arg)$_3$-NH$_2$;

(SEQ ID NO: 216)
Ac-c(Cys-Glu-His-D-2-Nal-Arg-Trp-Ala-Cys)-(Pro)$_2$-Lys-Asp-β-Ala-Tyr-Gly-(Arg)$_5$-Gln-(Arg)$_3$-NH$_2$;

(SEQ ID NO: 217)
Ac-c(Cys-Glu-His-D-2-Nal-Arg-Trp-Ala-Cys)-(Pro)$_2$-Arg-Asp-β-Ala-Tyr-Gly-(Arg)$_5$-Gln-(Arg)$_3$-NH$_2$;

(SEQ ID NO: 218)
Ac-c(Cys-Glu-His-D-2-Nal-Arg-Trp-Ala-Cys)-(Pro)$_2$-Lys-Asp-β-Ala-(Arg)$_5$-Gln-(Arg)$_4$-NH$_2$;

(SEQ ID NO: 219)
Ac-c(Cys-Glu-His-D-2-Nal-Arg-Trp-Ala-Cys)-(Pro)$_2$-Arg-Asp-β-Ala-(Arg)$_5$-Gln-(Arg)$_4$-NH$_2$;

(SEQ ID NO: 220)
Ac-c(Cys-Glu-His-D-2-Nal-Arg-Trp-Ala-Cys)-(Pro)$_2$-Lys-Asp-β-Ala-Tyr-Gly-(Arg)$_5$-Gln-(Arg)$_4$-NH$_2$;

(SEQ ID NO: 221)
Ac-c(Cys-Glu-His-D-2-Nal-Arg-Trp-Ala-Cys)-(Pro)$_2$-Arg-Asp-β-Ala-Tyr-Gly-(Arg)$_5$-Gln-(Arg)$_4$-NH$_2$;

(SEQ ID NO: 222)
Ac-c(Cys-Glu-His-D-2-Nal-Arg-1-Nal-Ala-Cys)-(Pro)$_2$-Lys-Asp-β-Ala-(Arg)$_5$-Gln-(Arg)$_4$-NH$_2$;

(SEQ ID NO: 223)
Ac-c(Cys-Glu-His-D-2-Nal-Arg-1-Nal-Ala-Cys)-(Pro)$_2$-Arg-Asp-β-Ala-(Arg)$_5$-Gln-(Arg)$_4$-NH$_2$;

(SEQ ID NO: 224)
Ac-c(Cys-Glu-His-D-2-Nal-Arg-1-Nal-Ala-Cys)-(Pro)$_2$-Arg-Asp-β-Ala-(Arg)$_6$-Gln-(Arg)$_3$-NH$_2$;

(SEQ ID NO: 225)
Ac-c(Cys-Glu-His-D-2-Nal-Arg-1-Nal-Ala-Cys)-(Pro)$_2$-Lys-Asp-β-Ala-Tyr-Gly-(Arg)$_5$-Gln-(Arg)$_3$-NH$_2$;

```
                                                        (SEQ ID NO: 226)
Ac-c(Cys-Glu-His-D-2-Nal-Arg-1-Nal-Ala-Cys)-(Pro)_2-Arg-Asp-β-Ala-Tyr-Gly-
(Arg)_5-Gln-(Arg)_3-NH_2;

(SEQ ID NO: 227)
Ac-c(Cys-Glu-His-D-2-Nal-Arg-1-Nal-Ala-Cys)-(Pro)_2-Lys-Asp-β-Ala-Tyr-Gly-
(Arg)_5-Gln-(Arg)_4-NH_2;

(SEQ ID NO: 228)
Ac-c(Cys-Glu-His-D-2-Nal-Arg-1-Nal-Ala-Cys)-(Pro)_2-Arg-Asp-β-Ala-Tyr-Gly-
(Arg)_5-Gln-(Arg)_4-NH_2;

(SEQ ID NO: 229)
Ac-c(Cys-Glu-His-D-2-Nal-Arg-1-Nal-Ala-Cys)-(Pro)_2-Lys-Asp-β-Ala-Tyr-Gly-
(Arg)_6-Gln-(Arg)_3-NH_2;

(SEQ ID NO: 230)
Ac-c(Cys-Glu-His-D-2-Nal-Arg-1-Nal-Ala-Cys)-(Pro)_2-Arg-Asp-β-Ala-Tyr-Gly-
(Arg)_6-Gln-(Arg)_3-NH_2;

(SEQ ID NO: 231)
Ac-c(Cys-Glu-His-D-2-Nal-Arg-2-Nal-Ala-Cys)-(Pro)_2-Arg-Asp-β-Ala-(Arg)_6-Gln-
(Arg)_3-NH_2;

(SEQ ID NO: 232)
Ac-c(Cys-Glu-His-D-2-Nal-Arg-2-Nal-Ala-Cys)-(Pro)_2-Lys-Asp-β-Ala-(Arg)_5-Gln-
(Arg)_4-NH_2;

(SEQ ID NO: 233)
Ac-c(Cys-Glu-His-D-2-Nal-Arg-2-Nal-Ala-Cys)-(Pro)_2-Arg-Asp-β-Ala-(Arg)_5-Gln-
(Arg)_4-NH_2;

(SEQ ID NO: 234)
Ac-c(Cys-Glu-His-D-2-Nal-Arg-2-Nal-Ala-Cys)-(Pro)_2-Lys-Asp-β-Ala-Tyr-Gly-
(Arg)_5-Gln-(Arg)_3-NH_2;

(SEQ ID NO: 235)
Ac-c(Cys-Glu-His-D-2-Nal-Arg-2-Nal-Ala-Cys)-(Pro)_2-Arg-Asp-β-Ala-Tyr-Gly-
(Arg)_5-Gln-(Arg)_3-NH_2;

(SEQ ID NO: 236)
Ac-c(Cys-Glu-His-D-2-Nal-Arg-2-Nal-Ala-Cys)-(Pro)_2-Lys-Asp-β-Ala-Tyr-Gly-
(Arg)_6-Gln-(Arg)_3-NH_2;

(SEQ ID NO: 237)
Ac-c(Cys-Glu-His-D-2-Nal-Arg-2-Nal-Ala-Cys)-(Pro)_2-Arg-Asp-β-Ala-Tyr-Gly-
(Arg)_6-Gln-(Arg)_3-NH_2;

(SEQ ID NO: 238)
Ac-c(Cys-Glu-His-D-2-Nal-Arg-2-Nal-Ala-Cys)-(Pro)_2-Lys-Asp-β-Ala-Tyr-Gly-
(Arg)_5-Gln-(Arg)_4-NH_2;

(SEQ ID NO: 239)
Ac-c(Cys-Glu-His-D-2-Nal-Arg-2-Nal-Ala-Cys)-(Pro)_2-Arg-Asp-β-Ala-Tyr-Gly-
(Arg)_5-Gln-(Arg)_4-NH_2;

(SEQ ID NO: 240)
Ac-c(Cys-Glu-His-D-2-Nal-Arg-Bal-Ala-Cys)-(Pro)_2-Lys-Asp-β-Ala-(Arg)_5-Gln-
(Arg)_4-NH_2;

(SEQ ID NO: 241)
Ac-c(Cys-Glu-His-D-2-Nal-Arg-Bal-Ala-Cys)-(Pro)_2-Arg-Asp-β-Ala-(Arg)_5-Gln-
(Arg)_4-NH_2;
```

-continued (SEQ ID NO: 242)
Ac-c(Cys-Glu-His-D-2-Nal-Arg-Bal-Ala-Cys)-(Pro)$_2$-Arg-Asp-β-Ala-Tyr-Gly-(Arg)$_5$-Gln-(Arg)$_3$-NH$_2$;

(SEQ ID NO: 243)
Ac-c(Cys-Glu-His-D-2-Nal-Arg-Bal-Ala-Cys)-(Pro)$_2$-Lys-Asp-β-Ala-Tyr-Gly-(Arg)$_5$-Gln-(Arg)$_4$-NH$_2$;

(SEQ ID NO: 244)
Ac-c(Cys-Glu-His-D-2-Nal-Arg-Bal-Ala-Cys)-(Pro)$_2$-Arg-Asp-β-Ala-Tyr-Gly-(Arg)$_5$-Gln-(Arg)$_4$-NH$_2$;

(SEQ ID NO: 245)
Ac-c(Cys-Glu-His-D-2-Nal-Arg-Bal-Ala-Cys)-(Pro)$_2$-Lys-Asp-β-Ala-Tyr-Gly-(Arg)$_6$-Gln-(Arg)$_3$-NH$_2$;

(SEQ ID NO: 246)
Ac-c(Cys-Glu-His-D-2-Nal-Arg-Bal-Ala-Cys)-(Pro)$_2$-Arg-Asp-β-Ala-Tyr-Gly-(Arg)$_6$-Gln-(Arg)$_3$-NH$_2$;

(SEQ ID NO: 247)
Ac-Nle-c(Cys-D-Ala-His-D-Phe-Arg-Trp-Cys)-(Doc)$_2$-Tyr-Gly-Arg-(Lys)$_2$-(Arg)$_2$-Gln-(Arg)$_3$-NH$_2$;

(SEQ ID NO: 248)
Ac-Nle-c(Cys-D-Ala-His-D-Phe-Arg-Trp-Cys)-β-Ala-Tyr-Gly-Arg-(Lys)$_2$-Arg-Gln-(Arg)$_4$-NH$_2$;

(SEQ ID NO: 249)
Ac-Nle-c(Cys-D-Ala-His-D-Phe-Arg-Trp-Cys)-Doc-Tyr-Gly-Arg-(Lys)$_2$-(Arg)$_2$-Gln-(Arg)$_3$-NH$_2$;

(SEQ ID NO: 250)
Ac-Nle-c(Cys-D-Ala-His-D-Phe-Arg-Trp-Cys)-β-Ala-(Arg)$_5$-Gln-(Arg)$_3$-NH$_2$;

(SEQ ID NO: 251)
Ac-Nle-c(Cys-D-Ala-His-D-Phe-Arg-Trp-Cys)-β-Ala-Gly-(Arg)$_5$-Gln-(Arg)$_3$-NH$_2$;

(SEQ ID NO: 252)
Ac-Nle-c(Cys-D-Ala-His-D-Phe-Arg-Trp-Cys)-β-Ala-Tyr-Gly-(Arg)$_5$-Gln-(Arg)$_3$-NH$_2$;

(SEQ ID NO: 253)
Ac-Nle-c(Cys-D-Ala-His-D-Phe-Arg-Trp-Cys)-β-Ala-Gly-(Arg)$_5$-Gln-(Arg)$_4$-NH$_2$;

(SEQ ID NO: 254)
Ac-Nle-c(Cys-D-Ala-His-D-Phe-Arg-Trp-Cys)-β-Ala-Tyr-Gly-(Arg)$_2$-Lys-(Arg)$_2$-Gln-(Arg)$_3$-NH$_2$;

(SEQ ID NO: 255)
Ac-Nle-c(Cys-D-Ala-His-D-Phe-Arg-Trp-Cys)-β-Ala-Tyr-Gly-Arg-Lys-(Arg)$_3$-Gln-(Arg)$_3$-NH$_2$;

(SEQ ID NO: 256)
Ac-Nle-c(Cys-D-Ala-His-D-Phe-Arg-Trp-Cys)-β-Ala-Gly-(Arg)$_2$-Lys-(Arg)$_2$-Gln-(Arg)$_3$-NH$_2$;

(SEQ ID NO: 257)
Ac-Nle-c(Cys-D-Ala-His-D-Phe-Arg-Trp-Cys)-β-Ala-Gly-Arg-Lys-(Arg)$_3$-Gln-(Arg)$_3$-NH$_2$;

(SEQ ID NO: 258)
Ac-Nle-c(Cys-D-Ala-His-D-Phe-Arg-Trp-Cys)-β-Ala-(Arg)$_2$-Lys-(Arg)$_2$-Gln-(Arg)$_3$-NH$_2$;

```
                                                      (SEQ ID NO: 259)
Ac-Nle-c(Cys-D-Ala-His-D-Phe-Arg-Trp-Cys)-β-Ala-Arg-Lys-(Arg)₃-Gln-(Arg)₃-
NH₂;

(SEQ ID NO: 260)
Ac-Nle-c(Cys-D-Ala-His-D-Phe-Arg-Trp-Cys)-(β-Ala)₂-(Arg)₅-Gln-(Arg)₃-NH₂;

(SEQ ID NO: 261)
Ac-Nle-c(Cys-D-Ala-His-D-Phe-Arg-Trp-Cys)-(β-Ala)₂-Gly-(Arg)₅-Gln-(Arg)₃-
NH₂;

(SEQ ID NO: 262)
Ac-Nle-c(Cys-D-Ala-His-D-Phe-Arg-Trp-Cys)-(β-Ala)₂-Tyr-Gly-(Arg)₅-Gln-(Arg)₃-
NH₂;

(SEQ ID NO: 263)
Ac-Nle-c(Cys-D-Ala-His-D-Phe-Arg-Trp-Cys)-Doc-(Arg)₅-Gln-(Arg)₃-NH₂;

(SEQ ID NO: 264)
Ac-Nle-c(Cys-D-Ala-His-D-Phe-Arg-Trp-Cys)-Doc-Gly-(Arg)₅-Gln-(Arg)₃-NH₂;

(SEQ ID NO: 265)
Ac-Nle-c(Cys-D-Ala-His-D-Phe-Arg-Trp-Cys)-Doc-Tyr-Gly-(Arg)₅-Gln-(Arg)₃-
NH₂;

(SEQ ID NO: 266)
Ac-Nle-c(Cys-D-Ala-His-D-Phe-Arg-Trp-Cys)-(Doc)₂-(Arg)₅-Gln-(Arg)₃-NH₂;

(SEQ ID NO: 267)
Ac-Nle-c(Cys-D-Ala-His-D-Phe-Arg-Trp-Cys)-(Doc)₂-Gly-(Arg)₅-Gln-(Arg)₃-NH₂;

(SEQ ID NO: 268)
Ac-Nle-c(Cys-D-Ala-His-D-Phe-Arg-Trp-Cys)-(Doc)₂-Tyr-Gly-(Arg)₅-Gln-(Arg)₃-
NH₂;

(SEQ ID NO: 269)
Ac-Nle-c(Cys-D-Ala-His-D-Phe-Arg-Trp-Cys)-β-Ala-(Arg)₅-Gln-(Arg)₄-NH₂;

(SEQ ID NO: 270)
Ac-Nle-c(Cys-D-Ala-His-D-Phe-Arg-Trp-Cys)-β-Ala-Tyr-Gly-(Arg)₅-Gln-(Arg)₄-
NH₂;

(SEQ ID NO: 271)
Ac-Nle-c(Cys-D-Ala-His-D-Phe-Arg-Trp-Cys)-(β-Ala)₂-(Arg)₅-Gln-(Arg)₄-NH₂;

(SEQ ID NO: 272)
Ac-Nle-c(Cys-D-Ala-His-D-Phe-Arg-Trp-Cys)-(β-Ala)₂-Gly-(Arg)₅-Gln-(Arg)₄-NH₂;

(SEQ ID NO: 273)
Ac-Nle-c(Cys-D-Ala-His-D-Phe-Arg-Trp-Cys)-(β-Ala)₂-Tyr-Gly-(Arg)₅-Gln-(Arg)₄-
NH₂;

(SEQ ID NO: 274)
Ac-Nle-c(Cys-D-Ala-His-D-Phe-Arg-Trp-Cys)-Doc-(Arg)₅-Gln-(Arg)₄-NH₂;

(SEQ ID NO: 275)
Ac-Nle-c(Cys-D-Ala-His-D-Phe-Arg-Trp-Cys)-Doc-Gly-(Arg)₅-Gln-(Arg)₄-NH₂;

(SEQ ID NO: 276)
Ac-Nle-c(Cys-D-Ala-His-D-Phe-Arg-Trp-Cys)-Doc-Tyr-Gly-(Arg)₅-Gln-(Arg)₄-
NH₂;

(SEQ ID NO: 277)
Ac-Nle-c(Cys-D-Ala-His-D-Phe-Arg-Trp-Cys)-(Doc)₂-(Arg)₅-Gln-(Arg)₄-NH₂;

(SEQ ID NO: 278)
Ac-Nle-c(Cys-D-Ala-His-D-Phe-Arg-Trp-Cys)-(Doc)₂-Gly-(Arg)₅-Gln-(Arg)₄-NH₂;

(SEQ ID NO: 279)
Ac-Nle-c(Cys-D-Ala-His-D-Phe-Arg-Trp-Cys)-(Doc)₂-Tyr-Gly-(Arg)₅-Gln-(Arg)₄-
NH₂;
```

```
Ac-Nle-c(Cys-His-D-Phe-Arg-Trp-Gaba-Cys)-β-Ala-Tyr-Gly-(Arg)₅-Gln-(Arg)₃-   (SEQ ID NO: 280)
NH₂;

Ac-Nle-c(Cys-His-D-Phe-Arg-Trp-Gaba-Cys)-β-Ala-(Arg)₅-Gln-(Arg)₃-NH₂;   (SEQ ID NO: 281)

Ac-Nle-c(Asp-His-D-Phe-Arg-Trp-Ala-Lys)-β-Ala-Tyr-Gly-(Arg)₅-Gln-(Arg)₃-   (SEQ ID NO: 282)
NH₂;

Ac-Nle-c(Asp-His-D-Phe-Arg-Trp-Ala-Lys)-β-Ala-(Arg)₅-Gln-(Arg)₃-NH₂;   (SEQ ID NO: 283)

Ac-Nle-c(Asp-His-D-Phe-Arg-Trp-Lys)-β-Ala-Tyr-Gly-(Arg)₅-Gln-(Arg)₃-NH₂;   (SEQ ID NO: 284)

Ac-Nle-c(Asp-His-D-Phe-Arg-Trp-Lys)-β-Ala-Gly-(Arg)₅-Gln-(Arg)₃-NH₂;   (SEQ ID NO: 285)

Ac-Nle-c(Asp-His-D-Phe-Arg-Trp-Lys)-β-Ala-(Arg)₅-Gln-(Arg)₃-NH₂;   (SEQ ID NO: 286)

Ac-Nle-c(Asp-His-D-Phe-Arg-Trp-Lys)-(β-Ala)₂-Tyr-Gly-(Arg)₅-Gln-(Arg)₃-NH₂;   (SEQ ID NO: 287)

Ac-Nle-c(Asp-His-D-Phe-Arg-Trp-Lys)-(β-Ala)₂-Gly-(Arg)₅-Gln-(Arg)₃-NH₂;   (SEQ ID NO: 288)

Ac-Nle-c(Asp-His-D-Phe-Arg-Trp-Lys)-(β-Ala)₂-(Arg)₅-Gln-(Arg)₃-NH₂;   (SEQ ID NO: 289)

Ac-Nle-c(Asp-His-D-Phe-Arg-Trp-Lys)-Doc-Tyr-Gly-(Arg)₅-Gln-(Arg)₃-NH₂;   (SEQ ID NO: 290)

Ac-Nle-c(Asp-His-D-Phe-Arg-Trp-Lys)-Doc-Gly-(Arg)₅-Gln-(Arg)₃-NH₂;   (SEQ ID NO: 291)

Ac-Nle-c(Asp-His-D-Phe-Arg-Trp-Lys)-Doc-(Arg)₅-Gln-(Arg)₃-NH₂;   (SEQ ID NO: 292)

Ac-Nle-c(Asp-His-D-Phe-Arg-Trp-Lys)-(Doc)₂-Tyr-Gly-(Arg)₅-Gln-(Arg)₃-NH₂;   (SEQ ID NO: 293)

Ac-Nle-c(Asp-His-D-Phe-Arg-Trp-Lys)-(Doc)₂-Gly-(Arg)₅-Gln-(Arg)₃-NH₂;   (SEQ ID NO: 294)

Ac-Nle-c(Asp-His-D-Phe-Arg-Trp-Lys)-(Doc)₂-(Arg)₅-Gln-(Arg)₃-NH₂;   (SEQ ID NO: 295)

Ac-Nle-c(Asp-His-D-Phe-Arg-Trp-Lys)-β-Ala-Tyr-Gly-(Arg)₅-Gln-(Arg)₄-NH₂;   (SEQ ID NO: 296)

Ac-Nle-c(Asp-His-D-Phe-Arg-Trp-Lys)-β-Ala-Gly-(Arg)₅-Gln-(Arg)₄-NH₂;   (SEQ ID NO: 297)

Ac-Nle-c(Asp-His-D-Phe-Arg-Trp-Lys)-β-Ala-(Arg)₅-Gln-(Arg)₄-NH₂;   (SEQ ID NO: 298)

Ac-Nle-c(Asp-His-D-Phe-Arg-Trp-Lys)-(β-Ala)₂-Tyr-Gly-(Arg)₅-Gln-(Arg)₄-NH₂;   (SEQ ID NO: 299)

Ac-Nle-c(Asp-His-D-Phe-Arg-Trp-Lys)-(β-Ala)₂-Gly-(Arg)₅-Gln-(Arg)₄-NH₂;   (SEQ ID NO: 300)

Ac-Nle-c(Asp-His-D-Phe-Arg-Trp-Lys)-(β-Ala)₂-(Arg)₅-Gln-(Arg)₄-NH₂;   (SEQ ID NO: 301)

Ac-Nle-c(Asp-His-D-Phe-Arg-Trp-Lys)-Doc-Tyr-Gly-(Arg)₅-Gln-(Arg)₄-NH₂;   (SEQ ID NO: 302)

Ac-Nle-c(Asp-His-D-Phe-Arg-Trp-Lys)-Doc-Gly-(Arg)₅-Gln-(Arg)₄-NH₂;   (SEQ ID NO: 303)

Ac-Nle-c(Asp-His-D-Phe-Arg-Trp-Lys)-Doc-(Arg)₅-Gln-(Arg)₄-NH₂;   (SEQ ID NO: 304)
```

```
                                                         (SEQ ID NO: 305)
Ac-Nle-c(Asp-His-D-Phe-Arg-Trp-Lys)-(Doc)2-Tyr-Gly-(Arg)5-Gln-(Arg)4-NH2;

(SEQ ID NO: 306)
Ac-Nle-c(Asp-His-D-Phe-Arg-Trp-Lys)-(Doc)2-Gly-(Arg)5-Gln-(Arg)4-NH2;

(SEQ ID NO: 307)
Ac-Nle-c(Asp-His-D-Phe-Arg-Trp-Lys)-(Doc)2-(Arg)5-Gln-(Arg)4-NH2;

(SEQ ID NO: 308)
Ac-Nle-c(Asp-His-D-Phe-Arg-Trp-β-Ala-Lys)-β-Ala-Tyr-Gly-(Arg)5-Gln-(Arg)3-
NH2;

(SEQ ID NO: 309)
Ac-Nle-c(Asp-His-D-Phe-Arg-Trp-β-Ala-Lys)-β-Ala-(Arg)5-Gln-(Arg)3-NH2;

(SEQ ID NO: 310)
Ac-Nle-c(Cys-His-D-Phe-Arg-Trp-Ahx-Cys)-β-Ala-Tyr-Gly-(Arg)5-Gln-(Arg)3-
NH2;

(SEQ ID NO: 311)
Ac-Nle-c(Cys-His-D-Phe-Arg-Trp-Ahx-Cys)-β-Ala-(Arg)5-Gln-(Arg)3-NH2;

(SEQ ID NO: 312)
D-Phe-c(Cys-His-D-Phe-Arg-Trp-β-Ala-D-Cys)-Thr-β-Ala-Tyr-Gly-(Arg)5-Gln-
(Arg)3- NH2;

(SEQ ID NO: 313)
D-Phe-c(Cys-His-D-Phe-Arg-Trp-β-Ala-D-Cys)-Thr-β-Ala-(Arg)5-Gln-(Arg)3-NH2;

(SEQ ID NO: 314)
Ac-Nle-c(Cys-His-D-Phe-Arg-Trp-Apn-Cys)-β-Ala-Tyr-Gly-(Arg)5-Gln-(Arg)3-
NH2;

(SEQ ID NO: 315)
Ac-Nle-c(Cys-His-D-Phe-Arg-Trp-Apn-Cys)-β-Ala-(Arg)5-Gln-(Arg)3-NH2;

(SEQ ID NO: 316)
Ac-Cha-c(Asp-His-D-Phe-Arg-Trp-Gaba-Lys)-β-Ala-Tyr-Gly- (Arg)5-Gln-(Arg)3-
NH2;

(SEQ ID NO: 317)
Ac-Cha-c(Asp-His-D-Phe-Arg-Trp-Gaba-Lys)-β-Ala-(Arg)5-Gln-(Arg)3-NH2;

(SEQ ID NO: 318)
Ac-Nle-c(Asp-His-D-Phe-Arg-Trp-Gaba-Lys)-β-Ala-Tyr-Gly-(Arg)5-Gln-(Arg)3-
NH2;

(SEQ ID NO: 319)
Ac-Nle-c(Asp-His-D-Phe-Arg-Trp-Gaba-Lys)-β-Ala-(Arg)5-Gln-(Arg)3-NH2;

(SEQ ID NO: 320)
Ac-Chg-c(Asp-His-D-Phe-Arg-Trp-Gaba-Lys)-β-Ala-Tyr-Gly-(Arg)5-Gln-(Arg)3-
NH2;

(SEQ ID NO: 321)
Ac-Chg-c(Asp-His-D-Phe-Arg-Trp-Gaba-Lys)-β-Ala-(Arg)5-Gln-(Arg)3-NH2;

(SEQ ID NO: 322)
Ac-hCha-c(Asp-His-D-Phe-Arg-Trp-Gaba-Lys)-β-Ala-Tyr-Gly-(Arg)5-Gln-(Arg)3-
NH2;

(SEQ ID NO: 323)
Ac-hCha-c(Asp-His-D-Phe-Arg-Trp-Gaba-Lys)-β-Ala-(Arg)5-Gln-(Arg)3-NH2;

(SEQ ID NO: 324)
Ac-hCha-c(Asp-His-D-Phe-Arg-Trp-Gaba-Lys)-(β-Ala)2-Tyr-Gly-(Arg)5-Gln-
(Arg)3- NH2;

(SEQ ID NO: 325)
Ac-hCha-c(Asp-His-D-Phe-Arg-Trp-Gaba-Lys)-(β-Ala)2-(Arg)5-Gln-(Arg)3-NH2;
```

```
                                                     (SEQ ID NO: 326)
Ac-hCha-c(Asp-His-D-Phe-Arg-Trp-Gaba-Lys)-Doc-Tyr-Gly-(Arg)5-Gln-(Arg)3-
NH2;

(SEQ ID NO: 327)
Ac-hCha-c(Asp-His-D-Phe-Arg-Trp-Gaba-Lys)-Doc-(Arg)5-Gln-(Arg)3-NH2;

(SEQ ID NO: 328)
Ac-hCha-c(Asp-His-D-Phe-Arg-Trp-Gaba-Lys)-(Doc)2-Tyr-Gly-(Arg)5-Gln-(Arg)3-
NH2;

(SEQ ID NO: 329)
Ac-hCha-c(Asp-His-D-Phe-Arg-Trp-Gaba-Lys)-(Doc)2-(Arg)5-Gln-(Arg)3-NH2;

(SEQ ID NO: 330)
Ac-hCha-c(Asp-His-D-Phe-Arg-Trp-Gaba-Lys)-β-Ala-Tyr-Gly-(Arg)5-Gln-(Arg)4-
NH2;

(SEQ ID NO: 331)
Ac-hCha-c(Asp-His-D-Phe-Arg-Trp-Gaba-Lys)-β-Ala-(Arg)5-Gln-(Arg)4-NH2;

(SEQ ID NO: 332)
Ac-hCha-c(Asp-His-D-Phe-Arg-Trp-Gaba-Lys)-(β-Ala)2-Tyr-Gly-(Arg)5-Gln-
(Arg)4- NH2;

(SEQ ID NO: 333)
Ac-hCha-c(Asp-His-D-Phe-Arg-Trp-Gaba-Lys)-(β-Ala)2-(Arg)5-Gln-(Arg)4-NH2;

(SEQ ID NO: 334)
Ac-hCha-c(Asp-His-D-Phe-Arg-Trp-Gaba-Lys)-Doc-Tyr-Gly-(Arg)5-Gln-(Arg)4-
NH2;

(SEQ ID NO: 335)
Ac-hCha-c(Asp-His-D-Phe-Arg-Trp-Gaba-Lys)-Doc-(Arg)5-Gln-(Arg)4-NH2;

(SEQ ID NO: 336)
Ac-hCha-c(Asp-His-D-Phe-Arg-Trp-Gaba-Lys)-(Doc)2-Tyr-Gly-(Arg)5-Gln-(Arg)4-
NH2;

(SEQ ID NO: 337)
Ac-hCha-c(Asp-His-D-Phe-Arg-Trp-Gaba-Lys)-(Doc)2-(Arg)5-Gln-(Arg)4-NH2;

(SEQ ID NO: 338)
Ac-D-Chg-c(Asp-His-D-Phe-Arg-Trp-Gaba-Lys)-β-Ala-Tyr-Gly-(Arg)5-Gln-(Arg)3-
NH2;

(SEQ ID NO: 339)
Ac-D-Chg-c(Asp-His-D-Phe-Arg-Trp-Gaba-Lys)-β-Ala-(Arg)5-Gln-(Arg)3-NH2;

(SEQ ID NO: 340)
Ac-hPhe-c(Asp-His-D-Phe-Arg-Trp-Gaba-Lys)-β-Ala-Tyr-Gly-(Arg)5-Gln-(Arg)3-
NH2;

(SEQ ID NO: 341)
Ac-hPhe-c(Asp-His-D-Phe-Arg-Trp-Gaba-Lys)-β-Ala-(Arg)5-Gln-(Arg)3-NH2;

(SEQ ID NO: 342)
Ac-Nle-c(Cys-His-D-Phe-Arg-D-Trp-Apn-Cys)-β-Ala-Tyr-Gly-(Arg)5-Gln-(Arg)3-
NH2;

(SEQ ID NO: 343)
Ac-Nle-c(Cys-His-D-Phe-Arg-D-Trp-Apn-Cys)-β-Ala-(Arg)5-Gln-(Arg)3-NH2;

(SEQ ID NO: 344)
Ac-Nle-c(Cys-His-D-Phe-Arg-D-Trp-Ahx-Cys)-β-Ala-Tyr-Gly-(Arg)5-Gln-(Arg)3-
NH2;

(SEQ ID NO: 345)
Ac-Nle-c(Cys-His-D-Phe-Arg-D-Trp-Ahx-Cys)-β-Ala-(Arg)5-Gln-(Arg)3-NH2;
```

-continued (SEQ ID NO: 346)
Ac-Nle-c(Cys-His-D-Phe-Arg-D-Trp-β-Ala-Cys)-β-Ala-Tyr-Gly-(Arg)$_5$-Gln-(Arg)$_3$-NH$_2$;

(SEQ ID NO: 347)
Ac-Nle-c(Cys-His-D-Phe-Arg-D-Trp-β-Ala-Cys)-β-Ala-(Arg)$_5$-Gln-(Arg)$_3$-NH$_2$;

(SEQ ID NO: 348)
Ac-Nle-c(Cys-D-Ala-His-D-Phe-Arg-Trp-Pen)-β-Ala-Tyr-Gly-(Arg)$_5$-Gln-(Arg)$_3$-NH$_2$;

(SEQ ID NO: 349)
Ac-Nle-c(Cys-D-Ala-His-D-Phe-Arg-Trp-Pen)-β-Ala-Gly-(Arg)$_5$-Gln-(Arg)$_3$-NH$_2$;

(SEQ ID NO: 350)
Ac-Nle-c(Cys-D-Ala-His-D-Phe-Arg-Trp-Pen)-β-Ala-(Arg)$_5$-Gln-(Arg)$_3$-NH$_2$;

(SEQ ID NO: 351)
Ac-Nle-c(Cys-D-Ala-His-D-Phe-Arg-Trp-Pen)-(β-Ala)$_2$-Tyr-Gly-(Arg)$_5$-Gln-(Arg)$_3$-NH$_2$;

(SEQ ID NO: 352)
Ac-Nle-c(Cys-D-Ala-His-D-Phe-Arg-Trp-Pen)-(β-Ala)$_2$-Gly-(Arg)$_5$-Gln-(Arg)$_3$-NH$_2$;

(SEQ ID NO: 353)
Ac-Nle-c(Cys-D-Ala-His-D-Phe-Arg-Trp-Pen)-(β-Ala)$_2$-(Arg)$_5$-Gln-(Arg)$_3$-NH$_2$;

(SEQ ID NO: 354)
Ac-Nle-c(Cys-D-Ala-His-D-Phe-Arg-Trp-Pen)-Doc-Tyr-Gly-(Arg)$_5$-Gln-(Arg)$_3$-NH$_2$;

(SEQ ID NO: 355)
Ac-Nle-c(Cys-D-Ala-His-D-Phe-Arg-Trp-Pen)-Doc-Gly-(Arg)$_5$-Gln-(Arg)$_3$-NH$_2$;

(SEQ ID NO: 356)
Ac-Nle-c(Cys-D-Ala-His-D-Phe-Arg-Trp-Pen)-Doc-(Arg)$_5$-Gln-(Arg)$_3$-NH$_2$;

(SEQ ID NO: 357)
Ac-Nle-c(Cys-D-Ala-His-D-Phe-Arg-Trp-Pen)-(Doc)$_2$-Tyr-Gly-(Arg)$_5$-Gln-(Arg)$_3$-NH$_2$;

(SEQ ID NO: 358)
Ac-Nle-c(Cys-D-Ala-His-D-Phe-Arg-Trp-Pen)-(Doc)$_2$-Gly-(Arg)$_5$-Gln-(Arg)$_3$-NH$_2$;

(SEQ ID NO: 359)
Ac-Nle-c(Cys-D-Ala-His-D-Phe-Arg-Trp-Pen)-(Doc)$_2$-(Arg)$_5$-Gln-(Arg)$_3$-NH$_2$;

(SEQ ID NO: 360)
D-Phe-c(Cys-His-D-(Et)Tyr-Arg-Trp-β-Ala-D-Cys)-β-Ala-Tyr-Gly-(Arg)$_5$-Gln-(Arg)$_3$-NH$_2$;

(SEQ ID NO: 361)
D-Phe-c(Cys-His-D-(Et)Tyr-Arg-Trp-β-Ala-D-Cys)-β-Ala-(Arg)$_5$-Gln-(Arg)$_3$-NH$_2$;

(SEQ ID NO: 362)
D-Phe-c(Cys-His-D-(Et)Tyr-Arg-Trp-β-Ala-D-Cys)-β-Ala-Gly-(Arg)$_5$-Gln-(Arg)$_3$-NH$_2$;

(SEQ ID NO: 363)
D-Phe-c(Cys-His-D-(Et)Tyr-Arg-Trp-β-Ala-D-Cys)-β-Ala-(Arg)$_5$-Gln-(Arg)$_4$-NH$_2$;

(SEQ ID NO: 364)
D-Phe-c(Cys-His-D-(Et)Tyr-Arg-Trp-β-Ala-D-Cys)-(β-Ala)$_2$-Tyr-Gly-(Arg)$_5$-Gln-(Arg)$_3$-NH$_2$;

(SEQ ID NO: 365)
D-Phe-c(Cys-His-D-(Et)Tyr-Arg-Trp-β-Ala-D-Cys)-(β-Ala)$_2$-(Arg)$_5$-Gln-(Arg)$_3$-NH$_2$;

-continued

D-Phe-c(Cys-His-D-(Et)Tyr-Arg-Trp-β-Ala-D-Cys)-(β-Ala)$_2$-Gly-(Arg)$_5$-Gln-(Arg)$_3$-NH$_2$;   (SEQ ID NO: 366)

D-Phe-c(Cys-His-D-(Et)Tyr-Arg-Trp-β-Ala-D-Cys)-(β-Ala)$_2$-(Arg)$_5$-Gln-(Arg)$_4$-NH$_2$;   (SEQ ID NO: 367)

D-Phe-c(Cys-His-D-(Et)Tyr-Arg-Trp-β-Ala-D-Cys)-Doc-Tyr-Gly-(Arg)$_5$-Gln-(Arg)$_3$-NH$_2$;   (SEQ ID NO: 368)

D-Phe-c(Cys-His-D-(Et)Tyr-Arg-Trp-β-Ala-D-Cys)-Doc-(Arg)$_5$-Gln-(Arg)$_3$-NH$_2$;   (SEQ ID NO: 369)

D-Phe-c(Cys-His-D-(Et)Tyr-Arg-Trp-β-Ala-D-Cys)-Doc-Gly-(Arg)$_5$-Gln-(Arg)$_3$-NH$_2$;   (SEQ ID NO: 370)

D-Phe-c(Cys-His-D-(Et)Tyr-Arg-Trp-β-Ala-D-Cys)-Doc-(Arg)$_5$-Gln-(Arg)$_4$-NH$_2$;   (SEQ ID NO: 371)

D-Phe-c(Cys-His-D-(Et)Tyr-Arg-Trp-β-Ala-D-Cys)-(Doc)$_2$-Tyr-Gly-(Arg)$_5$-Gln-(Arg)$_3$-NH$_2$;   (SEQ ID NO: 372)

D-Phe-c(Cys-His-D-(Et)Tyr-Arg-Trp-β-Ala-D-Cys)-(Doc)$_2$-(Arg)$_5$-Gln-(Arg)$_3$-NH$_2$;   (SEQ ID NO: 373)

D-Phe-c(Cys-His-D-(Et)Tyr-Arg-Trp-β-Ala-D-Cys)-(Doc)$_2$-Gly-(Arg)$_5$-Gln-(Arg)$_3$-NH$_2$;   (SEQ ID NO: 374)

D-Phe-c(Cys-His-D-(Et)Tyr-Arg-Trp-β-Ala-D-Cys)-(Doc)$_2$-(Arg)$_5$-Gln-(Arg)$_4$-NH$_2$;   (SEQ ID NO: 375)

D-Phe-c(Cys-His-D-(Et)Tyr-hArg-Trp-β-Ala-D-Cys)-Thr-β-Ala-Tyr-Gly-(Arg)$_5$-Gln-(Arg)$_3$-NH$_2$;   (SEQ ID NO: 376)

D-Phe-c(Cys-His-D-(Et)Tyr-hArg-Trp-β-Ala-D-Cys)-Thr-β-Ala-(Arg)$_5$-Gln-(Arg)$_3$-NH$_2$;   (SEQ ID NO: 377)

D-Phe-c(Cys-His-D-(Et)Tyr-hArg-Trp-β-Ala-D-Cys)-Thr-(β-Ala)$_2$-Tyr-Gly-(Arg)$_5$-Gln-(Arg)$_3$-NH$_2$;   (SEQ ID NO: 378)

D-Phe-c(Cys-His-D-(Et)Tyr-hArg-Trp-β-Ala-D-Cys)-Thr-(β-Ala)$_2$-(Arg)$_5$-Gln-(Arg)$_3$-NH$_2$;   (SEQ ID NO: 379)

D-Phe-c(Cys-His-D-(Et)Tyr-hArg-Trp-β-Ala-D-Cys)-Thr-Doc-Tyr-Gly-(Arg)$_5$-Gln-(Arg)$_3$-NH$_2$;   (SEQ ID NO: 380)

D-Phe-c(Cys-His-D-(Et)Tyr-hArg-Trp-β-Ala-D-Cys)-Thr-Doc-(Arg)$_5$-Gln-(Arg)$_3$-NH$_2$;   (SEQ ID NO: 381)

D-Phe-c(Cys-His-D-(Et)Tyr-hArg-Trp-β-Ala-D-Cys)-Thr-(Doc)$_2$-Tyr-Gly-(Arg)$_5$-Gln-(Arg)$_3$-NH$_2$;   (SEQ ID NO: 382)

D-Phe-c(Cys-His-D-(Et)Tyr-hArg-Trp-β-Ala-D-Cys)-Thr-β-Ala-Tyr-Gly-(Arg)$_5$-Gln-(Arg)$_4$-NH$_2$; (SEQ ID NO: 383)

D-Phe-c(Cys-His-D-(Et)Tyr-hArg-Trp-β-Ala-D-Cys)-Thr-β-Ala-(Arg)$_5$-Gln-(Arg)$_4$-NH$_2$; (SEQ ID NO: 384)

D-Phe-c(Cys-His-D-(Et)Tyr-hArg-Trp-β-Ala-D-Cys)-Thr-(β-Ala)$_2$-Tyr-Gly-(Arg)$_5$-Gln-(Arg)$_4$-NH$_2$; (SEQ ID NO: 385)

D-Phe-c(Cys-His-D-(Et)Tyr-hArg-Trp-β-Ala-D-Cys)-Thr-(β-Ala)$_2$-(Arg)$_5$-Gln-(Arg)$_4$-NH$_2$; (SEQ ID NO: 386)

D-Phe-c(Cys-His-D-(Et)Tyr-hArg-Trp-β-Ala-D-Cys)-Thr-Doc-Tyr-Gly-(Arg)$_5$-Gln-(Arg)$_4$-NH$_2$; (SEQ ID NO: 387)

D-Phe-c(Cys-His-D-(Et)Tyr-hArg-Trp-β-Ala-D-Cys)-Thr-Doc-(Arg)$_5$-Gln-(Arg)$_4$-NH$_2$; (SEQ ID NO: 388)

D-Phe-c(Cys-His-D-(Et)Tyr-hArg-Trp-β-Ala-D-Cys)-Thr-(Doc)$_2$-Tyr-Gly-(Arg)$_5$-Gln-(Arg)$_4$-NH$_2$; (SEQ ID NO: 389)

D-Phe-c(Cys-His-D-(Et)Tyr-hArg-Trp-β-Ala-D-Cys)-Thr-(Doc)$_2$-(Arg)$_5$-Gln-(Arg)$_4$-NH$_2$; (SEQ ID NO: 390)

D-Phe-c(Cys-His-D-(Et)Tyr-hArg-Bip-β-Ala-D-Cys)-Thr-β-Ala-Tyr-Gly-(Arg)$_5$-Gln-(Arg)$_3$-NH$_2$; (SEQ ID NO: 391)

D-Phe-c(Cys-His-D-(Et)Tyr-hArg-Bip-β-Ala-D-Cys)-Thr-β-Ala-Tyr-Gly-(Arg)$_5$-Gln-(Arg)$_4$-NH$_2$; (SEQ ID NO: 392)

D-Phe-c(Cys-His-D-(Et)Tyr-hArg-Bip-β-Ala-D-Cys)-Thr-β-Ala-(Arg)$_5$-Gln-(Arg)$_3$-NH$_2$; (SEQ ID NO: 393)

D-Phe-c(Cys-His-D-(Et)Tyr-hArg-Bip-β-Ala-D-Cys)-Thr-(β-Ala)$_2$-Tyr-Gly-(Arg)$_5$-Gln-(Arg)$_3$-NH$_2$; (SEQ ID NO: 394)

D-Phe-c(Cys-His-D-(Et)Tyr-hArg-Bip-β-Ala-D-Cys)-Thr-(β-Ala)$_2$-(Arg)$_5$-Gln-(Arg)$_3$-NH$_2$; (SEQ ID NO: 395)

D-Phe-c(Cys-His-D-(Et)Tyr-hArg-Bip-β-Ala-D-Cys)-Thr-Doc-Tyr-Gly-(Arg)$_5$-Gln-(Arg)$_3$-NH$_2$; (SEQ ID NO: 396)

D-Phe-c(Cys-His-D-(Et)Tyr-hArg-Bip-β-Ala-D-Cys)-Thr-Doc-Tyr-Gly-(Arg)$_5$-Gln-(Arg)$_4$-NH$_2$; (SEQ ID NO: 397)

D-Phe-c(Cys-His-D-(Et)Tyr-hArg-Bip-β-Ala-D-Cys)-Thr-Doc-(Arg)$_5$-Gln-(Arg)$_3$-NH$_2$; (SEQ ID NO: 398)

-continued (SEQ ID NO: 399)
D-Phe-c(Cys-His-D-(Et)Tyr-hArg-Bip-β-Ala-D-Cys)-Thr-(Doc)$_2$-Tyr-Gly-(Arg)$_5$-Gln-(Arg)$_3$-NH$_2$;

(SEQ ID NO: 400)
D-Phe-c(Cys-His-D-(Et)Tyr-hArg-Bip-β-Ala-D-Cys)-Thr-(Doc)$_2$-(Arg)$_5$-Gln-(Arg)$_3$-NH$_2$;

(SEQ ID NO: 401)
Ac-Nle-c(Cys-D-Ala-His-D-Phe-Arg-Trp-Gly-Cys)-β-Ala-Tyr-Gly-(Arg)$_5$-Gln-(Arg)$_3$-NH$_2$;

(SEQ ID NO: 402)
Ac-Nle-c(Cys-D-Ala-His-D-Phe-Arg-Trp-Gly-Cys)-β-Ala-(Arg)$_5$-Gln-(Arg)$_3$-NH$_2$;

(SEQ ID NO: 403)
Nle-c(Cys-His-D-Phe-Arg-Trp-Apn-Cys)-β-Ala-Tyr-Gly-(Arg)$_5$-Gln-(Arg)$_3$-NH$_2$;

(SEQ ID NO: 404)
Nle-c(Cys-His-D-Phe-Arg-Trp-Apn-Cys)-β-Ala-(Arg)$_5$-Gln-(Arg)$_3$-NH$_2$;

(SEQ ID NO: 405)
Nle-c(Cys-His-D-Phe-Arg-Trp-Apn-Cys)-(β-Ala)$_2$-Tyr-Gly-(Arg)$_5$-Gln-(Arg)$_3$-NH$_2$;

(SEQ ID NO: 406)
Nle-c(Cys-His-D-Phe-Arg-Trp-Apn-Cys)-(β-Ala)$_2$-(Arg)$_5$-Gln-(Arg)$_3$-NH$_2$;

(SEQ ID NO: 407)
Nle-c(Cys-His-D-Phe-Arg-Trp-Apn-Cys)-β-Ala-Tyr-Gly-(Arg)$_5$-Gln-(Arg)$_4$-NH$_2$;

(SEQ ID NO: 408)
Nle-c(Cys-His-D-Phe-Arg-Trp-Apn-Cys)-β-Ala-(Arg)$_5$-Gln-(Arg)$_4$-NH$_2$;

(SEQ ID NO: 409)
Nle-c(Cys-His-D-Phe-Arg-Trp-Apn-Cys)-(β-Ala)$_2$-Tyr-Gly-(Arg)$_5$-Gln-(Arg)$_4$-NH$_2$;

(SEQ ID NO: 410)
Nle-c(Cys-His-D-Phe-Arg-Trp-Apn-Cys)-(β-Ala)$_2$-(Arg)$_5$-Gln-(Arg)$_4$-NH$_2$;

(SEQ ID NO: 411)
Nle-c(Cys-His-D-Phe-Arg-Trp-Apn-Cys)-Doc-Tyr-Gly-(Arg)$_5$-Gln-(Arg)$_3$-NH$_2$;

(SEQ ID NO: 412)
Nle-c(Cys-His-D-Phe-Arg-Trp-Apn-Cys)-Doc-(Arg)$_5$-Gln-(Arg)$_3$-NH$_2$;

(SEQ ID NO: 413)
Nle-c(Cys-His-D-Phe-Arg-Trp-Apn-Cys)-(Doc)$_2$-Tyr-Gly-(Arg)$_5$-Gln-(Arg)$_3$-NH$_2$;

(SEQ ID NO: 414)
Nle-c(Cys-His-D-Phe-Arg-Trp-Apn-Cys)-(Doc)$_2$-(Arg)$_5$-Gln-(Arg)$_3$-NH$_2$;

(SEQ ID NO: 415)
Nle-c(Cys-His-D-Phe-Arg-Trp-Apn-Cys)-Doc-Tyr-Gly-(Arg)$_5$-Gln-(Arg)$_4$-NH$_2$;

(SEQ ID NO: 416)
Nle-c(Cys-His-D-Phe-Arg-Trp-Apn-Cys)-Doc-(Arg)$_5$-Gln-(Arg)$_4$-NH$_2$;

(SEQ ID NO: 417)
Nle-c(Cys-His-D-Phe-Arg-Trp-Apn-Cys)-(Doc)$_2$-Tyr-Gly-(Arg)$_5$-Gln-(Arg)$_4$-NH$_2$;

(SEQ ID NO: 418)
Nle-c(Cys-His-D-Phe-Arg-Trp-Apn-Cys)-(Doc)$_2$-(Arg)$_5$-Gln-(Arg)$_4$-NH$_2$;

(SEQ ID NO: 419)
Ac-Nle-c(Cys-D-Leu-His-D-Phe-Arg-Trp-Cys)-β-Ala-Tyr-Gly-(Arg)$_5$-Gln-(Arg)$_3$-NH$_2$;

(SEQ ID NO: 420)
Ac-Nle-c(Cys-D-Leu-His-D-Phe-Arg-Trp-Cys)-β-Ala-(Arg)$_5$-Gln-(Arg)$_3$-NH$_2$;

(SEQ ID NO: 421)
Ac-Nle-c(Cys-D-Leu-His-D-Phe-Arg-Trp-Cys)-(β-Ala)$_2$-Tyr-Gly-(Arg)$_5$-Gln-(Arg)$_3$-NH$_2$;

(SEQ ID NO: 422)
Ac-Nle-c(Cys-D-Leu-His-D-Phe-Arg-Trp-Cys)-(β-Ala)$_2$-(Arg)$_5$-Gln-(Arg)$_3$-NH$_2$;

```
                                                        (SEQ ID NO: 423)
Ac-Nle-c(Cys-D-Leu-His-D-Phe-Arg-Trp-Cys)-Doc-Tyr-Gly-(Arg)5-Gln-(Arg)3-
NH2;

(SEQ ID NO: 424)
Ac-Nle-c(Cys-D-Leu-His-D-Phe-Arg-Trp-Cys)-Doc-(Arg)5-Gln-(Arg)3-NH2;

(SEQ ID NO: 425)
Ac-Nle-c(Cys-D-Leu-His-D-Phe-Arg-Trp-Cys)-(Doc)2-Tyr-Gly-(Arg)5-Gln-(Arg)3-
NH2;

(SEQ ID NO: 426)
Ac-Nle-c(Cys-D-Leu-His-D-Phe-Arg-Trp-Cys)-(Doc)2-(Arg)5-Gln-(Arg)3-NH2;

(SEQ ID NO: 427)
Ac-Nle-c(Cys-D-Leu-His-D-Phe-Arg-Trp-Cys)-β-Ala-Tyr-Gly-(Arg)5-Gln-(Arg)4-
NH2;

(SEQ ID NO: 428)
Ac-Nle-c(Cys-D-Leu-His-D-Phe-Arg-Trp-Cys)-β-Ala-(Arg)5-Gln-(Arg)4-NH2;

(SEQ ID NO: 429)
Ac-Nle-c(Cys-D-Leu-His-D-Phe-Arg-Trp-Cys)-(β-Ala)2-Tyr-Gly-(Arg)5-Gln-(Arg)4-
NH2;

(SEQ ID NO: 430)
Ac-Nle-c(Cys-D-Leu-His-D-Phe-Arg-Trp-Cys)-(β-Ala)2-(Arg)5-Gln-(Arg)4-NH2;

(SEQ ID NO: 431)
Ac-Nle-c(Cys-D-Leu-His-D-Phe-Arg-Trp-Cys)-Doc-Tyr-Gly-(Arg)5-Gln-(Arg)4-
NH2;

(SEQ ID NO: 432)
Ac-Nle-c(Cys-D-Leu-His-D-Phe-Arg-Trp-Cys)-Doc-(Arg)5-Gln-(Arg)4-NH2;

(SEQ ID NO: 433)
Ac-Nle-c(Cys-D-Leu-His-D-Phe-Arg-Trp-Cys)-(Doc)2-Tyr-Gly-(Arg)5-Gln-(Arg)4-
NH2;

(SEQ ID NO: 434)
Ac-Nle-c(Cys-D-Leu-His-D-Phe-Arg-Trp-Cys)-(Doc)2-(Arg)5-Gln-(Arg)4-NH2;

(SEQ ID NO: 435)
Ac-Nle-c(Cys-D-Cha-His-D-Phe-Arg-Trp-Cys)-β-Ala-Tyr-Gly-(Arg)5-Gln-(Arg)3-
NH2;

(SEQ ID NO: 436)
Ac-Nle-c(Cys-D-Cha-His-D-Phe-Arg-Trp-Cys)-β-Ala-(Arg)5-Gln-(Arg)3-NH2;

(SEQ ID NO: 437)
Ac-Nle-c(Cys-D-Cha-His-D-Phe-Arg-Trp-Cys)-(β-Ala)2-Tyr-Gly-(Arg)5-Gln-
(Arg)3-NH2;

(SEQ ID NO: 438)
Ac-Nle-c(Cys-D-Cha-His-D-Phe-Arg-Trp-Cys)-(β-Ala)2-(Arg)5-Gln-(Arg)3-NH2;

(SEQ ID NO: 439)
Ac-Nle-c(Cys-D-Cha-His-D-Phe-Arg-Trp-Cys)-Doc-Tyr-Gly-(Arg)5-Gln-(Arg)3-
NH2;

(SEQ ID NO: 440)
Ac-Nle-c(Cys-D-Cha-His-D-Phe-Arg-Trp-Cys)-Doc-(Arg)5-Gln-(Arg)3-NH2;

(SEQ ID NO: 441)
Ac-Nle-c(Cys-D-Cha-His-D-Phe-Arg-Trp-Cys)-(Doc)2-Tyr-Gly-(Arg)5-Gln-(Arg)3-
NH2;

(SEQ ID NO: 442)
Ac-Nle-c(Cys-D-Cha-His-D-Phe-Arg-Trp-Cys)-(Doc)2-(Arg)5-Gln-(Arg)3-NH2;
```

-continued

Ac-Nle-c(Cys-D-Cha-His-D-Phe-Arg-Trp-Cys)-β-Ala-Tyr-Gly-(Arg)$_5$-Gln-(Arg)$_4$-NH$_2$;
(SEQ ID NO: 443)

Ac-Nle-c(Cys-D-Cha-His-D-Phe-Arg-Trp-Cys)-β-Ala-(Arg)$_5$-Gln-(Arg)$_4$-NH$_2$;
(SEQ ID NO: 444)

Ac-Nle-c(Cys-D-Cha-His-D-Phe-Arg-Trp-Cys)-(β-Ala)$_2$-Tyr-Gly-(Arg)$_5$-Gln-(Arg)$_4$-NH$_2$;
(SEQ ID NO: 445)

Ac-Nle-c(Cys-D-Cha-His-D-Phe-Arg-Trp-Cys)-(β-Ala)$_2$-(Arg)$_5$-Gln-(Arg)$_4$-NH$_2$;
(SEQ ID NO: 446)

Ac-Nle-c(Cys-D-Cha-His-D-Phe-Arg-Trp-Cys)-Doc-Tyr-Gly-(Arg)$_5$-Gln-(Arg)$_4$-NH$_2$;
(SEQ ID NO: 447)

Ac-Nle-c(Cys-D-Cha-His-D-Phe-Arg-Trp-Cys)-Doc-(Arg)$_5$-Gln-(Arg)$_4$-NH$_2$;
(SEQ ID NO: 448)

Ac-Nle-c(Cys-D-Cha-His-D-Phe-Arg-Trp-Cys)-(Doc)$_2$-Tyr-Gly-(Arg)$_5$-Gln-(Arg)$_4$-NH$_2$;
(SEQ ID NO: 449)

Ac-Nle-c(Cys-D-Cha-His-D-Phe-Arg-Trp-Cys)-(Doc)$_2$-(Arg)$_5$-Gln-(Arg)$_4$-NH$_2$;
(SEQ ID NO: 450)

Nle-c(Cys-His-D-Phe-Arg-Trp-Gaba-Cys)-β-Ala-Tyr-Gly-(Arg)$_5$-Gln-(Arg)$_3$-NH$_2$;
(SEQ ID NO: 451)

Nle-c(Cys-His-D-Phe-Arg-Trp-Gaba-Cys)-β-Ala-(Arg)$_5$-Gln-(Arg)$_3$-NH$_2$;
(SEQ ID NO: 452)

Nle-c(Cys-His-D-Phe-Arg-Trp-Gaba-Cys)-(β-Ala)$_2$-Tyr-Gly-(Arg)$_5$-Gln-(Arg)$_3$-NH$_2$;
(SEQ ID NO: 453)

Nle-c(Cys-His-D-Phe-Arg-Trp-Gaba-Cys)-(β-Ala)$_2$-(Arg)$_5$-Gln-(Arg)$_3$-NH$_2$;
(SEQ ID NO: 454)

Nle-c(Cys-His-D-Phe-Arg-Trp-Gaba-Cys)-β-Ala-Tyr-Gly-(Arg)$_5$-Gln-(Arg)$_4$-NH$_2$;
(SEQ ID NO: 455)

Nle-c(Cys-His-D-Phe-Arg-Trp-Gaba-Cys)-β-Ala-(Arg)$_5$-Gln-(Arg)$_4$-NH$_2$;
(SEQ ID NO: 456)

Nle-c(Cys-His-D-Phe-Arg-Trp-Gaba-Cys)-(β-Ala)$_2$-Tyr-Gly-(Arg)$_5$-Gln-(Arg)$_4$-NH$_2$;
(SEQ ID NO: 457)

Nle-c(Cys-His-D-Phe-Arg-Trp-Gaba-Cys)-(β-Ala)$_2$-(Arg)$_5$-Gln-(Arg)$_4$-NH$_2$;
(SEQ ID NO: 458)

Nle-c(Cys-His-D-Phe-Arg-Trp-Gaba-Cys)-Doc-Tyr-Gly-(Arg)$_5$-Gln-(Arg)$_3$-NH$_2$;
(SEQ ID NO: 459)

Nle-c(Cys-His-D-Phe-Arg-Trp-Gaba-Cys)-Doc-(Arg)$_5$-Gln-(Arg)$_3$-NH$_2$;
(SEQ ID NO: 460)

Nle-c(Cys-His-D-Phe-Arg-Trp-Gaba-Cys)-(Doc)$_2$-Tyr-Gly-(Arg)$_5$-Gln-(Arg)$_3$-NH$_2$;
(SEQ ID NO: 461)

Nle-c(Cys-His-D-Phe-Arg-Trp-Gaba-Cys)-(Doc)$_2$-(Arg)$_5$-Gln-(Arg)$_3$-NH$_2$;
(SEQ ID NO: 462)

Nle-c(Cys-His-D-Phe-Arg-Trp-Gaba-Cys)-Doc-Tyr-Gly-(Arg)$_5$-Gln-(Arg)$_4$-NH$_2$;
(SEQ ID NO: 463)

Nle-c(Cys-His-D-Phe-Arg-Trp-Gaba-Cys)-Doc-(Arg)$_5$-Gln-(Arg)$_4$-NH$_2$;
(SEQ ID NO: 464)

```
                                                      (SEQ ID NO: 465)
Nle-c(Cys-His-D-Phe-Arg-Trp-Gaba-Cys)-(Doc)2-Tyr-Gly-(Arg)5-Gln-(Arg)4-NH2;
or (SEQ ID NO: 466)
Nle-c(Cys-His-D-Phe-Arg-Trp-Gaba-Cys)-(Doc)2-(Arg)5-Gln-(Arg)4-NH2,
``` or pharmaceutically acceptable salts thereof.

In an example embodiment, the compounds useful for practicing the methods described herein are the compounds of Formula (IV):

```
(IV)
                                                      (SEQ ID NO: 614)
Ac-c(Cys-Glu-His-A1-Arg-A2-A3-Cys)-(Pro)2-Lys-Asp-
NH2
``` or pharmaceutically acceptable salts thereof. In Formula (IV):
- $A^1$ is the D-isomer of X-Phe or 2-Nal where X is halogen;
- $A^2$ is Bal, 1-Nal, 2-Nal, or Trp; and
- $A^3$ is Aib, Ala, β-Ala or Gly, In an example embodiments, the at least one of the following compounds is used:

```
                                                      (SEQ ID NO: 467)
Ac-c(Cys-Glu-His-D-4-Br-Phe-Arg-Trp-Gly-Cys)-
(Pro)2-Lys-Asp-NH2;

(SEQ ID NO: 468)
Ac-c(Cys-Glu-His-D-2-Nal-Arg-Trp-Ala-Cys)-(Pro)2-
Lys-Asp-NH2;

(SEQ ID NO: 469)
Ac-c(Cys-Glu-His-D-2-Nal-Arg-2-Nal-Ala-Cys)-(Pro)2-
Lys-Asp-NH2;

(SEQ ID NO: 470)
Ac-c(Cys-Glu-His-D-2-Nal-Arg-1-Nal-Ala-Cys)-(Pro)2-
Lys-Asp-NH2;

(SEQ ID NO: 471)
Ac-c(Cys-Glu-His-D-2-Nal-Arg-Bal-Ala-Cys)-(Pro)2-
Lys-Asp-NH2;

(SEQ ID NO: 472)
Ac-c(Cys-Glu-His-D-2-Nal-Arg-2-Nal-β-Ala-Cys)-
(Pro)2-Lys-Asp-NH2;
or (SEQ ID NO: 473)
Ac-c(Cys-Glu-His-D-2-Nal-Arg-2-Nal-Aib-Cys)-(Pro)2-
Lys-Asp-NH2;
``` or pharmaceutically acceptable salts thereof.

In example embodiments, an MC4R agonist useful for practicing the methods described herein is at least one compound modified with a hydantoin moiety according to Formula (V), (VI) or (VII), or a pharmaceutically acceptable salt, hydrate, solvate or a prodrug thereof.

Formula (V) is described below: (see WO2008/147556 or International Patent Application Number PCT/US08/06675 incorporated herein by reference in its entirety).

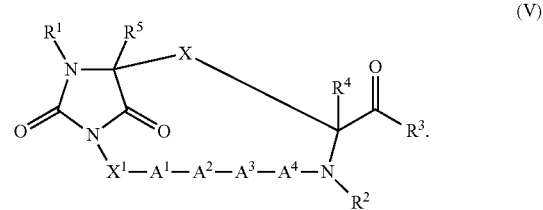

(V)

In Formula (V):
X is selected from the group consisting of —CH$_2$—S—S—CH$_2$—, —C(CH$_3$)$_2$—S—S—CH$_2$—, —CH$_2$—S—S—C(CH$_3$)$_2$—, —C(CH$_3$)$_2$—S—S—C(CH$_3$)$_2$—, —(CH$_2$)$_2$—S—S—CH$_2$—, —CH$_2$—S—S(CH$_2$)$_2$—, —(CH$_2$)$_2$—S—S—(CH$_2$)$_2$—, —C(CH$_3$)$_2$—S—S—(CH$_2$)$_2$—, —(CH$_2$)$_2$—S—S—C(CH$_3$)$_2$—, —(CH$_2$)$_r$—C(O)—NR$^8$—(CH$_2$)$_r$— and —(CH$_2$)$_r$—NR$^8$—C(O)—(CH$_2$)$_r$—;

$R^2$ each is, independently, H, (C$_1$-C$_{10}$)alkyl or substituted (C$_1$-C$_{10}$)alkyl;

$R^3$ is —OH or —NH$_2$;

$R^4$ and $R^5$ each is, independently, H, (C$_1$-C$_{10}$)alkyl or substituted (C$_1$-C$_{10}$)alkyl;

$X^1$ is

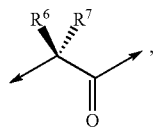

$A^1$ is H is, 2-Pal, 3-Pal, 4-Pal, (X$^1$, X$^2$, X$^3$, X$^4$, X$^5$)Phe, Taz, 2-Thi, 3-Thi or is deleted;

$A^2$ is D-Bal, D-1-Nal, D-2-Nal, D-Phe or D-(X$^1$, X$^2$, X$^3$, X$^4$, X$^5$)Phe;

$A^3$ is Arg, hArg, Dab, Dap, Lys or Orn;

$A^4$ is Bal, 1-Nal, 2-Nal, (X$^1$, X$^2$, X$^3$, X$^4$, X$^5$)Phe or Trp;

$R^6$ and $R^7$ each is, independently for each occurrence thereof, H, (C$_1$-C$_{10}$)heteroalkyl, aryl(C$_1$-C$_5$)alkyl, substituted (C$_1$-C$_{10}$)alkyl, substituted (C$_1$-C$_{10}$)heteroalkyl or substituted aryl(C$_1$-C$_5$)alkyl provided that $R^6$ and $R^7$ may be joined together to form a ring;

$R^8$ is H, (C$_1$-C$_{10}$)alkyl or substituted (C$_1$-C$_{10}$)alkyl;

r is, independently for each occurrence thereof, 1, 2, 3, 4 or 5; and t is, independently for each occurrence thereof, 1 or 2.

Compounds according the foregoing formula can include compounds wherein $X^1$ is selected from the group consisting of:

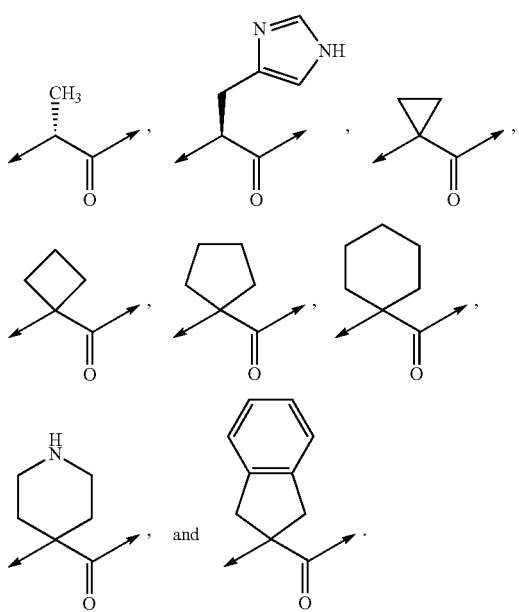

Representative embodiments of the foregoing class of compounds are as follows:

(SEQ ID NO: 474)
c[Hydantoin(C(O)-(Cys-D-Ala))-His-D-Phe-Arg-Trp-Cys]-NH₂;

(SEQ ID NO: 475)
c[Hydantoin(C(O)-(hCys-D-Ala))-His-D-Phe-Arg-Trp-Cys]-NH₂;

(SEQ ID NO: 476)
c[Hydantoin(C(O)-(Cys-D-Ala))-His-D-2-Nal-Arg-Trp-Cys]-NH₂;

(SEQ ID NO: 477)
c[Hydantoin(C(O)-(hCys-D-Ala))-His-D-2-Nal-Arg-Trp-Cys]-NH₂;

(SEQ ID NO: 478)
c[Hydantoin(C(O)-(Asp-D-Ala))-His-D-Phe-Arg-Trp-Lys]-NH₂;

(SEQ ID NO: 479)
c[Hydantoin(C(O)-(Asp-D-Ala))-His-D-Phe-Arg-Trp-Orn]-NH₂;

(SEQ ID NO: 480)
c[Hydantoin(C(O)-(Asp-D-Ala))-His-D-Phe-Arg-Trp-Dab]-NH₂;

(SEQ ID NO: 481)
c[Hydantoin(C(O)-(Asp-D-Ala))-His-D-Phe-Arg-Trp-Dap]-NH₂;

(SEQ ID NO: 482)
c[Hydantoin(C(O)-(Asp-His))-D-2-Nal-Arg-Trp-Lys]-NH₂;

(SEQ ID NO: 483)
c[Hydantoin(C(O)-(Asp-His))-D-Phe-Arg-Trp-Lys]-NH₂;

(SEQ ID NO: 484)
c[Hydantoin(C(O)-(Asp-A3c))-D-Phe-Arg-Trp-Lys]-NH₂;

(SEQ ID NO: 485)
c[Hydantoin(C(O)-(Asp-A5c))-D-Phe-Arg-Trp-Lys]-NH₂;

(SEQ ID NO: 486)
c[Hydantoin(C(O)-(Asp-A6c))-D-Phe-Arg-Trp-Lys]-NH₂;

(SEQ ID NO: 487)
c[Hydantoin(C(O)-(Asp-A3c))-D-2-Nal-Arg-Trp-Lys]-NH₂;

(SEQ ID NO: 488)
c[Hydantoin(C(O)-(Asp-A5c))-D-2-Nal-Arg-Trp-Lys]-NH₂;

(SEQ ID NO: 489)
c[Hydantoin(C(O)-(Asp-A6c))-D-2-Nal-Arg-Trp-Lys]-NH₂;

(SEQ ID NO: 490)
c[Hydantoin(C(O)-(Asp-Aic))-D-Phe-Arg-Trp-Lys]-NH₂;

(SEQ ID NO: 491)
c[Hydantoin(C(O)-(Asp-Apc))-D-Phe-Arg-Trp-Lys]-NH₂;

(SEQ ID NO: 492)
c[Hydantoin(C(O)-(Asp-Aic))-D-2-Nal-Arg-Trp-Lys]-NH₂;

(SEQ ID NO: 493)
c[Hydantoin(C(O)-(Asp-Apc))-D-2-Nal-Arg-Trp-Lys]-NH₂;

(SEQ ID NO: 494)
c[Hydantoin(C(O)-(Glu-D-Ala))-His-D-Phe-Arg-Trp-Orn]-NH₂;

(SEQ ID NO: 495)
c[Hydantoin(C(O)-(Glu-D-Ala))-His-D-Phe-Arg-Trp-Dab]-NH₂;

(SEQ ID NO: 496)
c[Hydantoin(C(O)-(Glu-D-Ala))-His-D-Phe-Arg-Trp-Dap]-NH₂;

(SEQ ID NO: 497)
c[Hydantoin(C(O)-(Glu-D-Ala))-His-D-Phe-Arg-Trp-Lys]-NH₂;

```
                                          (SEQ ID NO: 498)
c[Hydantoin(C(O)-(Glu-His))-D-Phe-Arg-Trp-Dap]-NH2;
or
                                          (SEQ ID NO: 499)
c[Hydantoin(C(O)-(Glu-His))-D-Phe-Arg-Trp-Lys]-NH2.
```

In an example embodiment, an MC4R agonist useful for practicing the methods described herein is at least one compound of Formula (VI), a pharmaceutically-acceptable salt, hydrate, solvate and/or prodrugs thereof (see WO2008/147556 or International Patent Application Number PCT/US08/06675 which is incorporated herein by reference in its entirety):

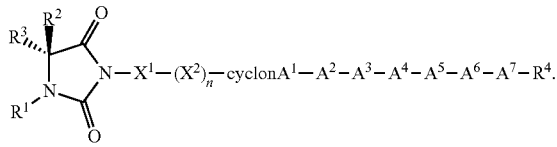

(VI)

In Formula (VI):
$X^1$ is

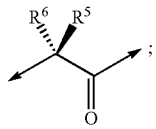

$X^2$ is

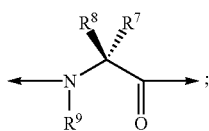

$A^1$ is Asp, Cys, D-Cys, Dab, Dap, Glu, Lys, Orn, Pen or D-Pen;
$A^2$ is an L- or D-amino acid;
$A^3$ is H is, 2-Pal, 3-Pal, 4-Pal, $(X^1, X^2, X^3, X^4, X^5)$Phe, Taz, 2-Thi or 3-Thi;
$A^4$ is D-Bal, D-1-Nal, D-2-Nal, D-Phe or D-$(X^1, X^2, X^3, X^4, X^5)$Phe;
$A^5$ is Arg, hArg, Dab, Dap, Lys or Orn;
$A^6$ is Bal, 1-Nal, 2-Nal, $(X^1, X^2, X^3, X^4, X^5)$Phe or Trp;
$A^7$ is Asp, Cys, D-Cys, Dab, Dap, Glu, Lys, Orn, Pen or D-Pen;
$R^1$ is H, $(C_1-C_{10})$alkyl or substituted $(C_1-C_{10})$alkyl;
$R^2$ and $R^3$ each is, independently, H, $(C_1-C_{10})$alkyl, $(C_1-C_{10})$heteroalkyl, aryl$(C_1-C_5)$alkyl, substituted $(C_1-C_{10})$alkyl, substituted $(C_1-C_{10})$heteroalkyl or substituted aryl$(C_1-C_5)$alkyl or $R^2$ and $R^3$ may be fused together form a cyclic moiety;
$R^4$ is OH, $NH_2$, $CO_2H$ or $C(O)NH_2$;
$R^5$ and $R^6$ each is, independently, H, $(C_1-00)$alkyl, $(C_1-C_{10})$heteroalkyl, aryl$(C_1-C_5)$alkyl, substituted $(C_1-C_{10})$alkyl, substituted $(C_1-C_{10})$heteroalkyl or substituted aryl$(C_1-C_5)$alkyl or $R^5$ and $R^6$ may be fused together form a cyclic moiety;
$R^7$ and $R^8$ each is, independently, H, $(C_1-C_{10})$alkyl, $(C_1-C_{10})$heteroalkyl, aryl$(C_1-C_5)$alkyl, substituted $(C_1-C_{10})$alkyl, substituted $(C_1-C_{10})$heteroalkyl or substituted aryl$(C_1-C_5)$alkyl; or $R^7$ and $R^8$ may be fused together form a cyclic moiety;
$R^9$ is H, $(C_1-C_{10})$alkyl or substituted $(C_1-C_{10})$alkyl; and
n is, independently for each occurrence thereof, 0, 1, 2, 3, 4, 5, 6 or 7;
or a pharmaceutically acceptable salt thereof.

Exemplary embodiments of the compounds of Formula (VI) are those compounds wherein:
$A^1$ is Cys;
$A^2$ is D-Ala, Asn, Asp, Gln, Glu or D-Phe;
$A^3$ is His;
$A^4$ is D-2-Nal or D-Phe;
$A^5$ is Arg;
$A^6$ is Trp; and
$A^7$ is Cys or Pen;
each of R', $R^2$, $R^3$, and $R^9$ is, independently, H;
$R^4$ is $C(O)NH_2$;
each of $R^5$ and $R^6$ is, independently, H, $(C_1-C_{10})$heteroalkyl, substituted $(C_1-C_{10})$alkyl or substituted $(C_1-C_{10})$heteroalkyl or $R^5$ and $R^6$ may be fused together form a cyclic moiety; and each of $R^7$ and $R^8$ is, independently, H, $(C_1-C_{10})$alkyl, $(C_1-C_{10})$heteroalkyl, substituted $(C_1-C_{10})$alkyl or substituted $(C_1-C_{10})$heteroalkyl;
or pharmaceutically acceptable salts thereof.

Example compounds of the immediately foregoing Formula (VI) include:

```
                                          (SEQ ID NO: 500)
Hydantoin(C(O)-(Arg-Gly))-c(Cys-Glu-His-D-Phe-Arg- Trp-Cys)-NH2;

(SEQ ID NO: 501)
Hydantoin(C(O)-(Nle-Gly))-c(Cys-Glu-His-D-Phe-Arg-

Trp-Cys)-NH2;

(SEQ ID NO: 502)
Hydantoin(C(O)-(Gly-Gly))-c(Cys-Glu-His-D-Phe-Arg-

Trp-Cys)-NH2;

(SEQ ID NO: 503)
Hydantoin(C(O)-(Nle-Gly))-c(Cys-D-Ala-His-D-Phe-

Arg-Trp-Cys)-NH2;

(SEQ ID NO: 504)
Hydantoin(C(O)-(Gly-Gly))-c(Cys-D-Ala-His-D-Phe-

Arg-Trp-Cys)-NH2;

(SEQ ID NO: 505)
Hydantoin(C(O)-(Nle-Gly))-c(Cys-D-Ala-His-D-Phe-

Arg-Trp-Pen)-NH2;

(SEQ ID NO: 506)
Hydantoin(C(O)-(Gly-Gly))-c(Cys-D-Ala-His-D-Phe-

Arg-Trp-Pen)-NH2;

(SEQ ID NO: 507)
Hydantoin(C(O)-(Ala-Gly))-c(Cys-D-Ala-His-D-Phe-

Arg-Trp-Cys)-NH2;
```

Hydantoin(C(O)-(D-Ala-Gly))-c(Cys-D-Ala-His-D-Phe-Arg-Trp-Cys)-NH$_2$; (SEQ ID NO: 508)

Hydantoin(C(O)-(Aib-Gly))-c(Cys-D-Ala-His-D-Phe-Arg-Trp-Cys)-NH$_2$; (SEQ ID NO: 509)

Hydantoin(C(O)-(Val-Gly))-c(Cys-D-Ala-His-D-Phe-Arg-Trp-Cys)-NH$_2$; (SEQ ID NO: 510)

Hydantoin(C(O)-(Ile-Gly))-c(Cys-D-Ala-His-D-Phe-Arg-Trp-Cys)-NH$_2$; (SEQ ID NO: 511)

Hydantoin(C(O)-(Leu-Gly))-c(Cys-D-Ala-His-D-Phe-Arg-Trp-Cys)-NH$_2$; (SEQ ID NO: 512)

Hydantoin(C(O)-(Gly-Gly))-c(Cys-Glu-His-D-2-Nal-Arg-Trp-Cys)-NH$_2$; (SEQ ID NO: 513)

Hydantoin(C(O)-(Nle-Gly))-c(Cys-Glu-His-D-2-Nal-Arg-Trp-Cys)-NH$_2$; (SEQ ID NO: 514)

Hydantoin(C(O)-(D-Arg-Gly))-c(Cys-Glu-His-D-Phe-Arg-Trp-Cys)-NH$_2$; (SEQ ID NO: 515)

Hydantoin(C(O)-(D-Arg-Gly))-c(Cys-D-Ala-His-D-Phe-Arg-Trp-Cys)-NH$_2$; (SEQ ID NO: 516)

Hydantoin(C(O)-(Arg-Gly))-c(Cys-D-Ala-His-D-Phe-Arg-Trp-Cys)-NH$_2$; (SEQ ID NO: 517)

Hydantoin(C(O)-(D-Arg-Gly))-c(Cys-D-Ala-His-D-2-Nal-Arg-Trp-Cys)-NH$_2$; (SEQ ID NO: 518)

Hydantoin(C(O)-(Arg-Gly))-c(Cys-D-Ala-His-D-2-Nal-Arg-Trp-Cys)-NH$_2$; (SEQ ID NO: 519)

Hydantoin(C(O)-(Ala-Nle))-c(Cys-Glu-His-D-Phe-Arg-Trp-Cys)-NH$_2$; (SEQ ID NO: 520)

Hydantoin(C(O)-(Val-Nle))-c(Cys-Glu-His-D-Phe-Arg-Trp-Cys)-NH$_2$; (SEQ ID NO: 521)

Hydantoin(C(O)-(Gly-Nle))-c(Cys-Glu-His-D-Phe-Arg-Trp-Cys)-NH$_2$; (SEQ ID NO: 522)

Hydantoin(C(O)-(A6c-Nle))-c(Cys-D-Ala-His-D-Phe-Arg-Trp-Cys)-NH$_2$; (SEQ ID NO: 523)

Hydantoin(C(O)-(Gly-Nle))-c(Cys-D-Ala-His-D-Phe-Arg-Trp-Cys)-NH$_2$; (SEQ ID NO: 524)

Hydantoin(C(O)-(Ala-Nle))-c(Cys-D-Ala-His-D-Phe-Arg-Trp-Cys)-NH$_2$; (SEQ ID NO: 525)

Hydantoin(C(O)-(D-Ala-Nle))-c(Cys-D-Ala-His-D-Phe-Arg-Trp-Cys)-NH$_2$; (SEQ ID NO: 526)

Hydantoin(C(O)-(Val-Nle))-c(Cys-D-Ala-His-D-Phe-Arg-Trp-Cys)-NH$_2$; (SEQ ID NO: 527)

Hydantoin(C(O)-(Leu-Nle))-c(Cys-D-Ala-His-D-Phe-Arg-Trp-Cys)-NH$_2$; (SEQ ID NO: 528)

Hydantoin(C(O)-(Cha-Nle))-c(Cys-D-Ala-His-D-Phe-Arg-Trp-Cys)-NH$_2$; (SEQ ID NO: 529)

Hydantoin(C(O)-(Aib-Nle))-c(Cys-D-Ala-His-D-Phe-Arg-Trp-Cys)-NH$_2$; (SEQ ID NO: 530)

Hydantoin(C(O)-(Gly-Arg))-c(Cys-Glu-His-D-Phe-Arg-Trp-Cys)-NH$_2$; (SEQ ID NO: 531)

Hydantoin(C(O)-(Gly-Arg))-c(Cys-Glu-His-D-2-Nal-Arg-Trp-Cys)-NH$_2$; (SEQ ID NO: 532)

Hydantoin(C(O)-(Gly-Arg))-c(Cys-D-Ala-His-D-Phe-Arg-Trp-Cys)-NH$_2$; (SEQ ID NO: 533)

Hydantoin(C(O)-(Gly-Arg))-c(Cys-D-Ala-His-D-2-Nal-Arg-Trp-Cys)-NH$_2$; (SEQ ID NO: 534)

Hydantoin(C(O)-(Gly-D-Arg))-c(Cys-Glu-His-D-Phe-Arg-Trp-Cys)-NH$_2$; (SEQ ID NO: 535)

Hydantoin(C(O)-(Gly-D-Arg))-c(Cys-D-Ala-His-D-Phe-Arg-Trp-Cys)-NH$_2$; (SEQ ID NO: 536)

Hydantoin(C(O)-(Gly-D-Arg))-c(Cys-D-Ala-His-D-2-Nal-Arg-Trp-Cys)-NH$_2$; (SEQ ID NO: 537)

Or

Hydantoin(C(O)-(Nle-Ala))-c(Cys-Glu-His-D-Phe-Arg-Trp-Cys)-NH$_2$; (SEQ ID NO: 538)

or a pharmaceutically acceptable salt thereof.

In some embodiments, the MC4R agonist comprises/is:

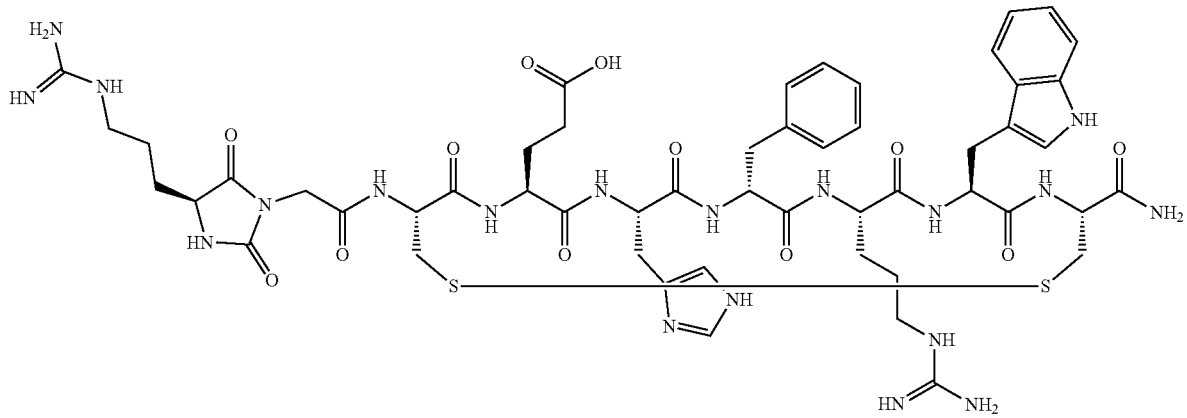 [SMILES: N=C(N)NCCC[C@@H]1NC(=O)[C@@H](Cc2ccccc2)NC(=O)[C@H](Cc2c[nH]cn2)NC(=O)[C@H](CCC(=O)O)NC(=O)[C@@H](NC(=O)CN2C(=O)N[C@@H](CCCNC(=N)N)C2=O)CSSC[C@@H](C(N)=O)NC(=O)[C@H](Cc2c[nH]c3ccccc23)NC1=O]

In an example embodiment, the MC4R agonists useful for practicing the methods described herein are compounds having a structure according to Formula (VII) as depicted below (see WO2008/147556 or International Patent Application Number PCT/US08/06675 which is incorporated herein by reference in its entirety):

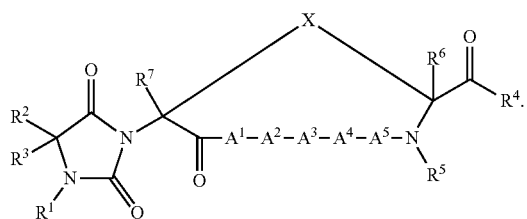

(VII)

wherein:
X is selected from the group consisting of $-CH_2-S-S-CH_2-$, $-C(CH_3)_2SSCH_2-$, $-CH_2-S-S-C(CH_3)_2-$, $-C(CH_3)_2-S-S-C(CH_3)_2-$, $-(CH_2)_2-S-S-CH_2-$, $-CH_2-S-S-(CH_2)_2-$, $-(CH_2)_2-S-S-(CH_2)_2-$, $-C(CH_3)_2-S-S-(CH_2)_2-$, $-(CH_2)_2-S-S-C(CH_3)_2-$, $-(CH_2)_r-C(O)-NR^8-(CH_2)_r-$ and $-(CH_2)_r-NR^8-C(O)-(CH_2)_r-$;

each of $R^1$ and $R^5$ is, independently, H, $(C_1-C_{10})$alkyl or substituted $(C_1-C_{10})$alkyl;

each of $R^2$ and $R^3$ is, independently, H, $(C_1-C_{10})$alkyl, $(C_1-00)$heteroalkyl, aryl$(C_1-C_5)$alkyl, substituted $(C_1-C_{10})$alkyl, substituted $(C_1-C_{10})$heteroalkyl or substituted aryl$(C_1-C_5)$alkyl or $R^2$ and $R^3$ may be fused together to form a ring;

$R^4$ is OH or $NH_2$;

each of $R^6$ and $R^7$ is, independently, H, $(C_1-C_{10})$alkyl or substituted $(C_1-C_{10})$alkyl;

$A^1$ is an L- or D-amino acid or deleted;

$A^2$ is H is, 2-Pal, 3-Pal, 4-Pal, $(X^1, X^2, X^3, X^4, X^5)$Phe, Taz, 2-Thi or 3-Thi;

$A^3$ is D-Bal, D-1-Nal, D-2-Nal, D-Phe or D-$(X^1, X^2, X^3, X^4, X^5)$Phe;

$A^4$ is Arg, hArg, Dab, Dap, Lys or Orn;

$A^5$ is Bal, 1-Nal, 2-Nal, $(X^1, X^2, X^3, X^4, X^5)$Phe or Trp;

r is, independently for each occurrence thereof, 1, 2, 3, 4 or 5; and t is, independently for each occurrence thereof, 1 or 2;

or pharmaceutically acceptable salts thereof.

In an example embodiment of the compounds of Formula (VII), $A^1$ is Ala, D-Ala, Asn, Asp, Gln, Glu or Gly.

Example compounds according to Formula (VII) include the following compounds:

```
                                      (SEQ ID NO: 539)
c[Hydantoin(C(O)-(Nle-Cys))-D-Ala-His-D-Phe-Arg- Trp-Cys]-NH2;

(SEQ ID NO: 540)
c[Hydantoin(C(O)-(Ala-Cys))-D-Ala-His-D-Phe-Arg-

Trp-Cys]-NH2;

(SEQ ID NO: 541)
c[Hydantoin(C(O)-(D-Ala-Cys))-D-Ala-His-D-Phe-Arg-

Trp-Cys]-NH2;

(SEQ ID NO: 542)
c[Hydantoin(C(O)-(Aib-Cys))-D-Ala-His-D-Phe-Arg-

Trp-Cys]-NH2;

(SEQ ID NO: 543)
c[Hydantoin(C(O)-(Val-Cys))-D-Ala-His-D-Phe-Arg-

Trp-Cys]-NH2;

(SEQ ID NO: 544)
c[Hydantoin(C(O)-(Abu-Cys))-D-Ala-His-D-Phe-Arg-

Trp-Cys]-NH2;

(SEQ ID NO: 545)
c[Hydantoin(C(O)-(Leu-Cys))-D-Ala-His-D-Phe-Arg-

Trp-Cys]-NH2;

(SEQ ID NO: 546)
c[Hydantoin(C(O)-(Ile-Cys))-D-Ala-His-D-Phe-Arg-

Trp-Cys]-NH2;

(SEQ ID NO: 547)
c[Hydantoin(C(O)-(Cha-Cys))-D-Ala-His-D-Phe-Arg-

Trp-Cys]-NH2;
```

```
                                                    (SEQ ID NO: 548)
c[Hydantoin(C(O)-(A6c-Cys))-D-Ala-His-D-Phe-Arg- Trp-Cys]-NH₂;

(SEQ ID NO: 549)
c[Hydantoin(C(O)-(Phe-Cys))-D-Ala-His-D-Phe-Arg-

Trp-Cys]-NH₂;

(SEQ ID NO: 550)
c[Hydantoin(C(O)-(Gly-Cys))-D-Ala-His-D-Phe-Arg-

Trp-Cys]-NH₂;
Or (SEQ ID NO: 551)
c[Hydantoin(C(O)-(Gly-Cys))-Glu-His-D-Phe-Arg-Trp- Cys]-NH₂;
``` or pharmaceutically acceptable salts thereof.

In an example embodiment, the MC4R agonist useful for practicing the methods described herein is at least one compound according to Formula (VIII) (see International Patent Application Number PCT/US08/07411, incorporated herein by reference in its entirety):

$$(R^2R^3)\text{-}A^0\text{-}A^1\text{-}c(A^2\text{-}A^3\text{-}A^4\text{-}A^5\text{-}A^6\text{-}A^7\text{-}A^8\text{-}A^9)\text{-}A^{10}\text{-}R^1 \quad \text{(VIII)}$$

In Formula (VIII):
$A^0$ is an aromatic amino acid
$A^1$ is Acc, HN—$(CH_2)_m$—C(O), an L- or D-amino acid;
$A^2$ is Asp, Cys, D-Cys, hCys, D-hCys, Glu, Pen, or D-Pen;
$A^3$ is Aib, Ala, β-Ala, Gaba, Gly or a D-amino acid;
$A^4$ is H is, 2-Pal, 3-Pal, 4-Pal, $(X^1, X^2, X^3, X^4, X^5)$Phe, Taz, 2-Thi, or 3-Thi;
$A^5$ is D-Bal, D-1-Nal, D-2-Nal, D-Phe, L-Phe, D-$(X^1, X^2, X^3, X^4, X^5)$Phe, L-Phe, D-Trp or D-(Et)Tyr;
$A^6$ is Arg, hArg, Dab, Dap, Lys, Orn, or HN—CH$((CH_2)_n$—N($R^4R^5$))—C(O);
$A^7$ is Bal, D-Bal, Bip, D-Bip, 1-Nal, D-1-Nal, 2-Nal, D-2-Nal, or D-Trp;
$A^8$ is Acc, Aha, Ahx, Ala, D-Ala, β-Ala, Apn, Gaba, Gly, HN—$(CH_2)_s$—C(O), or deleted;
$A^9$ is Cys, D-Cys, hCys, D-hCys, Dab, Dap, Lys, Orn, Pen, or D-Pen;
$A^{10}$ is Acc, HN—$(CH_2)$—C(O), L- or D-amino acid, or deleted;
$R^1$ is OH, or NH₂;
each of $R^2$ and $R^3$ is, independently for each occurrence selected from the group consisting of H, ($C_1$-$C_{30}$)alkyl, ($C_1$-$C_{30}$)heteroalkyl, ($C_1$-$C_{30}$)acyl, ($C_2$-$C_{30}$)alkenyl, ($C_2$-$C_{30}$)alkynyl, aryl($C_1$-$C_{30}$)alkyl, aryl($C_1$-$C_{30}$)acyl, substituted ($C_1$-$C_{30}$)alkyl, substituted ($C_1$-$C_{30}$)heteroalkyl, substituted ($C_1$-$C_{30}$)acyl, substituted ($C_2$-$C_{30}$)alkenyl, substituted ($C_2$-$C_{30}$)alkynyl, substituted aryl ($C_1$-$C_{30}$)alkyl, and substituted aryl($C_1$-$C_{30}$)acyl;
each of $R^4$ and $R^5$ is, independently for each occurrence, H, ($C_1$-$C_{40}$)alkyl, ($C_1$-$C_{40}$)heteroalkyl, ($C_1$-$C_{40}$)acyl, ($C_2$-$C_{40}$)alkenyl, ($C_2$-$C_{40}$)alkynyl, aryl($C_1$-$C_{40}$)alkyl, aryl($C_1$-$C_{40}$)acyl, substituted ($C_1$-$C_{40}$)alkyl, substituted ($C_1$-$C_{40}$)heteroalkyl, substituted ($C_1$-$C_{40}$)acyl, substituted ($C_2$-$C_{40}$)alkenyl, substituted ($C_2$-$C_{40}$)alkynyl, substituted aryl($C_1$-$C_{40}$)allyl, substituted aryl($C_1$-$C_{40}$) acyl, ($C_1$-$C_{40}$)alkylsulfonyl, or —C(NH)—NH₂;
m is, independently for each occurrence, 1, 2, 3, 4, 5, 6 or 7;
n is, independently for each occurrence, 1, 2, 3, 4 or 5;
s is, independently for each occurrence, 1, 2, 3, 4, 5, 6, or 7;
t is, independently for each occurrence, 1, 2, 3, 4, 5, 6, or 7;
$X^1$, $X^2$, $X^3$, $X^4$, and $X^5$ each is, independently for each occurrence, H, F, Cl, Br, I, ($C_{1-10}$)alkyl, substituted ($C_{1-10}$)alkyl, ($C_{2-10}$)alkenyl, substituted ($C_{2-10}$)alkenyl, ($C_{2-10}$)alkynyl, substituted ($C_{2-10}$)alkynyl, aryl, substituted aryl, OH, NH₂, NO₂, or CN.

In example embodiments of Formula (VIII),
(I) when $R^4$ is ($C_1$-$C_{40}$)acyl, aryl($C_1$-$C_{40}$)acyl, substituted ($C_1$-$C_{40}$)acyl, substituted aryl($C_1$-$C_{40}$)acyl, ($C_1$-$C_{40}$)alkylsulfonyl, or —C(NH)—NH₂, then $R^5$ is H or ($C_1$-$C_{40}$)alkyl, ($C_1$-$C_{40}$)heteroalkyl, ($C_2$-$C_{40}$)alkenyl, ($C_2$-$C_{40}$)alkynyl, aryl($C_1$-$C_{40}$)alkyl, substituted ($C_1$-$C_{40}$)alkyl, substituted ($C_1$-$C_{40}$)heteroalkyl, substituted ($C_2$-$C_{40}$)alkenyl, substituted ($C_2$-$C_{40}$)alkynyl, or substituted aryl($C_1$-$C_{40}$)alkyl;
(II) when $R^2$ is ($C_1$-$C_{30}$)acyl, aryl($C_1$-$C_{30}$)acyl, substituted ($C_1$-$C_{30}$)acyl, or substituted aryl($C_1$-$C_{30}$)acyl, then $R^3$ is H, ($C_1$-$C_{30}$)alkyl, ($C_1$-$C_{30}$)heteroalkyl, ($C_2$-$C_{30}$)alkenyl, ($C_2$-$C_{30}$)alkynyl, aryl($C_1$-$C_{30}$)alkyl, substituted ($C_1$-$C_{30}$)alkyl, substituted ($C_1$-$C_{30}$)heteroalkyl, substituted ($C_2$-$C_{30}$)alkenyl, substituted ($C_2$-$C_{30}$)alkynyl, or substituted aryl($C_1$-$C_{30}$)alkyl;
(III) when $A^2$ is Cys, D-Cys, hCys, D-hCys, Pen, or D-Pen, then $A^9$ is Cys, D-Cys, hCys, D-hCys, Pen, or D-Pen;
(IV) when $A^2$ is Asp or Glu, then $A^9$ is Dab, Dap, Orn, or Lys;
(V) when $A^8$ is Ala or Gly, then $A^1$ is not Nle; or pharmaceutically acceptable salts thereof.

In example embodiments of compounds of Formula (VIII):
$A^0$ is 1-Nal, 2-Nal, H is, Pff, Phe, Trp, or Tyr;
$A^1$ is Arg;
$A^2$ is Cys;
$A^3$ is D-Ala;
$A^4$ is H is;
$A^5$ is D-Phe
$A^6$ is Arg;
$A^7$ is Trp
$A^8$ is deleted;
$A^9$ is Cys; and
$A^{10}$ is deleted;
or pharmaceutically acceptable salts thereof.

Particular compounds of the immediately foregoing group of compounds are of the formula:

```
                                                    (SEQ ID NO: 552)
Ac-Tyr-Arg-c(Cys-D-Ala-His-D-Phe-Arg-Trp-Cys)-NH₂;

(SEQ ID NO: 553)
Ac-2-Nal-Arg-c(Cys-D-Ala-His-D-Phe-Arg-Trp-Cys)-

NH₂;

(SEQ ID NO: 554)
Ac-1-Nal-Arg-c(Cys-D-Ala-His-DPhe-Arg-Trp-Cys)-NH₂;

(SEQ ID NO: 555)
Ac-Phe-Arg-c(Cys-D-Ala-His-D-Phe-Arg-Trp-Cys)-NH₂;

(SEQ ID NO: 556)
Ac-Trp-Arg-c(Cys-D-Ala-His-D-Phe-Arg-Trp-Cys)-NH₂;

(SEQ ID NO: 557)
Ac-Pff-Arg-c(Cys-D-Ala-His-D-Phe-Arg-Trp-Cys)-NH₂;
```

-continued

H-His-Arg-c(Cys-D-Ala-His-D-Phe-Arg-Trp-Cys)-NH₂; (SEQ ID NO: 558)
or

Ac-His-Arg-c(Cys-D-Ala-His-D-Phe-Arg-Trp-Cys)-NH₂; (SEQ ID NO: 559)

or a pharmaceutically acceptable salt thereof.

In one example embodiment, the MC4R agonist is Ac-Arg-c(Cys-D-Ala-His-D-Phe-Arg-Trp-Cys)-NH₂ (SEQ ID NO: 140) or a pharmaceutically acceptable salt thereof. In another example embodiment, the MC4R agonist is Hydantoin(C(O)-(Arg-Gly))-c(Cys-Glu-His-D-Phe-Arg-Trp-Cys)-NH₂ (SEQ ID NO: 500) or a pharmaceutically acceptable salt thereof.

In some embodiments, the MC4R agonist is an agonist described in WO2014/144260 A1, incorporated herein by reference. Administration of a compound or pharmaceutically acceptable salt thereof or a composition comprising a compound or pharmaceutical salt of a compound of the invention useful to practice the methods described herein, can be continuous, hourly, four times daily, three time daily, twice daily, once daily, once every other day, twice weekly, once weekly, once every two weeks, once a month, or once every two months, or longer or some other intermittent dosing regimen.

Examples of administration of a compound or composition comprising a compound or pharmaceutical salt of a compound of the invention include peripheral administration. Examples of peripheral administration include oral, subcutaneous, intraperitoneal, intramuscular, intravenous, rectal, transdermal or intranasal forms of administration.

As used herein, peripheral administration can include all forms of administration of a compound or a composition comprising a compound of the instant invention which excludes intracranial administration. Examples of peripheral administration include, but are not limited to, oral, parenteral (e.g., intramuscular, intraperitoneal, intravenous or subcutaneous injection, extended release, slow release implant, depot and the like), nasal, vaginal, rectal, sublingual or topical routes of administration, including transdermal patch applications and the like.

The nomenclature used to define the peptides is that typically used in the art wherein the amino group at the N-terminus appears to the left and the carboxyl group at the C-terminus appears to the right. Where the amino acid has D and L isomeric forms, it is the L form of the amino acid that is represented unless otherwise explicitly indicated.

The compounds of the invention useful for practicing the methods described herein may possess one or more chiral centers and so exist in a number of stereoisomeric forms. All stereoisomers and mixtures thereof are included in the scope of the present invention. Racemic compounds may either be separated using preparative HPLC and a column with a chiral stationary phase or resolved to yield individual enantiomers utilizing methods known to those skilled in the art. In addition, chiral intermediate compounds may be resolved and used to prepare chiral compounds of the invention.

The compounds described herein may exist in one or more tautomeric forms. All tautomers and mixtures thereof are included in the scope of the present invention. For example, a claim to 2-hydroxypyridinyl would also cover its tautomeric form, a-pyridonyl.

Unless defined otherwise, all technical and scientific terms used herein have the same meaning as commonly understood by one of ordinary skill in the art to which this invention belongs. Also, all publications, patent applications, patents and other references mentioned herein are incorporated by reference in their entirety.

| Symbol | Meaning |
|---|---|
| Abu | α-aminobutyric acid |
| Ac | acyl group |
| Acc | 1-amino-1-cyclo(C₃-C₉)alkyl carboxylic acid |
| A3c | 1-amino-1cyclopropanecarboxylic acid |
| A4c | 1-amino-1-cyclobutanecarboxylic acid |
| A5c | 1-amino-1-cyclopentanecarboxylic acid |
| A6c | 1-amino-1-cyclohexanecarboxylic acid |
| Aha | 7-aminoheptanoic acid |
| Ahx | 6-aminohexanoic acid |
| Aib | α-aminoisobutyric acid |
| Aic | 2-aminoindan-2-carboxylic acid |
| Ala or A | Alanine |
| β-Ala | β-alanine |
| Apc | denotes the structure: |

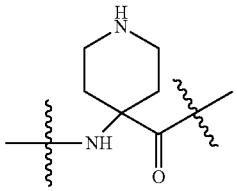 [SMILES: *NC1(C(*)=O)CCNCC1]

| | |
|---|---|
| Apn | 5-aminopentanoic acid (HN—(CH₂)₄—C(O) |
| Arg or R | Arginine |
| hArg | Homoarginine |
| Asn or N | Asparagine |
| Asp or D | aspartic acid |
| Bal | 3-benzothienylalanine |
| Bip | 4,4'-biphenylalanine, represented by the structure |

| | |
|---|---|
| Bpa | 4-benzoylphenylalanine |
| 4-Br-Phe | 4-bromo-phenylalanine |
| Cha | β-cyclohexylalanine |
| hCha | homo-cyclohexylalanine |
| Chg | Cyclohexylglycine |
| Cys or C | Cysteine |
| hCys | Homocysteine |
| Dab | 2,4-diaminobutyric acid |
| Dap | 2,3-diaminopropionic acid |
| Dip | β,β-diphenylalanine |
| Doc | 8-amino-3,6-dioxaoctanoic acid with the structure of: |

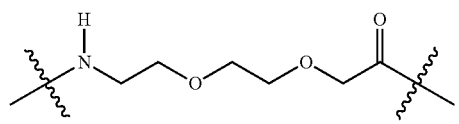 [SMILES: *NCCOCCOCC(*)=O]

| | |
|---|---|
| 2-Fua | β-(2-furyl)-alanine |
| Gaba | 4-aminobutyric acid |
| Gln or Q | Glutamine |
| Glu or E | glutamic acid |

| | |
|---|---|
| Gly or G | Glycine |
| His or H | Histidine |
| 3-Hyp | trans-3-hydroxy-L-proline, i.e., (2S,3S)-3-hydroxy-pyrrolidine-2-carboxylic acid |
| 4-Hyp | 4-hydroxyproline, i.e., (2S,4R)-4-hydorxypyrrolidine-2-carboxylic acid |
| Ile or I | Isoleucine |
| Leu or L | Leucine |
| hLeu | Homoleucine |
| Lys or K | Lysine |
| Met or M | Methionine |
| β-hMet | β-homomethionine |
| 1-Nal | β-(1-naphthyl)alanine |
| 2-Nal | β-(2-naphthyl)alanine |
| Nip | nipecotic acid |
| Nle | Norleucine |
| Ole | octahydroindole-2-carboxylic acid |
| Orn | Ornithine |
| 2-Pal | β-(2-pyridiyl)alanine |
| 3-Pal | β-(3-pyridiyl)alanine |
| 4-Pal | β-(4-pyridiyl)alanine |
| Pen | Penicillamine |
| Pff | (S)-pentafluorophenylalanine |
| Phe or F | Phenylalanine |
| hPhe | homophenylalanine |
| Pro or P | Proline |
| hProP | Homoproline |
| Ser or S | Serine |
| Tle | tert-Leucine |
| Taz | β-(4-thiazolypalanine |
| 2-Thi | β-(2-thienyl)alanine |
| 3-Thi | β-(3-thienyl)alanine |
| Thr or T | Threonine |
| Trp or W | Tryptopham |
| Tyr or Y | Tyrosine |
| D—(Et) Tyr | has a structure of 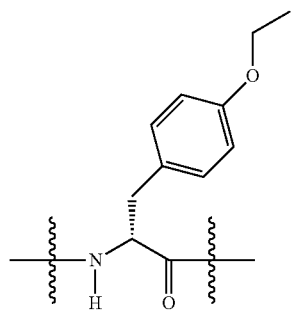 [SMILES: *N[C@H](Cc1ccc(OCC)cc1)C(*)=O] |
| Val or V | Valine |

Certain other abbreviations used herein are defined as follows:

Boc: tert-butyloxycarbonyl
Bzl: Benzyl
DCM: Dichloromethane
DIC: N,N-diisopropylcarbodiimide
DIEA: diisopropylethyl amine
Dmab: 4-{N-(1-(4,4-dimethyl-2,6-dioxocyclohexylidene)-3-methylbutyl)-amino}benzyl
DMAP: 4-(dimethylamino)pyridine
DMF: Dimethylformamide
DNP: 2,4-dinitrophenyl
Fm: Fluorenylmethyl
Fmoc: fluorenylmethyloxycarbonyl
For: Formyl
HBTU: 2-(1H-benzotriazole-1-yl)-1,1,3,3-tetramethyl-uronium hexafluorophosphate
cHex Cyclohexyl
HOAT: O-(7-azabenzotriazol-1-yl)-1,1,3,3-tetramethyl-uronium hexafluorophosphate
HOBt: 1-hydroxy-benzotriazole
MBNA 4-methylbenzhydrylamine
Mmt: 4-methoxytrityl
NMP: N-methylpyrrolidone
O-tBu oxy-tert-butyl
Pbf: 2,2,4,6,7-pentamethyldihydrobenzofuran-5-sulfonyl
PyBroP bromo-tris-pyrrolidino-phosphonium hexafluorophosphate
tBu: tert-butyl
TIS: triisopropylsilane
TOS: Tosyl
Trt Trityl
TFA: trifluoro acetic acide
TFFH: tetramethylfluoroforamidiaium hexafluorophosphate
Z: benzyloxycarbonyl Unless otherwise indicated, with the exception of the N-terminal amino acid, all abbreviations (e.g. Ala) of amino acids in this disclosure stand for the structure of —NH—C(R)(R')—CO—, wherein R and R' each is, independently, hydrogen or the side chain of an amino acid (e.g., R=CH₃ and R'=H for Ala), or R and R' may be joined to form a ring system.

For the N-terminal amino acid, the abbreviation stands for the structure of:

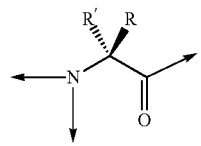

The designation "NH₂" in e.g., Ac-Nle-c(Cys-D-Ala-His-D-Phe-Arg-Trp-Cys)-NH₂ (SEQ ID NO:13), indicates that the C-terminus of the peptide is amidated. Ac-Nle-c(Cys-D-Ala-His-D-Phe-Arg-Trp-Cys) (SEQ ID NO:107), or alternatively Ac-Nle-c(Cys-D-Ala-His-D-Phe-Arg-Trp-Cys)-OH (SEQ ID NO:107), indicates that the C-terminus is the free acid.

"-c(Cys-Cys)-" or "-cyclo(Cys-Cys)-" denotes the structure:

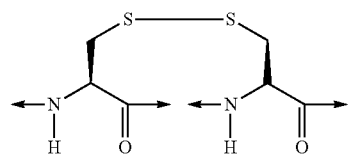

"-c(Cys-Pen)-" or "-cyclo(Cys-Pen)-" denotes the structure:

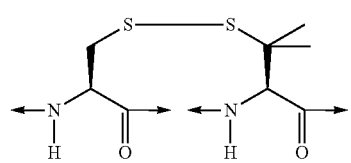

"-c(Asp-Lys)-" or "-cyclo(Asp-Lys)-" denotes the structure:

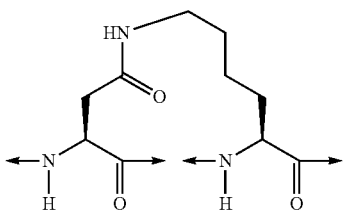

Applicants have devised the following shorthand used in naming the specific embodiments and/or species:

"Hydantoin-(C(O)-(A$^a$-A$^b$))" denotes the structure:

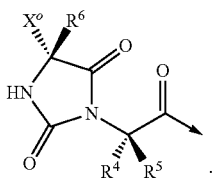

wherein amino acid "A$^a$" has the structure:

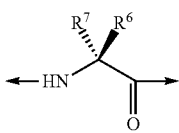

and amino acid "A$^b$" the structure:

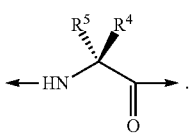

For example, "Hydantoin-(C(O)-Arg-A$^b$))" would have the following structure:

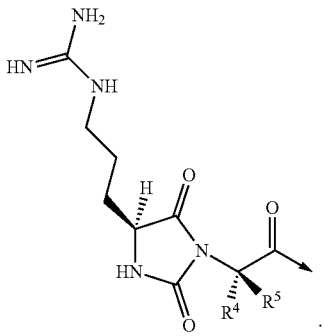

For example, "Hydantoin-(C(O)-(Arg-Gly))" would have the following structure:

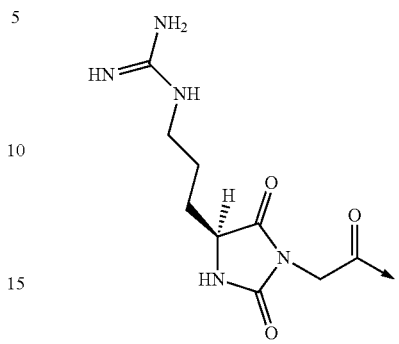

For example, a compound represented as "c[Hydantoin (C(O)-(Cys-A$^b$))-A$^1$-A$^2$-A$^3$-A$^4$-Cys]-" would have the following the structure:

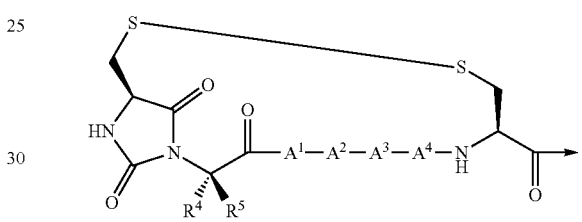

whereas a compound represented as "c[Hydantoin(C(O)-(A$^b$-Cys))-A$^1$-A$^2$-A$^3$-A$^4$-Cys]-" would have the structure:

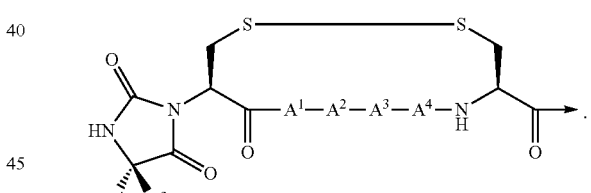

For further guidance, "c[Hydantoin(C(O)-(Asp-A$^b$))-A$^1$-A$^2$-A$^3$-A$^4$-Lys]-" represents the following compound:

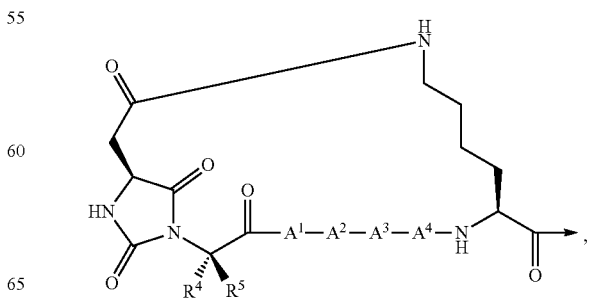

whereas "c[Hydantoin(C(O)-(Dap-A$^b$))-A$^1$-A$^2$-A$^3$-A$^4$-Asp]-" has the following formula:

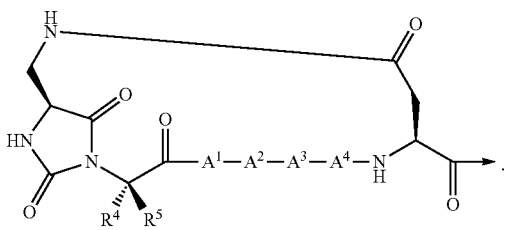

"Acyl" refers to R"—C(O)—, where R" is H, alkyl, substituted alkyl, heteroalkyl, substituted heteroalkyl, alkenyl, substituted alkenyl, aryl, alkylaryl, or substituted alklyaryl, and is indicated in the general formula of a particular embodiment as "Ac".

"Alkyl" refers to a hydrocarbon group containing one or more carbon atoms, where multiple carbon atoms if present are joined by single bonds. The alkyl hydrocarbon group may be straight-chain or contain one or more branches or cyclic groups.

"Hydroxyalkyl" refers to an alkyl group wherein one or more hydrogen atoms of the hydrocarbon group are substituted with one or more hydroxy radicals, such as hydroxymethyl, hydroxyethyl, hydroxypropyl, hydroxybutyl, hydroxypentyl, hydroxyhexyl and the like.

"Substituted alkyl" refers to an alkyl wherein one or more hydrogen atoms of the hydrocarbon group are replaced with one or more substituents selected from the group consisting of halogen, (i.e., fluorine, chlorine, bromine, and iodine), —OH, —CN, —SH, amine (e.g., —NH$_2$, —NHCH$_3$), —NO$_2$, guanidine, urea, amidine, and —C$_{1-20}$ alkyl, wherein said —C$_{1-20}$ alkyl optionally may be substituted with one or more substituents selected, independently for each occurrence, from the group consisting of halogens, —CF$_3$, —OCH$_3$, —OCF$_3$, and —(CH$_2$)$_{0-20}$—COOH. In different embodiments 1, 2, 3 or 4 substituents are present. The presence of —(CH$_2$)$_{0-20}$—COOH results in the production of an alkyl acid. Non-limiting examples of alkyl acids containing, or consisting of, —(CH$_2$)$_{0-20}$—COOH include 2-norbornane acetic acid, tert-butyric acid, 3-cyclopentyl propionic acid, and the like.

The term "halo" encompasses fluoro, chloro, bromo and iodo.

Guanidines are a group of organic compounds that share a common functional group with the general structure (R$^1$R$^2$N)(R$^3$R$^4$N)C=N—R$^5$. The central bond within this group is an imine, and the group is related structurally to amidines and ureas.

"Heteroalkyl" refers to an alkyl wherein one of more of the carbon atoms in the hydrocarbon group is replaced with one or more of the following groups: amino, amido, —O—, —S— or carbonyl. In different embodiments 1 or 2 heteroatoms are present.

"Substituted heteroalkyl" refers to a heteroalkyl wherein one or more hydrogen atoms of the hydrocarbon group are replaced with one or more substituents selected from the group consisting of halogen, (i.e., fluorine, chlorine, bromine, and iodine), —OH, —CN, —SH, —NH$_2$, —NHCH$_3$, —NO$_2$, and —C$_{1-20}$ alkyl, wherein said —C$_{1-20}$ alkyl optionally may be substituted with one or more substituents selected, independently for each occurrence, from the group consisting of halogens, —CF$_3$, —OCH$_3$, —OCF$_3$, and —(CH$_2$)$_{0-20}$—COOH. In different embodiments 1, 2, 3 or 4 substituents are present.

"Alkenyl" refers to a hydrocarbon group made up of two or more carbons where one or more carbon-carbon double bonds are present. The alkenyl hydrocarbon group may be straight-chain or contain one or more branches or cyclic groups.

"Substituted alkenyl" refers to an alkenyl wherein one or more hydrogens are replaced with one or more substituents selected from the group consisting of halogen (i.e., fluorine, chlorine, bromine, and iodine), —OH, —CN, —SH, —NH$_2$, —NHCH$_3$, —NO$_2$, and —C$_{1-20}$ alkyl, wherein said —C$_{1-20}$ alkyl optionally may be substituted with one or more substituents selected, independently for each occurrence, from the group consisting of halogens, —CF$_3$, —OCH$_3$, —OCF$_3$, and —(CH$_2$)$_{0-20}$—COOH. In different embodiments 1, 2, 3 or 4 substituents are present.

"Aryl" refers to an optionally substituted aromatic group with at least one ring having a conjugated pi-electron system, containing up to three conjugated or fused ring systems. Aryl includes carbocyclic aryl, heterocyclic aryl and biaryl groups. Preferably, the aryl is a 5- or 6-membered ring. Preferred atoms for a heterocyclic aryl are one or more sulfur, oxygen, and/or nitrogen. Non-limiting examples of aryl include phenyl, 1-naphthyl, 2-naphthyl, indole, quinoline, 2-imidazole, 9-anthracene, and the like. Aryl substituents are selected from the group consisting of —C$_{1-20}$ alkyl, —C$_{1-20}$ alkoxy, halogen (i.e., fluorine, chlorine, bromine, and iodine), —OH, —CN, —SH, —NH$_2$, —NO$_2$, —C$_{1-20}$ alkyl substituted with halogens, —CF$_3$, —OCF$_3$, and —(CH$_2$)$_{0-20}$—COOH. In different embodiments the aryl contains 0, 1, 2, 3, or 4 substituents.

"Alkylaryl" refers to an "alkyl" joined to an "aryl".

The term "(C$_{1-12}$) hydrocarbon moiety" encompasses alkyl, alkenyl and alkynyl and in the case of alkenyl and alkynyl there is C$_2$-C$_{12}$.

For the avoidance of doubt, unless otherwise indicated, the term substituted means substituted by one or more defined groups. In the case where groups may be selected from a number of alternative groups, the selected groups may be the same or different. For the avoidance of doubt, the term independently means that where more than one substituent is selected from a number of possible substituents, those substituents may be the same or different.

The pharmaceutically acceptable salts of the compounds of the invention which contain a basic center are, for example, non-toxic acid addition salts formed with inorganic acids such as hydrochloric, hydrobromic, hydroiodic, sulfuric and phosphoric acid, with carboxylic acids or with organo-sulfonic acids. Examples include the HCl, HBr, HI, sulfate or bisulfate, nitrate, phosphate or hydrogen phosphate, acetate, benzoate, succinate, saccharate, fumarate, maleate, lactate, citrate, tartrate, gluconate, camsylate, methanesulfonate, ethanesulfonate, benzenesulfonate, p-toluenesulfonate and pamoate salts. Compounds of the invention can also provide pharmaceutically acceptable metal salts, in particular non-toxic alkali and alkaline earth metal salts, with bases. Examples include the sodium, potassium, aluminum, calcium, magnesium, zinc and diethanolamine salts (Berge, S. M. et al., *J. Pharm. Sci.*, 66:1-19 (1977); Gould, P. L., *Intl J. Pharmaceutics*, 33:201-17 (1986); and Bighley, L. D. et al., *Encyclo. Pharma. Tech.*, Marcel Dekker Inc, New York, 13:453-97 (1996).

The pharmaceutically acceptable solvates of the compounds of the invention include the hydrates thereof. Also included within the scope of the invention and various salts of the invention are polymorphs thereof. Hereinafter, compounds their pharmaceutically acceptable salts, their solvates or polymorphs, defined in any aspect of the invention (except intermediate compounds in chemical processes) are referred to as "compounds of the invention".

Designation "(amino acid) n" means that an amino acid is repeated n times. For example, designation "(Pro)$_2$" or "(Arg)$_3$" mean that proline or arginine residues are repeated, respectively, two or three times.

MC4R agonists and pharmaceutically acceptable salts thereof described herein can also be used to treat individuals, including human subjects defective melanocortin receptor signaling, due to mutations/defects upstream of the MC4R. MC4R agonists and pharmaceutically acceptable salts thereof described herein can also be used to treat individuals, including human subjects that carry mutations in the genes coding for pro-opiomelanocortin (POMC) and leptin such that these mutations result in POMC haplo-insufficientcy or haplo-deficiency and/or leptin haplo-insufficiency or haplo-deficiency.

In one example embodiment, an MC4R agonist is a compound represented by structural formula (X):

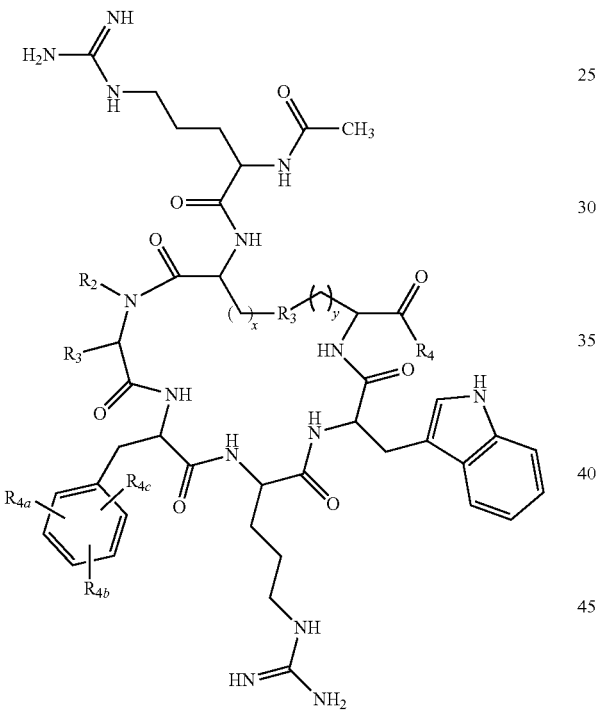

(X)

or a pharmaceutically acceptable salt thereof. In structural formula (X), the chemical substituents are defined as follows:

$R_1$ is —NH—C(O)— or —C(O)—NH—;

$R_2$ is —H, —CH$_2$—, or, $R^2$, together with $R^3$, forms a pyrrolidine ring optionally substituted with —OH;

$R_3$ is —(CH$_2$)$_2$— if $R_2$ is —CH$_2$—, and otherwise $R^3$ is selected from

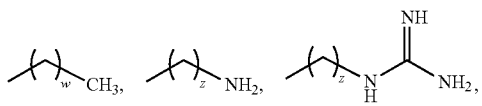

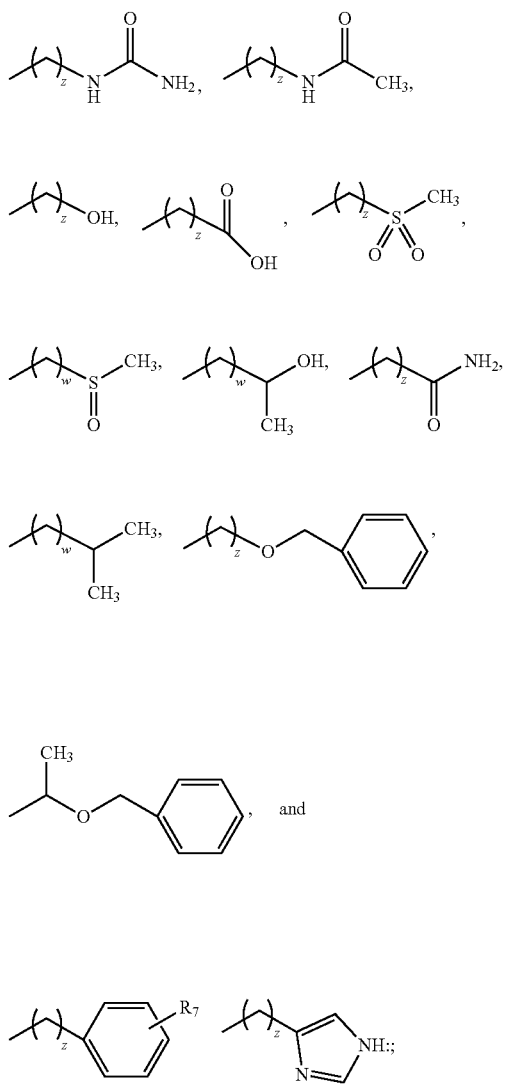

$R_{4a}$, $R_{4b}$, and $R_{4c}$ are each independently selected from hydrogen, halo, (C$_1$-C$_{10}$)alkyl-halo, (C$_1$-C$_{10}$)alkyl-dihalo, (C$_1$-C$_{10}$)alkyl-trihalo, (C$_1$-C$_{10}$)alkyl, (C$_1$-C$_{10}$) alkoxy, (C$_1$-C$_{10}$)alkylthio, aryl, aryloxy, nitro, nitrile, sulfoniamide, amino, hydroxyl, carboxy, and akoxycarbonyl. In one example embodiment, $R_{4a}$, $R_{4b}$, and $R_{4c}$ is not hydrogen.

$R_5$ is —OH or —N(R$_{6a}$)(R$_{6b}$);

$R_{6a}$ and $R_{6b}$ are each independently H or C$_1$ to C$_4$ linear, branched or cyclic alkyl chain;

$R_7$ is —H or —C(O)—NH$_2$;

w is in each instance independently 0 to 5;

x is 1 to 5;

y is 1 to 5;

z is in each instance independently 1 to 5.

An example of a compound of structural formula (X) is a cyclic peptide defined by structural formula (XI):

(XI)

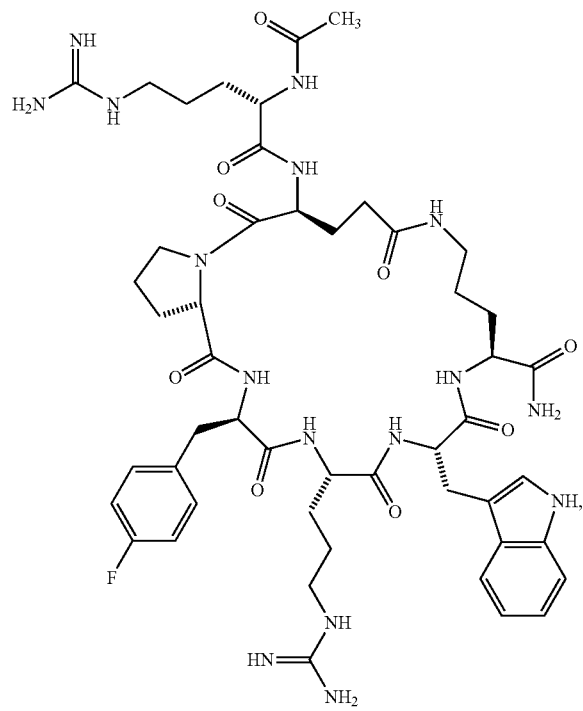

or a pharmaceutically acceptable salt thereof.

Pharmaceutical Compositions/Administration

In accordance with any method or composition described herein, in embodiments, provided herein is a unit dosage of a MC4R agonist described herein, e.g., setmelanotide. In embodiments, the unit dosage contains 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or 2 mg of the agonist. In embodiments, the unit dosage is suitable for injection, e.g., subcutaneous injection. In embodiments, the unit dosage is disposed in a delivery device suitable for injection, e.g., subcutaneous injection. In embodiments, the unit dosage is disposed in a syringe suitable for injection, e.g., subcutaneous injection, or a pen-type injector. Exemplary pen-type injectors are described, e.g., in U.S. Pat. Nos. 8,512,297B2, 5,688,251A, 5,820,602A, US2014/0163526A1, and U.S. Pat. No. 5,226,895A, incorporated herein by reference.

In embodiments, also provided herein is a pharmaceutical composition comprising a MC4R agonist described herein, e.g., setmelanotide. In embodiments, the pharmaceutical composition includes a therapeutically effective amount of a MC4R agonist described herein, e.g., setmelanotide. A therapeutically effective amount of the agonist can vary according to factors such as the disease state, age, sex, and weight of the individual, and the ability of the agonist to elicit a desired response in the individual, e.g., amelioration of at least one disorder parameter, e.g., a parameter of obesity or hyperphagia, or amelioration of at least one symptom of the disorder, e.g., obesity, hyperphagia, Prader Willi Syndrome (PWS), or other obesity-associated genetic disorder (e.g., POMC-null or PCSK1-null obesity, among others). In embodiments, a therapeutically effective amount is also one in which any toxic or a detrimental effect of the composition is outweighed by the therapeutically beneficial effects.

In certain embodiments, the agonist may be prepared with a carrier that will protect it against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., Sustained and Controlled Release Drug Delivery Systems, J. R. Robinson, ed., Marcel Dekker, Inc., New York, 1978.

In other embodiments, the agonist can be prepared as described in WO2014/144842, incorporated herein by reference. In embodiments, the agonist is prepared in a formulation comprising an anionic excipient, e.g., PEG-carboxylic acid, fatty acid having 10 or more carbon atoms, and/or anionic phospholipid. In embodiments, the anionic phospholipid is described in WO2014/144842 (e.g., at pages 7-9). In some embodiments, the anionic phospholipid is 1,2-distearoyl-sn-Glycero-3-Phosphoethanolamine (DSPE), optionally conjugated to polyethylene glycol (PEG), the structure of which is:

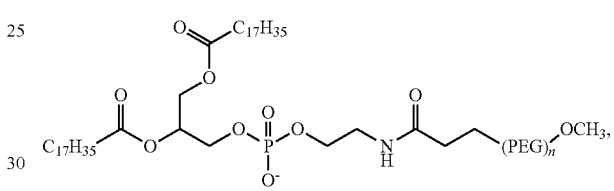

with the value of "n" varying with molecular weight. In embodiments, the fatty acid is described in WO2014/144842 (e.g., at page 9). In embodiments, the PEG-carboxylic acid is described in WO2014/144842 (e.g., at pages 9-11). In embodiments, the molar ratio of the agonist to the anionic excipient ranges from about 1:1 to about 1:10.

In embodiments, the agonist forms an ionic complex with the other components of the formulation, and e.g., provides a desirable pharmacokinetic profile for the agonist (e.g., extend duration of drug action and/or minimize adverse effects). In embodiments, the formulation is a sustained release formulation. In embodiments, the formulation provides reduced fluctuations in concentration of the agonist after administration.

A MC4R agonist described herein, e.g., setmelanotide, can be administered to a subject, e.g., human subject, by various methods. In embodiments, the route of administration is one of: intravenous injection or infusion, subcutaneous injection, or intramuscular injection. In embodiments, the route of administration is subcutaneous injection.

In embodiments, pharmaceutical compositions, e.g., comprising a MC4R agonist described herein, can be administered with medical devices. For example, compositions comprising the agonist can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of implants and modules include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Other such implants, delivery systems, and modules can also be used.

In embodiments, continuous administration can be indicated, e.g., via subcutaneous pump. In embodiments, the agonist is administered via a syringe (e.g., prefilled syringe), an implantable device, a needleness hypodermic injection device, an infusion pump (e.g., implantable infusion pump), or an osmotic delivery system.

In embodiments, the agonist is administered at a unit dosage, e.g., comprising 0.1-10 mg, e.g., 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.5, 3, 3.5, 4, 4.5, 5, 5.5, 6, 6.5, 7, 7.5, 8, 8.5, 9, 9.5, or 10 mg of the agonist, e.g., subcutaneously.

In embodiments, the agonist is administered in a bolus at a dose of between 0.1-10 mg, e.g., 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.5, 3, 3.5, 4, 4.5, 5, 5.5, 6, 6.5, 7, 7.5, 8, 8.5, 9, 9.5, or 10 mg of the agonist, e.g., subcutaneously.

In embodiments, the agonist is administered continuously, e.g., via a pump, e.g., subcutaneous pump.

In embodiments, the agonist, e.g., a unit dosage of the agonist, is disposed within a delivery device, e.g., a syringe (e.g., prefilled syringe), an implantable device, a needleness hypodermic injection device, an infusion pump (e.g., implantable infusion pump), or an osmotic delivery system.

In embodiments, a daily dosage of the agonist is administered, e.g., subcutaneously, to a subject. In embodiments, the daily dosage of the agonist is about 0.1 mg to about 10 mg, e.g., 0.1-0.2, 0.2-0.4, 0.4-0.6, 0.6-0.8, 0.8-1, 1-1.2, 1.2-1.5, 1.5-2, 2-2.5, 2.5-3, 3-3.5, 3.5-4, 4-4.5, 4.5-5, 5-5.5, 5.5-6, 6-6.5, 6.5-7, 7-7.5, 7.5-8, 8-8.5, 8.5-9, 9-9.5, 9.5-10 mg, e.g., administered subcutaneously.

In embodiments, the agonist, e.g., setmelanotide, is administered, e.g., via one or multiple administrations, over a period of at least 3 weeks, e.g., at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 weeks or more, or at least 1, 2, 3, 4, 5, 6, 7, 8, 8, 9, 10, 11, or 12 months or more, or at least 1, 2, 3, 4 years or more. In embodiments, where multiple administrations are provided of the agonist, the time interval in between any two of the administrations is at least 6 hours, e.g., 6 h, 12 h, 24 h, 1 day, 2 days, 3 days, 4 days, 5 days, 6 days, 7 days, 1 week, 2 weeks, 3 weeks, 4 weeks, or more. In embodiments, the interval in between any two of the administrations is 1 day.

Kits

A MC4R agonist described herein, e.g., setmelanotide, can be provided in a kit. The kit includes a MC4R agonist described herein and, optionally, a container, a pharmaceutically acceptable carrier and/or informational material. The informational material can be descriptive, instructional, marketing or other material that relates to the methods described herein and/or the use of the agonist for the methods described herein.

The informational material of the kits is not limited in its form. In one embodiment, the informational material can include information about production of the agonist, physical properties of the agonist, concentration, date of expiration, batch or production site information, and so forth. In one embodiment, the informational material relates to methods for administering the agonist, e.g., by a route of administration described herein and/or at a dose and/or dosing schedule described herein.

In one embodiment, the informational material can include instructions to administer an agonist described herein in a suitable manner to perform the methods described herein, e.g., in a suitable dose, dosage form, or mode of administration (e.g., a dose, dosage form, or mode of administration described herein). In another embodiment, the informational material can include instructions to administer an agonist to a suitable subject, e.g., a human, e.g., an obese human, e.g., severely obese human, e.g., having PWS or a genetic defect in one or more genes of the POMC-MC4R pathway.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about an agonist described herein and/or its use in the methods described herein. The informational material can also be provided in any combination of formats.

In addition to an agonist, the composition of the kit can include other ingredients, such as a surfactant, a lyoprotectant or stabilizer, an antioxidant, an antibacterial agent, a bulking agent, a chelating agent, an inert gas, a tonicity agent and/or a viscosity agent, a solvent or buffer, a stabilizer, a preservative, a pharmaceutically acceptable carrier and/or a second agent for treating a condition or disorder described herein. Alternatively, the other ingredients can be included in the kit, but in different compositions or containers than an agonist described herein.

In some embodiments, a component of the kit is stored in a sealed vial, e.g., with a rubber or silicone closure (e.g., a polybutadiene or polyisoprene closure). In some embodiments, a component of the kit is stored under inert conditions (e.g., under Nitrogen or another inert gas such as Argon). In some embodiments, a component of the kit is stored under anhydrous conditions (e.g., with a desiccant). In some embodiments, a component of the kit is stored in a light blocking container such as an amber vial.

An agonist described herein can be provided in any form, e.g., liquid, frozen, dried or lyophilized form. It is preferred that a composition including the agonist described herein be substantially pure and/or sterile. When an agonist described herein such as setmelanotide is provided in a liquid solution, the liquid solution preferably is an aqueous solution, with a sterile aqueous solution being preferred. In one embodiment, the agonist is supplied with a diluents or instructions for dilution. The diluent can include for example, a salt or saline solution, e.g., a sodium chloride solution having a pH between 6 and 9, lactated Ringer's injection solution, D5W, or PLASMA-LYTE A Injection pH 7.4® (Baxter, Deerfield, IL).

The kit can include one or more containers for the composition containing an agonist described herein. In some embodiments, the kit contains separate containers, dividers or compartments for the composition and informational material. For example, the composition can be contained in a bottle, vial, IV admixture bag, IV infusion set, piggyback set or syringe (e.g., prefilled syringe), and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In embodiments, the composition is contained in an injector device, e.g., a pen-type injector. The containers of the kits can be air tight, waterproof (e.g., impermeable to changes in moisture or evaporation), and/or light-tight.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples specifically point out various aspects of the present invention, and are not to be construed as limiting in any way the remainder of the disclosure.

Example 1: Treatment with a Melanocortin-4 Receptor (MC4R) Agonist in a POMC Deficient Patient with Severe Obesity and Hyperphagia Patients with POMC gene defects, such as POMC loss of function mutations, suffer from severe early onset obesity, hyperphagia, red hair, adrenal insufficiency, and ACTH deficiency. It is believed that the early onset obesity and hyperphagia is caused by a deficiency of POMC-derived peptides, such as MSH and ACTH, which are ligands to melanocortin receptors. MSH, a cleavage product of POMC, is the ligand of the hypothalamic MC4R, which is important for regulating feeding behavior and energy homeostasis. There is a need for a targeted replacement therapy for patients with genetic defects of the leptin-melanocortin pathway, such as patients with POMC loss of function mutations.

This example describes a study in which an adult POMC deficient patient was administered the MC4R agonist, setmelanotide (also called RM-493), having the sequence, Ac-Arg-c(Cys-D-Ala-His-D-Phe-Arg-Trp-Cys)-NH$_2$ (SEQ ID NO: 140). See, e.g., Chen et al. J. Clin. Endocrinol. Metab. 2015; 100:1639-45. The study was an investigator initiated, open label, phase 2, non-randomized proof of concept study (EudraCT No. 2014-002392-28; Clinical Trials Identifier No. NCT02507492) with three parts: pre-study evaluation, main study (about 13 weeks) and after a short interval off drug, a long-term extension phase.

In the pre-study period, baseline examinations were performed, including analysis of metabolic parameters, including OGTT, GnRH test, fasting blood glucose, Leptin measurements as well as bioelectrical impedance analysis (BIA, according standard protocols; Data-in, Nutriguard-MS), indirect calorimetry (CareFusion, VMAX® Encore system), heart rate and blood pressure monitoring (after the first injection and after each dosage escalation blood pressure was measured regularly over 12 hours; in addition, blood was measured at home 3 times daily) as well as a dermatological and psychological examination. All parameters were in the normal range with the exception of elevated fasting insulin reflecting insulin resistance. These measurements were repeated after 13 and 26 weeks of treatment. Baseline examination also included physical examination, e.g., measurement of height and body-weight. Setmelanotide treatment was started at a dose of 0.25 mg subcutaneously (s.c.) once daily. The dose escalated every 1-2 weeks after careful assessment of safety and weight loss. After the first injection and after each dosage escalation, blood pressure was measured regularly over 12 hours. In addition, blood was measured 3 times daily. Setmelanotide injections were given once a day.

After about 90 days of treatment (main study), assessments were repeated, including assessments of metabolic parameters, e.g., blood tests, skin examination, and psychological evaluation. Setmelanotide treatment was ended, and a rapid and large weight gain off-treatment was observed. Subsequently, setmelanotide treatment was continued for another 3 months (extension phase) along with continued assessments (of metabolic parameters). The hunger score was evaluated using a Likert hunger scale from 0 to 10 points (0=no hunger; 10=severe hunger). See, e.g., Sibilia. Psychologicol Topics 19 (2010), 2, 341-354.

Bioelectric Impedance Analysis (BIA) and indirect calorimetric analysis was performed according standard protocols, e.g., as described in Barak et al. JPEN J. Parenter. Enteral Nutr. 27.1(2003):43-6; and Compher et al. J. Am. Diet Assoc. 106.6(2006):881-903.

Statistical analysis: The values of systolic and diastolic blood pressure and heart rate were analyzed with a non-parametric student t-test.

MAINTAIN control group: The Maintain-Z-Project is a randomized controlled trial (ClinicalTrials.gov: NCT00850629) analyzing the effects of a multimodal lifestyle intervention on weight maintenance after weight loss of children and adolescents. The primary outcome was to describe the dynamic of hormonal and metabolic mechanisms counter-balancing sustained weight loss during puberty and adolescence. 147 participants reached the initial weight reduction of −0.2 BMI-standard deviation score (SDS) (weight reduction phase last in average 15.7±5.2 standard deviation (SD) weeks). Out of this study-cohort, 12 girls with extreme, but not monogenetic obesity (age 16.5±0.6 SD years; BMI 38.8±2.5 SD kg/m$^2$) were selected as control group for weight loss using the same study protocol (except GnRH-testing).

Results

Phenotype of the POMC Deficient Index Patient

The patient was a 21 year old woman, with a compound heterozygous loss of function POMC gene mutation (p.Lys51Term g.A6851>T, p.Arg145ProfsX12 g.7134delG). See, e.g., Krude et al. Nat. Genet. 1998; 19:155-7. Her older brother, who retrospectively was identified also as a carrier of compound heterozygous mutations, had died at 7 months of age due to liver failure caused by adrenal failure caused by a lack of adrenocorticotropic hormone (ACTH). As the patient was diagnosed with adrenal insufficiency early after birth, she was treated with hydrocortisone since she was three weeks old. After three months of age, development of obesity and severe hyperphagia was observed in the patient. At four years of age, a genetic analysis of the POMC gene in the patient identified a POMC gene defect. This was the first description of POMC loss of function mutation in humans.

Despite enormous efforts, where the patient received pharmacotherapy for adrenal insufficiency and received intense counseling for diet, exercise and behavioral appetite control, the patient was not able to stabilize her body-weight, except for brief periods of weight stabilization, during which she was never able to lose a substantial amount of body weight. In all cases of short-term weight loss, an immediate weight regain occurred in the patient. The extreme obesity resulted in moderate metabolic disturbances and a progressive distortion of her lower extremity, which necessitated several surgical orthopedic interventions. Similar to leptin deficient patients[1] (see, e.g., Farooqi et al. N. Engl. J. Med. 1999; 341:879-84), her pubertal development stopped at tanner stage 2 and menarche was still missing at the age of 21 years. She was treated with L-Thyroxine (175 µg/day) because of elevated TSH serum levels (range: 6-15 mU/l) and with hydrocortisone replacement (at a dose of 12.7 $mg/m^2$ BSA)).

Body Weight, Body Composition and Hunger Score

At baseline (prior to treatment with setmelanotide), the body weight of the patient was 155 kg with a height of 176.5 cm (BMI 49.8 $kg/m^2$; BMI standard deviation score (SDS)+ 4.52). At baseline, the patient was severely hyperphagic: her Likert hunger scale score was 9 out of 10 points (extreme hunger). Psychological evaluation constantly revealed extreme discomfort with her quality of life due to extreme obesity.

Weight Loss and Change in Hunger Scores

Setmelanotide was given subcutaneously once daily with a dose escalation starting with a low dose of 0.25 mg and weekly increments to 0.5 mg, 1.0 mg and finally 1.5 mg. Initially, with low dosage, the weight loss was moderate with only little changes in hunger. However, with increasing dosage, the patient noticed a clear reduction of hunger with 1 mg setmelanotide (5 out of 10 points), and her appetite was nearly completely abolished at the 1.5 mg dose (0 to 1 out of 10 points; no hunger). With this change in satiety, she reached a constant rate of weight loss of 2-3 kg per week at the 1.5 mg dose, leading to total weight loss of 25.8 kg after the first 13 weeks of treatment (16.7% of her initial body weight; end body weight 129.2 kg; BMI 41.5 kg/m2; BMI SDS+3.86).

Due to regulatory obligations, the clinical trial with setmelanotide treatment was stopped after 13 weeks. Soon after, the patient recognized markedly increased hunger (Likert hunger score 7 points) and regained weight (4.8 kg). The patient developed an acute situational depression as a result of this reversal in clinical course, and for this reason therapy was restarted (after three weeks off drug). Immediately after restart of setmelanotide (1 mg for 4 weeks and 1.5 mg thereafter) hunger decreased again and weight loss recommenced. During this second treatment phase the patient lost approximately 1-2 kg per week and reached a total loss of 35.9 kg body weight after 26 weeks of treatment (23.2% of her initial body weight). The patient has continued to lose weight since then and at 86 weeks of treatment has lost 60.5 kg of body weight. The patient remains responsive to the setmelanotide treatment.

Metabolism

Metabolic parameters and blood pressure were monitored. An oral glucose tolerance test was performed before the study start, after 13 weeks, and during the extension phase. During the study, the patient's blood glucose values remained always in the normal range (fasting and after glucose challenge). The pre-study elevated insulin levels demonstrating marked insulin resistance improved significantly under setmelanotide treatment.

Despite severe weight loss, the resting energy expenditure (REE)/kg lean body mass stayed relatively stable. This is in contrast to the significant reduction of REE after weight loss in common obese patients (see, e.g., Leibel et al. N Engl J Med 1995; 332:621-8; Johannsen et al. J Clin Endocrinol Metab 2012; 97:2489-96; Ebbeling et al. JAMA 2012; 307:2627-34; and de Jonge et al. Obesity (Silver Spring) 2012; 20:2384-9), which is thought to be one factor in regaining weight in normal obese patients. Also, in the POMC deficient subject, lean body mass was not greatly altered, and the reduction of body weight was mainly due to a loss of body-fat mass, which was accompanied by a significant decrease in serum leptin concentrations. Blood sugar values were relatively stable in all tests; insulin sensitivity improved significantly during the duration of setmelanotide treatment.

Cholesterol, HDL, LDL, and tryglyceride levels were also measured at 13 weeks and compared to baseline. HDL cholesterol and triglycerides did not change, while LDL cholesterol and total cholesterol were reduced, after a 13-week treatment with setmelanotide. Triglycerides, LDL and total cholesterol were further reduced after 26 weeks of treatment.

Blood Pressure

Blood pressure (BP) and heart rate (HR) during the study were assessed. In this study, blood pressure (BP) and heart rate (HR) were measured three times per day and over 12 hours after start of the therapy and after each dosage escalation.

There was no increase in blood pressure during all steps of dose escalation (analyzed with non-parametric student t-test). There were significant decreases in systolic and diastolic BP as well as HR.

Safety and Tolerability of Setmelanotide Treatment

Generally, setmelanotide treatment was well tolerated. The patient reported infrequent dry mouth. In general, there were no changes in safety laboratories of clinical concern.

Conclusions

As demonstrated herein, setmelanotide resulted in substantial reduction of weight and decreased hunger without adverse events. This study represents the first successful treatment of a POMC deficient patient with a targeted replacement therapy (MSH replacement therapy) with setmelanotide. The therapy using setmelanotide completely reversed hyperphagia and normalized insulin resistance caused by the disturbed hypothalamic leptin-melanocortin pathway in the POMC deficient patient. Treatment with setmelanotide resulted in an exceptional and sustained weight loss and termination of the life-long existing hyperphagia. The significant and continuous reduction of body weight while on therapy, which indicates a complete reversibility of the severe obesity, was comparable to if not greater than the changes observed after leptin administration to leptin deficient individuals. Treatment using setmelanotide can permit a normal long-term outcome and improvement of quality of life for the patient, who, prior to treatment, was at risk for severe comorbidities and a reduced life-expectancy.

In this study, the strong treatment effect was strongly supported by the long history of weight gain and severe hyperphagia prior to treatment. In addition, there was a strong dose-response for both hunger and weight loss in the dose escalation phase. The stopping of treatment in between the main study (first 13 weeks) and the extension phase allowed the patient to serve as her own "control". There was an immediate and rapid increase in hunger and weight after a short term withdrawal and a rapid response to re-treatment, thereby demonstrating the strong effect of setmelanotide. Quality of life improved dramatically after the initiation of setmelanotide treatment. The sustained weight loss under setmelanotide was surprising. Diet induced weight loss in patients with common obesity is generally accompanied by significant counter-regulatory effects, including reduction in resting energy expenditure (REE) and increases in hunger that lead to weight regain in the majority of patients. See, e.g., Johannsen et al. J. Clin. Endocrinol. Metab. 2012; 97:2489-96. Weight loss as observed in this patient under treatment with the MC4R agonist setmelanotide did not result in counter-regulatory responses even after more than 26 weeks of therapy and tremendous reduction of body weight. These data show that setmelanotide (RM-493) treatment also benefits obese individuals in avoiding weight regain after a period of significant weight loss. This is consistent with reports showing that the leptin-melanocortin signaling cascade plays an important role in the regulation of weight regain and energy expenditure after a period of severe weight loss e.g. caused by a dietary intervention (Rosenbaum et al. JCI, 2005; Kissileff et al. Am J Clin Nutr 2012).

Compared to wild-type obese patients administered setmelanotide, the weight loss seen in the POMC deficient patient was much greater. For example, as described in Example 3, wild-type obese patients given setmelanotide exhibited weight loss of about 0.6 to about 0.9 kg per week. In this example, the POMC deficient patient treated with setmelanotide exhibited weight loss of about 2-2.5 kg per week. This data show that POMC deficient (e.g., POMC null genotype) subjects are hyperresponsive to MC4R agonists such as setmelanotide, compared to wild-type obese patients, e.g., who do not have a POMC deficiency (e.g., POMC null genotype). As POMC operates upstream of the MC4R, deficiencies in other genes in the POMC-MC4R pathway upstream of MC4R likely also convey hyperresponsiveness to MC4R agonists such as setmelanotide, when compared to wild-type obese patients.

POMC deficiency is a childhood onset "ultra-rare disease", which has been reported in only approximately 15-20 children, of whom only three so far have reached adulthood. No adult-diagnosed patients have been reported to date. The efficacy and safety demonstrated in this study on an adult POMC deficient human are likely applicable to pediatric subjects and/or those subjects having other deficiencies of the hypothalamic leptin-melanocortin pathway, e.g., that lead to reduced or impaired POMC function or signaling, altered POMC processing, reduced hypothalamic POMC expression (e.g., which can be caused by genetic and epigenetic variations in the POMC gene, such as POMC heterozygous variant carriers); in subjects with mutations in the leptin receptor gene; in subjects with functional hypothalamic syndromes, such as Prader-Willi syndrome or PCSK1 deficiency; or in subject with MC4R mutations or other defects that impact functioning of the POMC-MC4R pathway.

Example 2: A Melanocortin 4 Receptor (MC4R) Agonist is Effective in a Mouse Model (Magel2-Null) of Prader-Willi Syndrome (PWS)

PWS is a contiguous gene disorder resulting from the loss of expression of several paternally inherited genes in a ~2 Mb region on chromosome 15 (15q11.2-13), known as the PWS region. The maternal genes at this locus are normally inactive. See, e.g., Elena et al. J of Obesity (2012). The PWS region includes several protein coding genes, along with DNA regions that generate long noncoding RNAs, numerous small nucleolar RNA (snoRNAs), and antisense transcripts. The inactivation of this 2 Mb region, which normally expresses several gene products, brings about the PWS symptoms. Symptoms associated with PWS are described herein.

Deficiency in the function of the MAGEL2 gene, located in the 2 Mb PWS locus, is likely causative for a number of the signs and symptoms in PWS patients. Magel2-null mice recapitulate many aspects of the PWS phenotype (Bischof et. al., Hum Mol Gen, 2007, Vol 16, no 22, 2713-2719). Magel2-null mice start with a failure to thrive phenotype (including growth retardation and reduced food intake) in the neonatal phase, followed by excessive weight gain after weaning associated with only moderately increased food intake. These progressive changes in energy metabolism mimic what is observed in human PWS, leading to significantly increased adiposity through adulthood. Magel2-null mice also exhibit delayed gonadal development, altered behavior with increased anxiety, and defects in the hypothalamic-pituitary axis—all features reminiscent of defects in the PWS. Mechanistically, the failure to thrive phase of Magel2-null mice aligns with the period where the POMC neurons still respond normally to the anorectic hormone leptin. However, POMC neurons in Magel2-null mice lose the ability to respond to leptin at about 8 weeks of age, leading progressively to significant changes in body composition and a profound increase in fat mass (Pravdivyi et. al., Hum Mol Gen, 2015 May 14, 1-8). Thus, the loss of function noted in the POMC neurons of Magel2-null mice may recapitulate important aspects of the PWS phenotype, mimicking progression from an early life failure to thrive phenotype into later metabolic disturbances and obesity. Magel2-null mice are a relevant rodent model of PWS.

Methods

Experiments were performed to determine the effect of a MC4R agonist, setmelanotide, on Magel2-null mice. Setmelanotide was evaluated in wild type and Magel2-null mice. Adult mice (N=6 per group) were acclimated to metabolic chambers, and food intake and energy expenditure (kcal/h) were measured over time. Mice were 8 weeks old. At this age, Magel2-null mice do not yet show the moderate hyperphagia noted later in life in this animal model. Vehicle and drug (setmelanotide) were administered intraperitoneally (i.p.) (n=6 for each treatment). A 0.1 mg/kg dose of setmelanotide was injected i.p. before the start of the dark cycle in the mice.

Food intake (cumulative in grams (g)) through 3 hours post dose and overnight cumulative food intake were assessed. Energy expenditure was also measured after dosing. Post-setmelanotide treatment data were compared to the data from post-vehicle injections in the same groups of mice. Statistical analysis was by two-way ANOVA followed by Bonferroni post-testing.

Results

Figure 1B:
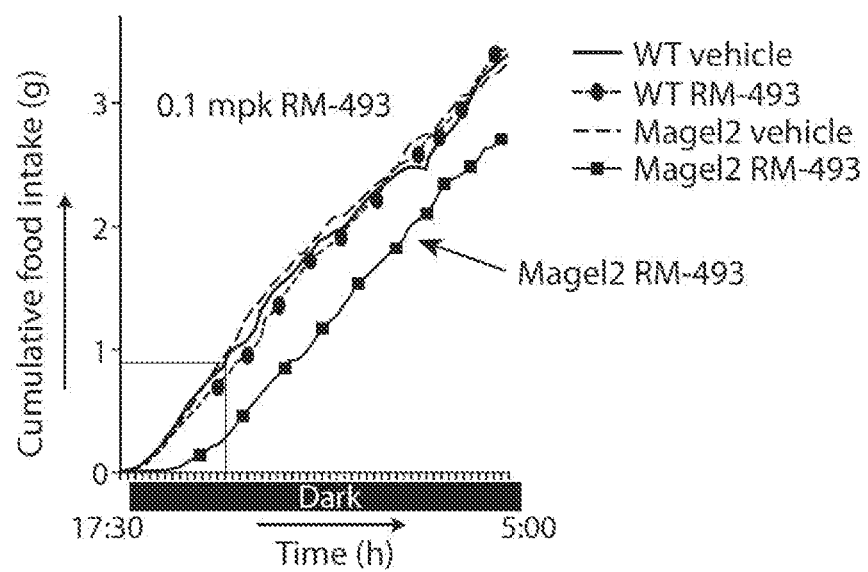

A 0.1 mg/kg dose of setmelanotide significantly suppressed spontaneous food intake in Magel2-null mice (~75% decrease over the first 3 hours; P<0.05) (FIG. 1A). This food intake suppression persisted throughout the dark cycle (FIG. 1B). Setmelanotide also increased energy expenditure by 11% at 3 hours post-dosing in Magel2-null mice compared to vehicle-dosed Magel2-null mice. Thus, setmelanotide decreased food intake and increased energy expenditure in Magel2-null mice.

In addition, Magel2-null mice were much more sensitive than wildtype mice to setmelanotide, as wildtype mice dosed with 0.1 mg/kg retained normal levels of food intake and did not respond to this dose of setmelanotide (FIGS. 1A-B). These data show that Magel2-null mice, a model for PWS in humans, were surprisingly sensitive to MSH "replacement therapy" with setmelanotide. This is likely in part due to the lack of expression of the anorectic hormone MSH in PWS patients due to dysfunctional POMC hypothalamic neurons (Pravdivyi et. al., Hum Mol Gen, 2015 May 14, 1-8). The large effects on food intake suppression noted in Magel2-null mice compared to wild type mice observed here show that setmelanotide treatment as replacement of missing MSH signaling may impact key efficacy endpoints in PWS patients, e.g., by restoring signaling downstream of the defective POMC neurons.

Conclusions

Magel2-null mice are a robust and relevant model for PWS. Treatment of Magel2-null mice with 0.1 mg/kg setmelanotide showed a statistically significant decrease in cumulative food intake (P<0.05). These data demonstrate that the MC4R agonist setmelanotide is effective in a mouse model of PWS, and suggest that setmelanotide may be efficacious in treating PWS, e.g., reducing appetite and hyperphagia behaviors in addition to modulating body weight in PWS patients. Also, Magel2-null mice were much more responsive to setmelanotide (e.g., in decreasing food intake) than wild-type obese mice.

Example 3: MC4R Agonist Effect on Wild-Type Obese Patients

The effect of MC4R agonist setmelanotide on wild-type obese human patients was assessed. The patients were treated with placebo or setmelanotide twice daily (BID) at 0.01 mg/kg or 0.015 mg/kg. There were 9 patients in each treatment group (6 with setmelanotide and 3 with placebo).

Figure 2:
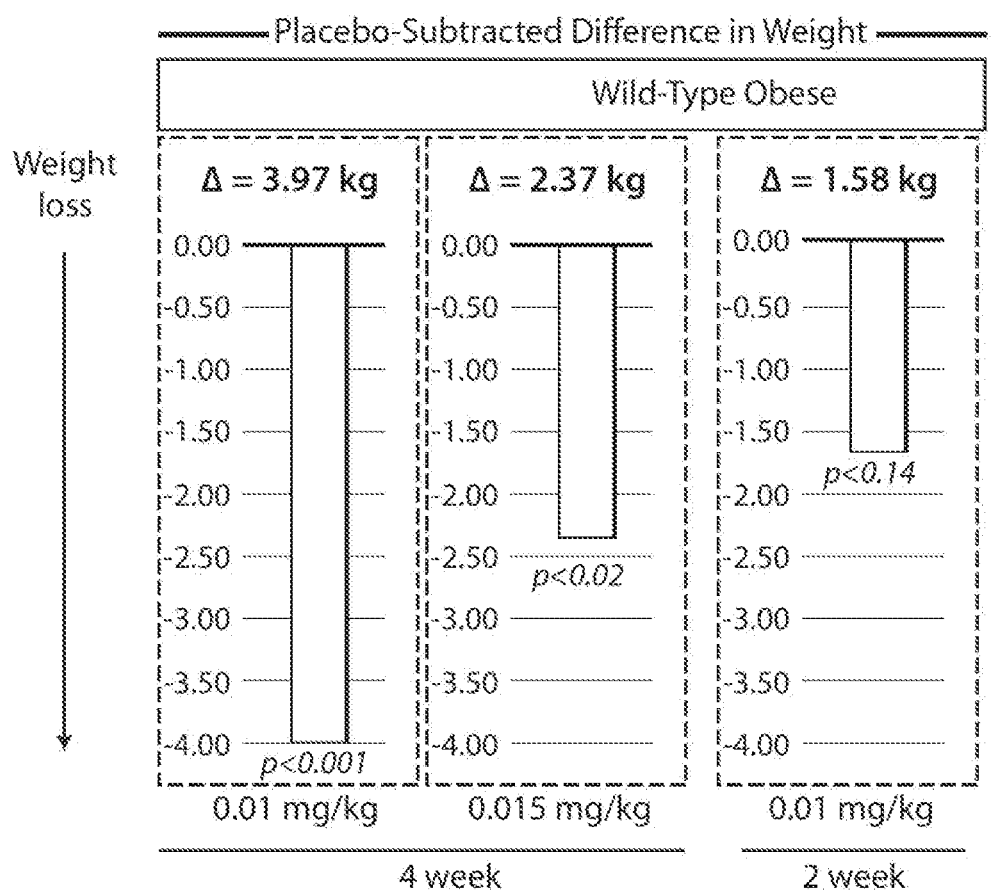
FIG. 2 is a set of graphs showing the change in body weight in wild-type obese humans after 2 or 4 weeks of treatment with setmelanotide.

The amount of weight loss was determined after 2 weeks or after 4 weeks of treatment. FIG. 2 shows the placebo-subtracted differences in weight of the wild-type obese patients after administration with setmelanotide at various doses after 2 or 4 weeks. The weight loss among the wild-type obese patients was about 0.6 to about 0.9 kg per week.

Example 4: Treatment of PWS

PWS is a rare genetic disorder that causes life-threatening obesity. It is believed that defects in the MC4 pathway are a cause of the weight and appetite abnormalities in PWS.

A phase 2 clinical trial is conducted to evaluate the safety and efficacy of setmelanotide on weight and eating behaviors (weight reduction and food-related behaviors) in obese patients with Prader-Willi syndrome (PWS). The trial is a double-blind, placebo-controlled parallel group study with a randomized placebo-controlled withdrawal phase and open label active treatment extension. The trial assesses the effect of setmelanotide as a replacement therapy for the treatment of severe obesity and hyperphagia in PWS, using a personalized medicine approach to restore lost function believed to be caused by a defect in the MC4 signaling pathway.

About 36 obese adolescent and adult patients with PWS are enrolled in the trial. Setmelanotide is administered once daily by subcutaneous injection for up to 10 weeks of treatment. After a two-week placebo-controlled baseline period, patients are randomized into one of three of the following treatment groups: 1) setmelanotide at 0.5 mg daily, 2) setmelanotide at 1.5 mg daily, and 3) placebo daily. After treatment for four weeks, patients are evaluated at the primary efficacy timepoint for weight, hyperphagia, and body composition. After the four weeks, patients are subjected to a 2-week randomized withdrawal period, where 50% of the patients are in a double-blind withdrawal (50% patients given setmelanotide and 50% patients given placebo). Following the 2-week withdrawal period, patients are treated with a 2-week active dose extension period.

PWS obese patients may exhibit a response (e.g., greater response, e.g., greater efficacy) to setmelanotide than obese patients that do not have PWS.

Example 5: Treatment of POMC-Null Obesity (POMC Deficiency)

POMC-null obesity is a very rare, life-threatening genetic disorder for which there have been no reported effective treatments. POMC-null patients lack a functioning POMC gene and have severe, early-onset obesity and extreme hunger. It is believed that these symptoms are due to a genetic defect in the MC4 pathway.

An open-label phase 2 clinical trial is conducted to evaluate the safety and efficacy of setmelanotide on weight and appetite in POMC-null patients.

About six obese adolescent and adult patients with POMC-null genetic defects are expected to be enrolled in the trial. Setmelanotide is administered once daily by subcutaneous injection for up to 13 weeks.

Patients are monitored for body weight, hunger level, waist circumference, daily food intake, blood pressure (systolic and diastolic), and heart rate before, during, and after the course of treatment. Adverse events are also monitored during and after the course of treatment to evaluate safety.

POMC-null obese patients may exhibit a response, e.g., greater response, e.g., efficacy, to setmelanotide than obese patients that are not POMC-null.

Example 6. The Effect of Varying Concentrations of Setmelanotide on Food Intake in Wild-Type and db/db Mice (Leptin Receptor Deficient Mice)

Mice carrying the db/db mutation lack the letptin receptor gene. It was postulated that these mice would be particularly sensitive to the MC4R agonist setmelanotide.

To determine this, wild-type and db/db mice were exposed to vehicle or varying concentrations of setmelanotide (0.0554 mpk; 0.137 mpk, 0.344 mpk, or 1.37 mpk), and their food intake was measured over four hours.

Figure 3A:
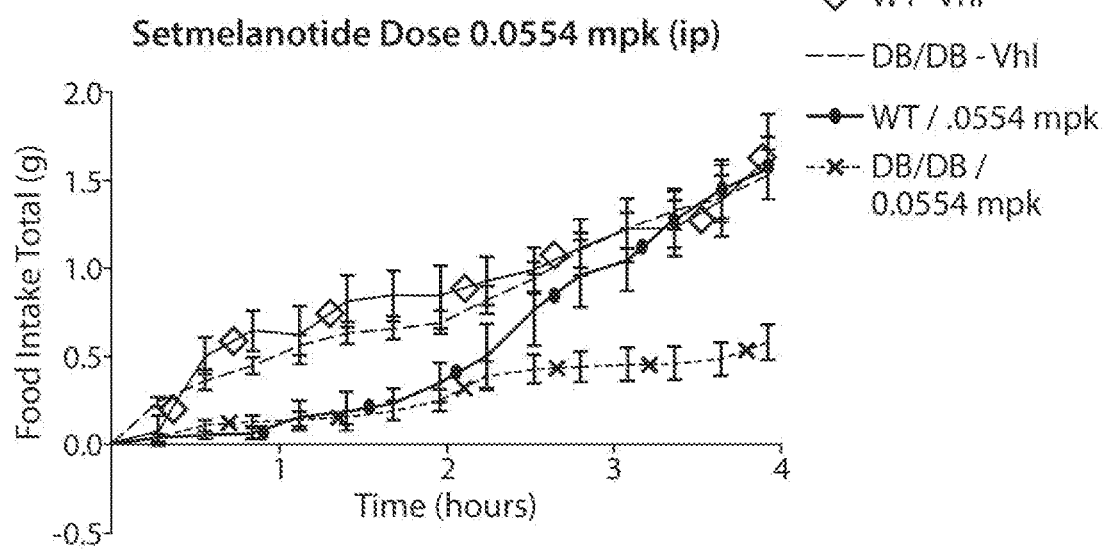
FIGS. 3A-D show food intake over time in wild-type and db/db mice administered vehicle or setmelanotide.

The results are shown in FIGS. 3A-F. For instance, at the 0.0544 mpk dose, the wildtype and vehicle treated mice showed identical food intake at the 4 hour timepoint, while the food intake in the db/db mice was significantly suppressed at the end of the 4 hour time period, by about 80% (FIG. 3A). Decreased food intake in wild-type mice was observed with this dose of drug at 1 and 2 hours, although food intake approached wt amounts after three hours and was indistinguishable from vehicle-treated wt and DB/DV mice at 4 hours. vehicle.

Figure 3B:
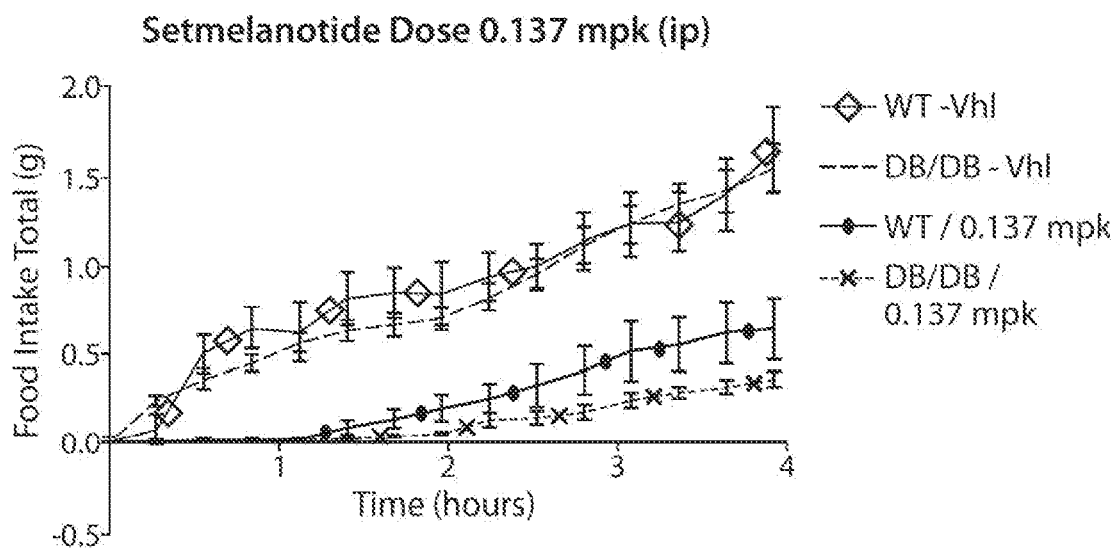
Figure 3C:
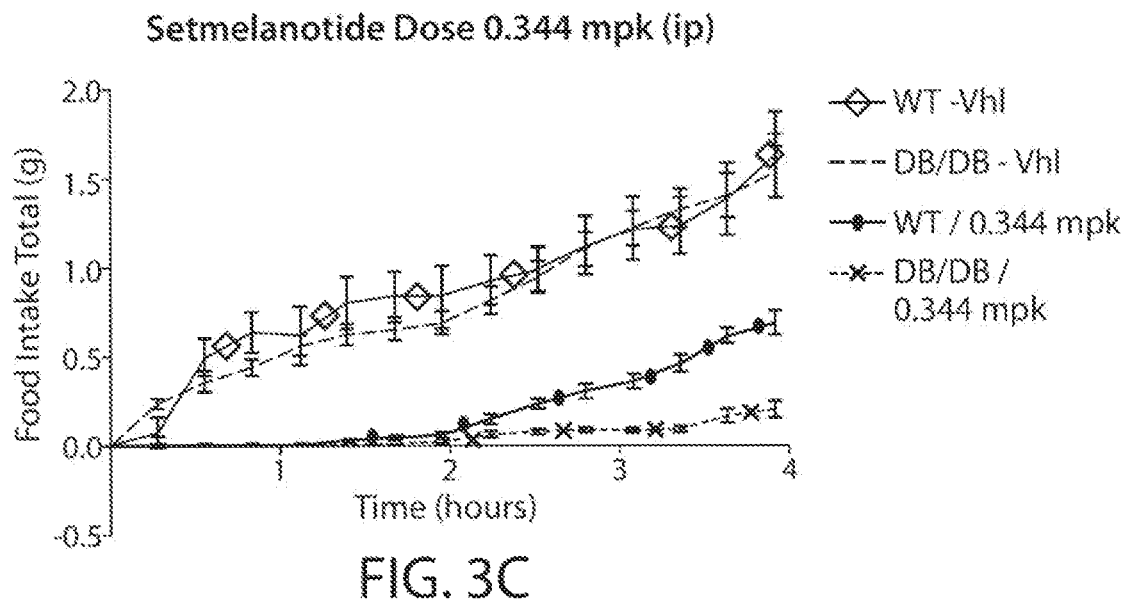
Figure 3D:
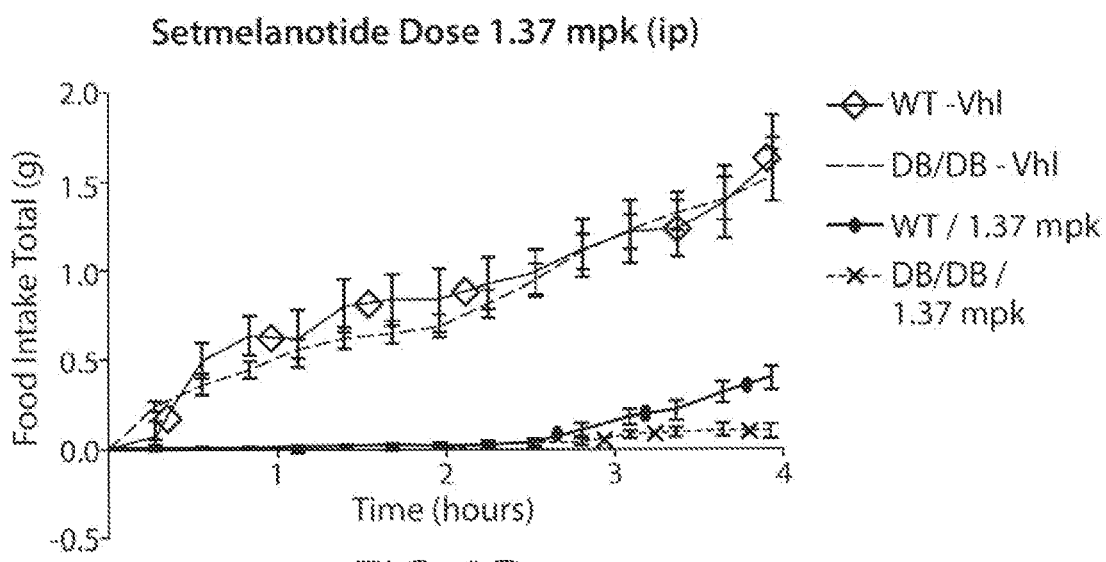
Figure 3E:
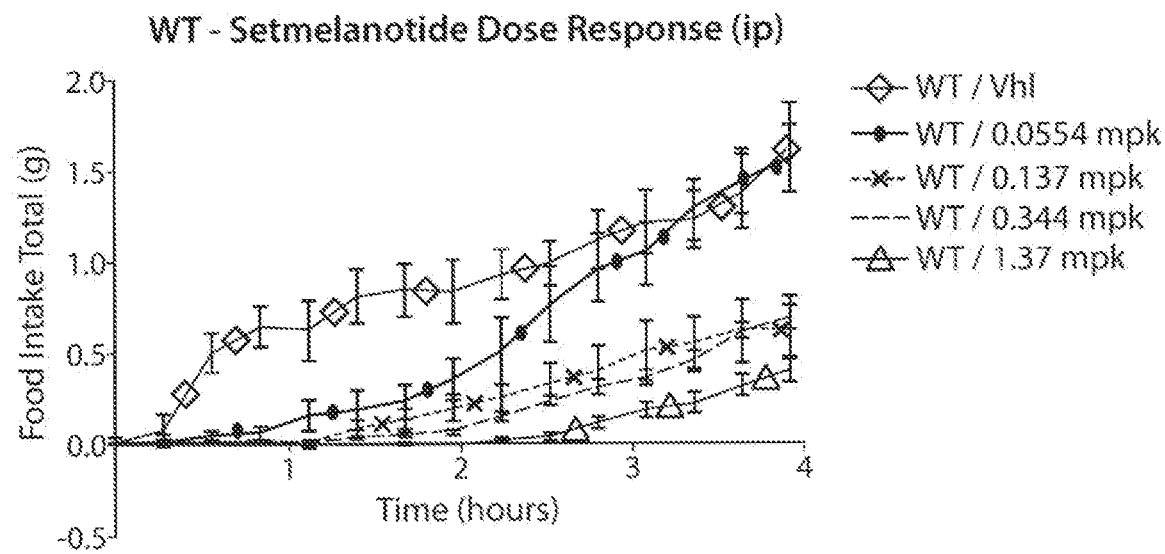
FIGS. 3E- and 3F are graphs that summarize the effects of food intake over time in wild-type (FIG. 3E) or db/db mice (FIG. 3F) administered vehicle or 0.0554 mpk, 0.137 mpk, 0.344 mpk or 1.37 mpk setmelanotide.
Figure 3F:
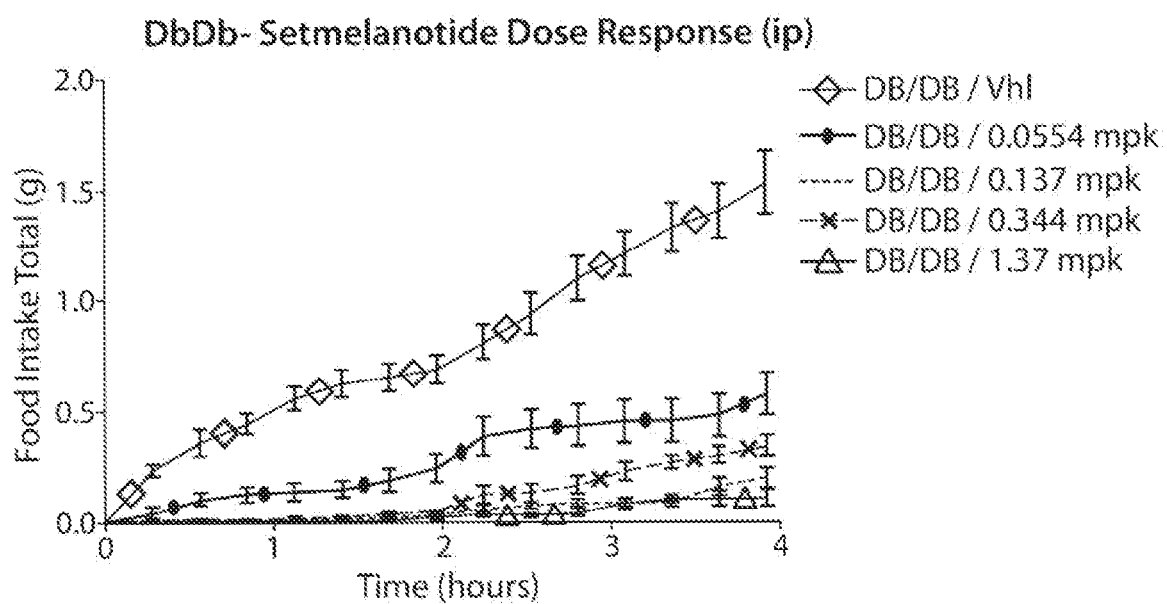

Suppression of food intake was even more pronounced at higher doses of setmelanotide (FIGS. 3B-3D). Higher doses of setmelanotide (0.137 mpk, 0/344 mpk, and 1.37 mpk) lead to significantly decreased food intake in wt mice as well as db/db mice when compared to vehicle-treated wt and db/db mice. Dose responses for wt and db/db mice for the setmelanotide concentrations tested are shown in FIGS. 3E and 3F, respectively. For all concentrations db/db mice always show a more profound suppression of foodintake than wildtype mice treated with setmelanotide.

These results demonstrate that wildtype mice consumed less food when exposed to increasing concentrations of setmelanotide. In addition, these results show that db/db mice are hypersensitive to the effects of this MC4R agonist.

EQUIVALENTS

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

The invention claimed is:

1. A method of treating a disorder in a subject in need thereof, comprising:

administering an agonist of the melanocortin-4 receptor (MC4R) at a daily dosage of about 0.1 mg to about 10 mg, wherein the disorder is characterized by one or more mutations in a gene associated with Bardet-Biedl syndrome, wherein the agonist is a MC4R agonist having a structure of Formula (I)

$$(R^2R^3)\text{-}A^1\text{-}c(A^2\text{-}A^3\text{-}A^4\text{-}A^5\text{-}A^6\text{-}A^7\text{-}A^8\text{-}A^9)\text{-}A^{10}\text{-}R^1 \quad (I),$$

wherein:

$A^1$ is Acc, HN—(CH$_2$)$_m$—C(O), L- or D-amino acid, or deleted;

$A^2$ is Cys, D-Cys, hCys, D-hCys, Pen, D-Pen, Asp, or Glu;

$A^3$ is Gly, Ala, β-Ala, Gaba, Aib, D-amino acid, or deleted;

$A^4$ is H is, 2-Pal, 3-Pal, 4-Pal, Taz, 2-Thi, 3-Thi, or (X$^1$, X$^2$, X$^3$, X$^4$, X$^5$)Phe;

$A^5$ is D-Phe, D-1-Nal, D-2-Nal, D-Trp, D-Bal, D-(X$^1$, X$^2$, X$^3$, X$^4$, X$^5$)Phe, L-Phe or D-(Et)Tyr;

$A^6$ is Arg, hArg, Dab, Dap, Lys, Orn, or HN—CH((CH$_2$)$_n$—N(R$^4$R$^5$))—C(O);

$A^7$ is Trp, 1-Nal, 2-Nal, Bal, Bip, D-Trp, D-2-Nal, D-Bal or D-Bip;

$A^8$ is Gly, D-Ala, Acc, Ala, 13-Ala, Gaba, Apn, Ahx, Aha, HN—(CH$_2$)$_s$—C(O), or deleted;

$A^9$ is Cys, D-Cys, hCys, D-hCys, Pen, D-Pen, Dab, Dap, Orn, or Lys;

$A^{10}$ is Acc, HN—(CH$_2$)$_r$—C(O), L- or D-amino acid, or deleted;

$R^1$ is OH or NH$_2$;

each of $R^2$ and $R^3$ is, independently for each occurrence, selected from the group consisting of H, (C$_1$-C$_{30}$)alkyl, (C$_1$-C$_{30}$)heteroalkyl, (C$_1$-C$_{30}$)acyl, (C$_2$-C$_{30}$)alkenyl, (C$_2$-C$_{30}$)alkynyl, aryl(C$_1$-C$_{30}$)alkyl, aryl(C$_1$-C$_{30}$)acyl, substituted (C$_1$-C$_{30}$)alkyl, substituted (C$_1$-C$_{30}$)heteroalkyl, substituted (C$_1$-C$_{30}$)acyl, substituted (C$_2$-C$_{30}$)alkenyl, substituted (C$_2$-C$_{30}$)alkynyl, substituted aryl(C$_1$-C$_{30}$)alkyl, and substituted aryl(C$_1$-C$_{30}$)acyl;

each of $R^4$ and $R^5$ is, independently for each occurrence, H, (C$_1$-C$_{40}$)alkyl, (C$_1$-C$_{40}$)heteroalkyl, (C$_1$-C$_{40}$)acyl, (C$_2$-C$_{40}$)alkenyl, (C$_2$-C$_{40}$)alkynyl, aryl(C$_1$-C$_{40}$)alkyl, aryl(C$_1$-C$_{40}$)acyl, substituted (C$_1$-C$_{40}$)alkyl, substituted (C$_1$-C$_{40}$)heteroalkyl, substituted (C$_1$-C$_{40}$)acyl, substituted (C$_2$-C$_{40}$)alkenyl, substituted (C$_2$-C$_{40}$)alkynyl, substituted aryl(C$_1$-C$_{40}$)alkyl, substituted aryl(C$_1$-C$_{40}$)acyl, (C$_1$-C$_{40}$)alkylsulfonyl, or —C(NH)—NH$_2$;

m is, independently for each occurrence, 1, 2, 3, 4, 5, 6 or 7;

n is, independently for each occurrence, 1, 2, 3, 4 or 5;

s is, independently for each occurrence, 1, 2, 3, 4, 5, 6, or 7;

t is, independently for each occurrence, 1, 2, 3, 4, 5, 6, or 7;

$X^1$, $X^2$, $X^3$, $X^4$, and $X^8$ each is, independently for each occurrence, H, F, Cl, Br, I, $(C_{1-10})$alkyl, substituted $(C_{1-10})$alkyl, $(C_{2-10})$alkenyl, substituted $(C_{2-10})$alkenyl, $(C_{2-10})$alkynyl, substituted $(C_{2-10})$alkynyl, aryl, substituted aryl, OH, $NH_2$, $NO_2$, or CN.

2. The method of claim 1, comprising administering the MC4R agonist in a unit dosage suitable for injection.

3. The method of claim 2, wherein the unit dosage is disposed within a delivery device.

4. The method of claim 1, wherein the MC4R agonist is administered subcutaneously.

5. The method of claim 1, wherein the subject is obese.

6. The method of claim 1, wherein the subject has a body mass index (BMI) greater than 35 kg/m² prior to administration of the agonist or at the time of the first administration.

7. The method of claim 1, wherein:
   (i) the subject has failed one or more previous therapies prior to administration of the agonist or at the time of the first administration;
   (ii) the subject has a lower body weight after administration of the agonist than before administration of the agonist;
   (iii) administration of the agonist results in a reduction of weight in the subject compared to the weight of the subject before treatment of about 1 kg to 3 kg after 1 week of treatment;
   (iv) administration of the agonist results in weight loss in the subject at a rate of about 1-2 kg/week;
   (v) administration of the agonist results in a reduction in hunger level in the subject compared to the hunger level of the subject before treatment;
   (vi) administration of the agonist results in a significant decrease in resting energy expenditure (REE) in the subject;
   (vii) administration of the agonist results in an increase in resting energy expenditure (REE) in the subject as compared to a control REE;
   (viii) administration of the agonist results in a reduction in food intake by the subject compared to a control;
   (ix) administration of the agonist results in a reduction in food intake of at least 100 kilocalories compared to a control;
   (x) administration of the agonist results in a reduction in waist circumference of the subject compared to a control;
   (xi) administration of the agonist results in a reduction in waist circumference of at least 2 cm in the subject compared to a control;
   (xii) administration of the agonist results in no detectable increase in blood pressure of the subject compared to the blood pressure of the subject prior to treatment;
   (xiii) administration of the agonist results in a reduction in blood pressure of the subject compared to the blood pressure of the subject prior to treatment;
   (xiv) administration of the agonist results in a reduction in systolic blood of the subject of at least 3 mmHg compared to the blood pressure of the subject prior to treatment; or
   (xv) administration of the agonist results in a reduction in diastolic blood pressure of the subject of at least 4 mmHg compared to the blood pressure of the subject prior to treatment.

8. The method of claim 1, wherein the subject is a mammal.

9. The method of claim 1, wherein the agonist is Ac-Arg-c(Cys-D-Ala-His-D-Phe-Arg-Trp-Cys)-$NH_2$ (SEQ ID NO: 140).

10. The method of claim 1, wherein the disorder is characterized by one or mutations in a BBS1-19, or 20 gene.

11. The method of claim 10, wherein the subject is or is identified as being:
   (i) a heterozygous carrier of the mutation(s), further characterized by having one functional BBS1-19, or 20 allele and one non-functional BBS1-19, or 20 allele;
   (ii) a compound heterozygous carrier of the mutation(s), e.g., having two non-functional BBS1-19, or 20 alleles, further characterized by having a BBS1-19, or 20 null genotype; or
   (iii) a homozygous carrier of the mutation(s), further characterized by having a BBS1-19, or 20 null genotype.

12. The method of claim 1, wherein the disorder comprises Laurence-Moon-Biedl syndrome.

13. The method of claim 1, wherein the one or more mutations comprise non-coding variants in one or more of the BBS1-19, or 20 genes.

14. The method of claim 1, wherein the disorder comprises Bardet-Biedl syndrome.

15. The method of claim 1, wherein the disorder is characterized by defective cilia or ciliary dysregulation.

16. The method of claim 1, wherein the defective cilia comprise defective neuronal cilia.

17. The method of claim 1, wherein the disorder further comprises impaired leptin signaling.

18. The method of claim 1, wherein the disorder further comprises hyperleptinemia.

19. The method of claim 2, wherein the unit dosage comprises between about 0.1 to about 0.2 mg of the agonist.

20. The method of claim 1, wherein:
   $R^1$ is $NH_2$;
   $R^2$ is —H and $R^3$ is acyl;
   $A^1$ is Arg;
   $A^2$ is Cys;
   $A^3$ is Ala;
   $A^4$ is His;
   $A^5$ is D-Phe;
   $A^6$ is Arg;
   $A^7$ is Trp;
   $A^8$ is deleted; and/or
   $A^9$ is Cys.

21. A method of treating a disorder in a subject in need thereof, comprising:
   administering an agonist of the melanocortin-4 receptor (MC4R) at a daily dosage of about 0.1 mg to about 10 mg,
   wherein the agonist is Ac-Arg-c(Cys-D-Ala-His-D-Phe-Arg-Trp-Cys)-$NH_2$ (SEQ ID NO: 140), and the disorder is characterized by one or more mutations in a gene associated with Alstrom syndrome.

* * * * *